(12) United States Patent
Shen et al.

(10) Patent No.: US 11,440,886 B2
(45) Date of Patent: Sep. 13, 2022

(54) ANTI-INFLAMMATORY COMPOUND, AND PREPARATION AND USE THEREOF

(71) Applicant: E-Nitiate Biopharmaceuticals (Hangzhou) Co., Ltd., Hangzhou (CN)

(72) Inventors: Wang Shen, Zhejiang (CN); Pengfei Liu, Zhejiang (CN); Jinping Zhu, Zhejiang (CN); Qiuping Luo, Zhejiang (CN); Pingbo Ke, Zhejiang (CN); Yufei Liu, Zhejiang (CN); Jida Shen, Zhejiang (CN)

(73) Assignee: E-Nitiate Biopharmaceuticals (Hangzhou) Co., Ltd., Hangzhou (CN)

( * ) Notice: Subject to any disclaimer, the term of this patent is extended or adjusted under 35 U.S.C. 154(b) by 0 days.

(21) Appl. No.: 16/993,289

(22) Filed: Aug. 14, 2020

(65) Prior Publication Data

US 2020/0377460 A1   Dec. 3, 2020

Related U.S. Application Data

(63) Continuation-in-part of application No. PCT/CN2019/078964, filed on Mar. 21, 2019.

(30) Foreign Application Priority Data

Apr. 26, 2018   (CN) .......................... 201810386572.6

(51) Int. Cl.
C07D 213/68   (2006.01)
C07D 405/12   (2006.01)
C07D 409/12   (2006.01)

(52) U.S. Cl.
CPC ......... *C07D 213/68* (2013.01); *C07D 405/12* (2013.01); *C07D 409/12* (2013.01)

(58) Field of Classification Search
CPC ... C07D 409/12; C07D 405/12; C07D 213/38
See application file for complete search history.

(56) References Cited

FOREIGN PATENT DOCUMENTS

| | | |
|---|---|---|
| CN | 102603544 | 7/2012 |
| CN | 103748073 | 4/2014 |
| EP | 0376724 A3 | 9/1991 |
| JP | H0228185 | 1/1990 |
| RU | 2009113585 A | 10/2010 |
| WO | 9923075 | 5/1999 |
| WO | 2004005258 A1 | 1/2004 |

OTHER PUBLICATIONS

Banker et al., Prodrugs, Modern Pharmaceutics, 3rd edition, Revised and Expanded, pp. 451 and 596.*
Jordan "Tamoxifen . . . " Nature Rev. v.2. p. 205-913 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982, 1996.*
Bundgaard, Design of Prodrugs, Chapter 1, p. 1, 1985.*
Silverman, Prodrugs and Drug Delivery Systems, The Organic Chemistry of Drug Design and Drug action, Chapter 8, pp. 352-400, 1992.*
Xu, Tetrahedron Letters, vol. 55, 7194-7197, 2014. (Year: 2014).*
Bebbington et al., "3,5 Disubstituted-4-hydroxyphenyls Linked to 3-Hydroxy-2-methyl-4(1H)-pyridinone: Potent Inhibitors of Lipid Peroxidation and Cell Toxicity," J. Med. Chem. 2000, 43, 2779-2782, 4 pages.
European Patent Office, International Search Report and Written Opinion, International Application No. PCT/CN2019/078964, dated Jul. 5, 2021, 9 pages.
Hall et al., "The Synthesis and Molecular Structure of 1-(3,4-Dihydroxyphenethyl)-3-hydroxy-2-methylpyridin-4(1H)-one Hydrochloride Methanol Solvate," Crystals, 2013, 3, 333-338, 6 pages.
Australia Patent Office; First Office Action; dated Jun. 3, 2021; 7 pages.
CAS Registry No. 1405726-89-7; STN Entry Date Nov. 25, 2012; 4(1H)-Pyridinone, 1-[2-amino-2-(3,4-dimethoxyphenyl)ethyl].
CAS Registry No. 1408687-07-9; STN Entry Date Dec. 2, 2012; 4(1H)-Pyridinone, 1-[2-(3,4-dimethoxyphenyl)-2-hydroxyethyl].
CAS Registry No. 1479671-43-6; STN Entry Date Nov. 24, 2013; 4(1H)-Pyridinone, 1-[2-(3,4-dimethoxyphenyl)-2-(methylamino)ethyl].
Russia Patent Office; First Office Action; dated Apr. 14, 2021; 31 pages.
English Translation of RU 2009113585A1 as published as US 20090281131A1.
James M. Butler, et al., "Increased leukocyte histamine release with elevated cyclic AMP-phosphodiesterase activity in atopic dermatitis." Journal of Allergy and Clinical Immunology, vol. 71, No. 5, May 1983, pp. 490-497.

(Continued)

*Primary Examiner* — D Margaret M Seaman
(74) *Attorney, Agent, or Firm* — Umberg Zipser LLP; Jason Tejani

(57) ABSTRACT

The present invention provides an anti-inflammatory compound, which is a compound having a structure (I) as shown below:

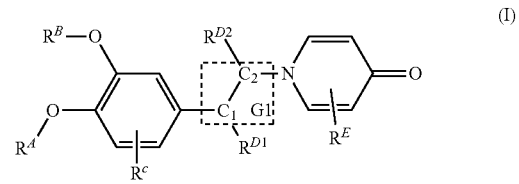

The compound is a target that is important for autoimmune activation, and that has strong inhibitory effect on PDE4 and penetrates the skin easily, and is a new type anti-inflammatory compound that is easily degraded.

14 Claims, No Drawings

(56) References Cited

OTHER PUBLICATIONS

Florian Gantner, et al., "In vitro differentiation of human monocytes to macrophages: change of PDE profile and its relationship to suppression of tumour necrosis factor-alpha release by PDE inhibitors." British Journal of Pharmacology, vol. 121, May 1997, pp. 221-231.

Gordon Dent, et al., "Suppression of human eosinophil respiratory burst and cyclic AMP hydrolysis by inhibitors of type IV phosphodiesterase: interaction with the beta adrenoceptor agonist albuterol." Journal of Pharmacology and Experimental Therapeutics, vol. 271, Dec. 1993, pp. 1167-1174.

Kevin D. Cooper, et al., "Phosphodiesterase inhibition by Ro 20-1724 reduces hyper-IgE synthesis by atopic dermatitis cells in vitro." Journal of Investigative Dermatology, vol. 84, Jun. 1985, pp. 477-482.

Amy S. Paller, et al., "Efficacy and safety of crisaborole ointment, a novel, nonsteroidal phosphodiesterase 4 (PDE4) inhibitor for the topical treatment of atopic dermatitis (AD) in children and adults." Journal of the American Academy of Dermatology, vol. 75, No. 3, Sep. 2016, pp. 494-503.

Buzhe Xu, et al., "A Facile Synthesis of Novel Tricyclic 4-Pyridones." Tetrahedron Letters, vol. 55, No. 52, Nov. 10, 2014, pp. 7194-7197.

\* cited by examiner

ANTI-INFLAMMATORY COMPOUND, AND PREPARATION AND USE THEREOF

CROSS-REFERENCE TO RELATED APPLICATION

This application is a continuation-in-part application of and claims the priority benefit of international application of PCT application serial no. PCT/CN2019/078964, filed on Mar. 21, 2019, which claims the priority benefit of China application no. 201810386572.6, filed on Apr. 26, 2018. The entirety of each of the above mentioned patent applications is hereby incorporated by reference herein and made a part of this specification.

BACKGROUND OF THE INVENTION

1. Field of the Invention

The present invention relates to the field of pharmaceutical chemistry, and in particular to an anti-inflammatory compound, a preparation method, and use thereof in the treatment of inflammatory dermatological diseases, such as atopic dermatitis and psoriasis.

2. Description of Related Art

Inflammation caused by human autoimmune conditions is a major factor causing many human diseases. People with degenerative diseases usually exhibit excessive levels of pro-inflammatory modulators in their blood. A class of such pro-inflammatory modulators are cytokines. Cytokines include pro-inflammatory cytokines (including IL-1, IL-1β, IL-2, IL-3, IL-6, IL-7, IL-9, IL-12, IL-17, IL-18, IL-23, TNF-α, LT, LIF, oncoproteins and IFN-); anti-inflammatory cytokines (IL-4, IL-10, IL-11, IL-13 and TGF-β); and chemokines (IL-8, Gro-a, MIP-1, MCP-1, ENA-78 and RANTES).

In many situations of inflammation, pro-inflammatory cytokines, especially TNF-α, IL-1β and IL-6, and anti-inflammatory cytokine IL-10, show important roles in the pathogenesis of various inflammation-related diseases and can thus be used as potential therapeutic agents. For example, elevated levels of pro-inflammatory cytokines (INF-α, IFN, IL-1, IL-2, IL-6, and IL-12) and chemokines (IL-8, MCP-1, and RANTES) have been observed in inflammation-related diseases, such as eczema, psoriasis, enteritis, Graves' disease, and Hashimoto thyroiditis, with simultaneous increases in their soluble TNF receptors, IL-1 receptor antagonists, and anti-inflammatory cytokine IL-10. It has been confirmed that IL-10 inhibits the increase in production of pro-inflammatory cytokines in LPMC culture in vitro and in patients.

Phosphodiesterase (PDE) isozymes are involved in the regulation of signal transduction cascade in cells by regulating the cyclic nucleotide level. So far, a family of 11 PDE isozyme genes have been identified. The difference between these isozymes lies in their cell distribution and biochemical functions. High PDE4 activity was found in leukocytes of patients with atopic dermatitis, particularly children (Butler, J M, et al., J. Allergy Clin. Immunol. 1983, 71: 490-497). PDE4 is a main isozyme in inflammatory cells, such as monocytes and monocyte-derived macrophages (Gantner et al., Br. J. Pharmacol., 1997, 121: 221-231), eosinophils (Dent et al., J. Pharmacol. Exp. Ther., 1994, 271: 1167-1174) and B lymphocytes (Cooper et al., J. Invest. Dermatol., 1985, 84: 477-482). PDE4 inhibitors show a highly potent anti-inflammatory effect by increasing the intracellular cAMP level. By inhibiting cAMP degradation, the PDE4 inhibitors can regulate intracellular functions (e.g., reduce peroxide production) and gene transcription (e.g., inhibit the synthesis and/or release of inflammatory cytokines). Because PDE4 is also expressed in keratinocytes, these cells can be used as other possible pharmacological targets for controlling inflammatory skin diseases using PDE4 inhibitors.

PDE4 inhibitors are useful in diseases related to eosinophil activity, particularly inflammatory tracheal diseases, such as bronchial asthma, allergic rhinitis, allergic conjunctivitis, atopic dermatitis, eczema, allergic angiitis, inflammation and proliferative skin diseases, such as psoriasis or keratosis. These compounds can be administered possibly in the form of oral, transdermal, topical, inhalable and intranasal preparations.

In recent years, great changes have taken place in the treatment of inflammation-related diseases. Due to the more and more attention paid to the severity of these diseases and the insight into the important role of cytokines in their immune pathogenesis by the patients and physicians, many drugs targeting cytokines are available in the clinic and some are available in the market to treat these diseases related to the autoimmune system. Most of the efforts are focused on targeting TNF-α and IL-1. At present, many drugs are available on the market. For example, TNF-α inhibitors such as Etanercept (Enbrel), infliximab (Remicade) and adalimumab (Humira), certolizumab pegol (Cimzia) can be used for treating immune system-related diseases such as rheumatic arthritis, psoriasis and irritant enteritis; and several drugs targeting IL-1 (Anakinra (Kineret)), IL-4 (dupilumab (Dupixent)), IL-6 (tocilizumab (Actemra), and siltuximab (Sylvant)), or IL-12/IL-23 (Ustekinumab (Stelara)) and Alefacept (Amevive) inhibiting T immune cells can be used for treating various immune diseases.

However, when these monoclonal antibody products are systemically administered, the immunity of patients is inhibited, resulting in infection or other systemic side effects. Therefore, these drugs are clinically approved for treating patients with moderate to severe inflammatory diseases. Most patients with psoriasis and eczema are mild to moderate, so these drugs cannot help them.

Crisaborole, a PDE4 inhibitor, has proved its efficacy and safety in the treatment of mild to moderate eczema in children and adults in Phase III clinical trials (research project Nos.: AD-301 and AD-302) of eczema (also known as allergic dermatitis, atopic dermatitis, or atopic dermatitis) (Paller A S et al., J Am Acad Dermatol. 2016; 75(3): 494-503). PDE4 is a key regulatory point for the production of inflammatory cytokines in eczema, which mainly acts by degrading cyclic adenosine monophosphate. In circulating inflammatory cells in patients with eczema, the PDE4 activity increases, and in-vitro tests show that when PDE4 in monocytes is inhibited, the release of cytokines that promote inflammatory response decreases.

Crisaborole has been proved to have good safety, but limited clinical effect, as indicated by a clinical effect on eczema that is only about 10% higher than that of the blank control. Also, a large proportion (about 50%) of patients cannot benefit from Crisaborole. Crisaborole has an insignificant clinical effect in the treatment of psoriasis due to the low activity (where the enzyme inhibition activity is about 100 nM, and the cell activity inhibiting cytokine release is about 500 nM) (not approved for treating psoriasis).

In view of this, it can be found that the existing drugs for eczema and psoriasis cannot meet the needs of patients, particularly the majority of mild-moderate patients, and more effective and safe topical drugs are still needed to be developed to treat most mild-moderate inflammatory skin diseases (such as psoriasis, eczema, etc.).

SUMMARY OF THE INVENTION

The present invention provides a novel anti-inflammatory drug that has a potent inhibition effect on PDE4, an important target for autoimmune activation, and is easy to penetrate the skin, and readily degrade.

The present invention provides an anti-inflammatory compound, which is a compound having a structure shown below:

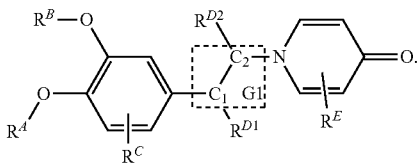

In the structural formula, $R^A$ is hydrogen, alkyl, or aryl, and in the above groups one or more hydrogen atom(s) attached to carbon in the groups is/are optionally substituted with alkyl, cycloalkyl, aryl, or halogen, the alkyl is an alkyl group having 1 to 15 carbon atoms, generally a group having the general formula $C_nH_{2n+1}$—, and preferably a linear or branched alkyl group where n is not greater than 6;

the aryl group is selected from any aromatic groups consisting of pure carbocyclic or heterocyclic ring(s) with 5-24 carbon atoms, such as cyclopentadienyl, phenyl, naphthyl, quinolinyl, pyrrolyl, pyridinyl, furyl, and the like; and the "one or more hydrogen atom(s) attached to carbon in the groups is/are optionally substituted with alkyl (which generally refers to an alkyl group with no more than 10 carbon atoms), cycloalkyl (three-, four-, five-, six-, or seven-membered), heterocycloalkyl (aza/thia/oxa-three/four/five/six/seven-membered), aryl (which generally refers to an aryl group having 5 to 20 carbon atoms), or halogen (fluoro, chloro, bromo, iodo)" means the forms of substitution of hydrogen on an alkyl group, for example, —CH$_2$Cl, —CH$_2$CH$_2$Cl, —CH$_2$(Br)CH$_3$, —CH$_2$CH$_2$F, —CHF$_2$, —CH(CH$_3$)CHF$_2$, —CH(Ph)CH$_3$,

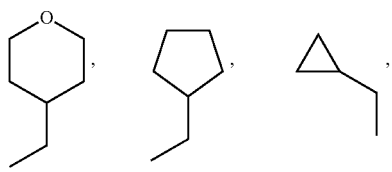

or —CH$_2$Ph, or the forms of substitution of hydrogen on an aromatic group, for example,

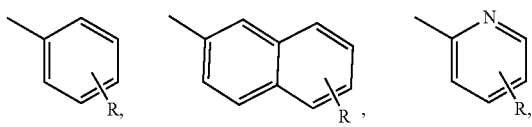

-continued

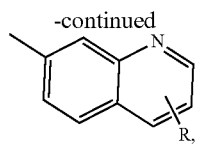

in which R is any one or several substituting alkyl groups (generally having no more than 6 carbon atoms), cycloalkyl groups (generally three-, four-, five-, or six-membered, which may be heterocycloalkyl), aryl groups (which generally refers to an aryl group having 5 to 20 carbon atoms, and may be heteroaryl), and halogen on the aromatic ring.

$R^B$ is hydrogen, alkyl, cycloalkyl, heterocycloalkyl, aryl, alkenyl, or alkynyl, and in the above groups one or more hydrogen atom(s) attached to carbon in the groups is/are optionally substituted with alkyl, cycloalkyl, heterocycloalkyl, aryl, or halogen, and one or more carbon atom(s) in the groups is/are optionally substituted with sulfur, sulfoxide, sulfone, or sulfonyl; or $R^B$ is a hydroxyl protecting group, where the alkyl is as defined in the scenario of $R^A$;

the aryl is as defined in the scenario of $R^A$;

the cycloalkyl refers to a three-membered, four-membered, five-membered, or six-membered ring;

the heterocycloalkyl refers to an oxa/aza/thia three-membered, four-membered, five-membered, or six-membered ring;

the alkenyl may be selected from linear or branched alkenyl with 2-10 carbon atoms, such as ethenyl (—═), 2-propenyl (—CH$_2$—═), 2-butenyl (—CH$_2$—═—CH$_3$), 3-butenyl (—CH$_2$—CH$_2$—═), cyclopentenyl

and the like;

the alkynyl may be selected from linear or branched alkynyl with 2-10 carbon atoms, such as ethynyl

2-propynyl

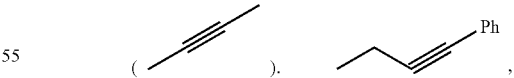

and the like;

the "one or more hydrogen atom(s) attached to carbon in the groups is/are optionally substituted with alkyl, cycloalkyl, heterocycloalkyl, aryl, or halogen" has the same meaning as in the scenario of $R^A$;

the "one or more carbon atom(s) in the groups is/are optionally substituted with sulfur, sulfoxide, sulfone, or sulfonyl refers to a situation in which one or more carbon atom(s) such as $C_1$ and $C_2$ on the structure

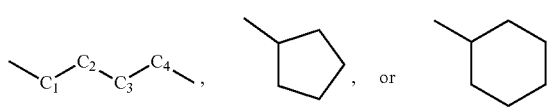

is/are replaced by S, (S=O), or (O=S=O), for example,

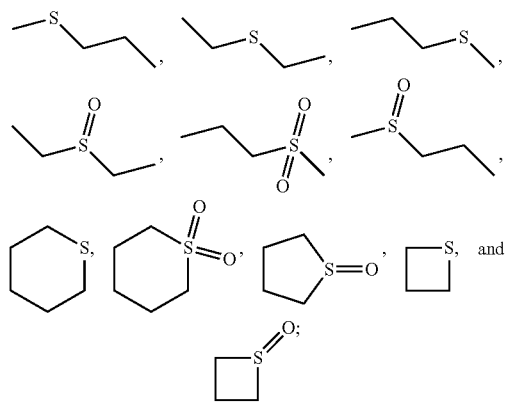

and the hydroxyl protecting group means that a protectant reacts with a hydroxyl group to converts the hydroxyl group into silicon ether, benzyl ether, methyl ether, allyl ether and other forms, so that it is not affected by oxidation, reduction and other reactions.

$R^C$ is hydrogen, alkyl, halogen, alkoxy, or cyano, where the alkyl is selected from a linear or branched alkyl group with 1-20 carbon atoms; and the alkoxy refers to the group —O—R, in which R is a branched or linear alkyl group with 1-20 carbon atoms;

$R^{D1}$ is hydrogen, oxygen, nitrogen, hydroxy, cyano, amino, amido, alkyl, aryl, an ester group, carboxyl, alkynyl, or alkenyl, and in the above groups one or more hydrogen atom(s) attached to carbon/oxygen (that is, hydrogen in —OH)/nitrogen (that is, hydrogen in —NH$_2$, —NH(R), or =NH) in the groups is/are optionally substituted with alkyl, cycloalkyl, alkynyl, alkenyl, aryl, halogen, sulfonyl, a sulfoxide group, or an ether group, and one or more carbon atom(s) in the groups is/are optionally substituted with sulfur, sulfoxide, sulfone, or sulfonyl, where the alkyl is as defined in the scenario of $R^A$;

the amino refers to —NH$_2$;

the amido refers to a group denoted by

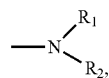

in which $R_1$ and $R_2$ may be any substituent, such as alkyl, aryl, and the like;

the aryl is as defined in the scenario of $R^A$;

the alkenyl is as defined in the scenario of $R^B$;

the alkynyl is as defined in the scenario of $R^B$;

the ester group refers to a group denoted by

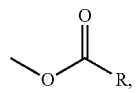

in which R is alkyl, cycloalkyl, heterocycloalkyl, aryl, heteroaryl, and the like, where the alkyl is as defined in the scenario of $R^B$, and the aryl is as defined in the scenario of $R^B$;

in the "one or more hydrogen atom(s) attached to carbon/oxygen/nitrogen in the groups is/are optionally substituted with alkyl, cycloalkyl, alkynyl, alkenyl, aryl, halogen, sulfonyl, a sulfoxide group, or an ether group", the alkyl, cycloalkyl, aryl, and halogen are as defined in the scenario of $R^A$;

the alkynyl generally refers to an alkynyl substituent with no more than 20 carbon atoms, and may be

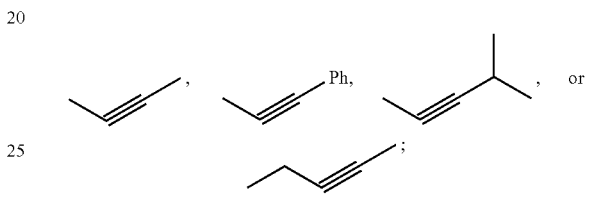

the alkenyl generally refers to an alkenyl substituent with no more than 20 carbon atoms, and may be

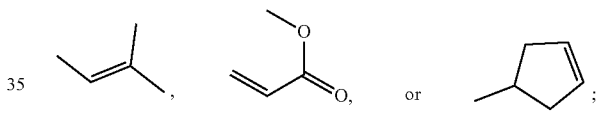

and the ether group generally refers to an ether substituent with no more than 20 carbon atoms, and may be (—O—R); and the "one or more carbon atom(s) in the groups is/are optionally substituted with sulfur, sulfoxide, sulfone, or sulfonyl" has the same meaning as in the scenario of $R^B$.

$C_1$—$R^{D1}$ bond is a single bond, or a double bond (e.g. C=O, C=N, and the like);

$R^{D2}$ is hydrogen, cyano, alkyl, cycloalkyl, aryl, an ester group, or carboxyl, and in the above groups one or more hydrogen atom(s) attached to carbon/oxygen/nitrogen in the groups is/are optionally substituted with alkyl, cycloalkyl, alkynyl, alkenyl, aryl, halogen, sulfonyl, a sulfoxide group, or an ether group, where the amino, amido, alkyl, cycloalkyl, aryl, ester group, "one or more hydrogen atom(s) attached to carbon/oxygen/nitrogen in the groups is/are optionally substituted with alkyl, cycloalkyl, alkynyl, alkenyl, aryl, halogen, sulfonyl, a sulfoxide group, or an ether group" have the same meaning as those in the scenario of $R^{D1}$.

G1 is a single bond, a double bond or a ring comprising $C_1$ and $C_2$, where the ring may be a ring-opening product of $C_1$ and $C_2$ double bonds, for example, cyclopropane, and propylene oxide; or a cyclization reaction product of a compound having a double bond or a triple bond such as cis-butadiene, cyclopentene and the like with $C_1$=$C_2$ double bond.

$R^E$ is a group where one or more hydrogen atom(s) attached to carbon on the pyridinone ring of G1 is/are substituted with alkyl, aryl, cyano, or halogen, where the alkyl, aryl and halogen are as defined in the scenario of $R^A$.

Further, the anti-inflammatory compound provided in the present invention is further characterized by G1 that is a three-membered ring, and having a specific structure shown below:

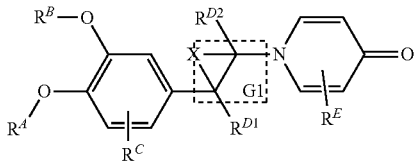

in which X is carbon, oxygen, nitrogen, or sulfur.

In addition, the present invention also provides a method for preparing the anti-inflammatory compound, which comprises: using 3-hydroxybenzaldehyde derivative A as a starting material, and substituting the hydrogen in the hydroxyl group of the 3-hydroxybenzaldehyde derivative A with $R^B$ to obtain an intermediate product B;

reacting the intermediate product B in the presence of trimethylsilyl cyanide to obtain an intermediate product C;

reducing the intermediate product C to obtain an intermediate product D having an amino group; and reacting the amino group in the intermediate product D with a six-membered oxygen-containing cyclic compound to obtain a type-A target product, where the 3-hydroxybenzaldehyde derivative A is a compound having a structure shown below:

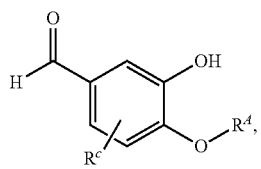

the intermediate product B is a compound having a structure shown below:

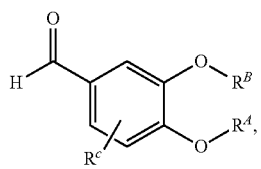

the intermediate product C is a compound having a structure shown below:

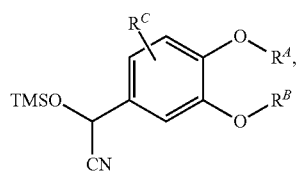

the intermediate product D is a compound having a structure shown below:

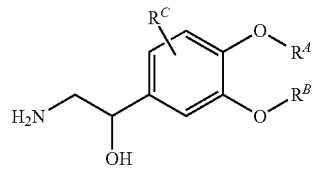

the type-A target product is a compound having a structure shown below:

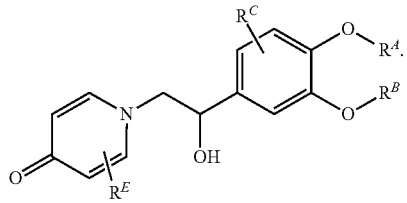

In addition, the present invention also provides a method for preparing the anti-inflammatory compound, which comprises subjecting the hydroxyl group on the middle bridge of the type-A target product to an addition/substitution reaction to obtain a type-A-1 target product, where the type-A-1 target product is a compound having a structure shown below:

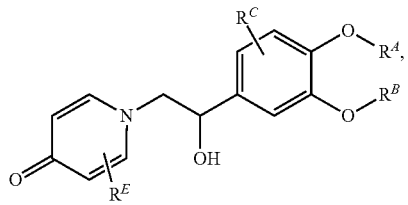

in which $R_d$ is alkyl, cycloalkyl, or an ester group, and in the above groups one or more hydrogen atom(s) attached to carbon in the groups is/are optionally substituted with alkyl, alkynyl, alkenyl, cycloalkyl, aryl, halogen, hydroxy, thio, cyano, or thioalkyl.

In addition, the present invention also provides a method for preparing the anti-inflammatory compound, which comprises oxidizing the hydroxyl group on the middle bridge of the type-A target product to obtain a type-B target product, where the type-B target product is a compound having a structure shown below:

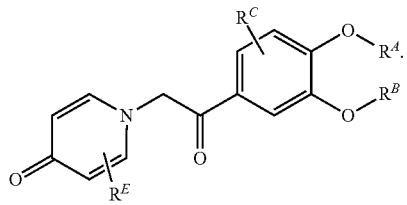

In addition, the present invention also provides a method for preparing the anti-inflammatory compound, which comprises deprotecting the group $R^B$ that is a hydroxyl protecting group on the type-B target product to obtain a type-B-1 target product, where the type-B-1 target product is a compound having a structure shown below:

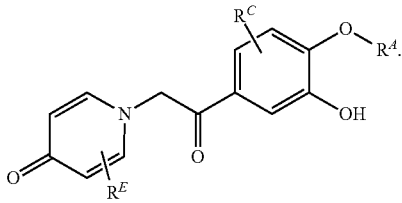

In addition, the present invention also provides a method for preparing the anti-inflammatory compound, which comprises subjecting the hydroxyl group on the phenyl ring of the type B-1 target product to an addition/substitution reaction to obtain a type B-2 target product, where the type-B-2 target product is a compound having a structure shown below:

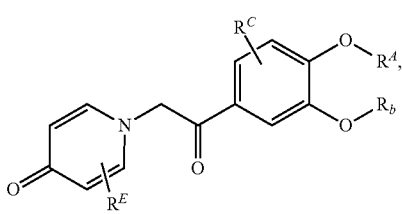

in which $R_d$ is alkyl, cycloalkyl, or an ester group, and in the above groups one or more hydrogen atom(s) attached to carbon in the groups is/are optionally substituted with alkyl, alkynyl, alkenyl, cycloalkyl, aryl, halogen, hydroxy, thio, cyano, or thioalkyl.

In addition, the present invention also provides a method for preparing the anti-inflammatory compound, which comprises oximating the carbonyl group on the middle bridge of the type-B target product to obtain a type B-3 target product, where the type-B-3 target product is a compound having a structure shown below:

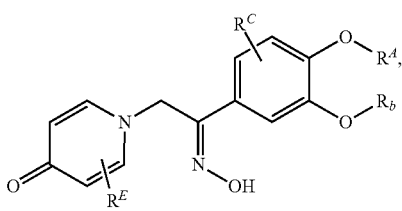

In addition, the present invention also provides a method for preparing the anti-inflammatory compound, which comprises subjecting the hydroxyl group on the oxime of the type-B-3 target product to an addition/substitution reaction to obtain a type-B-4 target product, where the type-B-4 target product is a compound having a structure shown below:

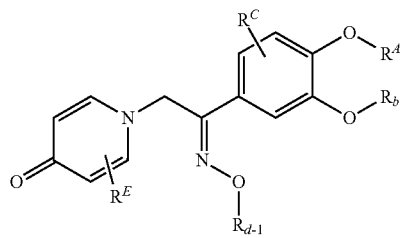

in which $R_{d-1}$ is alkyl, cycloalkyl, or an ester group, and in the above groups one or more hydrogen atom(s) attached to carbon in the group is/are optionally substituted with alkyl, alkynyl, alkenyl, cycloalkyl, heterocycloalkyl, aryl, halogen, hydroxy, thio, cyano, or thioalkyl.

In addition, the present invention also provides a method for preparing the anti-inflammatory compound, which comprises: using a 3-hydroxyacetophenone derivative I as a starting material, and substituting the hydrogen in the hydroxyl group of the 3-hydroxyacetophenone derivative I with $R^B$, to obtain an intermediate product II;

reacting the intermediate product II in the presence of a halogenating agent to obtain an intermediate product III; and reacting the halogen in the intermediate product III with a six-membered oxygen-containing cyclic compound to obtain a type-B target product, where the 3-hydroxyacetophenone derivative I is a compound having a structure shown below:

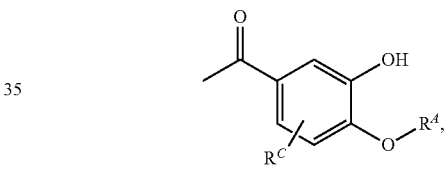

the intermediate product II is a compound having a structure shown below:

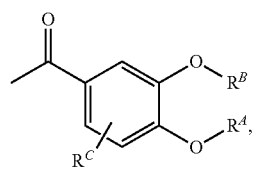

the intermediate product III is a compound having a structure shown below:

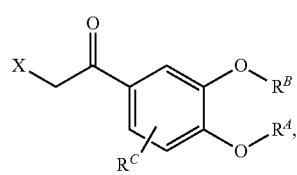

in which X is halogen.

In addition, the present invention also provides a method for preparing the anti-inflammatory compound, which comprises removing the hydroxyl group on the middle bridge of the type-A target product to obtain a type-C target product, or reducing and then eliminating the carbonyl group on the middle bridge of the type-B target product to obtain a type-C target product, where the type-C target product is a compound having a structure shown below:

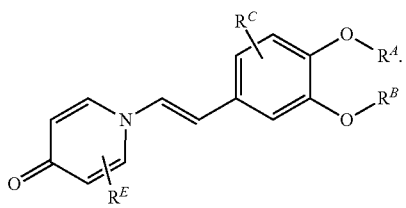

In addition, the present invention also provides a method for preparing the anti-inflammatory compound, which comprises reducing and then eliminating the carbonyl group on the middle bridge of the type-B-2 target product to obtain a type-C-1 target product, where the type-C-1 target product is a compound having a structure shown below:

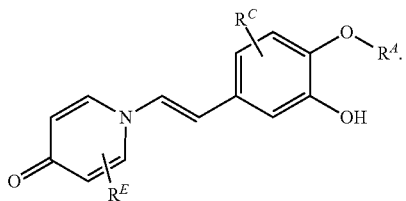

In addition, the present invention also provides a method for preparing the anti-inflammatory compound, which comprises subjecting the hydroxyl group on the phenyl ring of the type C-1 target product to an addition/substitution reaction to obtain a type C-2 target product, where the type-C-2 target product is a compound having a structure shown below:

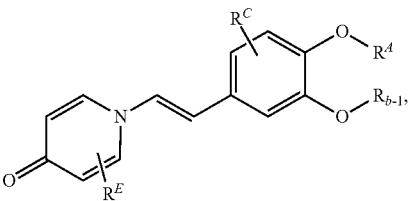

in which $R_{b-1}$ is alkyl, cycloalkyl, or an ester group, and in the above groups one or more hydrogen atom(s) attached to carbon in the groups is/are optionally substituted with alkyl, alkynyl, alkenyl, cycloalkyl, heterocycloalkyl, aryl, halogen, hydroxy, thio, cyano, or thioalkyl.

In addition, the present invention also provides a method for preparing the anti-inflammatory compound, which comprises reacting the carbonyl group on the middle bridge of the type-B target product with a halogenating reagent to obtain an intermediate product X1; and replacing the halogen in the intermediate product X1 to obtain a type-C-3 target product, where the intermediate product X1 is a compound having a structure shown below:

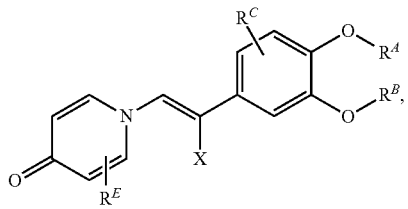

in which X is halogen; and where the type-C-3 target product is a compound having a structure shown below:

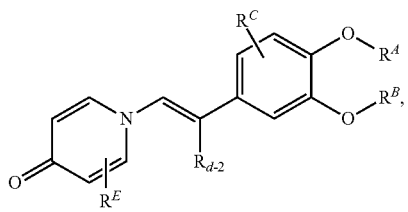

in which $R_d$-2 is aryl, alkyl, cycloalkyl, an ether group, or an ester group where one or more hydrogen atom(s) attached to carbon in the groups is/are optionally substituted with alkyl, alkynyl, alkenyl, cycloalkyl, aryl, halogen, hydroxy, thio, cyano, or thioalkyl.

In addition, the present invention also provides a method for preparing the anti-inflammatory compound, which comprises: reacting an acetophenone derivative 1 as a starting material with trimethylsilyl cyanide, to obtain an intermediate product 2;

reducing the intermediate product 2 to obtain an intermediate product 3; and reacting the amino group in the intermediate product 3 with a six-membered oxygen-containing cyclic compound to obtain a type-A' target product, where the acetophenone derivative 1 is a compound having a structure shown below:

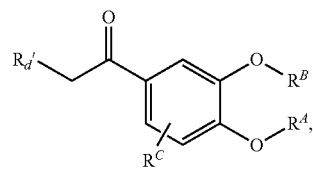

in which $R_d'$ is hydrogen, alkyl, aryl, alkynyl, or alkenyl, and in the above groups one or more hydrogen atom(s) attached to carbon in the group is/are substituted with alkyl, alkynyl, alkenyl, cycloalkyl, aryl, halogen, hydroxy, thio, cyano, or thioalkyl;

the intermediate product 2 is a compound having a structure shown below:

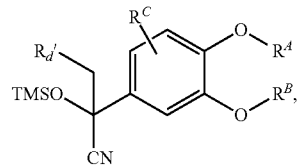

the intermediate product 3 is a compound having a structure shown below:

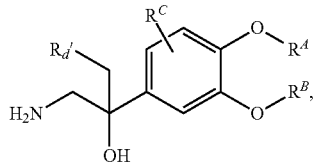

the type-A' target product is a compound having a structure shown below:

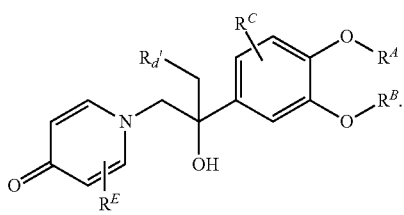

In addition, the present invention also provides a method for preparing the anti-inflammatory compound, which comprises removing the hydroxyl group on the middle bridge of the type-A' target product to obtain a type-C' target product, where the type-C' target product is a compound having a structure shown below:

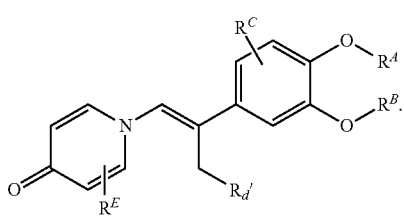

In addition, the present invention also provides a method for preparing the anti-inflammatory compound, which comprises reacting the carbonyl group on the middle bridge of the type-B target product with trimethylsilyl cyanide to obtain an intermediate product Y1; and subjecting the intermediate product Y1 to reduction and elimination to obtain a type-C" target product, where the intermediate product Y1 is a compound having a structure shown below:

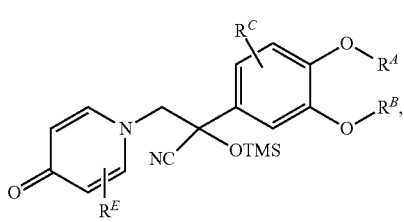

the type-C" target product is a compound having a structure shown below:

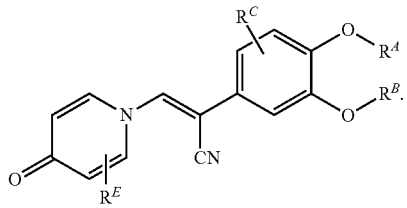

In addition, the present invention also provides a method for preparing the anti-inflammatory compound, which comprises reacting a six-membered N-acetonitrile compound Z1 with a benzaldehyde derivative Z2 to obtain a type-C2" target product, where the six-membered N-acetonitrile compound Z1 is a compound having a structure shown below:

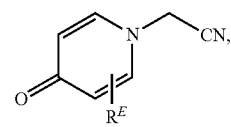

the benzaldehyde derivative Z2 is a compound having a structure shown below:

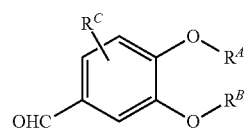

the type-C2" target product is a compound having a structure shown below:

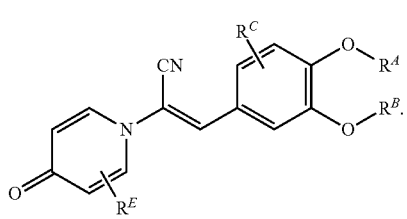

In addition, the present invention also provides a method for preparing the anti-inflammatory compound, which comprises: esterifying a cinnamic acid derivative 1 as a starting material, to obtain an intermediate product 2;

forming a ring from the double bond on the intermediate product 2 to obtain an intermediate product 3;

hydrolyzing the terminal ester group of the intermediate product 3 to give an intermediate product 4 having a carboxyl group;

aminating the terminal carboxyl group of the intermediate product 4 to obtain an intermediate product 5; and reacting the intermediate product 5 with a six-membered oxygen-containing cyclic compound to obtain a type-D target product, where the cinnamic acid derivative 1 is a compound having a structure shown below:

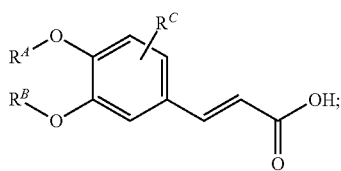

the intermediate product 2 is a compound having a structure shown below:

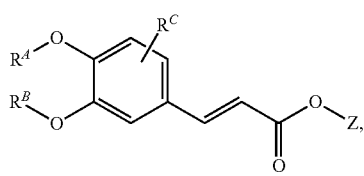

in which Z is alkyl;

the intermediate product 3 is a compound having a structure shown below:

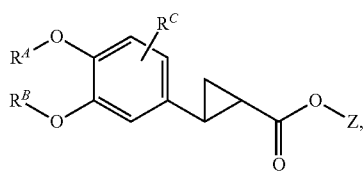

the intermediate product 4 is a compound having a structure shown below:

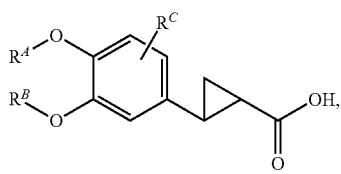

the intermediate product 5 is a compound having a structure shown below:

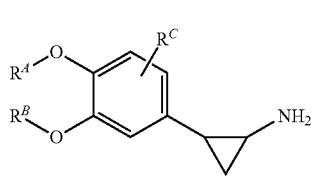

the type-D target product is a compound having a structure shown below:

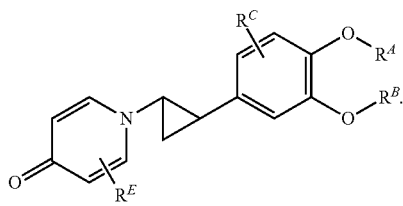

In addition, the present invention also provides use of the anti-inflammatory compound as a PDE4 inhibitor.

In addition, the present invention also provides use of the anti-inflammatory compound in the treatment of inflammatory skin diseases.

In addition, the present invention also provides a drug comprising 0.01-10% of the anti-inflammatory compound mentioned above; and other components selected from a surfactant, a lipid compound, and an auxiliary agent;

where the amount of the surfactant accounts for 10-30% of the total weight of the drug;

the amount of the lipid compound accounts for 50-85% of the total weight of the drug; and the amount of the auxiliary agent accounts for 10-30% of the total weight of the drug.

Function and Effect:

The present invention provides a novel anti-inflammatory compound that has a potent inhibition effect on PDE4, an important target for autoimmune activation, and is easy to penetrate the skin, and readily degradable. It is more effective than existing drugs (such as Eucrisa) or has fewer side effects than existing drugs (such as hormones, and tacrolimus), thus being a topical drug for treating eczema having good effects and no toxic side effects.

DESCRIPTION OF THE EMBODIMENTS

Example 1

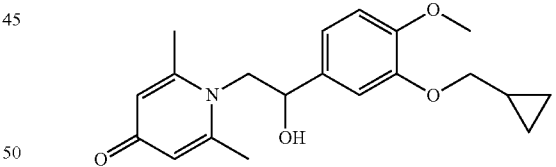

The specific reaction scheme is as shown below:

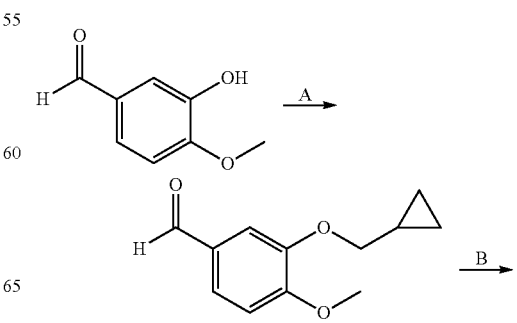

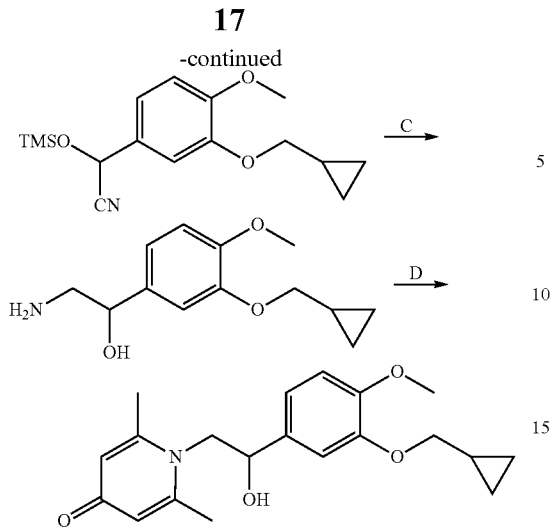

Step A:

At room temperature, 3-hydroxy-4-methoxybenzaldehyde (3.04 g, 20 mmol) was dissolved in acetonitrile (80 mL), and then potassium carbonate (5.52 g, 40 mmol) and bromomethylcyclopropane (4.05 g, 30 mmol) were added in sequence, and heated to 80° C. for 3 hours with stirring under nitrogen atmosphere. After the reaction was completed, a saturated aqueous sodium chloride solution (60 mL) was added, and extracted with dichloromethane (3×100 mL). The organic phases were combined, dried over anhydrous sodium sulfate, filtered, rotary dried, and purified by column chromatography to obtain 3-cyclopropylmethoxy-4-methoxybenzaldehyde (3.50 g, 85%).

Step B:

3-cyclopropylmethoxy-4-methoxybenzaldehyde (3.09 g, 15 mmol) was dissolved in dichloromethane (30 mL); and under nitrogen atmosphere, triethyl amine (4.16 mL, 30 mmol) and trimethylsilyl cyanide (3.75 g, 30 mmol) were added, and stirred for 6 hours at room temperature. The reaction solution was concentrated and rotary dried to obtain a crude product of 2-(3-cyclopropylmethoxy-4-methoxyphenyl)-2-trimethylsiloxyacetonitrile, which was directly used in the next reaction.

Step C:

2-(3-cyclopropylmethoxy-4-methoxyphenyl)-2-trimethylsiloxyacetonitrile (4.57 g, 15 mmol) obtained in the above step was dissolved in anhydrous tetrahydrofuran (50 mL), and then lithium aluminum hydride (1.14 g, 30 mmol) was added portion-wise in an ice bath, and stirred overnight at room temperature. After the reaction was completed, water (1.2 mL), an aqueous sodium hydroxide solution (1.2 mL, 15%), and water (3.6 mL) were added in sequence, stirred for half an hour, dried over anhydrous sodium sulfate, filtered, and rotary dried to obtain a crude product of 2-amino-1-(3-cyclopropylmethoxy-4-methoxyphenyl)ethanol.

Step D:

2-amino-1-(3-(cyclopropylmethoxy)-4-methoxyphenyl) ethanol obtained in the above step was dissolved in ethanol (20 mL), and then 2,6-dimethyl-4H-pyran-4-one (1 g, 10.41 mmol) and an aqueous sodium hydroxide solution (2 M, 20 mL) were added, and stirred overnight at 60° C. After the reaction was completed, the reaction solution was rotary dried, and purified by column chromatography to obtain 1-(2-(3-cyclopropylmethoxy-4-methoxyphenyl)-2-hydroxyethyl)-2,6, dimethylpyridin-4(1H)-one (2.01 g, yield 58%, white solid). $^1$H NMR (400 MHz, CDCl$_3$) δ 7.03 (d, J=1.6 Hz, 2H), 6.90 (dd, J=8.0, 1.6 Hz, 2H), 6.87 (d, J=8.0 Hz, 2H), 6.05 (s, 2H), 5.03 (dd, J=9.6, 3.2 Hz, 1H), 4.03 (dd, J=15.2, 10.0 Hz, 1H), 3.93-3.84 (m, 6H), 2.47 (s, 6H), 1.39-1.26 (m, 1H), 0.69-0.64 (m, 2H), 0.40-0.36 (m, 2H); LC-MS: m/z 344.2 [M+H]$^+$.

Example 2

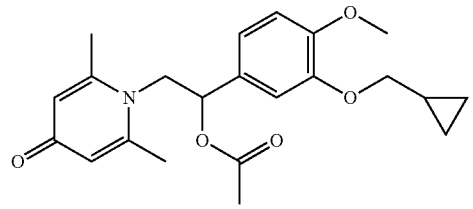 [SMILES: COc1ccc(C(Cn2c(C)cc(=O)cc2C)OC(C)=O)cc1OCC1CC1]

(1-(3-cyclopropylmethoxy-4methoxyphenyl)-2-(2,6-dimethyl-4-carbonylpyridin-1(4H)-yl)ethyl) acetate The specific reaction scheme is as shown below:

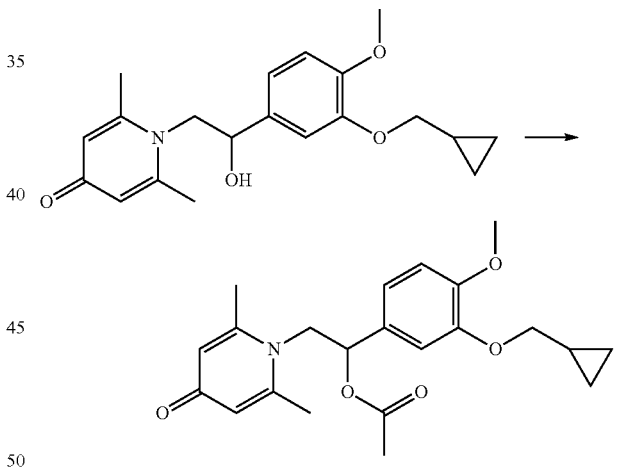

The compound 1-(2-(3-cyclopropylmethoxy-4-methoxyphenyl)-2-hydroxyethyl)pyridin-4(1H)-one (343 mg, 1.0 mmol) was dissolved in dichloromethane (8 mL), and then acetyl chloride (118 mg, 1.5 mmol) and triethyl amine (202 mg, 2.0 mmol) were added in sequence, and stirred overnight at room temperature. After the reaction was completed, the reaction solution was rotary dried, and purified by reverse-phase HPLC to obtain (1-(3-cyclopropylmethoxy-4methoxyphenyl)-2-(2,6-dimethyl-4-carbonylpyridin-1 (4H)-yl)ethyl) acetate (116 mg, yield 30%, pale yellow oil). $^1$H NMR (400 MHz, CD$_3$OD) δ 7.05-6.96 (m, 5H), 6.12-6.08 (m, 1H), 4.82-4.75 (m, 1H), 4.62-4.56 (m, 1H), 3.86-3.83 (m, 5H), 2.75 (s, 6H), 2.03 (s, 3H) 1.29-1.21 (m, 1H), 0.64-0.60 (m, 2H), 0.37-0.33 (m, 2H); LC-MS: m/z 386.2 [M+H]$^+$.

Example 3

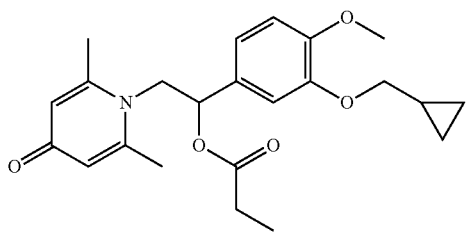 [SMILES: CCC(=O)OC(Cn1c(C)cc(=O)cc1C)c1ccc(OC)c(OCC2CC2)c1]

(1-(3-cyclopropylmethoxy-4methoxyphenyl)-2-(2,6-dimethyl-4-carbonylpyridin-1(4H)-yl)ethyl) propionate The specific reaction scheme is as shown below:

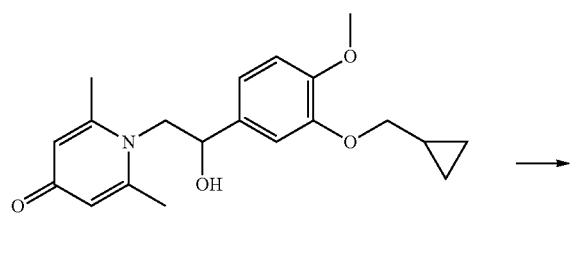

The compound 1-(2-(3-cyclopropylmethoxy-4-methoxyphenyl)-2-hydroxyethyl)pyridin-4(1H)-one (343 mg, 1.0 mmol) was dissolved in dichloromethane (8 mL), and then propionyl chloride (139 mg, 1.5 mmol) and triethyl amine (202 mg, 2.0 mmol) were added in sequence, and stirred overnight at room temperature. After the reaction was completed, the reaction solution was rotary dried, and purified by reverse-phase HPLC to obtain (1-(3-cyclopropylmethoxy-4methoxyphenyl)-2-(2,6-dimethyl-4-carbonylpyridin-1(4H)-yl) ethyl) propionate (140 mg, yield 35%, pale yellow oil). $^1$H NMR (400 MHz, CD$_3$OD) δ 7.05-6.97 (m, 5H), 6.15-6.12 (m, 1H), 4.82-4.76 (m, 1H), 4.64-4.59 (m, 1H), 3.86-3.83 (m, 5H), 2.77 (s, 6H), 2.38-2.29 (m, 2H), 1.29-1.24 (m, 1H), 1.05-1.01 (m, 3H), 0.64-0.60 (m, 2H), 0.36-0.33 (m, 2H); LC-MS: m/z 399.9 [M+H]$^+$.

Example 4

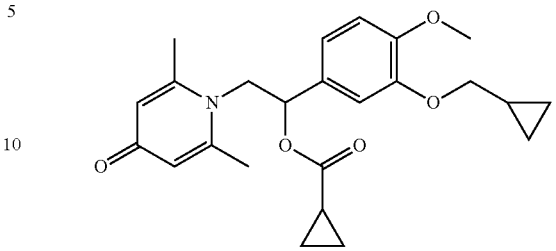

(1-(3-cyclopropylmethoxy-4methoxyphenyl)-2-(2,6-dimethyl-4-carbonylpyridin-1(4H)-yl)ethyl) cyclopropylcarboxylate The specific reaction scheme is as shown below:

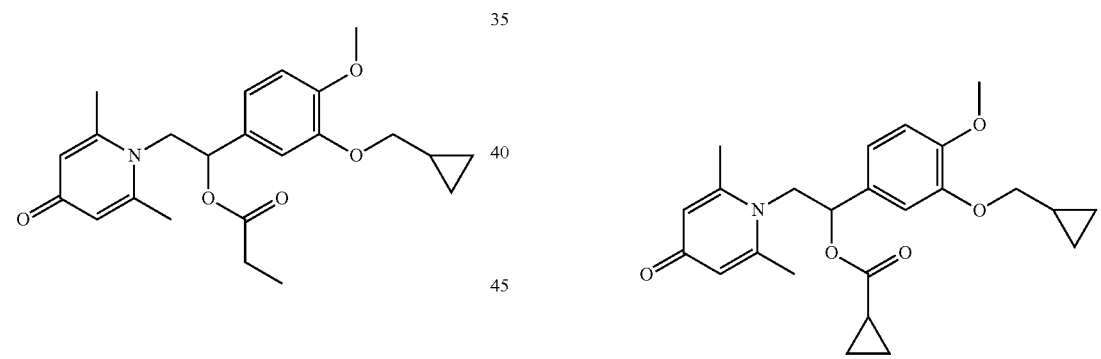

The compound 1-(2-(3-cyclopropylmethoxy-4-methoxyphenyl)-2-hydroxyethyl)pyridin-4(1H)-one (343 mg, 1.0 mmol) was dissolved in dichloromethane (8 mL), and then cyclopropanecarbonyl chloride (157 mg, 1.5 mmol) and triethyl amine (202 mg, 2.0 mmol) were added in sequence, and stirred overnight at room temperature. After the reaction was completed, the reaction solution was rotary dried, and purified by reverse-phase HPLC to obtain (1-(3-cyclopropylmethoxy-4methoxyphenyl)-2-(2,6-dimethyl-4-carbonylpyridin-1(4H)-yl)ethyl) cyclopropylcarboxylate (103 mg, yield 25%, pale yellow oil). $^1$H NMR (400 MHz, CD$_3$OD) δ 7.04-7.01 (m, 2H), 6.95 (s, 1H), 6.35 (s, 2H), 6.11-6.06 (m, 1H), 4.56-4.50 (m, 1H), 4.37-4.32 (m, 1H), 3.89-3.81 (m, 5H), 2.53 (s, 6H), 0.92-0.81 (m, 6H), 0.66-0.62 (m, 2H), 0.39-0.36 (m, 2H); LC-MS: m/z 412.2 [M+H]$^+$.

Example 5

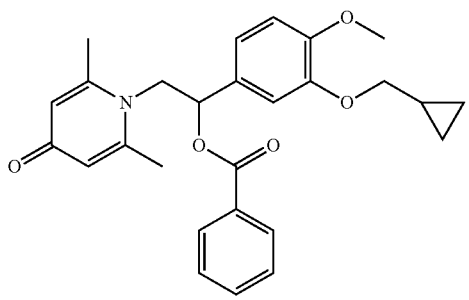 [SMILES: COc1ccc(C(Cn2c(C)cc(=O)cc2C)OC(=O)c2ccccc2)cc1OCC1CC1]

(1-(3-cyclopropylmethoxy-4methoxyphenyl)-2-(2,6-dimethyl-4-carbonylpyridin-1(4H)-yl)ethyl) benzoate The specific reaction scheme is as shown below:

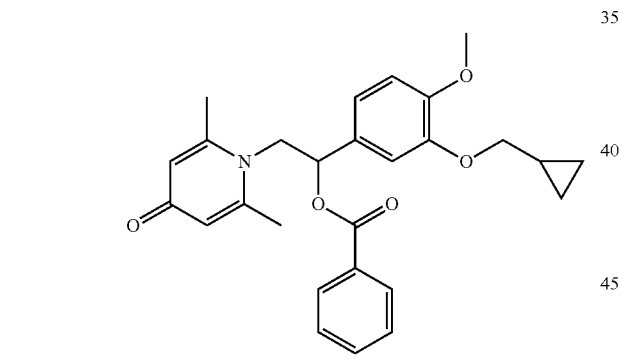

The compound 1-(2-(3-cyclopropylmethoxy-4-methoxyphenyl)-2-hydroxyethyl)pyridin-4(1H)-one (343 mg, 1.0 mmol) was dissolved in dichloromethane (8 mL), and then benzoyl chloride (211 mg, 1.5 mmol) and triethyl amine (202 mg, 2.0 mmol) were added in sequence and stirred overnight at room temperature. After the reaction was completed, the reaction solution was rotary dried, and purified by reverse-phase HPLC to obtain (1-(3-cyclopropylmethoxy-4methoxyphenyl)-2-(2,6-dimethyl-4-carbonylpyridin-1(4H)-yl) ethyl) benzoate (94 mg, yield 21%, white solid). $^1$H NMR (400 MHz, CD$_3$OD) δ 8.04-8.00 (m, 2H), 7.70-7.65 (m, 1H), 7.56-7.51 (m, 2H), 7.22 (dd, J=8.4, 2.0 Hz, 1H), 7.12 (d, J=2.0 Hz, 1H), 7.08 (d, J=8.4 Hz, 1H), 7.00 (s, 2H), 6.48-6.44 (m, 1H), 5.00-4.93 (m, 1H), 4.81-4.75 (m, 1H), 3.91-3.87 (m, 5H), 2.82 (s, 6H), 2.03 (s, 3H) 1.32-1.25 (m, 1H), 0.66-0.61 (m, 2H), 0.39-0.35 (m, 2H); LC-MS: m/z 448.2 [M+H]$^+$.

Example 6

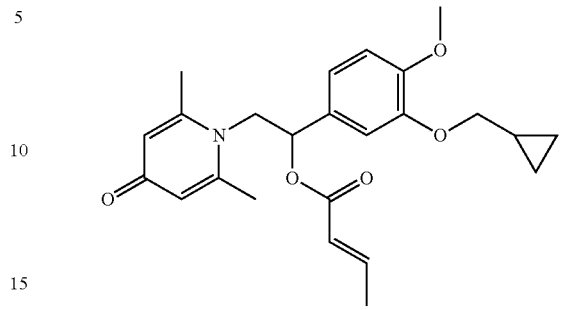

(1-(3-cyclopropylmethoxy-4methoxyphenyl)-2-(2,6-dimethyl-4-carbonylpyridin-1(4H)-yl)ethyl) crotonate The specific reaction scheme is as shown below:

The compound 1-(2-(3-cyclopropylmethoxy-4-methoxyphenyl)-2-hydroxyethyl)pyridin-4(1H)-one (343 mg, 1.0 mmol) was dissolved in dichloromethane (8 mL), and then crotonyl chloride (157 mg, 1.5 mmol) and triethyl amine (202 mg, 2.0 mmol) were added in sequence, and stirred overnight at room temperature. After the reaction was completed, the reaction solution was rotary dried, and purified by reverse-phase HPLC to obtain (1-(3-cyclopropylmethoxy-4methoxyphenyl)-2-(2,6-dimethyl-4-carbonylpyridin-1 (4H)-yl)ethyl) crotonate (127 mg, yield 31%, white solid). $^1$H NMR (400 MHz, CDCl$_3$) δ 6.87 (d, J=8.4 Hz, 1H), 6.82 (dd, J=8.4, 2.0 Hz, 1H), 6.77 (d, J=2.0 Hz, 1H), 6.33 (s, 2H), 5.98-5.89 (m, 1H), 5.86-5.76 (m, 1H), 4.37-4.28 (m, 1H), 4.13-4.04 (m, 1H), 3.88 (s, 3H), 3.84 (d, J=6.8 Hz, 2H), 2.37 (s, 6H), 1.33-1.28 (m, 1H), 0.69-0.64 (m, 2H), 0.39-0.35 (m, 2H); LC-MS: m/z 412.2 [M+H]$^+$.

Example 7

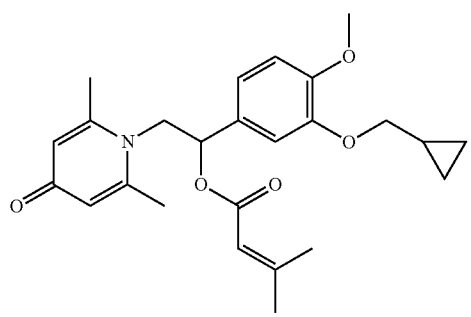 [SMILES: COc1ccc(C(Cn2c(C)cc(=O)cc2C)OC(=O)C=C(C)C)cc1OCC1CC1]

(1-(3-cyclopropylmethoxy-4methoxyphenyl)-2-(2,6-dimethyl-4-carbonylpyridin-1(4H)-yl)ethyl) 3-methylcrotonate The specific reaction scheme is as shown below:

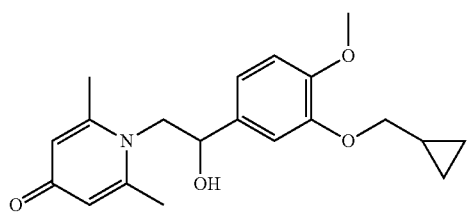

The compound 1-(2-(3-cyclopropylmethoxy-4-methoxyphenyl)-2-hydroxyethyl)pyridin-4(1H)-one (343 mg, 1.0 mmol) was dissolved in dichloromethane (8 mL), and then 3-methylcrotonyl chloride (178 mg, 1.5 mmol) and triethyl amine (202 mg, 2.0 mmol) were added in sequence, and stirred overnight at room temperature. After the reaction was completed, the reaction solution was rotary dried, and purified by reverse-phase HPLC to obtain (1-(3-cyclopropylmethoxy-4methoxyphenyl)-2-(2,6-dimethyl-4-carbonylpyridin-1(4H)-yl)ethyl)3-methyl crotonate (137 mg, yield 32%, white solid). $^1$H NMR (400 MHz, CDCl$_3$) δ 6.87 (d, J=8.4 Hz, 1H), 6.83 (dd, J=8.4, 2.0 Hz, 1H), 6.78 (d, J=2.0 Hz, 1H), 6.28 (s, 2H), 5.90 (dd, J=9.2, 4.8 Hz, 1H), 4.91 (s, 1H), 4.30 (dd, J=15.2, 9.2 Hz, 1H), 4.05 (dd, J=15.2, 4.8 Hz, 1H), 3.88 (s, 3H), 3.83 (d, J=7.2 Hz, 2H), 3.02 (s, 2H), 2.37 (s, 6H), 1.69 (s, 3H), 1.35-1.27 (m, 1H), 0.69-0.64 (m, 2H), 0.39-0.35 (m, 2H); LC-MS: m/z 426.2 [M+H]$^+$.

Example 8

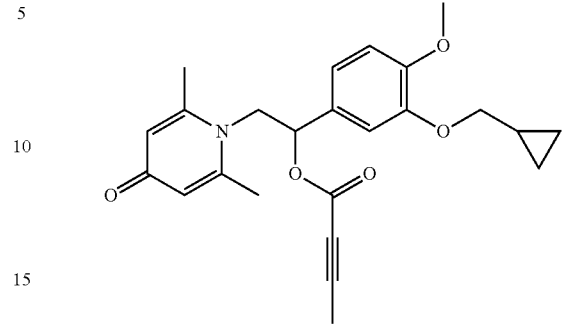

(1-(3-cyclopropylmethoxy-4methoxyphenyl)-2-(2,6-dimethyl-4-carbonylpyridin-1(4H)-yl)ethyl) but-2-ynoate The specific reaction scheme is as shown below:

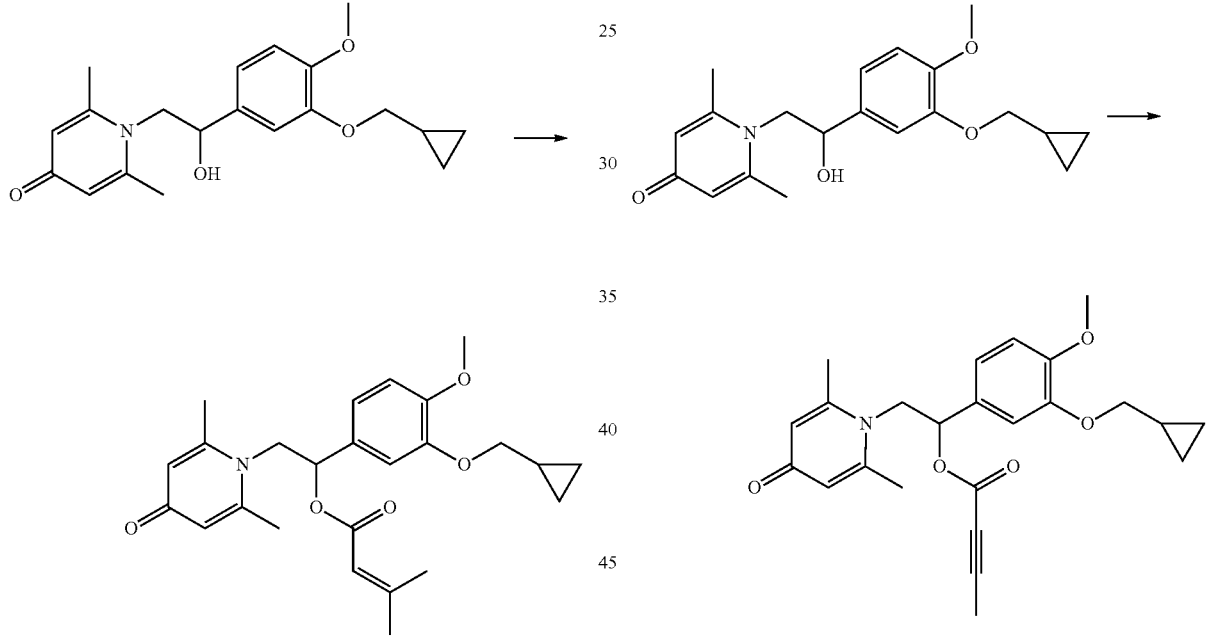

The compound 1-(2-(3-cyclopropylmethoxy-4-methoxyphenyl)-2-hydroxyethyl)pyridin-4(1H)-one (197 mg, 0.69 mmol) and 2-butynoic acid (72 mg, 0.86 mmol) were dissolved in dichloromethane (10 mL), and then 4-dimethylaminopyridine (105 mg, 0.86 mmol) and 1-(3-dimethylaminopropyl)-3-ethylcarbodiimide hydrochloride (165 mg, 0.86 mmol) were added in sequence, and stirred overnight at 30° C. After the reaction was completed, the reaction solution was rotary dried, and purified by reverse-phase HPLC to obtain (1-(3-cyclopropylmethoxy-4methoxyphenyl)-2-(2,6-dimethyl-4-carbonylpyridin-1 (4H)-yl)ethyl) but-2-ynoate (37 mg, 9%, white solid). $^1$H NMR (400 MHz, CDCl$_3$) δ 6.88-6.82 (m, 2H), 6.77 (d, J=1.6 Hz, 1H), 6.22 (s, 2H), 5.90 (dd, J=8.4, 5.2 Hz, 1H), 4.31 (dd, J=15.2, 8.4 Hz, 1H), 4.04 (dd, J=15.2, 5.2 Hz, 1H), 3.88 (s, 3H), 3.84 (d, J=7.2 Hz, 2H), 2.33 (s, 6H), 2.01 (s, 3H), 1.32-1.28 (m, 1H), 0.69-0.64 (m, 2H), 0.39-0.35 (m, 2H). LC-MS: m/z 410.4 [M+H]$^+$.

Example 9

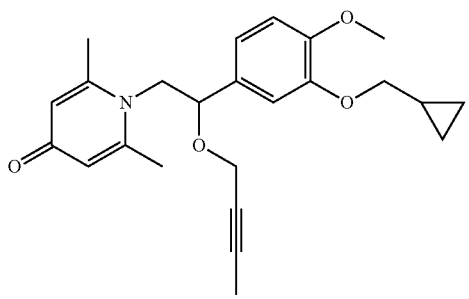 [SMILES: CC#CCOC(Cn1c(C)cc(=O)cc1C)c1ccc(OC)c(OCC2CC2)c1]

1-(2-(but-2-yn-1-yloxy)-2-(3-cyclopropylmethoxy-4-methoxyphenyl)ethyl)-2,26-dimethylpyridin-4-(1H)-one The specific reaction scheme is as shown below:

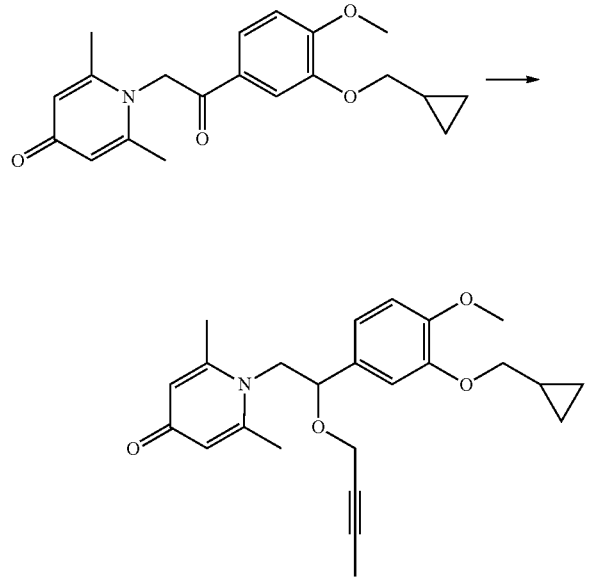

The compound 1-(2-(3-cyclopropylmethoxy-4-methoxyphenyl)-2-hydroxyethyl)pyridin-4(1H)-one (50 mg, 0.15 mmol) was dissolved in N,N-dimethylformamide (5 mL), and then 1-bromo-2-butyne (40 mg, 0.30 mmol) and cesium carbonate (98 mg, 0.30 mmol) were added and stirred overnight at 80° C. under nitrogen atmosphere. After the reaction was completed, saturated saline (10 mL) was added, and extracted with dichloromethane (3×10 mL).

The organic phases were combined, and dried over anhydrous sodium sulfate. Filtration, rotary drying, and purification by reverse-phase HPLC gave 1-(2-(but-2-yn-1-yloxy)-2-(3-cyclopropylmethoxy-4-methoxyphenyl)ethyl)-2,26-dimethylpyridin-4-(1H)-one (19 mg, yield 32%, pale yellow oil). $^1$H NMR (400 MHz, CDCl$_3$) δ 6.89 (d, J=7.6 Hz, 1H), 6.84-6.81 (m, 2H), 6.58 (s, 2H), 4.70-4.66 (m, 1H), 4.30-4.24 (m, 1H), 4.14-4.08 (m, 1H), 4.05-4.00 (m, 1H), 3.91-3.86 (m, 5H), 3.82-3.77 (m, 1H), 2.45 (s, 6H), 1.37-1.31 (m, 1H), 1.27 (s, 3H), 0.72-0.66 (m, 2H), 0.42-0.38 (m, 2H); LC-MS: m/z 396.1 [M+H]$^+$.

Example 10

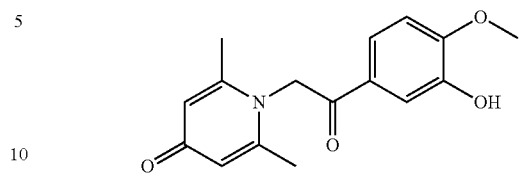

1-(2-(3-hydroxy-4-methoxyphenyl)-2-oxoethyl)-2,6-dimethylpyridin-4(1H)-one

The specific reaction scheme is as shown below:

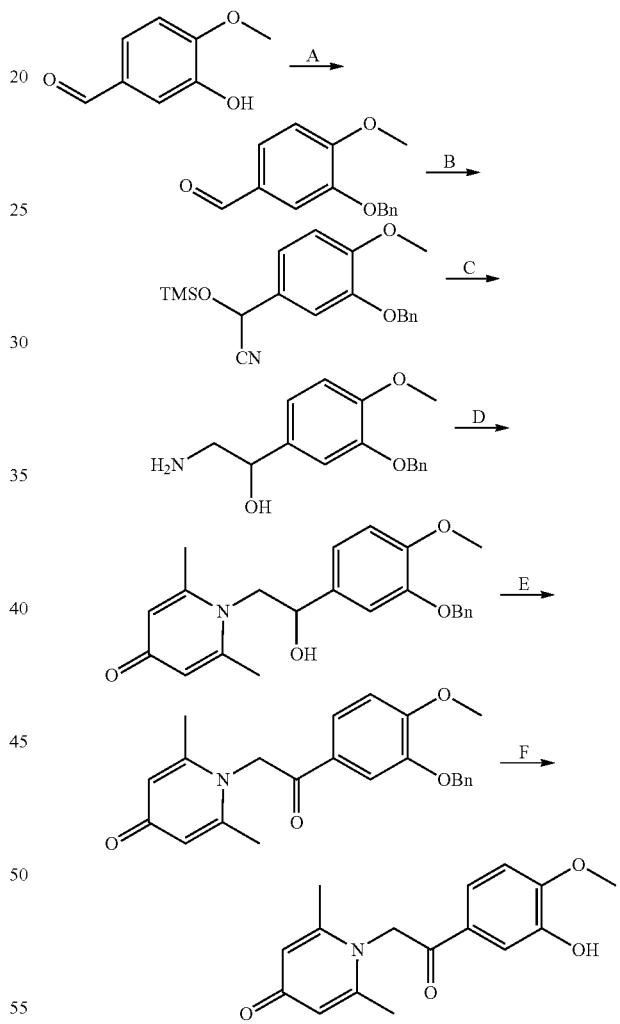

Step A:

At room temperature, 3-hydroxy-4-methoxybenzaldehyde (1.52 g, 10 mmol) was dissolved in acetonitrile (40 mL), and then potassium carbonate (2.76 g, 20 mmol) and benzyl bromide (2.56 g, 15 mmol) were added in sequence, and heated to 80° C. for 3 hours with stirring under nitrogen atmosphere. After the reaction was completed, aqueous sodium chloride solution (30 mL) was added, and extracted with dichloromethane (3×50 mL). The organic phases were combined, dried over anhydrous sodium sulfate, filtered, rotary dried, and purified by column chromatography to obtain 3-benzoxy-4-methoxybenzaldehyde (2.30 g, 95%, white solid).

Step B:

3-benzoxy-4-methoxybenzaldehyde (2.30 g, 9.5 mmol) was dissolved in dichloromethane (30 mL), and then triethyl amine (1.92 g, 19 mmol) and trimethylsilyl cyanide (2.82 g, 28.5 mmol) were added in sequence in an ice bath and stirred for 16 hours under nitrogen atmosphere at room temperature. After the reaction was completed, direct rotary drying gave 2-(3-benzoxy-4-methoxyphenyl)-2-trimethylsiloxyacetonitrile, which was directly used in the next reaction.

Step C:

2-(3-benzoxy-4-methoxyphenyl)-2-trimethylsiloxyacetonitrile obtained in the above step was dissolved in anhydrous tetrahydrofuran (40 mL), and lithium aluminum hydride (1.08 g, 28.5 mmol) was added portion-wise in an ice bath and stirred overnight at room temperature. After the reaction was completed, water (1.1 mL), an aqueous sodium hydroxide solution (1.1 mL, 15%), and water (3.3 mL) were added in sequence, stirred for half an hour, dried over anhydrous sodium sulfate, filtered, and rotary dried to obtain a crude product of 2-amino-1-(3-benzoxy-4-methoxyphenyl)ethanol, which was directly used in the next reaction.

Step D:

2-Amino-1-(3-benzoxy-4-methoxyphenyl)ethanol obtained in the above step was dissolved in ethanol (60 mL), and then 2,6-dimethyl-4H-pyran-4-one (1.24 g, 10 mmol), sodium hydroxide (800 mg, 20 mmol) and water (10 mL) were added in sequence, heated to 60° C., and stirred overnight under nitrogen atmosphere. After the reaction was completed, the reaction solution was rotary dried, and purified by column chromatography to obtain 1-(2-(3-benzoxy-4-methoxyphenyl)-2-hydroxyethyl)-2,6-dimethylpyridin-4(1H)-one (1.62 g, 45%, white solid). LC-MS m/z 380.2 [M+H]$^+$.

Step E:

1-(2-(3-benzoxy-4-methoxyphenyl)-2-hydroxyethyl)-2,6-dimethylpyridin-4(1H)-one (1.62 g, 4.26 mmol) was dissolved in dichloromethane (30 mL), and then the Dess-Martin Periodinane (2.16 g, 5.11 mmol) was added and stirred at room temperature for 2 hours. The reaction solution was filtered, and washed with saturated brine. The organic phase was dried over anhydrous sodium sulfate, filtered, rotary dried, and purified by column chromatography to obtain 1-(2-(3-benzoxy-4-methoxyphenyl)-2-oxoethyl)-2,6-dimethylpyridin-4(1H)-one (1.37 g, yield 85%, white solid). LC-MS m/z 378.2 [M+H]$^+$.

Step F:

The compound 1-(2-(3-benzoxy-4-methoxyphenyl)-2-oxoethyl)-2,6-dimethylpyridin-4(1H)-one (1.37 g, 3.61 mmol) was dissolved in methanol (50 mL), then Pd/C (137 mg) and triethyl amine (1 mL) were added, and hydrogen was introduced. The system was stirred overnight at room temperature. After the reaction was completed, the reaction solution was filtered, rotary dried, and purified by reverse-phase HPLC to obtain 1-(2-(3-hydroxy-4-methoxyphenyl)-2-oxoethyl)-2,6-dimethylpyridin-4(1H)-one (660 mg, yield 64%, gray solid). $^1$H NMR (400 MHz, CD$_3$OD) δ 7.73 (dd, J=8.4, 2.0 Hz, 1H), 7.53 (d, J=2.0 Hz, 1H), 7.12 (d, J=8.4 Hz, 1H), 7.04 (s, 2H), 5.97 (s, 2H), 3.98 (s, 3H), 2.51 (s, 6H); LC-MS: m/z 288.2 [M+H]$^+$.

Example 11

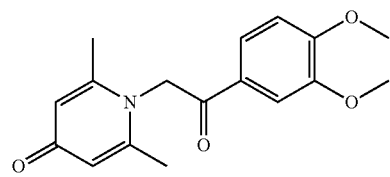

1-(2-(3,4-dimethoxyphenyl)-2-oxoethyl)-2,6-dimethylpyridin-4(1H)-one

The specific reaction scheme is as shown below:

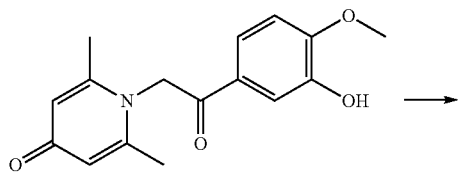

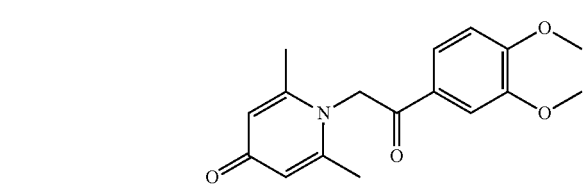 [SMILES: COc1ccc(C(=O)Cn2c(C)cc(=O)cc2C)cc1OC]

The compound 1-(2-(3-hydroxy-4-methoxyphenyl)-2-oxoethyl)-2,6-dimethylpyridin-4(1H)-one (28 mg, 0.1 mmol) was dissolved in N,N-dimethylformamide (5 mL), and then iodomethane (19 mg, 0.13 mmol) and potassium carbonate (21 mg, 0.15 mmol) were added and stirred for 1 hr at room temperature under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3,4-dimethoxyphenyl)-2-oxoethyl)-2,6-dimethylpyridin-4(1H)-one (10 mg, yield 30%, pale yellow oil). $^1$H NMR (400 MHz, CD$_3$OD) δ 7.85 (dd, J=8.4, 2.0 Hz, 1H), 7.60 (d, J=2.0 Hz, 1H), 7.15 (d, J=8.4 Hz, 1H), 7.05 (s, 2H), 6.02 (s, 2H), 4.07 (s, 3H), 3.96 (s, 3H), 2.52 (s, 6H); LC-MS: m/z 302.1 [M+H]$^+$.

Example 12

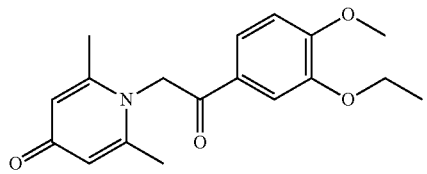 [SMILES: CCOc1cc(C(=O)Cn2c(C)cc(=O)cc2C)ccc1OC]

1-(2-(3-ethoxy-4-methoxyphenyl)-2-oxoethyl)-2,6-dimethylpyridin-4(1H)-one
The specific reaction scheme is as shown below:

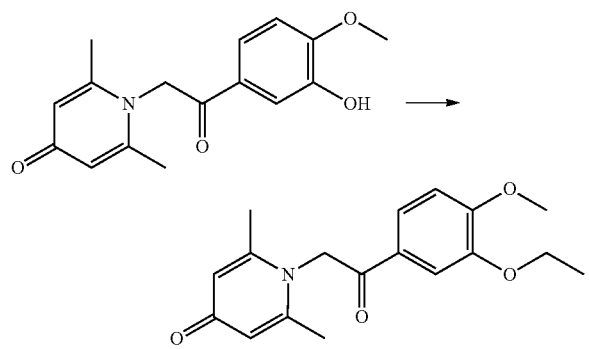

The compound 1-(2-(3-hydroxy-4-methoxyphenyl)-2-oxoethyl)-2,6-dimethylpyridin-4(1H)-one (28 mg, 0.1 mmol) was dissolved in N,N-dimethylformamide (5 mL), and then iodoethane (21 mg, 0.13 mmol) and potassium carbonate (21 mg, 0.15 mmol) were added and stirred for 1 hr at room temperature under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-ethoxy-4-methoxyphenyl)-2-oxoethyl)-2,6-dimethylpyridin-4(1H)-one (15 mg, yield 48%, pale yellow oil). $^1$H NMR (400 MHz, CDCl$_3$) δ 8.04 (s, 1H), 7.65 (d, J=8.0 Hz, 1H), 7.02 (s, 2H), 6.91 (d, J=8.0 Hz, 1H), 6.15 (s, 2H), 4.32 (q, J=6.0 Hz, 2H), 3.92 (s, 3H), 2.62 (s, 6H), 1.51 (t, J=6.0 Hz, 1H); LC-MS m/z 316.1 [M+H]$^+$.

Example 13

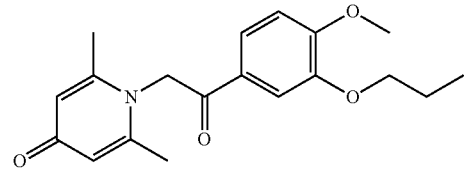 [SMILES: CCCOc1cc(C(=O)Cn2c(C)cc(=O)cc2C)ccc1OC]

1-(2-(3-propoxy-4-methoxyphenyl)-2-oxoethyl)-2,6-dimethylpyridin-4(1H)-one
The specific reaction scheme is as shown below:

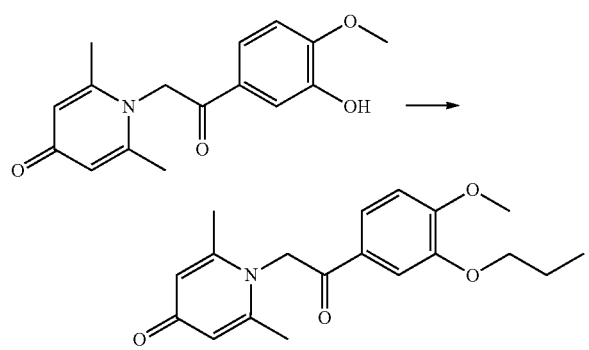

The compound 1-(2-(3-hydroxy-4-methoxyphenyl)-2-oxoethyl)-2,6-dimethylpyridin-4(1H)-one (20 mg, 0.07 mmol) was dissolved in N,N-dimethylformamide (5 mL), and then bromopropane (10 mg, 0.08 mmol) and potassium carbonate (15 mg, 0.11 mmol) were added and stirred for 2 hours at room temperature under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-propoxy-4-methoxyphenyl)-2-oxoethyl)-2,6-dimethylpyridin-4(1H)-one (8 mg, yield 34%, white solid). $^1$H NMR (400 MHz, CD$_3$OD) δ 7.22 (d, J=2.0 Hz, 1H), 7.14 (dd, J=8.4, 2.0 Hz, 1H), 7.01 (d, J=8.4 Hz, 1H), 6.38 (s, 2H), 6.02 (s, 2H), 4.03 (t, J=6.4 Hz, 2H), 3.89 (s, 3H), 2.37 (s, 6H), 1.90-1.80 (m, 2H), 1.08 (t, J=7.2 Hz, 3H); LC-MS: m/z 330.2 [M+H]$^+$.

Example 14

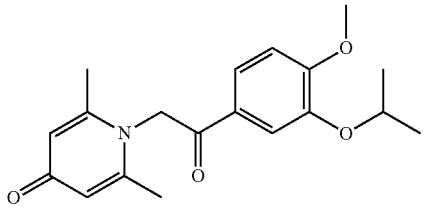 [SMILES: COc1ccc(C(=O)Cn2c(C)cc(=O)cc2C)cc1OC(C)C]

1-(2-(3-isopropoxy-4-methoxyphenyl)-2-oxoethyl)-2,6-dimethylpyridin-4(1H)-one
The specific reaction scheme is as shown below:

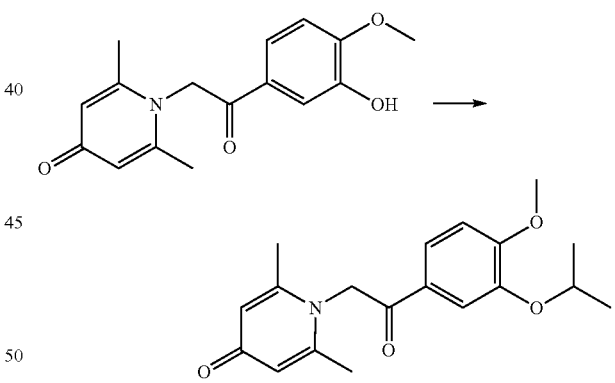

The compound 1-(2-(3-hydroxy-4-methoxyphenyl)-2-oxoethyl)-2,6-dimethylpyridin-4(1H)-one (35 mg, 0.12 mmol) was dissolved in N,N-dimethylformamide (5 mL), and then bromo-isopropane (17 mg, 0.14 mmol) and potassium carbonate (25 mg, 0.18 mmol) were added, and stirred for 2 hours at room temperature under nitrogen atmosphere. After the reaction was completed, saturated saline (10 mL) was added, and extracted with dichloromethane (3×10 mL).
The organic phases were combined, and dried over anhydrous sodium sulfate. Filtration, rotary drying, and purification by reverse-phase HPLC gave 1-(2-(3-isopropoxy-4-methoxyphenyl)-2-oxoethyl)-2,6-dimethylpyridin-4(1H)-one (10 mg, yield 63%, white solid). $^1$H NMR (400 MHz, CDCl$_3$) δ 7.02 (dd, J=8.4, 2.0 Hz, 1H), 6.98 (d, J=2.0 Hz, 1H), 6.91 (d, J=8.4 Hz, 1H), 6.76 (d, J=14.4 Hz, 1H), 6.60

(d, J=14.4 Hz, 1H), 6.30 (s, 2H), 4.69-4.60 (m, 1H), 3.90 (s, 3H), 2.57 (s, 6H), 1.35 (d, J=6.0 Hz, 6H); LC-MS: m/z 330.2 [M+H]⁺.

Example 15

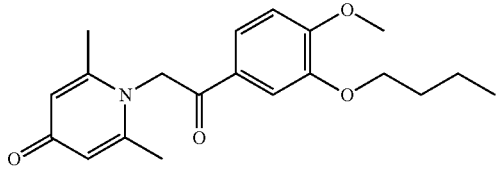 [SMILES: CCCCOc1cc(C(=O)Cn2c(C)cc(=O)cc2C)ccc1OC]

1-(2(3-n-butoxy-4-methoxyphenyl)-2-oxoethyl)-2,6-dimethylpyridin-4(1H)-one

The specific reaction scheme is as shown below:

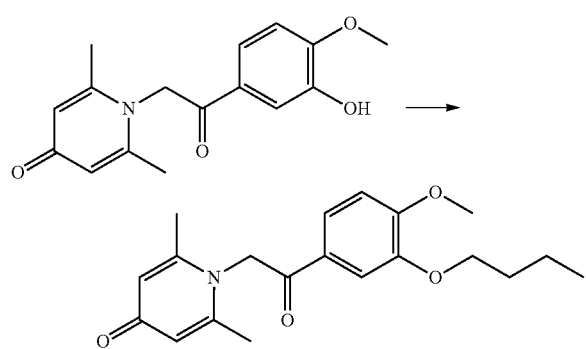

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then bromo-isopropane (95 mg, 0.7 mmol) and potassium carbonate (37 mg, 0.7 mmol) were added, and stirred for 2 hours at room temperature under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-n-butoxy-4-methoxyphenyl)-2-oxoethyl)-2,6-dimethylpyridin-4(1H)-one (26 mg, yield 42%, white solid). ¹H NMR (400 MHz, CD₃OD) δ 7.85 (dd, J=8.4, 2.0 Hz, 1H), 7.60 (d, J=2.0 Hz, 1H), 7.15 (d, J=8.4 Hz, 1H), 7.05 (s, 2H), 6.02 (s, 2H), 4.07 (t, J=6.4 Hz, 2H), 3.96 (s, 3H), 2.52 (s, 6H), 1.84-1.77 (m, 2H), 1.58-1.48 (m, 2H), 0.95 (t, J=7.2 Hz, 3H); LC-MS: m/z 344.1 [M+H]⁺.

Example 16

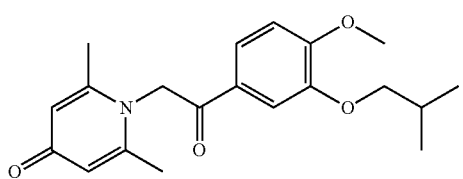

1-(2-(3-iso-butoxy-4-methoxyphenyl)-2-oxoethyl)-2,6-dimethylpyridin-4(1H)-one

The specific reaction scheme is as shown below:

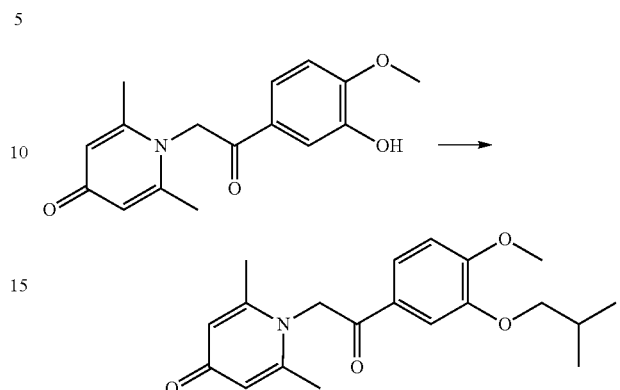

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then bromo-isobutane (27 mg, 0.2 mmol) and potassium carbonate (37 mg, 0.27 mmol) were added, and stirred for 2 hours at room temperature under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-iso-butoxy-4-methoxyphenyl)-2-oxoethyl)-2,6-dimethylpyridin-4(1H)-one (25 mg, yield 40%, white solid). ¹H NMR (400 MHz, CDCl₃) δ 7.02 (dd, J=8.4, 2.0 Hz, 1H), 6.98 (d, J=2.0 Hz, 1H), 6.91 (d, J=8.4 Hz, 1H), 6.76 (d, J=14.4 Hz, 1H), 6.60 (d, J=14.4 Hz, 1H), 6.30 (s, 2H), 3.92 (s, 3H), 3.81 (d, J=6.8 Hz, 2H), 2.27 (s, 6H), 2.25-2.17 (m, 1H), 1.08 (d, J=6.8 Hz, 6H); LC-MS: m/z 344.1 [M+H]⁺.

Example 17

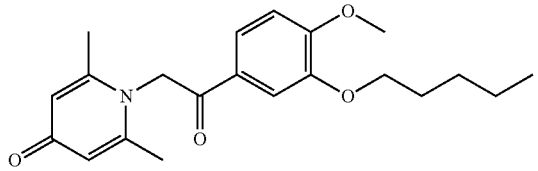 [SMILES: CCCCCOc1cc(C(=O)Cn2c(C)cc(=O)cc2C)ccc1OC]

1-(2-(3-n-pentyloxy-4-methoxyphenyl)-2-oxoethyl)-2,6-dimethylpyridin-4(1H)-one

The specific reaction scheme is as shown below:

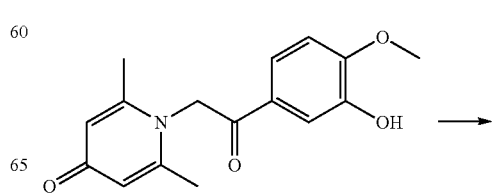

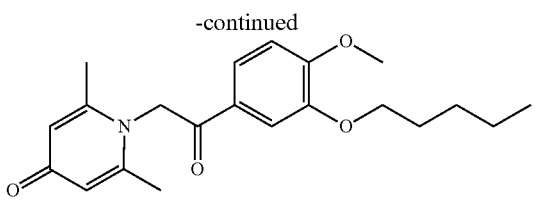

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then 1-bromopentane (105 mg, 0.7 mmol) and potassium carbonate (97 mg, 0.7 mmol) were added, and stirred for 5 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-n-pentyloxy-4-methoxyphenyl)-2-oxoethyl)-2,6-dimethylpyridin-4(1H)-one (20 mg, yield 32%, white solid). $^1$H NMR (400 MHz, CD$_3$OD) δ 7.85 (dd, J=8.4, 2.0 Hz, 1H), 7.60 (d, J=2.0 Hz, 1H), 7.15 (d, J=8.4 Hz, 1H), 7.07 (s, 2H), 6.03 (s, 2H), 4.06 (t, J=6.4 Hz, 2H), 3.96 (s, 3H), 2.53 (s, 6H), 1.86-1.79 (m, 2H), 1.52-1.36 (m, 4H), 0.95 (t, J=7.2 Hz, 3H); LC-MS: m/z 358.1 [M+H]$^+$.

Example 18

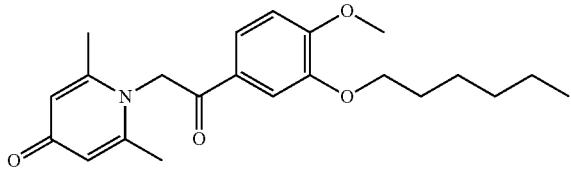 [SMILES: CCCCCCOc1cc(C(=O)Cn2c(C)cc(=O)cc2C)ccc1OC]

1-(2-(3-n-hexyloxy-4-methoxyphenyl)-2-oxoethyl)-2,6-dimethylpyridin-4(1H)-one

The specific reaction scheme is as shown below:

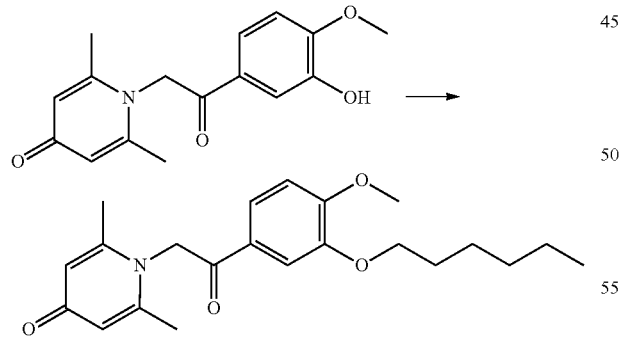

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then 1-bromon-hexane (115 mg, 0.7 mmol) and potassium carbonate (97 mg, 0.7 mmol) were added and stirred for 5 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-n-hexyloxy-4-methoxyphenyl)-2-oxoethyl)-2,6-dimethylpyridin-4(1H)-one (43 mg, yield 66%, white solid). $^1$H NMR (400 MHz, CD$_3$OD) δ 7.85 (dd, J=8.4, 2.0 Hz, 1H), 7.60 (d, J=2.0 Hz, 1H), 7.15 (d, J=8.4 Hz, 1H), 7.08 (s, 2H), 6.04 (s, 2H), 4.07 (t, J=6.4 Hz, 2H), 3.96 (s, 3H), 2.53 (s, 6H), 1.86-1.78 (m, 2H), 1.54-1.46 (m, 2H), 1.40-1.34 (m, 4H), 0.93 (t, J=7.2 Hz, 3H); LC-MS: m/z 372.0 [M+H]$^+$.

Example 19

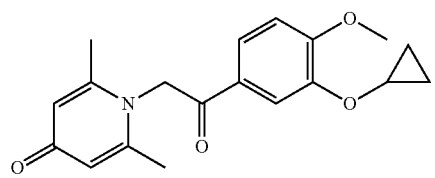 [SMILES: COc1ccc(C(=O)Cn2c(C)cc(=O)cc2C)cc1OC1CC1]

1-(2-(3-cyclopropyloxy-4-methoxyphenyl)-2-oxoethyl)-2,6-dimethylpyridin-4(1H)-one The specific reaction scheme is as shown below:

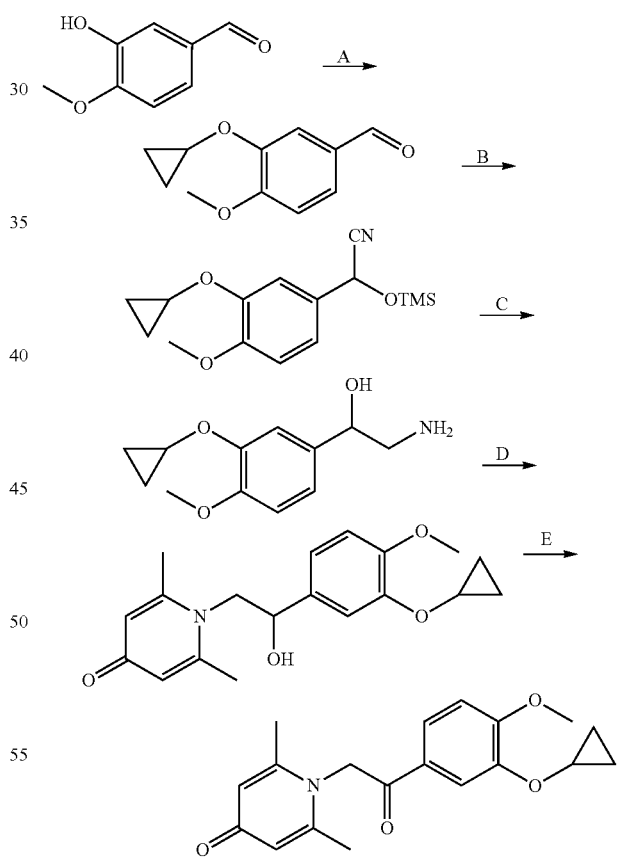

Step A:

The compound 3-hydroxy-4-methoxybenzaldehyde (1 g, 6.6 mmol), bromo-cyclopropane (2.4 mg, 19.8 mmol), cesium carbonate (6.5 g, 19.8 mmol), and potassium iodide (168 mg, 0.15 mmol) were dissolved in N, N-dimethylformamide (10 mL), stirred for 1 hr in a sealed tube at 180° C. under nitrogen atmosphere, then heated to 220° C., and stirred for another 1 hr. After the reaction was completed, saturated saline (20 mL) was added, and extracted with dichloromethane (3×20 mL). The organic phases were combined, and dried over anhydrous sodium sulfate. Filtration, rotary drying, and purification by column chromatography gave 3-cyclopropyloxy-4-methoxybenzaldehyde (170 mg, yield 13%, pale yellow oil). LC-MS: m/z 193.4 [M+H]$^+$.

Step B:

3-cyclopropyloxy-4-methoxybenzaldehyde (170 mg, 0.88 mmol) was dissolved in dichloromethane (4 mL); and under nitrogen atmosphere, triethyl amine (356 mg, 3.52 mmol) and trimethylsilyl cyanide (349 mg, 3.52 mmol) were added, and stirred for 6 hours at room temperature. After the reaction was completed, the reaction solution was concentrated and rotary dried to obtain 2-(3-cyclopropyloxy-4-methoxyphenyl)-2-trimethylsiloxyacetonitrile, which was directly used in the next reaction.

Step C:

2-(3-cyclopropyloxy-4-methoxyphenyl)-2-trimethylsiloxyacetonitrile obtained in the above step was dissolved in anhydrous tetrahydrofuran (20 mL), and then lithium aluminum hydride (100 mg, 2.6 mmol) was added portion-wise in an ice bath and stirred overnight at room temperature. After the reaction was completed, water (0.1 mL), an aqueous sodium hydroxide solution (0.1 mL, 15%), and water (0.3 mL) were added in sequence, stirred for half an hour, dried over anhydrous sodium sulfate, and filtered. The filtrate was rotary dried to obtain a crude product of 2-amino-1-(3-cyclopropyloxy-4-methoxyphenyl)ethanol (300 mg).

Step D:

2-Amino-1-(3-(cyclopropyloxy)-4-methoxyphenyl)ethanol obtained in the above step was dissolved in ethanol (5 mL), and then 2,6-dimethyl-4H-pyran-4-one (124 mg, 1 mmol) and aqueous sodium hydroxide solution (2 M, 2 mL) were added, and stirred overnight at 60° C. The reaction was complete as indicated by LCMS. The reaction solution was rotary dried, and purified by column chromatography to obtain 1-(2-(3-cyclopropyloxy-4-methoxyphenyl)-2-hydroxyethyl)-2,6-dimethylpyridin-4(1H)-one (100 mg, 34%, white solid). LC-MS: m/z 330.1 [M+1-1]$^+$.

Step E:

1-(2-(3-cyclopropylmethoxy-4-methoxyphenyl)-2-hydroxyethyl)-2,6-dimethylpyridin-4(1H)-one (30 mg, 0.1 mmol) was dissolved in dichloromethane (5 mL), and stirred for 2 hours at normal temperature. After the reaction was completed, the reaction solution was filtered, rotary dried, and purified by reverse-phase HPLC to obtain 1-(2-(3-cyclopropyloxy-4-methoxyphenyl)-2-oxoethyl)-2,6-dimethylpyridin-4(1H)-one (15 mg, yield 45%, white solid). $^1$H NMR (400 MHz, CD$_3$OD) δ 7.97 (dd, J=8.4, 2.0 Hz, 1H), 7.96 (d, J=2.0 Hz, 1H), 7.25 (d, J=8.4 Hz, 1H), 6.44 (s, 2H), 5.75 (s, 2H), 4.02 (s, 3H), 2.32 (s, 6H), 2.23-2.19 (m, 1H), 0.94-0.90 (m, 4H); LC-MS: m/z 328.1 [M+H]$^+$.

Example 20

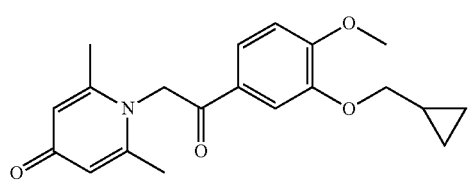 [SMILES: COc1ccc(C(=O)Cn2c(C)cc(=O)cc2C)cc1OCC1CC1]

1-(2-(3-cyclopropylmethoxy-4-methoxyphenyl)-2-oxo)ethyl-2,6-dimethylpyridin-4(1H)-one The specific reaction scheme is as shown below:

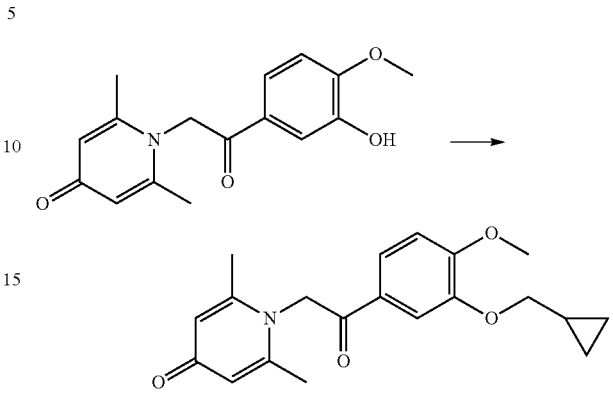

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then bromomethylcyclopropane (27 mg, 0.2 mmol) and potassium carbonate (37 mg, 0.27 mmol) were added, and stirred for 2 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-cyclopropylmethoxy-4-methoxyphenyl)-2-oxoethyl)-2,6-dimethylpyridin-4(1H)-one (36 mg, yield 62%, white solid). $^1$H NMR (400 MHz, DMSO-d$_6$) δ 7.79 (dd, J=8.4, 2.0 Hz, 1H), 7.50 (d, J=2.0 Hz, 1H), 7.16 (d, J=8.4 Hz, 1H), 5.99 (s, 2H), 5.62 (s, 2H), 3.90 (s, 3H), 3.53 (d, J=6.8 Hz, 2H), 2.11 (s, 6H), 1.26-1.21 (m, 1H), 0.62-0.56 (m, 2H), 0.36-0.31 (m, 2H); LC-MS: m/z 342.1 [M+H]$^+$.

Example 21

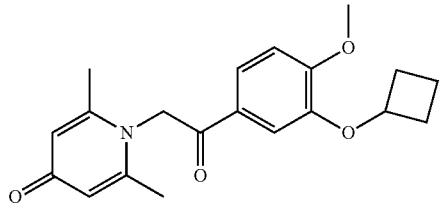 [SMILES: COc1ccc(C(=O)Cn2c(C)cc(=O)cc2C)cc1OC1CCC1]

The specific reaction scheme is as shown below:

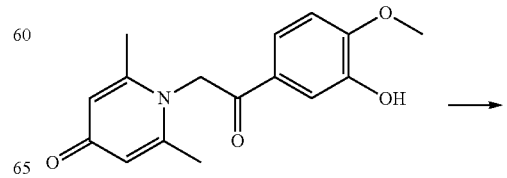

-continued

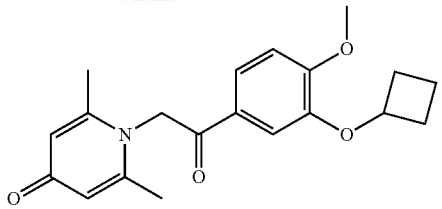

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then cyclobutyl bromide (69 mg, 0.51 mmol) and potassium carbonate (71 mg, 0.51 mmol) were added and stirred for 5 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-cyclobutyloxy-4-methoxyphenyl)-2-oxoethyl)-2,6-dimethylpyridin-4(1H)-one (16 mg, yield 26%, white solid). $^1$H NMR (400 MHz, CD$_3$OD) δ 7.85 (d, J=8.4 Hz, 1H), 7.45 (s, 1H), 7.14 (d, J=8.4 Hz, 1H), 7.04 (s, 2H), 5.99 (s, 2H), 4.79-4.73 (m, 1H), 3.96 (s, 3H), 2.51 (s, 6H), 2.51-2.45 (m, 1H), 2.23-2.13 (m, 1H), 1.91-1.83 (m, 1H), 1.79-1.70 (m, 1H); LC-MS: m/z 342.1 [M+H]$^+$.

Example 22

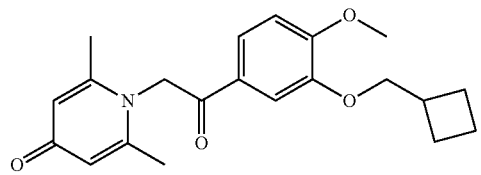 [SMILES: COc1ccc(C(=O)Cn2c(C)cc(=O)cc2C)cc1OCC1CCC1]

1-(2-(3-cyclobutylmethoxy-4-methoxyphenyl)-2-oxo)ethyl-2,6-dimethylpyridin-4(1H)-one The specific reaction scheme is as shown below:

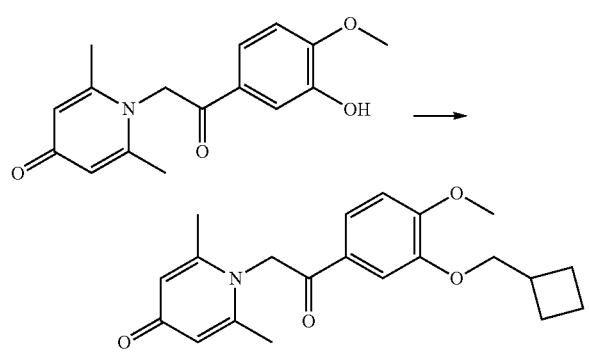

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then bromomethylcyclobutane (76 mg, 0.51 mmol) and potassium carbonate (71 mg, 0.51 mmol) were added, and stirred for 4 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-cyclobutylmethoxy-4-methoxyphenyl)-2-oxoethyl)-2,6-dimethylpyridin-4(1H)-one (16 mg, yield 24%, white solid). $^1$H NMR (400 MHz, CD$_3$OD) δ 7.84 (d, J=8.4 Hz, 1H), 7.61 (s, 1H), 7.14 (d, J=8.4 Hz, 1H), 6.91 (s, 2H), 5.95 (s, 2H), 4.04 (d, J=6.8 Hz, 2H), 3.95 (s, 3H), 2.84-2.78 (m, 1H), 2.47 (s, 6H), 2.20-2.10 (m, 2H), 2.02-1.86 (m, 4H); LC-MS: m/z 356.2 [M+H]$^+$.

Example 23

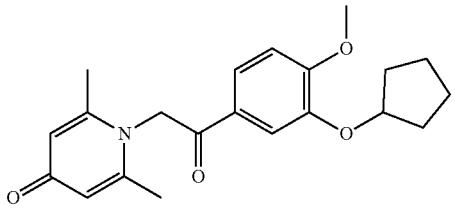 [SMILES: COc1ccc(C(=O)Cn2c(C)cc(=O)cc2C)cc1OC1CCCC1]

1-(2-(3-cyclopentyloxy-4-methoxyphenyl)-2-oxoethyl)-2,6-dimethylpyridin-4(1H)-one The specific reaction scheme is as shown below:

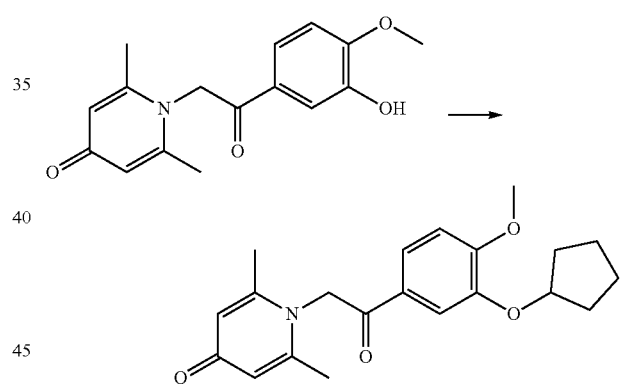

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then bromocyclopentane (76 mg, 0.51 mmol) and potassium carbonate (71 mg, 0.51 mmol) were added, and stirred for 4 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-cyclopentyl-4-methoxyphenyl)-2-oxoethyl)-2,6-dimethylpyridin-4(1H)-one (20 mg, yield 33%, white solid). $^1$H NMR (400 MHz, CD$_3$OD) δ 7.84 (dd, J=8.4, 2.0 Hz, 1H), 7.60 (d, J=2.0 Hz, 1H), 7.14 (d, J=8.4 Hz, 1H), 6.39 (s, 2H), 5.71 (s, 2H), 4.95-4.91 (m, 1H), 3.96 (s, 3H), 2.31 (s, 6H), 2.01-1.80 (m, 6H), 1.71-1.61 (m, 2H); LC-MS m/z 356.2 [M+H]$^+$.

Example 24

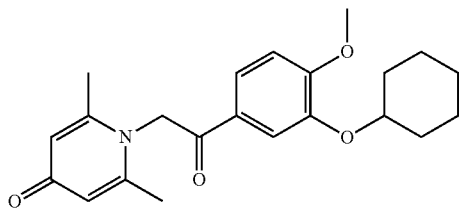 [SMILES: COc1ccc(C(=O)Cn2c(C)cc(=O)cc2C)cc1OC1CCCCC1]

1-(2-(3-cyclohexyloxy-4-methoxyphenyl)-2-oxoethyl)-2,6-dimethylpyridin-4(1H)-one The specific reaction scheme is as shown below:

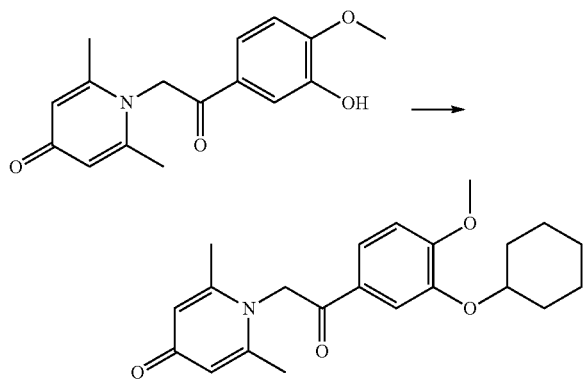

The compound 1-(2-(3-hydroxy-4-methoxyphenyl)-2-oxoethyl)-2,6-dimethylpyridin-4(1H)-one (50 mg, 0.17 mmol) was dissolved in N,N-dimethylformamide (5 mL), and then bromocycloohexane (83 mg, 0.51 mmol) and potassium carbonate (71 mg, 0.51 mmol) were added, and stirred for 4 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-cyclohexyloxy-4-methoxyphenyl)-2-oxoethyl)-2,6-dimethylpyridin-4(1H)-one (8 mg, yield 13%, white solid). $^1$H NMR (400 MHz, CD$_3$OD) δ 7.86 (d, J=8.4 Hz, 1H), 7.63 (s, 1H), 7.16 (d, J=8.4 Hz, 1H), 7.04 (s, 2H), 6.00 (s, 2H), 4.39-4.32 (m, 1H), 3.95 (s, 3H), 2.52 (s, 6H), 2.02-1.93 (m, 2H), 1.86-1.77 (m, 2H), 1.62-1.52 (m, 2H), 1.45-1.28 (m, 4H); LC-MS m/z 370.2 [M+H]$^+$.

Example 25

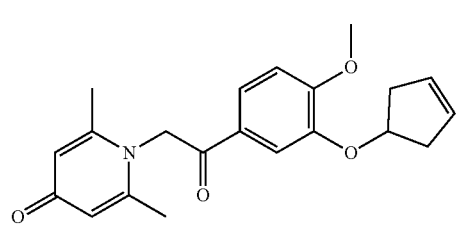 [SMILES: COc1ccc(C(=O)Cn2c(C)cc(=O)cc2C)cc1OC1CC=CC1]

1-(2-(3-(cyclopent-3-en-1-yloxy)-4-methoxyphenyl)-2-oxoethyl)-2,6-dimethylpyridin-4(1H)-one The specific reaction scheme is as shown below:

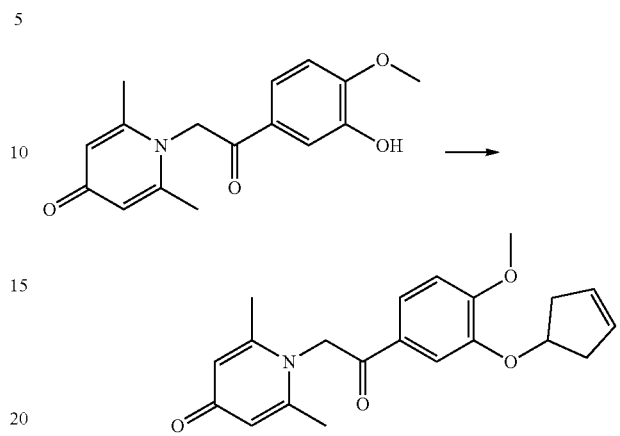

The compound 1-(2-(3-hydroxy-4-methoxyphenyl)-2-oxoethyl)-2,6-dimethylpyridin-4(1H)-one (30 mg, 0.11 mmol) was dissolved in acetonitrile (5 mL), and then cyclopent-3-en-1-yl methanesulfonate (68 mg, 0.42 mmol) and potassium carbonate (58 mg, 0.42 mmol) were added, and stirred overnight at 80° C. under nitrogen atmosphere. After the reaction was completed, the reaction solution was filtered, rotary dried, and purified by reverse-phase HPLC to obtain 1-(2-(3-(cyclopent-3-en-1-yloxy)-4-methoxyphenyl)-2-oxoethyl)-2,6-dimethylpyridin-4(1H)-one (12 mg, yield 32%, white solid). $^1$H NMR (400 MHz, CDCl$_3$) δ 7.85 (d, J=8.4 Hz, 1H), 7.55 (s, 1H), 7.18 (s, 2H), 7.01 (d, J=8.4 Hz, 1H), 6.04-5.91 (m, 2H), 5.77 (s, 2H), 5.17-5.11 (m, 1H), 3.96 (s, 3H), 2.95-2.89 (m, 2H), 2.63-2.60 (m, 2H), 2.53 (s, 6H); LC-MS m/z 354.2 [M+H]$^+$.

Example 26

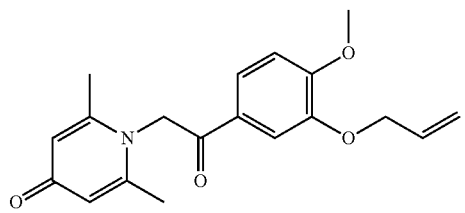 [SMILES: C=CCOc1cc(C(=O)Cn2c(C)cc(=O)cc2C)ccc1OC]

1-(2-(3-allyloxy-4-methoxyphenyl)-2-oxoethyl)-2,6-dimethylpyridin-4(1H)-one

The specific reaction scheme is as shown below:

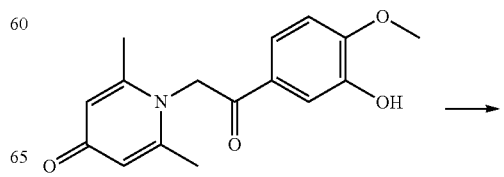

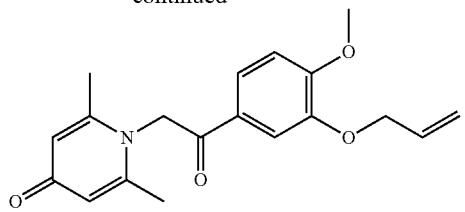

The compound 1-(2-(3-hydroxy-4-methoxyphenyl)-2-oxoethyl)-2,6-dimethylpyridin-4(1H)-one (50 mg, 0.18 mmol) was dissolved in N,N-dimethylformamide (5 mL), and then 3-bromopropene (26 mg, 0.21 mmol) and potassium carbonate (37 mg, 0.27 mmol) were added, and stirred overnight at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-allyloxy-4-methoxyphenyl)-2-oxoethyl)-2,6-dimethylpyridin-4(1H)-one (25 mg, yield 42%, white solid). $^1$H NMR (400 MHz, CD$_3$OD) δ 7.83 (d, J=8.4 Hz, 1H), 7.61 (s, 1H), 7.13 (d, J=8.4 Hz, 1H), 6.34 (s, 2H), 6.14-6.03 (m, 1H), 5.68 (s, 2H), 5.43 (d, J=17.2 Hz, 1H), 5.27 (d, J=10.4 Hz, 1H), 4.64 (d, J=4.8 Hz, 2H), 3.95 (s, 3H), 2.26 (s, 6H). LC-MS m/z 328.2 [M+H]$^+$.

Example 27

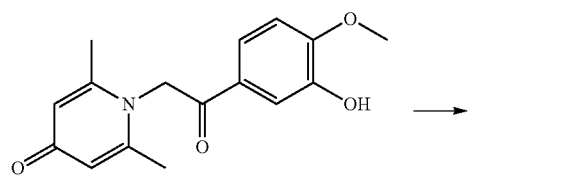

1-(2-(3-((3-methylbut-2-en-1-yl)oxy)-4-methoxyphenyl)-2-oxoethyl)-2,6-dimethylpyridin-4(1H)-one The specific reaction scheme is as shown below:

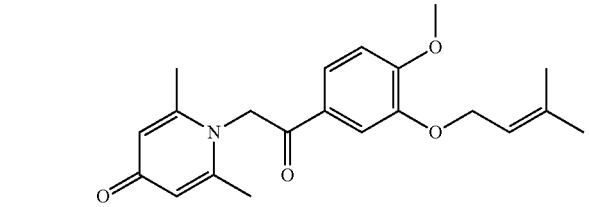 [SMILES: COc1ccc(C(=O)Cn2c(C)cc(=O)cc2C)cc1OCC=C(C)C]

The compound 1-(2-(3-hydroxy-4-methoxyphenyl)-2-oxoethyl)-2,6-dimethylpyridin-4(1H)-one (50 mg, 0.18 mmol) was dissolved in N,N-dimethylformamide (5 mL), and then 1-bromo-3-methyl-2-butene (31 mg, 0.21 mmol) and potassium carbonate (37 mg, 0.27 mmol) were added, and stirred for 1 hr 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-((3-methylbut-2-en-1-yl)oxy)-4-methoxyphenyl)-2-oxoethyl)-2,6-dimethylpyridin-4(1H)-one (25 mg, yield 40%, white solid). $^1$H NMR (400 MHz, CDCl$_3$) δ 7.63 (d, J=8.4 Hz, 1H), 7.55 (d, J=2.0 Hz, 1H), 6.96 (d, J=8.4 Hz, 1H), 6.32 (s, 2H), 5.51 (d, J=6.8 Hz, 1H), 5.32 (s, 2H), 4.65 (d, J=6.8 Hz, 2H), 3.98 (s, 3H), 2.21 (s, 6H), 1.79 (s, 3H), 1.77 (s, 3H); LC-MS m/z 356.2 [M+H]$^+$.

Example 28

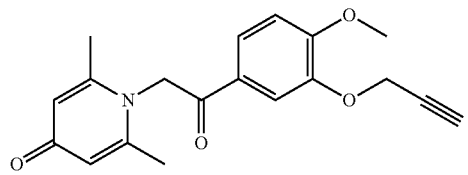 [SMILES: C#CCOc1cc(C(=O)Cn2c(C)cc(=O)cc2C)ccc1OC]

1-(2-(3-propargyloxy-4-methoxyphenyl)-2-oxoethyl)-2,6-dimethylpyridin-4(1H)-one

The specific reaction scheme is as shown below:

The compound 1-(2-(3-hydroxy-4-methoxyphenyl)-2-oxoethyl)-2,6-dimethylpyridin-4(1H)-one (50 mg, 0.18 mmol) was dissolved in N,N-dimethylformamide (5 mL), and then propargyl bromide (25 mg, 0.21 mmol) and potassium carbonate (37 mg, 0.27 mmol) were added, and stirred for 4 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-propargyloxy-4-methoxyphenyl)-2-oxoethyl)-2,6-dimethylpyridin-4(1H)-one (21 mg, yield 35%, white solid). $^1$H NMR (400 MHz, CDCl$_3$) δ 7.82 (d, J=8.0 Hz, 1H), 7.70 (s, 1H), 7.04 (d, J=8.0 Hz, 1H), 7.03 (s, 2H), 5.78 (s, 2H), 4.85 (d, J=2.4 Hz, 2H), 4.00 (s, 3H), 2.56 (t, J=2.4 Hz, 3H), 2.46 (s, 6H); LC-MS: m/z 326.3 [M+H]$^+$.

Example 29

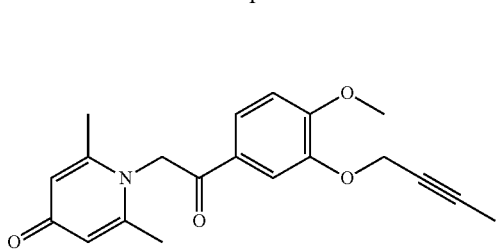

1-(2-(3-(but-2-yn-1-yloxy)-4-methoxyphenyl)-2-oxoethyl)-2,6-dimethylpyridin-4(1H)-one The specific reaction scheme is as shown below:

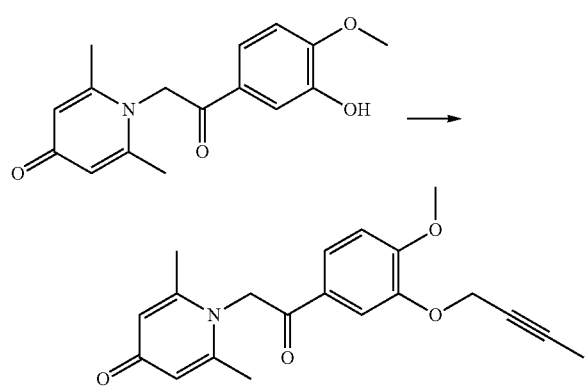

The compound 1-(2-(3-hydroxy-4-methoxyphenyl)-2-oxoethyl)-2,6-dimethylpyridin-4(1H)-one (50 mg, 0.18 mmol) was dissolved in N,N-dimethylformamide (5 mL), and then 1-bromo-2-butyne (83 mg, 0.70 mmol) and potassium carbonate (97 mg, 0.70 mmol) were added, and stirred for 2 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-(but-2-yn-1-yloxy)-4-methoxyphenyl)-2-oxoethyl)-2,6-dimethylpyridin-4(1H)-one (14 mg, yield 23%, white solid). $^1$H NMR (400 MHz, CD$_3$OD) δ 7.90 (dd, J=8.4, 2.0 Hz, 1H), 7.72 (d, J=2.0 Hz, 1H), 7.18 (d, J=8.4 Hz, 1H), 7.09 (s, 2H), 6.03 (s, 2H), 4.78 (q, J=2.4 Hz, 2H), 3.96 (s, 3H), 2.54 (s, 6H), 1.82 (t, J=2.4 Hz, 3H); LC-MS: m/z 340.0 [M+H]$^+$.

Example 30

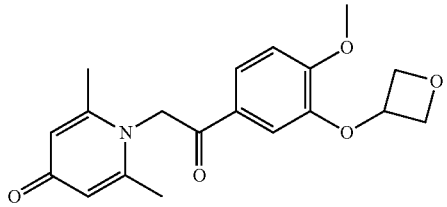 [SMILES: COc1ccc(C(=O)Cn2c(C)cc(=O)cc2C)cc1OC1COC1]

1-(2-(3-(oxacyclobutan-3-yl-oxy)-4-methoxyphenyl)-2-oxoethyl)-2,6-dimethylpyridin-4(1H)-one

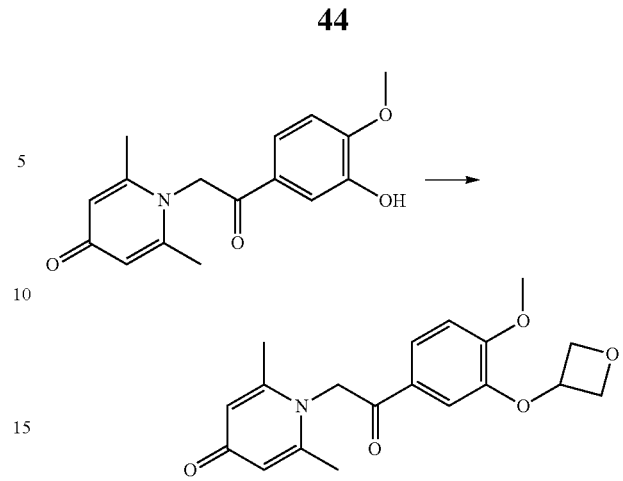

The compound 1-(2-(3-hydroxy-4-methoxyphenyl)-2-oxoethyl)-2,6-dimethylpyridin-4(1H)-one (158 mg, 0.55 mmol), oxacyclobutan-3-ol (81.4 mg, 1.1 mmol) and triphenylphosphine (288 mg, 1.1 mmol) were dissolved in anhydrous tetrahydrofuran (10 mL), the reaction solution was cooled in an ice bath, diisopropyl azodicarboxylate (222 mg, 1.1 mmol) was added dropwise over 5 min under nitrogen atmosphere, and then reacted for 24 hours at room temperature. After the reaction was completed, saturated saline (20 mL) was added, and extracted with dichloromethane (3×10 mL). The organic phases were combined, and dried over anhydrous sodium sulfate. Filtration, rotary drying, and purification by reverse-phase HPLC gave 1-(2-(3-(oxacyclobutan-3-yl-oxy)-4-methoxyphenyl)-2-oxoethyl)-2,6-dimethylpyridin-4(1H)-one (45 mg, yield 24%, white solid). $^1$H NMR (400 MHz, CD$_3$OD) δ 7.84 (dd, J=8.4, 2.0 Hz, 1H), 7.31 (d, J=2.0 Hz, 1H), 7.23 (d, J=8.4 Hz, 1H), 7.13 (s, 2H), 6.06 (s, 2H), 5.38-5.32 (m, 1H), 5.06-5.02 (m, 2H), 4.78-4.75 (m, 2H), 4.00 (s, 3H), 2.56 (s, 6H); LC-MS: m/z 344.4 [M+H]$^+$.

Example 31

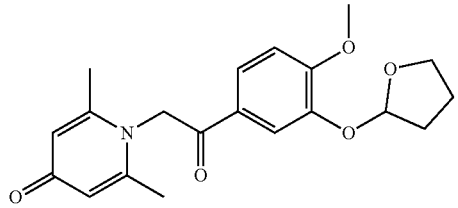 [SMILES: COc1ccc(C(=O)Cn2c(C)cc(=O)cc2C)cc1OC1CCCO1]

1-(2-(3-(tetrahydrofuran-2-yl)oxy-4-methoxyphenyl)-2-oxoethyl)-2,6-dimethylpyridin-4(1H)-one The specific reaction scheme is as shown below:

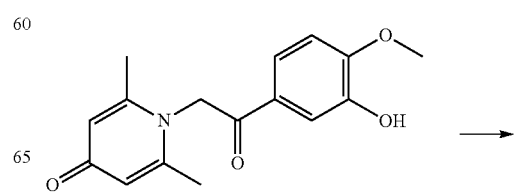

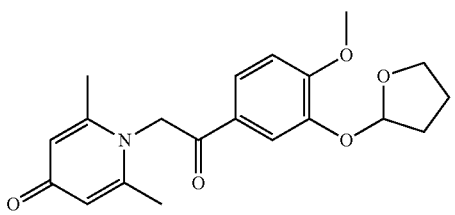

The compound 1-(2-(3-hydroxy-4-methoxyphenyl)-2-oxoethyl)-2,6-dimethylpyridin-4(1H)-one (50 mg, 0.17 mmol) was dissolved in dichloromethane (5 mL), and then 2,3-dihydrofuran (68 mg, 0.42 mmol) and pyridinium toluene-4-sulphonate (4.6 mg, 0.018 mmol) were added, and stirred overnight at room temperature. After the reaction was completed, the reaction solution was filtered, rotary dried, and purified by reverse-phase HPLC to obtain 14243-(tetrahydrofuran-2-yl)oxy-4-methoxyphenyl)-2-oxoethyl)-2,6-dimethylpyridin-4(1H)-one (28 mg, yield 44%, white solid). $^1$H NMR (400 MHz, CD$_3$OD) δ 7.87 (dd, J=8.4, 2.0 Hz, 1H), 7.81 (d, J=2.0 Hz, 1H), 7.15 (d, J=8.4 Hz, 1H), 6.40 (s, 2H), 5.87 (d, J=4.4 Hz, 1H), 5.70 (s, 2H), 4.07-4.02 (m, 1H), 3.97-3.92 (m, 1H), 3.94 (s, 3H), 2.31-2.11 (m, 4H), 2.29 (s, 6H); LC-MS m/z 358.1 [M+H]$^+$.

Example 32

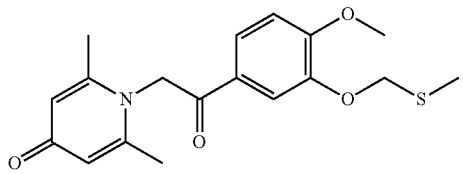 [SMILES: COc1ccc(C(=O)Cn2c(C)cc(=O)cc2C)cc1OCSC]

1-(2-(3-methylthiomethoxy-4-methoxyphenyl)-2-oxoethyl)-2,6-dimethylpyridin-4(1H)-one

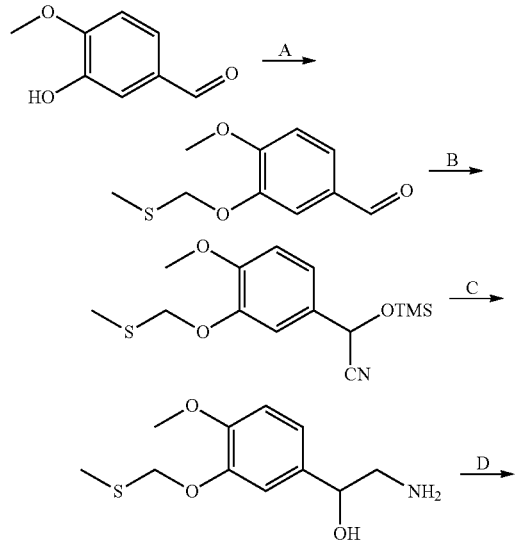

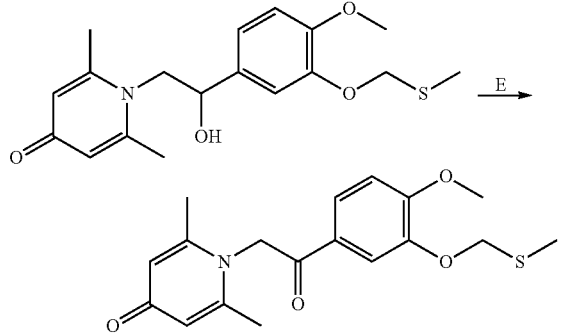

Step A:
Under nitrogen atmosphere, 3-hydroxy-4-methoxybenzaldehyde (2 g, 13 mmol) was dissolved in N,N-dimethylformamide (20 mL), and then chloromethyl methyl sulfide (1.5 g, 15.6 mmol) and cesium carbonate (6 g, 19.5 mmol) were added and stirred overnight at room temperature under nitrogen atmosphere. After the reaction was completed, saturated saline (40 mL) was added, and extracted with dichloromethane (3×30 mL). The organic phases were combined, and dried over anhydrous sodium sulfate. Filtration, rotary drying, and purification by column chromatography gave 3-methylthiomethoxy-4-methoxybenzaldehyde (1.7 g, yield 61%, yellow oil). LC-MS: m/z 213.1 [M+H]$^+$.

Step B:
3-methylthiomethoxy-4-methoxybenzaldehyde (1.7 g, 8 mmol) was dissolved in dichloromethane (20 mL); and under nitrogen atmosphere, triethyl amine (1.6 g, 16 mmol) and trimethylsilyl cyanide (1.6 g, 16 mmol) were added, and stirred for 6 hours at room temperature. The reaction solution was concentrated and rotary dried to obtain 2-(3-methylthiomethoxy-4-methoxyphenyl)-2-trimethylsiloxyacetonitrile, which was directly used in the next reaction.

Step C:
2-(3-Methylthiomethoxy-4-methoxyphenyl)-2-trimethylsiloxyacetonitrile obtained in the above step was dissolved in anhydrous tetrahydrofuran (50 mL), and then lithium aluminum hydride (608 mg, 16 mmol) was added portionwise in an ice bath and stirred overnight at room temperature. After the reaction was completed, water (0.6 mL), an aqueous sodium hydroxide solution (0.6 mL, 15%), and water (1.8 mL) were added in sequence, stirred for half an hour, dried over anhydrous sodium sulfate, and filtered. The filtrate was rotary dried to obtain a crude product of 2-amino-1-(3-methylthiomethoxy-4-methoxyphenyl)ethanol.

Step D:
2-Amino-1-(3-(methylthiomethoxy)-4-methoxyphenyl) ethanol obtained in the above step was dissolved in ethanol (10 mL), and then 2,6-dimethyl-4-pyranone (1.24 g, 10 mmol) and an aqueous sodium hydroxide solution (2 M, 10 mL) were added, and stirred overnight at 60° C. The reaction was complete as indicated by LCMS. The reaction solution was rotary dried, and purified by column chromatography to obtain 1-(2-(3-methylthiomethoxy-4-methoxyphenyl)-2-hydroxyethyl)-2,6-dimethylpyridin-4(1H)-one (1 g, 35%). LC-MS: m/z 350.1 [M+H]$^+$.

Step E:
1-(2-(3-methylthiomethoxy-4-methoxyphenyl)-2-hydroxyethyl)-2,6-dimethylpyridin-4(1H)-one (50 mg, 0.14 mmol) was dissolved in dimethylsulfoxide (5 mL), and then sulfur trioxide pyridine complex (111 mg, 0.7 mmol) in DMSO (2.5 mL) was slowly added and stirred overnight at normal temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-methylthiomethoxy-4-methoxyphenyl)-2-oxoethyl)-2,6-dimethylpyridin-4(1H)-one (25 mg, yield 51%, white solid). $^1$H NMR (400 MHz, CDCl$_3$) δ 7.67 (dd, J=8.4, 2.0 Hz, 1H), 7.55 (d, J=2.0 Hz, 1H), 7.00 (d, J=8.4 Hz, 1H), 6.28 (s, 2H), 5.31 (s, 2H), 5.23 (s, 2H), 3.93 (s, 3H), 3.68 (s, 3H), 2.12 (s, 6H); LC-MS: m/z 348.2 [M+H]$^+$.

mmol) was dissolved in dichloromethane (10 mL), and then the Dess-Martin Periodinane (85 mg, 0.2 mmol) was added and stirred at room temperature for 2 hours. The reaction solution was filtered, and washed with saturated brine. The organic phase was dried over anhydrous sodium sulfate, filtered, rotary dried, and purified by reverse-phase HPLC to obtain 1-(2-(3-methylsulfoxidemethoxy-4-methoxyphenyl)-2-oxoethyl)-2,6-dimethylpyridin-4(1H)-one (10 mg, yield 37%, white solid). $^1$H NMR (400 MHz, CDCl$_3$) δ 7.93 (d, J=2.0 Hz, 1H), 7.74 (dd, J=8.4, 2.0 Hz, 1H), 6.98 (d, J=8.4 Hz, 1H), 6.26 (s, 2H), 5.25 (s, 2H), 5.23 (s, 2H), 3.93 (s, 3H), 3.68 (s, 3H), 2.12 (s, 6H); LC-MS: m/z 364.2 [M+H]$^+$.

Example 33

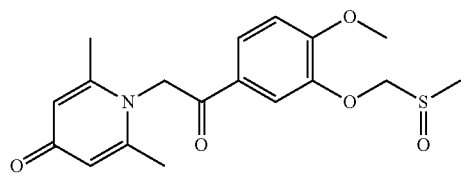 [SMILES: COc1ccc(C(=O)Cn2c(C)cc(=O)cc2C)cc1OCS(C)=O]

1-(2-(3-methylsulfoxidemethoxy-4-methoxyphenyl)-2-oxoethyl)-2,6-dimethylpyridin-4(1H)-one The specific reaction scheme is as shown below:

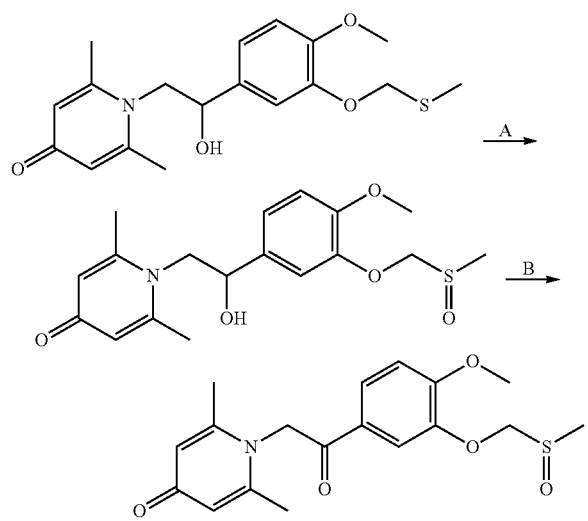

Step A:
1-(2-(3-methylthiomethoxy-4-methoxyphenyl)-2-hydroxyethyl)-2,6-dimethylpyridin-4(1H)-one (100 mg, 0.29 mmol) was dissolved in dichloromethane (5 mL), and then 85% m-chloroperoxybenzoic acid (56 mg, 0.28 mmol) was added and stirred at room temperature for 2 hours. Then, a saturated aqueous sodium sulfite solution (5 mL) was added and stirred for 10 min. The reaction solution was extracted with dichloromethane (3×10 mL). The organic phases were combined, and dried over anhydrous sodium sulfate. Filtration, rotary drying, and purification by column chromatography gave 1-(2(3-methylsulfoxidemethoxy-4-methoxyphenyl)-2-hydroxyethyl)-2,6-dimethylpyridin-4(1H)-one (38 mg, yield 36%, white solid). LC-MS: m/z 366.2 [M+H]$^+$.

Step B:
1-(2(3-methylsulfoxidemethoxy-4-methoxyphenyl)-2-hydroxyethyl)-2,6-dimethylpyridin-4(1H)-one (38 mg, 0.1

Example 34

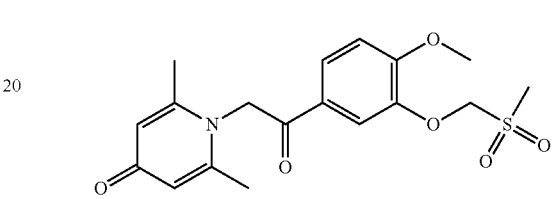

1-(2-(3-methylsulfonemethoxy-4-methoxyphenyl)-2-oxoethyl)-2,6-dimethylpyridin-4(1H)-one The specific reaction scheme is as shown below:

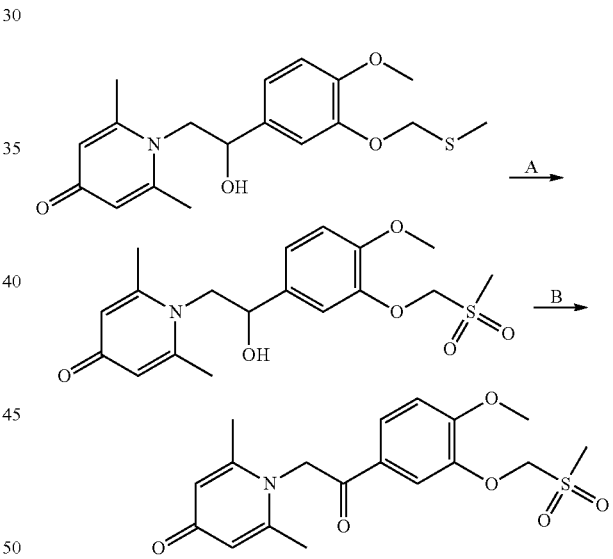

Step A:
1-(2-(3-methylthiomethoxy-4-methoxyphenyl)-2-hydroxyethyl)-2,6-dimethylpyridin-4(1H)-one (100 mg, 0.29 mmol) was dissolved in dichloromethane (5 mL), and then 85% m-chloroperoxybenzoic acid (176 mg, 0.87 mmol) was added and stirred overnight at room temperature. Then, a saturated aqueous sodium sulfite solution (10 mL) was added and stirred for 10 min. The reaction solution was extracted with dichloromethane (3×10 mL). The organic phases were combined, and dried over anhydrous sodium sulfate. Filtration, rotary drying, and purification by column chromatography gave 1-(2-(3-methylsulfonemethoxy-4-methoxyphenyl)-2-hydroxyethyl)-2,6-dimethylpyridin-4(1H)-one (50 mg, yield 55%, white solid). LC-MS: m/z 382.2 [M+H]$^+$.

Step B:

1-(2-(3-methylsulfonemethoxy-4-methoxyphenyl)-2-hydroxyethyl)-2,6-dimethylpyridin-4(1H)-one (50 mg, 0.13 mmol) was dissolved in dichloromethane (10 mL), and then the Dess-Martin Periodinane (110 mg, 0.26 mmol) was added and stirred at room temperature for 2 hours. The reaction solution was filtered, and washed with saturated brine. The organic phase was dried over anhydrous sodium sulfate, filtered, rotary dried, and purified by reverse-phase HPLC to obtain 1-(2-(3-methylsulfoxidemethoxy-4-methoxyphenyl)-2-oxoethyl)-2,6-dimethylpyridin-4(1H)-one (30 mg, yield 61%, white solid). $^1$H NMR (400 MHz, CDCl$_3$) δ 7.84 (dd, J=8.4, 2.0 Hz, 1H), 7.70 (d, J=2.0 Hz, 1H), 7.10 (d, J=8.4 Hz, 1H), 6.26 (s, 2H), 5.35 (s, 2H), 5.23 (s, 2H), 3.98 (s, 3H), 3.78 (s, 3H), 2.25 (s, 6H); LC-MS: m/z 380.1 [M+H]$^+$.

Example 35

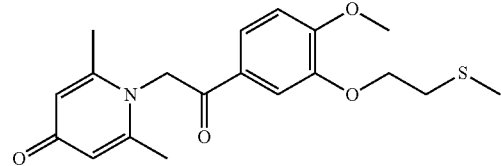 [SMILES: COc1ccc(C(=O)Cn2c(C)cc(=O)cc2C)cc1OCCSC]

1-(2-(3-methylthioethoxy-4-methoxyphenyl)-2-oxoethyl)-2,6-dimethylpyridin-4(1H)-one The specific reaction scheme is as shown below:

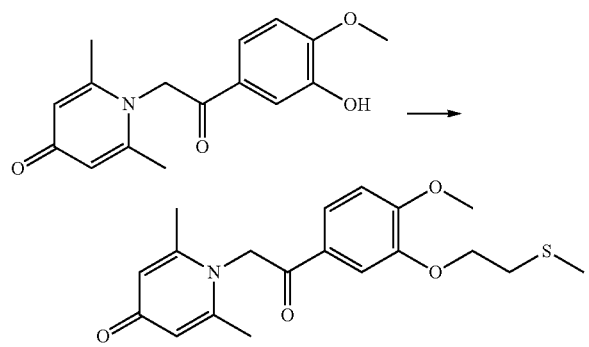

The compound 1-(2-(3-hydroxy-4-methoxyphenyl)-2-oxoethyl)-2,6-dimethylpyridin-4(1H)-one (287 mg, 1 mmol) was dissolved in N, N-dimethylformamide (5 mL), and then chloroethyl methyl sulfide (166 mg, 1.5 mmol) and potassium carbonate (276 mg, 2 mmol) were added and stirred for 2 hours at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave 1-(2-(3-methylthioethoxy-4-methoxyphenyl)-2-oxoethyl)-2,6-dimethylpyridin-4(1H)-one 200 mg, yield 55%, white solid). $^1$H NMR (400 MHz, CDCl$_3$) δ 7.66 (dd, J=8.4, 2.0 Hz, 1H), 7.56 (d, J=2.0 Hz, 1H), 6.98 (d, J=8.4 Hz, 1H), 6.28 (s, 2H), 5.31 (s, 2H), 4.27 (t, J=6.8 Hz, 2H), 3.98 (s, 3H), 2.95 (t, J=6.8 Hz, 2H), 2.24 (s, 3H), 2.19 (s, 6H); LC-MS: m/z 362.2 [M+H]$^+$.

Example 36

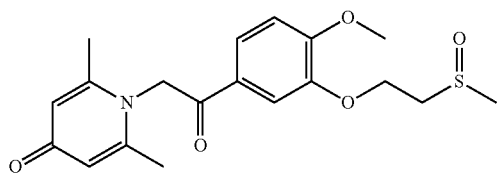 [SMILES: COc1ccc(C(=O)Cn2c(C)cc(=O)cc2C)cc1OCCS(C)=O]

1-(2-(3-methylsulfoxideethoxy-4-methoxyphenyl)-2-oxoethyl)-2,6-dimethylpyridin-4(1H)-one The specific reaction scheme is as shown below:

The compound 1-(2-(3-methylthioethoxy-4-methoxyphenyl)-2-oxoethyl)-2,6-dimethylpyridin-4(1H)-one (50 mg, 0.15 mmol) was dissolved in dichloromethane (5 mL), and then 85% m-chloroperoxybenzoic acid (28 mg, 0.14 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoxideethoxy-4-methoxystyryl)-2,6-dimethylpyridin-4(1H)-one (20 mg, yield 40%, colorless oil). $^1$H NMR (400 MHz, CDCl$_3$) δ 7.71 (dd, J=8.4, 2.0 Hz, 1H), 7.66 (d, J=2.0 Hz, 1H), 6.99 (d, J=8.4 Hz, 1H), 6.26 (s, 2H), 5.32 (s, 2H), 4.57-4.54 (m, 2H), 3.97 (s, 3H), 3.35-3.31 (m, 1H), 3.15-3.09 (m, 1H), 2.75 (s, 3H), 2.18 (s, 6H); LC-MS: m/z 378.2 [M+H]$^+$.

Example 37

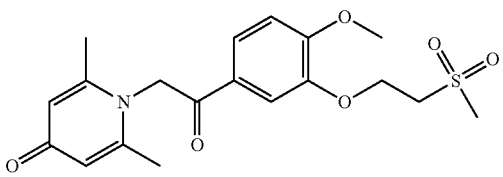 [SMILES: COc1ccc(C(=O)Cn2c(C)cc(=O)cc2C)cc1OCCS(C)(=O)=O]

1-(2-(3-methylsulfoneethoxy-4-methoxyphenyl)-2-oxo-ethyl)-2,6-dimethylpyridin-4(1H)-one The specific reaction scheme is as shown below:

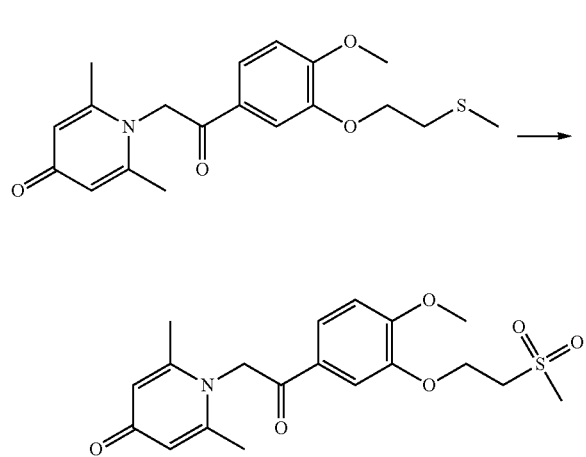

The compound 1-(2-(3-methylthioethoxy-4-methoxyphenyl)-2-oxoethyl)-2,6-dimethylpyridin-4(1H)-one (50 mg, 0.15 mmol) was dissolved in dichloromethane (5 mL), and then 85% m-chloroperoxybenzoic acid (71 mg, 0.35 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoneethoxy-4-methoxystyryl)-2,6-dimethylpyridin-4(1H)-one (20 mg, yield 36%, white solid). $^1$H NMR (400 MHz, CDCl$_3$) δ 7.74 (dd, J=8.4, 2.0 Hz, 1H), 7.60 (d, J=2.0 Hz, 1H), 7.00 (d, J=8.4 Hz, 1H), 6.26 (s, 2H), 5.30 (s, 2H), 4.53 (t, J=4.2 Hz, 2H), 3.95 (s, 3H), 3.51 (t, J=4.2 Hz, 2H), 3.18 (s, 3H), 2.18 (s, 6H); LC-MS: m/z 394.2 [M+H]$^+$.

Example 38

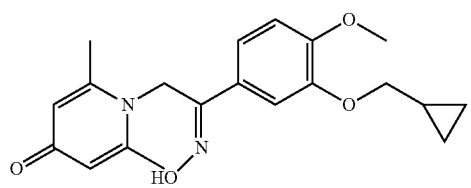 [SMILES: COc1ccc(/C(Cn2c(C)cc(=O)cc2C)=N/O)cc1OCC1CC1]

(Z)-1-(2-(3-cyclopropylmethoxy-4-methoxyphenyl)-2-(hydroxyimido)ethyl)-2,6-dimethylpyridin-4(1H)-one

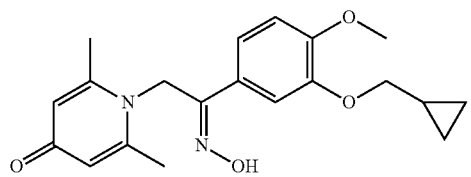 [SMILES: COc1ccc(/C(Cn2c(C)cc(=O)cc2C)=N\O)cc1OCC1CC1]

(E)-1-(2-(3-cyclopropylmethoxy-4-methoxyphenyl)-2-(hydroxyimido)ethyl)-2,6-dimethylpyridin-4(1H)-one The specific reaction scheme is as shown below:

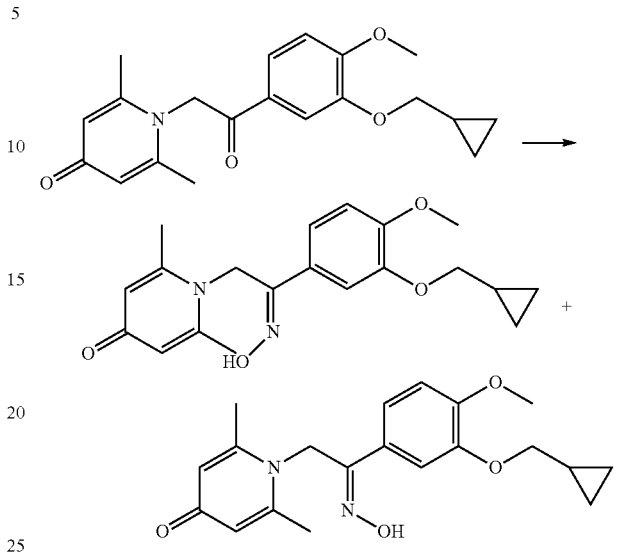

The compound 1-(2-(3-cyclopropylmethoxy-4-methoxyphenyl)-2-oxoethyl)-2,6-dimethylpyridin-4(1H)-one (341 mg, 1 mmol) and hydroxylamine hydrochloride (139 mg, 2 mmol) were dissolved in pyridine (10 mL), and refluxed for 24 hours under nitrogen atmosphere. After the reaction was completed, pyridine was rotary dried, and the reaction solution was purified by reverse-phase HPLC to obtain (Z)-1-(2-(3-cyclopropylmethoxy-4-methoxyphenyl)-2-(hydroxyimido)ethyl)-2,6-dimethylpyridin-4(1H)-one (96 mg, yield 27%, white solid) and (E)-1-(2-(3-cyclopropylmethoxy-4-methoxyphenyl)-2-(hydroxyimido)ethyl)-2,6-dimethylpyridin-4(1H)-one (43 mg, yield 12%, white solid).

(Z)-1-(2-(3-cyclopropylmethoxy-4-methoxyphenyl)-2-(hydroxyimido)ethyl)-2,6-dimethylpyridin-4(1H)-one. $^1$H NMR (400 MHz, CDCl$_3$) δ 7.45 (d, J=2.0 Hz, 1H), 7.30 (d, J=8.4 Hz, 1H), 6.93 (dd, J=8.4, 2.0 Hz, 1H), 6.48 (s, 2H), 5.00 (s, 2H), 3.92 (s, 3H), 3.89 (d, J=6.8 Hz, 2H), 2.41 (s, 6H), 1.42-1.32 (m, 1H), 0.68-0.62 (m, 2H), 0.40-0.35 (m, 2H); LC-MS: m/z 357.4 [M+H]$^+$.

(E)-1-(2-(3-cyclopropylmethoxy-4-methoxyphenyl)-2-(hydroxyimido)ethyl)-2,6-dimethylpyridin-4(1H)-one. $^1$H NMR (400 MHz, CDCl$_3$) δ 7.50 (d, J=2.0 Hz, 1H), 7.13 (d, J=8.4 Hz, 1H), 6.93 (dd, J=8.4, 2.0 Hz, 1H), 6.49 (s, 2H), 5.00 (s, 2H), 3.92 (s, 3H), 3.89 (d, J=6.8 Hz, 2H), 2.41 (s, 6H), 1.42-1.32 (m, 1H), 0.68-0.62 (m, 2H), 0.40-0.35 (m, 2H); LC-MS: m/z 357.4 [M+H]$^+$.

Example 39

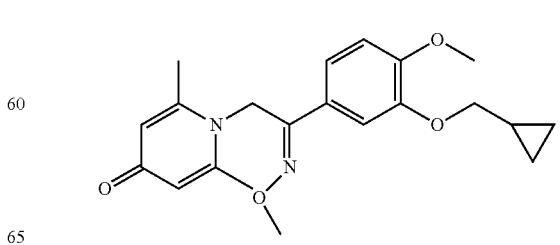

53

(Z)-1-(2-(3-cyclopropylmethoxy-4-methoxyphenyl)-2-(methoxyimido)ethyl)-2,6-dimethylpyridin-4(1H)-one The specific reaction scheme is as shown below:

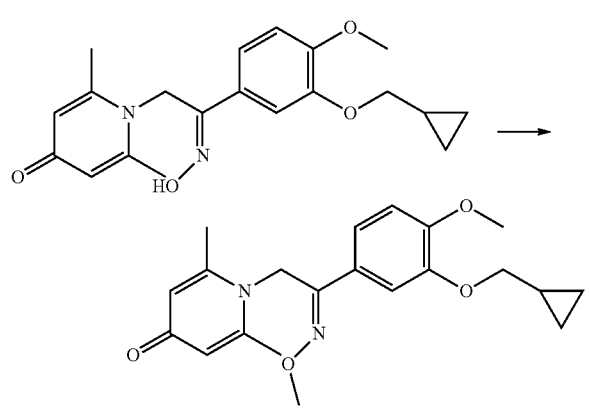

The compound (Z)-1-(2-(3-cyclopropylmethoxy-4-methoxyphenyl)-2-(hydroxyimido)ethyl)-2,6-dimethylpyridin-4(1H)-one (36 mg, 0.1 mmol) was dissolved in N,N-dimethylformamide (2 mL), and then 60% sodium hydride (12 mg, 0.3 mmol) was added at 0° C., and stirred for half an hour. Then, iodomethane (28.4 mg, 0.2 mmol) was added, and stirred at room temperature for 4 hours. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (Z)-1-(2-(3-cyclopropylmethoxy-4-methoxyphenyl)-2-(methoxyimido)ethyl)-2,6-dimethylpyridin-4(1H)-one (20 mg, yield 55%, white solid). $^1$H NMR (400 MHz, CDCl$_3$) δ 7.46 (d, J=2.0 Hz, 1H), 7.32 (d, J=8.4 Hz, 1H), 7.02 (dd, J=8.4, 2.0 Hz, 1H), 6.52 (s, 2H), 5.02 (s, 2H), 3.93 (s, 3H), 3.92 (s, 3H), 3.89 (d, J=6.8 Hz, 2H), 2.45 (s, 6H), 1.32-1.23 (m, 1H), 0.70-0.65 (m, 2H), 0.50-0.38 (m, 2H); LC-MS: m/z 371.2 [M+H]$^+$.

Example 40

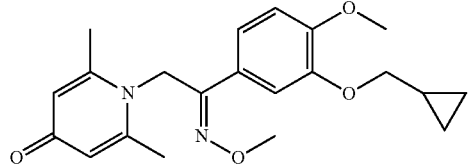 [SMILES: CO/N=C(/Cn1c(C)cc(=O)cc1C)c1ccc(OC)c(OCC2CC2)c1]

(E)-1-(2-(3-cyclopropylmethoxy-4-methoxyphenyl)-2-(hydroxymethylimido) ethyl)-2,6-dimethylpyridin-4(1H)-one The specific reaction scheme is as shown below:

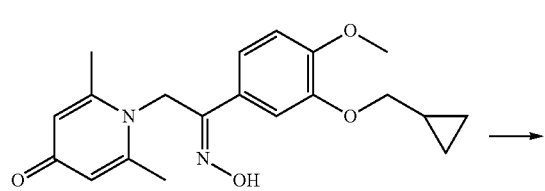

54

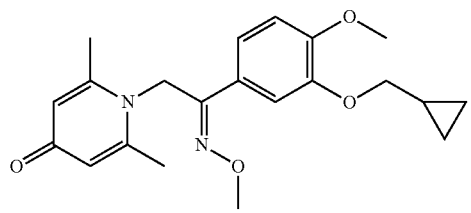

The compound (E)-1-(2-(3-cyclopropylmethoxy-4-methoxyphenyl)-2-(hydroxyimido)ethyl)-2,6-dimethylpyridin-4(1H)-one (36 mg, 0.1 mmol) was dissolved in N,N-dimethylformamide (2 mL), and then 60% sodium hydride (12 mg, 0.3 mmol) was added at 0° C., and stirred for half an hour. Then, iodomethane (28.4 mg, 0.2 mmol) was added, and stirred at room temperature for 4 hours. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (Z)-1-(2-(3-cyclopropylmethoxy-4-methoxyphenyl)-2-(methoxyimido)ethyl)-2,6-dimethylpyridin-4(1H)-one (18 mg, yield 49%, white solid). $^1$H NMR (400 MHz, CDCl$_3$) δ 7.51 (d, J=2.0 Hz, 1H), 7.11 (d, J=8.4 Hz, 1H), 7.00 (dd, J=8.4, 2.0 Hz, 1H), 6.46 (s, 2H), 5.00 (s, 2H), 3.95 (s, 3H), 3.93 (s, 3H), 3.88 (d, J=6.8 Hz, 2H), 2.49 (s, 6H), 1.42-1.32 (m, 1H), 0.68-0.62 (m, 2H), 0.40-0.35 (m, 2H); LC-MS: m/z 371.2 [M+H]$^+$.

Example 41

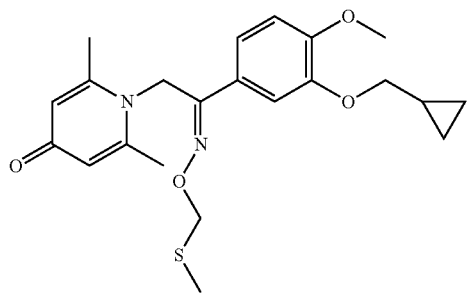

(Z)-1-(2-(3-cyclopropylmethoxy-4-methoxyphenyl)-2-(methylthiomethoxyimido)ethyl)-2,6-dimethylpyridin-4(1H)-one The specific reaction scheme is as shown below:

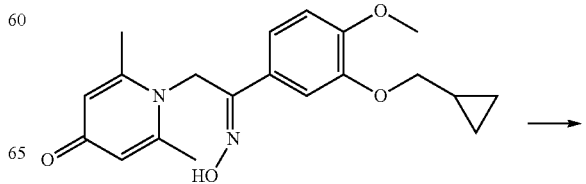

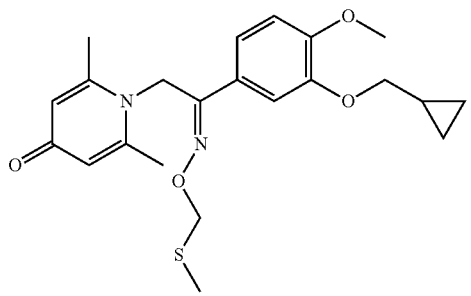 [SMILES: COc1ccc(/C(Cn2c(C)cc(=O)cc2C)=N/OCSC)cc1OCC1CC1]

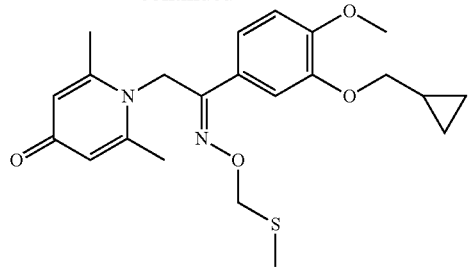 [SMILES: COc1ccc(/C(Cn2c(C)cc(=O)cc2C)=N\OCSC)cc1OCC1CC1]

The compound (Z)-1-(2-(3-cyclopropylmethoxy-4-methoxyphenyl)-2-(hydroxyimido)ethyl)-2,6-dimethylpyridin-4(1H)-one (300 mg, 0.84 mmol) was dissolved in N,N-dimethylformamide (5 mL), and then cesium carbonate (548 mg, 1.68 mmol) and chloromethylmethyl sulfide (122 mg, 1.26 mmol) were added, and stirred overnight at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (Z)-1-(2-(3-cyclopropylmethoxy-4-methoxyphenyl)-2-(methylthiomethoxyimido)ethyl)-2,6-dimethylpyridin-4(1H)-one (200 mg, yield 57%, white solid). $^1$H NMR (400 MHz, CD$_3$OD) δ 7.23 (d, J=8.4 Hz, 1H), 7.18 (s, 1H), 7.08 (d, J=8.4 Hz, 1H), 6.96 (s, 2H), 6.35 (s, 2H), 5.18 (s, 2H), 3.91 (s, 2H), 3.85 (d, J=6.8 Hz, 2H), 2.47 (s, 6H), 2.40 (s, 3H), 1.36-1.28 (m, 1H), 0.69-0.64 (m, 2H), 0.35-0.32 (m, 2H); LC-MS: m/z 417.1 [M+H]$^+$.

Example 42

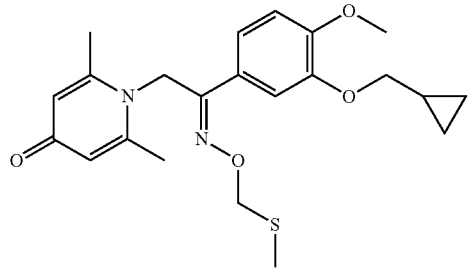

(E)-1-(2-(3-cyclopropylmethoxy-4-methoxyphenyl)-2-(methylthiomethoxyimido)ethyl)-2,6-dimethylpyridin-4(1H)-one The specific reaction scheme is as shown below:

The compound (E)-1-(2-(3-cyclopropylmethoxy-4-methoxyphenyl)-2-(hydroxyimido)ethyl)-2,6-dimethylpyridin-4(1H)-one (36 mg, 0.1 mmol) was dissolved in N,N-dimethylformamide (2 mL), and then cesium carbonate (65 mg, 0.2 mmol) and chloromethylmethyl sulfide (15 mg, 0.15 mmol) were added. and stirred overnight at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (Z)-1-(2-(3-cyclopropylmethoxy-4-methoxyphenyl)-2-(methylthiomethoxyimido)ethyl)-2,6-dimethylpyridin-4(1H)-one (20 mg, yield 48%, white solid). $^1$H NMR (400 MHz, CD$_3$OD) δ 7.36 (d, J=8.4 Hz, 1H), 7.25 (s, 1H), 6.88 (d, J=8.4 Hz, 1H), 6.86 (s, 2H), 6.38 (s, 2H), 5.10 (s, 2H), 3.96 (s, 2H), 3.90 (d, J=6.8 Hz, 2H), 2.47 (s, 6H), 2.40 (s, 3H), 1.36-1.28 (m, 1H), 0.69-0.64 (m, 2H), 0.35-0.32 (m, 2H); LC-MS: m/z 417.1 [M+H]$^+$.

Example 43

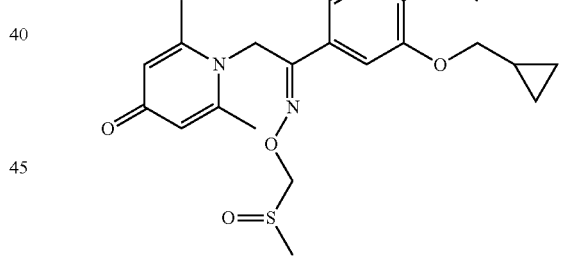

(Z)-1-(2-(3-cyclopropylmethoxy-4-methoxyphenyl)-2-(methylsulfoxidemethoxyimido)ethyl)-2,6-dimethylpyridin-4(1H)-one The specific reaction scheme is as shown below:

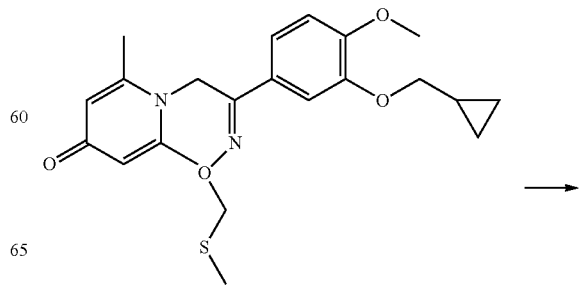

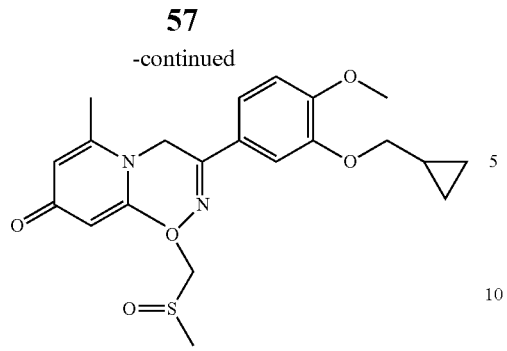

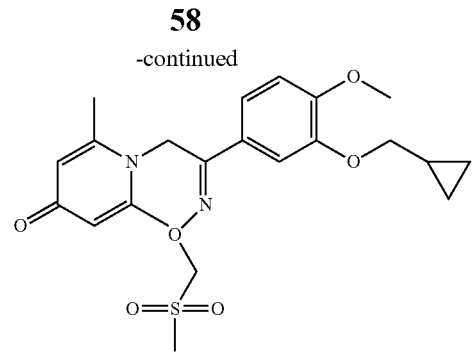

The compound (Z)-1-(2-(3-cyclopropylmethoxy-4-methoxyphenyl)-2-(methylthiomethoxyimido)ethyl)-2,6-dimethylpyridin-4(1H)-one (42 mg, 0.1 mmol) was dissolved in dichloromethane (5 mL), and then 85% m-chloroperoxybenzoic acid (18 mg, 0.09 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (Z)-1-(2-(3-cyclopropylmethoxy-4-methoxyphenyl)-2-(methylsulfoxidemethoxyimido)ethyl)-2,6-dimethylpyridin-4(1H)-one (20 mg, yield 46%, white solid). $^1$H NMR (400 MHz, DMSO-$d_6$) δ 7.28 (d, J=8.4 Hz, 1H), 7.21 (s, 1H), 6.96 (d, J=8.4 Hz, 1H), 6.90 (s, 2H), 6.36 (s, 2H), 5.15 (s, 2H), 3.94 (s, 2H), 3.88 (d, J=6.8 Hz, 2H), 2.46 (s, 6H), 2.42 (s, 3H), 1.38-1.30 (m, 1H), 0.69-0.65 (m, 2H), 0.38-0.33 (m, 2H); LC-MS: m/z 433.2 [M+H]$^+$.

The compound (Z)-1-(2-(3-cyclopropylmethoxy-4-methoxyphenyl)-2-(methylthiomethoxyimido)ethyl)-2,6-dimethylpyridin-4(1H)-one (42 mg, 0.1 mmol) was dissolved in dichloromethane (5 mL), and then 85% m-chloroperoxybenzoic acid (61 mg, 0.3 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (Z)-1-(2-(3-cyclopropylmethoxy-4-methoxyphenyl)-2-(methylsulfonemethoxyimido)ethyl)-2,6-dimethylpyridin-4(1H)-one (26 mg, yield 58%, white solid). $^1$H NMR (400 MHz, DMSO-$d_6$) δ 7.23 (d, J=8.4 Hz, 1H), 7.18 (s, 1H), 7.08 (d, J=8.4 Hz, 1H), 6.96 (s, 2H), 6.35 (s, 2H), 5.18 (s, 2H), 3.91 (s, 2H), 3.85 (d, J=6.8 Hz, 2H), 2.47 (s, 6H), 2.40 (s, 3H), 1.36-1.28 (m, 1H), 0.69-0.64 (m, 2H), 0.35-0.32 (m, 2H); LC-MS: m/z 449.2 [M+H]$^+$.

Example 44

Example 45

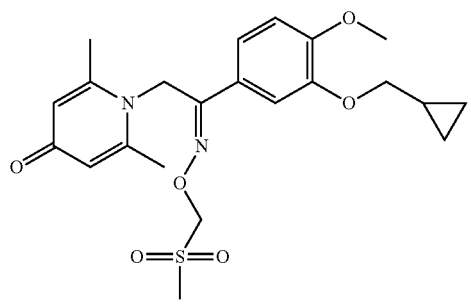 [SMILES: COc1ccc(/C(Cn2c(C)cc(=O)cc2C)=N/OCS(C)(=O)=O)cc1OCC1CC1]

(Z)-1-(2-(3-cyclopropylmethoxy-4-methoxyphenyl)-2-(methylsulfonemethoxyimido)ethyl)-2,6-dimethylpyridin-4(1H)-one The specific reaction scheme is as shown below:

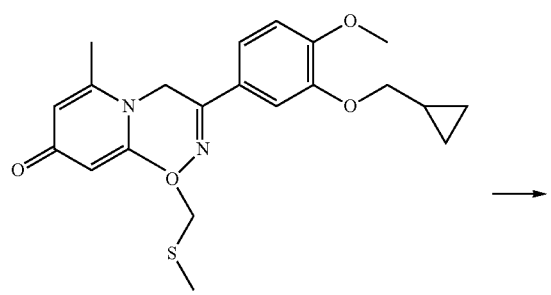

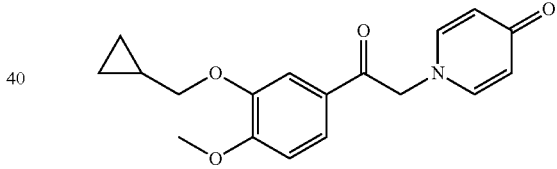

1-(2-(3-cyclopropylmethoxy-4-methoxyphenyl)-2-oxoethyl)pyridin-4(1H)-one

The specific reaction scheme is as shown below:

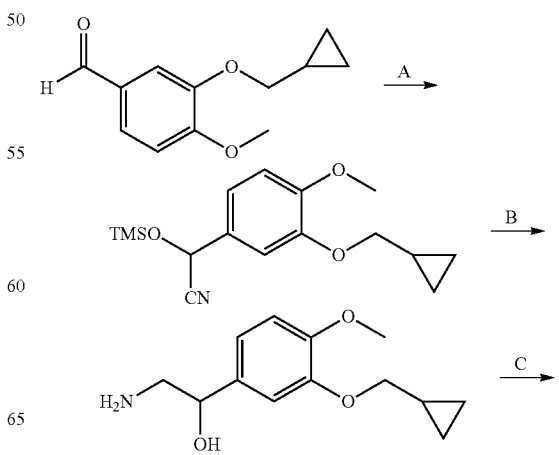

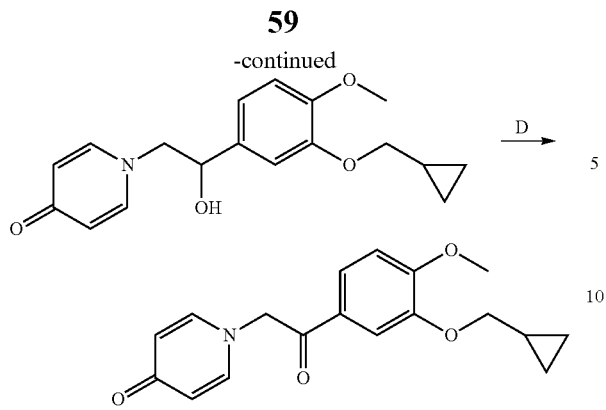

Step A:

3-cyclopropylmethoxy-4-methoxybenzaldehyde (3.09 g, 15 mmol) was dissolved in dichloromethane (30 mL); and under nitrogen atmosphere, triethyl amine (4.16 mL, 30 mmol) and trimethylsilyl cyanide (3.75 g, 30 mmol) were added, and stirred for 6 hours at room temperature. The reaction solution was concentrated and rotary dried to obtain 2-(3-cyclopropylmethoxy-4-methoxyphenyl)-2-trimethylsiloxyacetonitrile, which was directly used in the next reaction.

Step B:

The compound 2-(3-cyclopropylmethoxy-4-methoxyphenyl)-2-trimethylsiloxyacetonitrile (4.57 g, 15 mmol) was dissolved in anhydrous tetrahydrofuran (50 mL), and then lithium aluminum hydride (1.14 g, 30 mmol) was added portion-wise in an ice bath, and stirred overnight at room temperature. After the reaction was completed, water (1.2 mL), an aqueous sodium hydroxide solution (1.2 mL, 15%), and water (3.6 mL) were added in sequence, stirred for half an hour, dried over anhydrous sodium sulfate, filtered, and rotary dried to obtain a crude product of 2-amino-1-(3-cyclopropylmethoxy-4-methoxyphenyl)ethanol.

Step C:

The compound 2-amino-1-(3-(cyclopropylmethoxy)-4-methoxyphenyl)ethanol was dissolved in ethanol (20 mL), and then pyrone (1 g, 10.41 mmol) and aqueous sodium hydroxide solution (2M, 20 mL) were added, and stirred overnight at 60° C. The reaction was complete as indicated by LCMS. The reaction solution was rotary dried, and purified by column chromatography to obtain 1-(2-(3-cyclopropylmethoxy-4-methoxyphenyl)-2-hydroxyethyl)pyridin-4(1H)-one (2 g, 63%). LC-MS: m/z 316.2 [M+H]$^+$.

Step D:

The compound 1-(2-(3-cyclopropylmethoxy-4-methoxyphenyl)-2-hydroxyethyl)pyridin-4(1H)-one (280 mg, 0.88 mmol) was dissolved in dichloromethane (10 mL); and under nitrogen atmosphere, Dess-Martin Periodinane (746 mg, 1.76 mmol) was added and stirred for 3 hours at room temperature. After the reaction was completed, the reaction solution was concentrated, rotary dried, and purified by column chromatography to obtain 1-(2-(3-cyclopropylmethoxy-4-methoxyphenyl)-2-oxoethyl)pyridin-4(1H)-one (50 mg, yield 18%, white solid). $^1$H NMR (400 MHz, DMSO-d$_6$) δ 7.83 (d, J=7.6 Hz, 2H), 7.68 (dd, J=8.4, 1.2 Hz, 1H), 7.45 (d, J=1.2 Hz, 1H), 7.16 (d, J=8.4 Hz, 1H), 6.47 (d, J=7.6 Hz, 2H), 5.72 (s, 2H), 3.89 (s, 3H), 3.87 (d, J=6.8 Hz, 2H), 1.26-1.21 (m, 1H), 0.62-0.56 (m, 2H), 0.36-0.31 (m, 2H); LC-MS: m/z 314.1 [M+H]$^+$.

Example 46

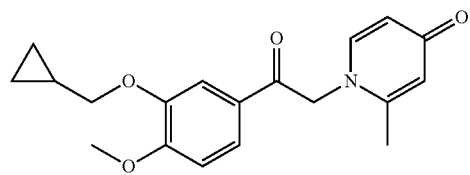 [SMILES: COc1ccc(C(=O)Cn2ccc(=O)cc2C)cc1OCC1CC1]

1-(2-(3-cyclopropylmethoxy-4-methoxyphenyl)-2-oxoethyl)-2-methylpyridin-4(1H)-one The specific reaction scheme is as shown below.

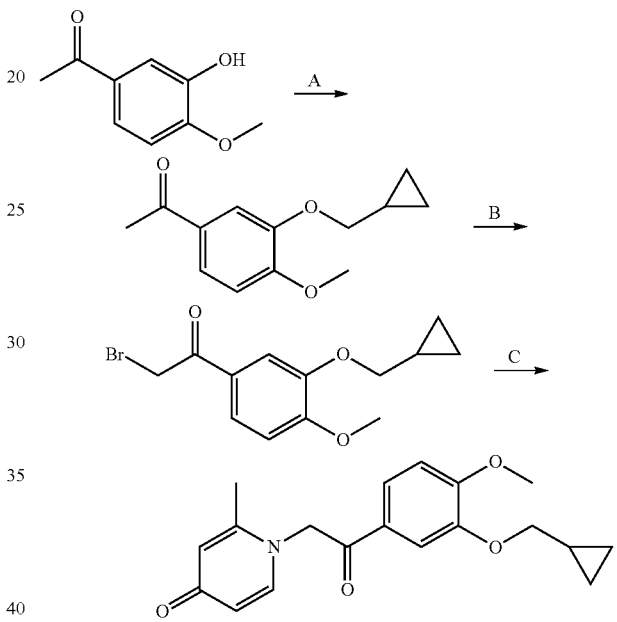

Step A:

3-hydroxy-4-methoxyacetophenone (1.66 g, 10 mmol) was dissolved in acetonitrile (30 mL); and under nitrogen atmosphere, potassium carbonate (2.76 g, 20 mmol) and bromomethylcyclopropane (2.0 g, 15 mmol) were added, and stirred for 6 hours at 80° C. The reaction solution was filtered. The filtrate was concentrated, rotary dried, and purified by column chromatography to obtain 1-(3-cyclopropylmethoxy-4-methoxyphenyl)ethanone (2.1 g, yield 95%, white solid).

Step B:

The compound 1-(3-cyclopropylmethoxy-4-methoxyphenyl)ethanone (2.2 g, 10 mmol) was dissolved in methanol (30 mL), and then N-bromosuccinimide (2.14 g, 12 mmol) and p-toluenesulfonic acid (1.7 g, 10 mmol) were added to the solution and reacted at 65° C. for hours. After the reaction was completed, the reaction solution was concentrated, rotary dried, and purified by column chromatography to obtain 2-bromo-1-(3-cyclopropylmethoxy-4-methoxyphenyl)ethanone (800 mg, yield 27%, white solid).

Step C:

The compound 2-bromo-1-(3-cyclopropylmethoxy-4-methoxyphenyl)ethanone (185 mg, 1.5 mmol) and 4-methoxy-2methylpyridine (500 mg, 1.67 mmol) were dissolved in acetonitrile (10 mL), and stirred at 80° C. for 48 hours. After the reaction was completed, the reaction solution was concentrated, rotary dried, and purified by column chromatography to obtain 1-(2-(3-cyclopropylmethoxy-4-methoxyphenyl)-2-oxoethyl)-2-methylpyridin-4(1H)-one (300 mg, yield 61%, white solid). $^1$H NMR (400 MHz, DMSO-$d_6$) δ 7.76 (dd, J=8.4, 2.0 Hz, 1H), 7.67 (d, J=8.4 Hz, 1H), 7.55 (d, J=1.2 Hz, 1H), 7.12 (d, J=8.8 Hz, 2H), 6.42-6.38 (m, 2H), 5.72 (s, 2H), 3.95 (s, 3H), 3.91 (d, J=6.8 Hz, 2H), 2.24 (s, 3H), 1.34-1.24 (m, 1H), 0.66-0.60 (m, 2H), 0.39-0.34 (m, 2H); LC-MS: m/z 328.1 [M+H]$^+$.

Example 47

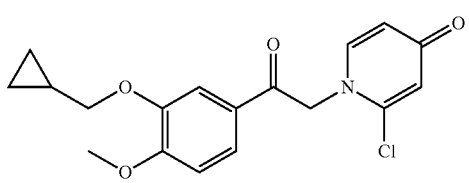

1-(2-(3-cyclopropylmethoxy-4-methoxyphenyl)-2-oxoethyl)-2-chloropyridin-4(1H)-one The specific reaction scheme is as shown below:

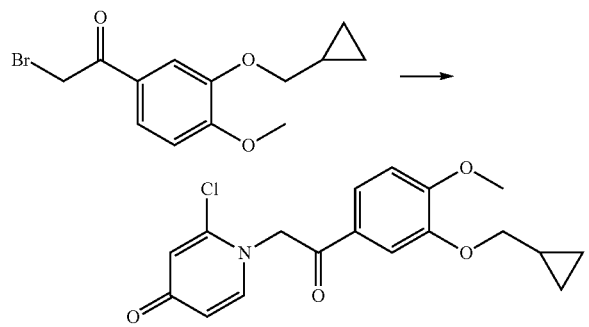

2-bromo-1-(3-cyclopropylmethoxy-4-methoxyphenyl)ethanone (594 mg, 2 mmol) and 4-methoxy-2chloropyridine (288 mg, 2 mmol) were dissolved in acetonitrile (10 mL), and stirred at 80° C. for 48 hours. After the reaction was completed, the reaction solution was concentrated, rotary dried, and purified by column chromatography to obtain 1-(2-(3-cyclopropylmethoxy-4-methoxyphenyl)-2-oxoethyl)-2-chloropyridin-4(1H)-one (117 mg, yield 17%, white solid). $^1$H NMR (400 MHz, DMSO-$d_6$) δ 7.73 (d, J=7.6 Hz, 2H), 7.47 (d, J=2.0 Hz, 1H), 7.16 (d, J=8.4 Hz, 1H), 6.38 (d, J=2.4 Hz, 1H), 6.18 (dd, J=8.0, 2.4 Hz, 1H), 5.77 (s, 2H), 3.89 (s, 3H), 3.87 (d, J=6.8 Hz, 2H), 1.27-1.22 (m, 1H), 0.62-0.56 (m, 2H), 0.36-0.32 (m, 2H); LC-MS: m/z 348.0 [M+H]$^+$.

Example 48

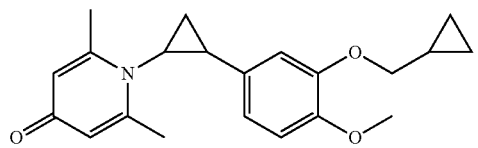 [SMILES: COc1ccc(C2CC2n2c(C)cc(=O)cc2C)cc1OCC1CC1]

1-(2-(3-cyclopropylmethoxy-4-methoxyphenyl)cyclopropyl)-2,6-dimethylpyridin-4(1H)-one

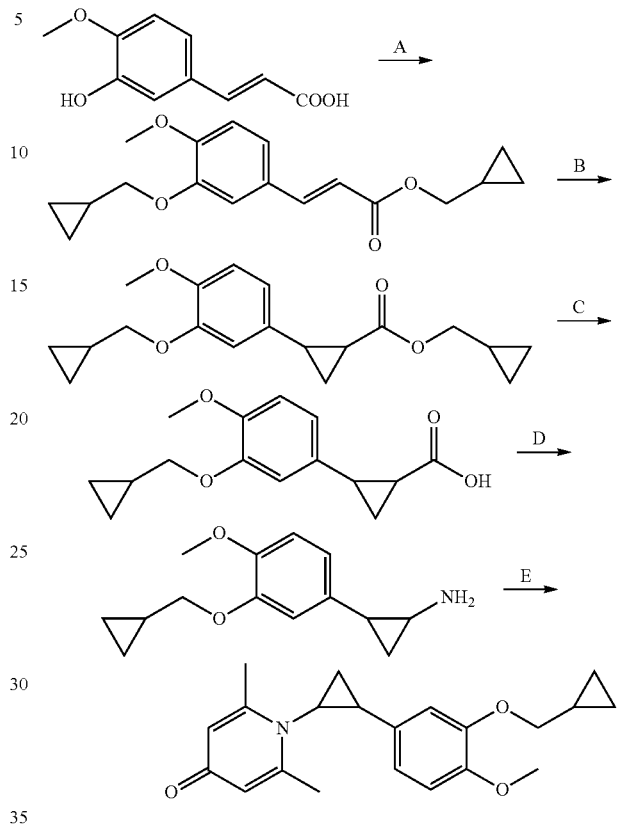

Step A:

3-hydroxy-4-methoxycinnamic acid (194 mg, 1 mmol) was dissolved in N,N-dimethylformamide (5 mL), and then bromomethylcyclopropane (338 mg, 2.5 mmol) and potassium carbonate (414 mg, 3 mmol) were added. The reaction solution was stirred overnight at 80° C. under nitrogen atmosphere. After the reaction was completed, saturated saline (10 mL) was added, and extracted with ethyl acetate (3×10 mL). The organic phases were combined, dried over anhydrous sodium sulfate, filtered, rotary dried, and purified by column chromatography to obtain cyclopropylmethyl 3-cyclopropylmethoxy-4-methoxycinnamate (200 mg, yield 61%, yellow liquid). LC-MS: m/z 303.3 [M+H]$^+$.

Step B:

Under nitrogen atmosphere, dimethylsulfoxide (4 mL), 60% sodium hydride (28.8 mg, 0.36 mmol) and trimethylsulfoxonium iodide (160 mg, 0.36 mmol) were stirred for 20 min at room temperature. A solution (2 mL) of cyclopropylmethyl 3-cyclopropylmethyl-4-methoxycinnamate (200 mg, 0.66 mmol) in tetrahydrofuran was slowly added. After the dropwise addition, the reaction solution was stirred at room temperature for 1 hr, then heated to 50° C. and continuously stirred for 1 hr. After the reaction was completed, the reaction solution was poured into iced water, and extracted with ethyl acetate (3×10 mL). The organic phases were combined, dried over anhydrous sodium sulfate, filtered, rotary dried, and purified by column chromatography to obtain cyclopropylmethyl 2-(3-cyclopropylmethoxy-4-methoxyphenyl)cyclopropylcarboxylate (80 mg, yield 56%, white solid). LC-MS: m/z 317.3 [M+H]$^+$.

Step C:

Cyclopropylmethyl 2-(3-cyclopropylmethoxy-4-methoxyphenyl)cyclopropylcarboxylate (80 mg, 0.25 mmol) was dissolved in methanol (2 mL), and then a sodium hydroxide solution (2N, 1 mL) was added, and stirred for 2 hr under reflux. After the reaction was completed, saturated saline (10 mL) was added, and extracted with dichloromethane (3×10 mL). The organic phases were combined, and dried over anhydrous sodium sulfate. Filtration, rotary drying, and purification gave 2-(3-cyclopropylmethoxy-4-methoxyphenyl)cyclopropylcarboxylic acid (50 mg, yield 76%, white solid).

Step D:

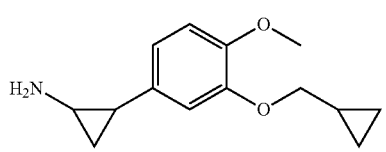 [SMILES: COc1ccc(C2CC2N)cc1OCC1CC1]

2-(3-cyclopropylmethoxy-4-methoxyphenyl)cyclopropylcarboxylic acid (50 mg, 0.19 mmol) was dissolved in 1,4-dioxane (2 mL), and then triethyl amine (26 mg, 0.26 mmol) and diphenylphosphoryl azide (64 mg, 0.26 mmol) were added. This reaction solution was stirred for 16 hours at room temperature, then heated to 80° C. and stirred for 1 hr. A mixture of 10% hydrochloric acid in 1,4-dioxane was added and continuously stirred at room temperature for 18 hours. After the reaction was completed, the reaction was quenched by adding a sodium hydroxide solution (1 mL, 3N), and extracted with dichloromethane (3×10 mL). The organic phases were combined, and dried over anhydrous sodium sulfate. Filtration, rotary drying, and purification gave 2-(3-cyclopropylmethoxy-4-methoxyphenyl)cyclopropylamine (12 mg, yield: 25%, yellow oil).

Step E

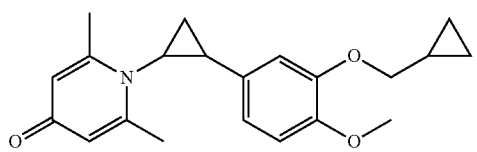 [SMILES: COc1ccc(C2CC2n2c(C)cc(=O)cc2C)cc1OCC1CC1]

The compound 2-(3-cyclopropylmethoxy-4-methoxyphenyl)cyclopropylamine (60 mg, 0.24 mmol) was dissolved in ethanol (3 mL), and then 2,6-dimethyl-4H-pyran-4-one (45 mg, 0.36 mmol) and sodium hydroxide (20 mg, 0.48 mmol) were added, and stirred overnight at 60° C. The reaction was complete as indicated by LCMS. The reaction solution was rotary dried, and purified to obtain 1-(2-(3-cyclopropylmethoxy-4-methoxyphenyl)cyclopropyl)-2,6-dimethylpyridin-4(1H)-one (10 mg, yield 11%, yellow oil). $^1$H NMR (400 MHz, CD$_3$OD) δ 6.83 (d, J=8.8 Hz, 1H), 6.75-6.58 (m, 2H), 6.18 (s, 2H), 3.76 (d, J=6.8 Hz, 2H), 3.73 (s, 3H), 2.40 (s, 6H), 1.63-1.54 (m, 2H), 1.29-1.12 (m, 2H), 0.54-0.48 (m, 2H), 0.26-0.22 (m, 2H); LC-MS: m/z 340.0 [M+H]$^+$.

Example 49

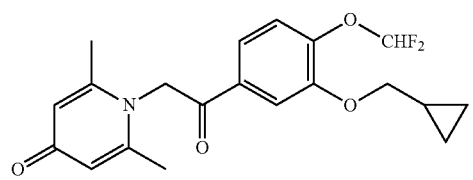 [SMILES: Cc1cc(=O)cc(C)n1CC(=O)c1ccc(OC(F)F)c(OCC2CC2)c1]

1-(2-(3-cyclopropylmethoxy-4-difluoromethoxyphenyl)-2-oxoethyl)-2,6-dimethylpyridin-4(1H)-one The specific reaction scheme is as shown below:

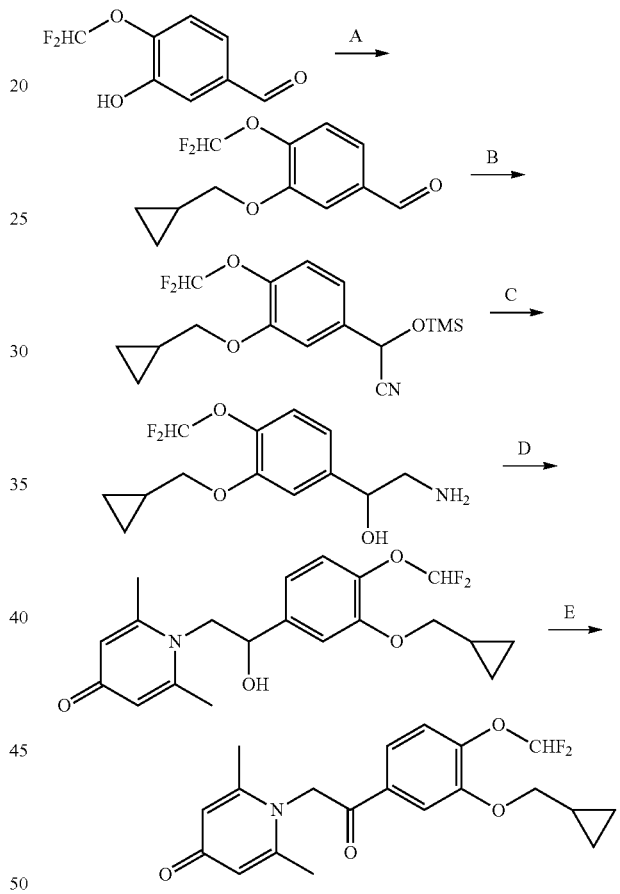

Step A:

At room temperature, 3-hydroxy-4-difluoromethoxybenzaldehyde (1.88 g, 10.0 mmol) was dissolved in acetonitrile (10 mL), and then potassium carbonate (2.07 g, 15.0 mmol) and bromomethylcyclopropane (1.76 g, 13.0 mmol) were added in sequence, and heated to 80° C. for 3 hours with stirring under nitrogen atmosphere. After the reaction was completed, saturated saline (30 mL) was added, and extracted with ethyl acetate (3×60 mL). The organic phases were combined, dried over anhydrous sodium sulfate, filtered, rotary dried, and purified by reverse-phase HPLC to obtain 3-cyclopropylmethoxy-4-difluoromethoxybenzaldehyde (2.20 g, 91%). LC-MS: m/z 243.2 [M+H]$^+$.

Step B:

The compound 3-cyclopropylmethoxy-4-difluoromethoxybenzaldehyde (2.20 g, 9.1 mmol) was dissolved in dichloromethane (30 mL), and then triethyl amine (1.84 g, 18.2 mmol) and trimethylsilyl cyanide (2.7 g, 27.3 mmol) were added in sequence in an ice bath and stirred for 16 hours under nitrogen atmosphere at room temperature. After the reaction was completed, the reaction solution was directly rotary dried to obtain the product 2-(3-cyclopropylmethoxy-4-difluoromethoxyphenyl)-2-trimethylsiloxyacetonitrile (3.1 g, 100%), which was directly used in the next reaction.

Step C:

The compound 2-(3-cyclopropylmethoxy-4-difluoromethoxyphenyl)-2-trimethylsiloxyacetonitrile (3.1 g, 9.1 mmol) was dissolved in anhydrous tetrahydrofuran (50 mL), and then lithium aluminum hydride (1.04 g, 27.3 mmol) was added portion-wise in an ice bath, and stirred overnight at room temperature. After the reaction was completed, the reaction solution was diluted with anhydrous tetrahydrofuran (200 mL), and extracted with water (1 mL). An aqueous sodium hydroxide solution (3 mL, 1M) and then water (3 mL) were added, stirred for half an hour, dried over anhydrous sodium sulfate, filtered, and rotary dried to obtain a crude product of 2-amino-1-(3-cyclopropylmethoxy-4-difluoromethoxyphenyl)ethanol (2.70 g, 100%). LC-MS: m/z 258.1 [M−18+1]$^+$.

Step D:

The compound 2-amino-1-(3-cyclopropylmethoxy-4-difluoromethoxyphenyl)ethanol (2.70 g, 9.1 mmol) was dissolved in ethanol (30 mL), and then 2,6-dimethyl-4H-pyran-4-one (1.86 g, 15.0 mmol), sodium hydroxide (0.60 g, 15.0 mmol) and water (10 mL) were added in sequence, heated to 60° C., and stirred for 16 hours under nitrogen atmosphere. After the reaction was completed, the reaction solution was rotary dried, and purified to obtain 1-(2-(3-cyclopropylmethoxy-4-difluoromethoxyphenyl)-2-hydroxyethyl)-2,6-dimethylpyridin-4(1H)-one (2.4 g, 69%). LC-MS: m/z 380.2 [M+H]$^+$.

Step E

The compound 1-(2-(3-cyclopropylmethoxy-4-difluoromethoxyphenyl)-2-hydroxyethyl)-2,6-dimethylpyridin-4(1H)-one (50 mg, 0.13 mmol) was dissolved in dichloromethane (10 mL), and then the Dess-Martin Periodinane (110 mg, 0.26 mmol) was added and stirred at room temperature for 2 hours. The reaction solution was filtered, and washed with saturated brine. The organic phase was dried over anhydrous sodium sulfate, filtered, rotary dried, and purified by reverse-phase HPLC to obtain 1-(2-(3-cyclopropylmethoxy-4-difluoromethoxyphenyl)-2-oxoethyl)-2,6-dimethylpyridin-4(1H)-one (35 mg, yield 72%, white solid). $^1$H NMR (400 MHz, CDCl$_3$) δ 7.66 (s, 2H), 7.64 (d, J=8.4 Hz, 1H), 7.33 (d, J=8.4 Hz, 1H), 6.79 (t, $J_{H-F}$=74.4 Hz, 1H), 6.45 (s, 2H), 5.50 (s, 2H), 3.99 (d, J=7.2 Hz, 2H), 2.26 (s, 6H) 1.37-1.28 (m, 1H), 0.72-0.66 (m, 2H), 0.43-0.37 (m, 2H); LC-MS: m/z 378.3 [M+H]$^+$.

Example 50

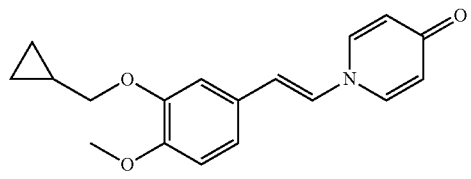 [SMILES: COc1ccc(/C=C/n2ccc(=O)cc2)cc1OCC1CC1]

(E)-1-(3-cyclopropylmethoxy-4-methoxystyryl)pyridin-4(1H)-one

The specific reaction scheme is as shown below:

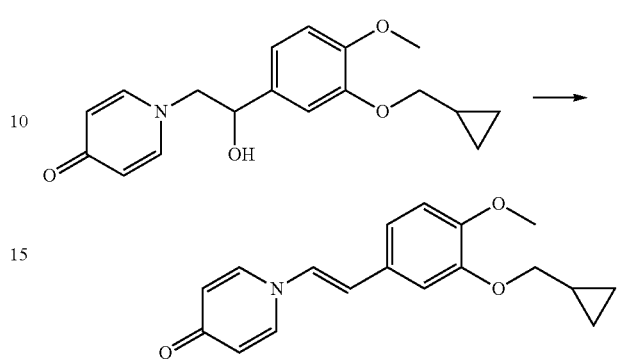

The compound 1-(2-(3-cyclopropylmethoxy-4-methoxyphenyl)-2-hydroxyethyl)pyridin-4(1H)-one (270 mg, 0.86 mmol) and p-toluenesulfonic acid (443 mg, 2.58 mmol) were dissolved in toluene (5 mL), and stirred overnight under reflux. After the reaction was completed, the reaction solution was filtered, rotary dried, and purified by reverse-phase HPLC to obtain (E)-1-(3-cyclopropylmethoxy-4-methoxystyryl)pyridin-4(1H)-one (50 mg, yield 20%, white solid). $^1$H NMR (400 MHz, DMSO-d$_6$) δ 8.02 (d, J=7.6 Hz, 2H), 7.52 (d, J=14.4 Hz, 1H), 7.10 (s, 1H), 6.97-6.93 (m, 2H), 6.85 (d, J=14.4 Hz, 1H), 6.21 (d, J=7.6 Hz, 2H), 3.83 (d, J=7.2 Hz, 2H), 3.77 (s, 3H), 1.26-1.21 (m, 1H), 0.62-0.56 (m, 2H), 0.36-0.31 (m, 2H); LC-MS: m/z 298.1 [M+H]$^+$.

Example 51

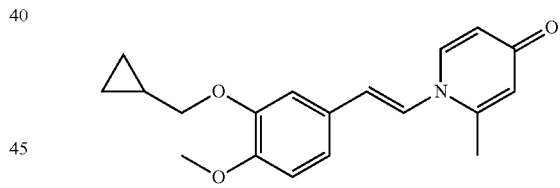

(E)-1-(3-cyclopropylmethoxy-4-methoxystyryl)-2-methylpyridin-4(1H)-one

The specific reaction scheme is as shown below:

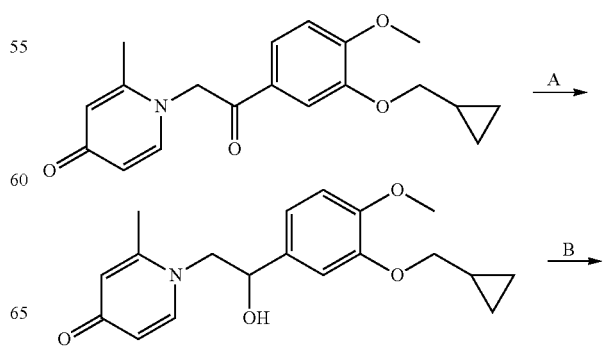

-continued

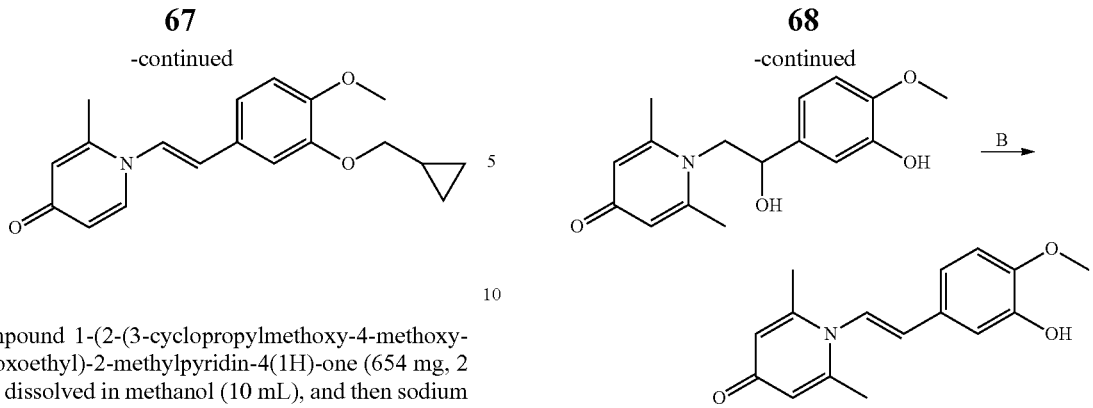

Step A:

The compound 1-(2-(3-cyclopropylmethoxy-4-methoxyphenyl)-2-oxoethyl)-2-methylpyridin-4(1H)-one (654 mg, 2 mmol) was dissolved in methanol (10 mL), and then sodium borohydride (114 mg, 3 mmol) was added portion-wise and stirred at room temperature for 3 hours.

After the reaction was completed, a saturated ammonium chloride solution (20 mL) was added, and the reaction solution was filtered, concentrated, and purified by column chromatography to obtain 1-(2-(3-cyclopropylmethoxy-4-methoxyphenyl)-2-hydroxyethyl)-2-methylpyridin-4(1H)-one (620 mg, yield 95%, white solid). LC-MS: m/z 330.4 [M+H]$^+$

Step B:

The compound 1-(2-(3-cyclopropylmethoxy-4-methoxyphenyl)-2-hydroxyethyl)-2-methylpyridin-4(1H)-one (620 mg, 1.88 mmol) and p-toluenesulfonic acid (970 mg, 5.64 mmol) were dissolved in toluene (15 mL), and stirred overnight under reflux. After the reaction was completed, the reaction solution was filtered, rotary dried, and purified by reverse-phase HPLC to obtain (E)-1-(3-cyclopropylmethoxy-4-methoxystyryl)-2-methylpyridin-4(1H)-one (520 mg, yield 84%, white solid). $^1$H NMR (400 MHz, DMSO-d$_6$) δ 8.32 (d, J=7.2 Hz, 1H), 7.65 (d, J=14.0 Hz, 1H), 7.22 (d, J=1.6 Hz, 1H), 7.12 (dd, J=8.4, 1.6 Hz, 1H), 7.00 (d, J=8.4 Hz, 1H), 6.95 (d, J=14.0 Hz, 1H), 6.66-6.62 (m, 2H), 3.86 (d, J=7.2 Hz, 2H), 3.81 (s, 3H), 2.51 (s, 3H), 1.28-1.22 (m, 1H), 0.62-0.57 (m, 2H), 0.36-0.31 (m, 2H); LC-MS: m/z 312.1 [M+H]$^+$.

Example 52

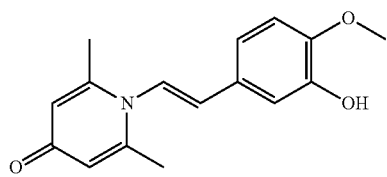 [SMILES: COc1ccc(/C=C/n2c(C)cc(=O)cc2C)cc1O]

(E)-1-(3-hydroxy-4-methoxystyryl)-2-methylpyridin-4(1H)-one

The specific reaction scheme is as shown below:

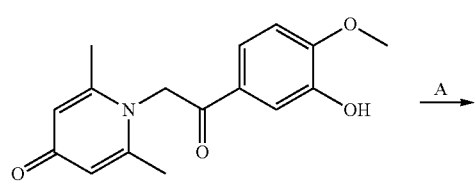

Step A:

The compound 1-(2-(3-cyclopropylmethoxy-4-methoxyphenyl)-2-oxoethyl)-2-methylpyridin-4(1H)-one (5.74 g, 20 mmol) was dissolved in methanol (100 mL), and then sodium borohydride (1.14 g, 30 mmol) was added portion-wise and stirred at room temperature for 3 hours. After the reaction was completed, a saturated ammonium chloride solution (20 mL) was added, and the reaction solution was filtered, concentrated, and purified by column chromatography to obtain 1-(2-(3-hydroxy-4-methoxyphenyl)-2-hydroxyethyl)-2,6-dimethylpyridin-4(1H)-one (5.09 g, yield 88%, colorless oil). LC-MS: m/z 290.4 [M+H]$^+$.

Step B:

The compound 1-(2-(3-cyclopropylmethoxy-4-methoxyphenyl)-2-hydroxyethyl)-2-methylpyridin-4(1H)-one (5.09 g, 17.6 mmol) and p-toluenesulfonic acid (9.08 g, 52.8 mmol) were dissolved in toluene (100 mL), and stirred overnight under reflux. After the reaction was completed, the reaction solution was filtered, rotary dried, and purified by reverse-phase HPLC to obtain (E)-1-(3-cyclopropylmethoxy-4-methoxystyryl)-2-methylpyridin-4(1H)-one (3.05 g, yield 64%, gray solid). $^1$H NMR (400 MHz, DMSO-d$_6$) δ 7.34 (s, 1H), 7.16 (s, 2H), 7.05 (d, J=14.0 Hz, 1H), 6.91 (d, J=8.4 Hz, 1H), 6.84 (d, J=8.4 Hz, 1H), 6.62 (d, J=14.0 Hz, 1H), 3.92 (s, 2H), 2.48 (s, 6H); LC-MS: m/z 272.1 [M+H]$^+$.

Example 53

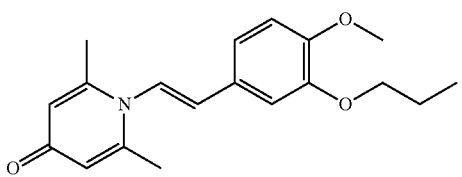

(E)-1-(3-propoxy-4-methoxystyryl)-2,6-dimethylpyridin-4(1H)-one

The specific reaction scheme is as shown below:

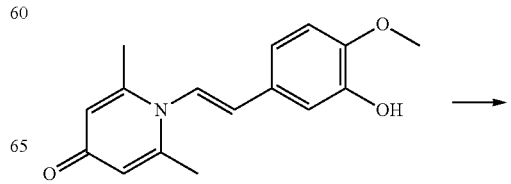

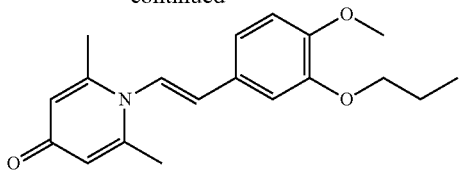

The compound (E)-1-(3-hydroxy-4-methoxystyryl)-2,6-dimethylpyridin-4(1H)-one (50 mg, 0.17 mmol) was dissolved in N,N-dimethylformamide (5 mL), and then bromopropane (34.5 mg, 0.28 mmol) and cesium carbonate (117 mg, 0.36 mmol) were added, and stirred for 2 hours at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-propoxy-4-methoxystyryl)-2,6-dimethylpyridin-4(1H)-one (25 mg, yield 44%, white solid). $^1$H NMR (400 MHz, CD$_3$OD) δ 7.22 (d, J=2.0 Hz, 1H), 7.14 (dd, J=8.4, 2.0 Hz, 1H), 7.09 (d, J=14.2 Hz, 1H), 7.01 (d, J=8.4 Hz, 1H), 6.77 (d, J=14.2 Hz, 1H), 6.38 (s, 2H), 4.03 (t, J=6.4 Hz, 2H), 3.89 (s, 3H), 2.37 (s, 6H), 1.90-1.80 (m, 2H), 1.08 (t, J=7.2 Hz, 3H); LC-MS: m/z 314.2 [M+1-1]$^+$.

Example 54

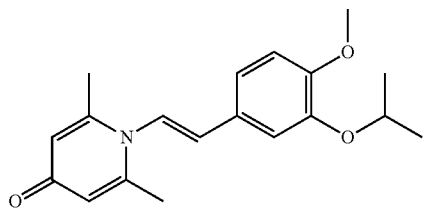 [SMILES: COc1ccc(/C=C/n2c(C)cc(=O)cc2C)cc1OC(C)C]

(E)-1-(3-isopropoxy-4-methoxystyryl)-2,6-dimethylpyridin-4(1H)-one

The specific reaction scheme is as shown below:

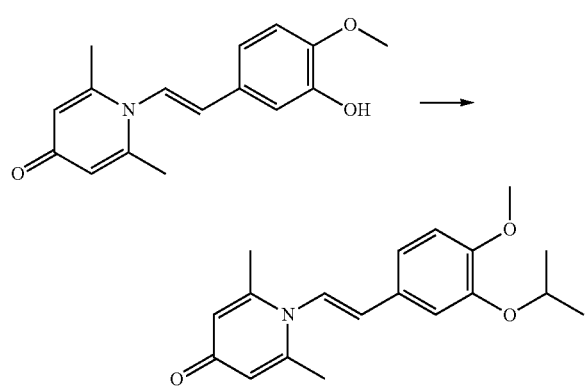

The compound (E)-1-(3-hydroxy-4-methoxystyryl)-2,6-dimethylpyridin-4(1H)-one (50 mg, 0.17 mmol) was dissolved in N,N-dimethylformamide (5 mL), and then bromoisopropane (34.5 mg, 0.28 mmol) and cesium carbonate (117 mg, 0.36 mmol) were added, and stirred for 2 hours at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-isopropoxy-4-methoxystyryl)-2,6-dimethylpyridin-4(1H)-one (8 mg, yield 14%, colorless oil). $^1$H NMR (400 MHz, CD$_3$OD) δ 7.26 (d, J=2.0 Hz, 1H), 7.22 (dd, J=8.4, 2.0 Hz, 1H), 7.21 (d, J=14.4 Hz, 1H), 7.05 (d, J=8.4 Hz, 1H), 6.97 (s, 2H), 6.89 (d, J=14.4 Hz, 1H), 4.69-4.60 (m, 1H), 3.90 (s, 3H), 2.57 (s, 6H), 1.35 (d, J=6.0 Hz, 6H). LC-MS: m/z 314.2 [M+H]$^+$.

Example 55

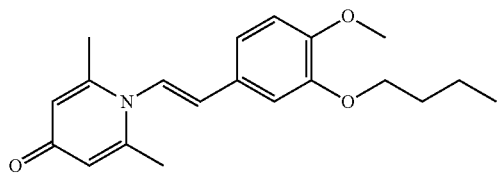 [SMILES: CCCCOc1cc(/C=C/n2c(C)cc(=O)cc2C)ccc1OC]

(E)-1-((3-n-butoxy-4-methoxy)-styryl)-2,6-dimethylpyridin-4(1H)-one

The specific reaction scheme is as shown below:

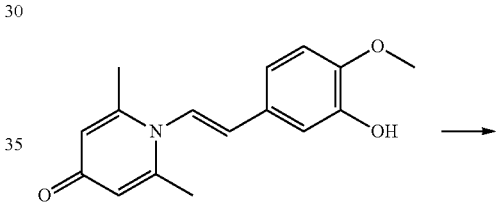

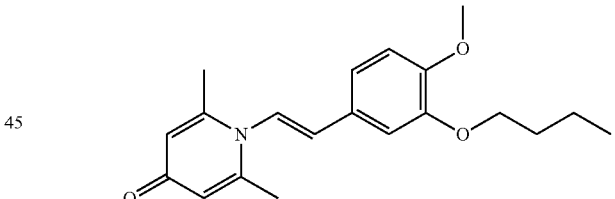

The compound (E)-1-(3-hydroxy-4-methoxystyryl)-2,6-dimethylpyridin-4(1H)-one (50 mg, 0.17 mmol) was dissolved in N,N-dimethylformamide (5 mL), and then n-butyl bromide (38 mg, 0.28 mmol) and cesium carbonate (117 mg, 0.36 mmol) were added, and stirred for 2 hours at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-n-butoxy-4-methoxystyryl)-2,6-dimethylpyridin-4(1H)-one (20 mg, yield 34%, white solid). $^1$H NMR (400 MHz, DMSO-d$_6$) δ 7.57 (s, 2H), 7.27 (d, J=14.4 Hz, 1H), 7.10 (d, J=1.6 Hz, 1H), 7.04-6.98 (m, 2H), 6.95 (d, J=14.4 Hz, 1H), 4.34 (t, J=6.4 Hz, 2H), 3.82 (s, 3H), 2.60 (s, 6H), 1.82-1.75 (m, 2H), 1.50-1.40 (m, 2H), 0.96 (t, J=7.2 Hz, 1H); LC-MS: m/z 328.2 [M+H]$^+$.

Example 56

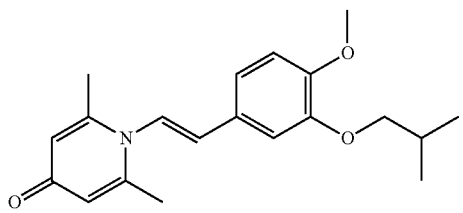 [SMILES: COc1ccc(/C=C/n2c(C)cc(=O)cc2C)cc1OCC(C)C]

(E)-1-(3-iso-butoxy-4-methoxystyryl)-2,6-dimethylpyridin-4(1H)-one

The specific reaction scheme is as shown below:

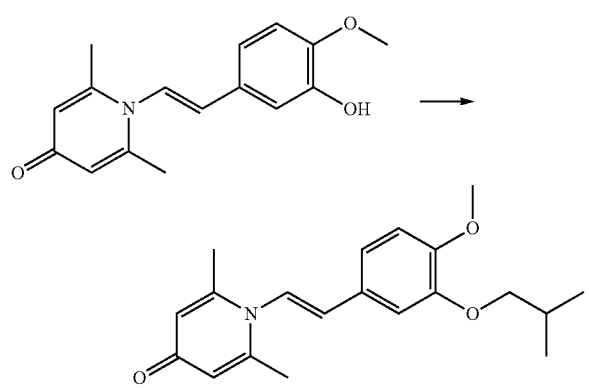

The compound (E)-1-(3-hydroxy-4-methoxystyryl)-2,6-dimethylpyridin-4(1H)-one (50 mg, 0.17 mmol) was dissolved in N,N-dimethylformamide (5 mL), and then bromoisobutane (38 mg, 0.28 mmol) and cesium carbonate (117 mg, 0.36 mmol) were added, and stirred for 2 hours at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-iso-butoxy-4-methoxystyryl)-2,6-dimethylpyridin-4(1H)-one (25 mg, yield 42%, white solid). $^1$H NMR (400 MHz, CDCl$_3$) δ 7.02 (dd, J=8.4, 2.0 Hz, 1H), 6.98 (d, J=2.0 Hz, 1H), 6.91 (d, J=8.4 Hz, 1H), 6.76 (d, J=14.4 Hz, 1H), 6.60 (d, J=14.4 Hz, 1H), 6.30 (s, 2H), 3.92 (s, 3H), 3.81 (d, J=6.8 Hz, 2H), 2.27 (s, 6H), 2.24-2.17 (m, 1H), 1.08 (d, J=6.8 Hz, 6H); LC-MS: m/z 328.2 [M+H]$^+$.

Example 57

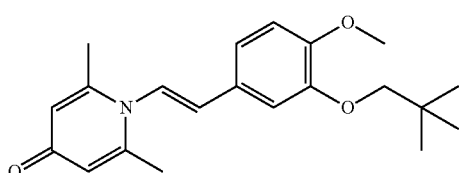

(E)-1-((3-neopentyloxy-4-methoxy)-styryl)-2,6-dimethylpyridin-4(1H)-one

The specific reaction scheme is as shown below:

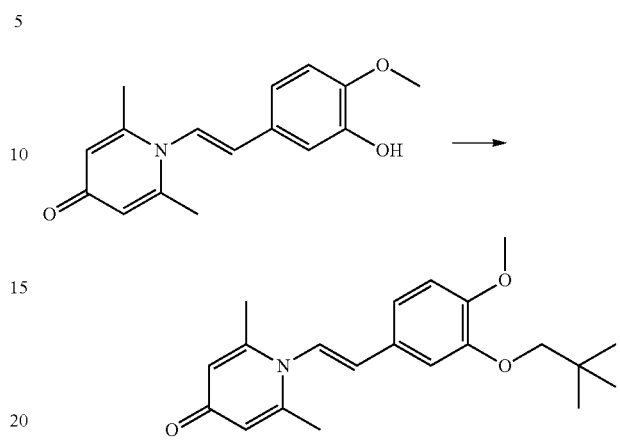

The compound (E)-1-(3-hydroxy-4-methoxystyryl)-2,6-dimethylpyridin-4(1H)-one (200 mg, 0.74 mmol) was dissolved in N,N-dimethylformamide (5 mL), and then bromoneopentane (224 mg, 1.48 mmol) and cesium carbonate (117 mg, 0.36 mmol) were added, and stirred for 24 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-neopentyloxy-4-methoxystyryl)-2,6-dimethylpyridin-4(1H)-one (20 mg, yield 8%, white solid). $^1$H NMR (400 MHz, CDCl$_3$) δ 7.25 (s, 2H), 7.05-7.00 (m, 2H), 6.97 (d, J=14.4 Hz, 1H), 6.90 (d, J=8.4 Hz, 1H), 6.70 (d, J=14.4 Hz, 1H), 3.91 (s, 3H), 3.68 (s, 2H), 2.54 (s, 6H), 1.08 (s, 9H); LC-MS m/z 342.3 [M+H]$^+$.

Example 58

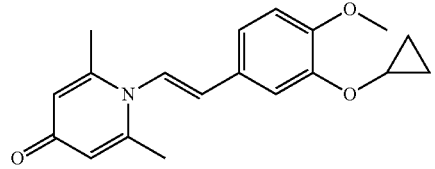 [SMILES: COc1ccc(/C=C/n2c(C)cc(=O)cc2C)cc1OC1CC1]

(E)-1-(3-cyclopropyloxy-4-methoxystyryl)-2,6-dimethylpyridin-4(1H)-one

The specific reaction scheme is as shown below:

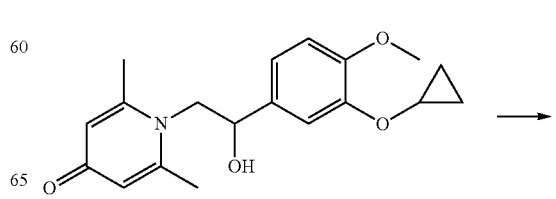

-continued

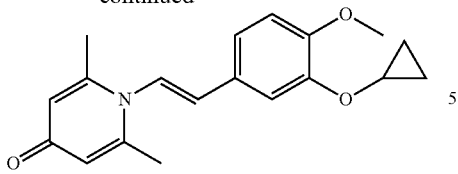

The compound 1-(2-(3-cyclopropylmethoxy-4-methoxyphenyl)-2-hydroxyethyl)-2,6-dimethylpyridin-4(1H)-one (100 mg, 0.3 mmol) and p-toluenesulfonic acid (68.4 mg, 0.6 mmol) were dissolved in toluene (5 mL), and then N,N-dimethylformamide (1 mL) was added and stirred overnight under reflux. After the reaction was completed, the reaction solution was filtered, rotary dried, and purified by reverse-phase HPLC to obtain (E)-1-(3-cyclopropyloxy-4-methoxystyryl)-2,6-dimethylpyridin-4(1H)-one (50 mg, yield 53%, white solid). $^1$H NMR (400 MHz, CD$_3$OD) δ 7.15 (s, 1H), 7.12 (d, J=8.4 Hz, 1H), 7.06 (d, J=14.4 Hz, 1H), 6.98 (d, J=8.4 Hz, 1H), 6.85 (d, J=14.4 Hz, 1H), 6.32 (s, 2H), 4.02 (s, 3H), 2.32 (s, 6H), 2.23-2.19 (m, 1H), 0.94-0.90 (m, 4H); LC-MS m/z 312.3 [M+H]$^+$.

Example 59

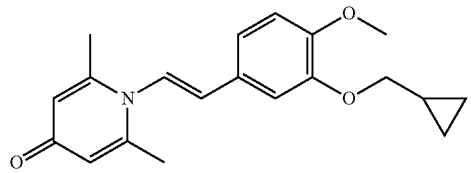 [SMILES: COc1ccc(/C=C/n2c(C)cc(=O)cc2C)cc1OCC1CC1]

(E)-1-(3-cyclopropylmethoxy-4-methoxystyryl)-2,6-dimethylpyridin-4(1H)-one

The specific reaction scheme is as shown below:

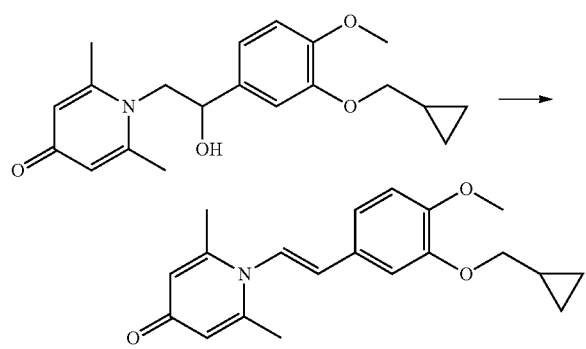

The compound 1-(2-(3-cyclopropylmethoxy-4-methoxyphenyl)-2-hydroxyethyl)-2,6-dimethylpyridin-4(1H)-one (186 mg, 0.54 mmol) and p-toluenesulfonic acid (140 mg, 0.81 mmol) were dissolved in toluene (5 mL), and then N,N-dimethylformamide (1 mL) was added and stirred overnight under reflux. After the reaction was completed, the reaction solution was filtered, rotary dried, and purified by reverse-phase HPLC to obtain (E)-1-(3-cyclopropylmethoxy-4-methoxystyryl)-2,6-dimethylpyridin-4(1H)-one (80 mg, yield 45%, white solid). $^1$H NMR (400 MHz, CD$_3$OD) δ 7.13 (dd, J=8.4, 2.0 Hz, 1H), 7.19 (d, J=2.0 Hz, 1H), 7.07 (d, J=14.4 Hz, 1H), 7.11 (s, 2H), 6.99 (d, J=8.4 Hz, 1H), 6.75 (d, J=14.4 Hz, 1H), 6.41 (s, 2H), 3.89 (d, J=7.2 Hz, 2H), 3.87 (s, 3H), 2.36 (s, 6H), 1.33-1.24 (m, 1H), 0.65-0.60 (m, 2H), 0.38-0.34 (m, 2H); LC-MS: m/z 326.1 [M+H]$^+$.

Example 60

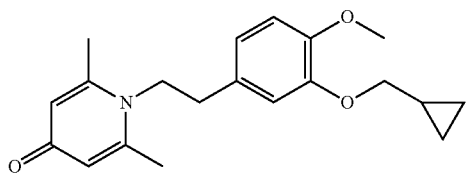 [SMILES: COc1ccc(CCn2c(C)cc(=O)cc2C)cc1OCC1CC1]

(E)-1-(3-cyclopropylmethoxy-4-methoxyphenethyl)-2,6-dimethylpyridin-4(1H)-one

The specific reaction scheme is as shown below:

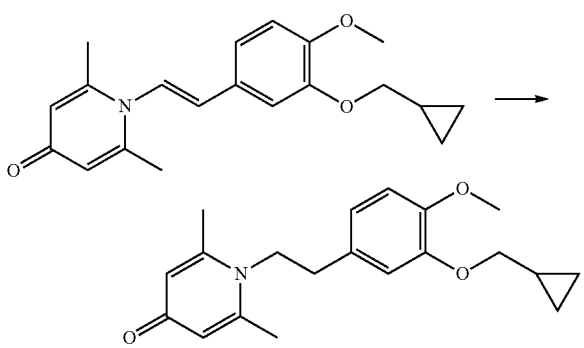

The compound (E)-1-(3-cyclopropyloxy-4-methoxystyryl)-2,6-dimethylpyridin-4(1H)-one (10 mg, 0.03 mmol) was dissolved in ethanol (3 mL), and then Pd/C (50 mg) was added, and stirred for 2 hours under hydrogen atmosphere at room temperature. After the reaction was completed, the reaction solution was filtered, rotary dried, and purified by reverse-phase HPLC to obtain (E)-1-(3-cyclopropylmethoxy-4-methoxyphenethyl)-2,6-dimethylpyridin-4(1H)-one (2.9 mg, yield 30%, colorless oil). $^1$H NMR (400 MHz, CD$_3$OD) δ 7.13 (dd, J=8.4, 2.0 Hz, 1H), 7.19 (d, J=2.0 Hz, 1H), 7.11 (s, 2H), 6.99 (d, J=8.4 Hz, 1H), 6.41 (s, 2H), 3.89 (d, J=7.2 Hz, 2H), 3.87 (s, 3H), 2.89-2.83 (m, 2H), 2.83-2.77 (m, 2H), 2.36 (s, 6H), 1.33-1.24 (m, 1H), 0.65-0.60 (m, 2H), 0.38-0.34 (m, 2H); LC-MS: m/z 328.1 [M+H]$^+$.

Example 61

(E)-1-(3-cyclobutyloxy-4-methoxy-styryl)-2,6-dimethylpyridin-4(1H)-one

The specific reaction scheme is as shown below:

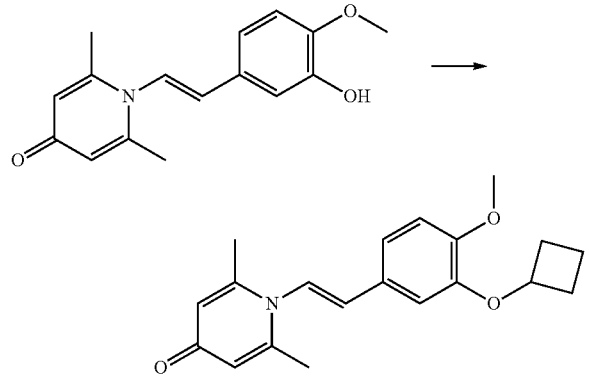

The compound (E)-1-(3-hydroxy-4-methoxystyryl)-2,6-dimethylpyridin-4(1H)-one (100 mg, 0.37 mmol) was dissolved in N,N-dimethylformamide (5 mL), and then bromocyclobutane (100 mg, 0.74 mmol) and cesium carbonate (241 mg, 0.74 mmol) were added, and stirred for 4 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-cyclobutyloxy-4-methoxy-styryl)-2,6-dimethylpyridin-4(1H)-one (18 mg, yield 15%, white solid). $^1$H NMR (400 MHz, CD$_3$OD) δ 7.13 (dd, J=8.4, 2.0 Hz, 1H), 7.05 (d, J=14.4 Hz, 1H), 7.03 (d, J=2.0 Hz, 1H), 6.99 (d, J=8.4 Hz, 1H), 6.75 (d, J=14.4 Hz, 1H), 6.36 (s, 2H), 4.78-4.71 (m, 1H), 3.86 (s, 3H), 2.52-2.44 (m, 2H), 2.34 (s, 6H), 2.22-2.12 (m, 2H), 1.89-1.81 (m, 1H), 1.77-1.65 (m, 1H); LC-MS m/z 326.2 [M+1-1]$^+$.

Example 62

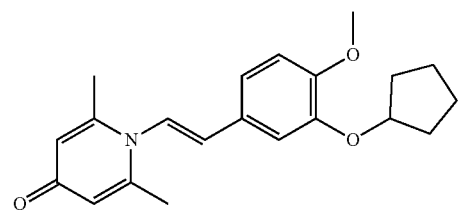 [SMILES: COc1ccc(/C=C/n2c(C)cc(=O)cc2C)cc1OC1CCCC1]

(E)-1-((3-cyclopentyloxy-4-methoxy)-styryl)-2,6-dimethylpyridin-4(1H)-one

The specific reaction scheme is as shown below:

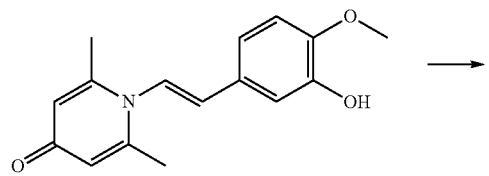

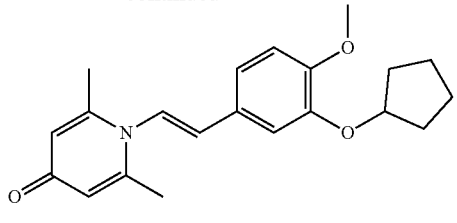

The compound (E)-1-(3-hydroxy-4-methoxystyryl)-2,6-dimethylpyridin-4(1H)-one (100 mg, 0.37 mmol) was dissolved in N,N-dimethylformamide (5 mL), and then bromocyclopentane (110 mg, 0.74 mmol) and cesium carbonate (241 mg, 0.74 mmol) were added, and stirred for 4 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-cyclopentyloxy-4-methoxy-styryl)-2,6-dimethylpyridin-4(1H)-one (25 mg, yield 20%, pale yellow solid). $^1$H NMR (400 MHz, CD$_3$OD) δ 7.16 (s, 1H), 7.13 (d, J=8.4 Hz, 1H), 7.06 (d, J=14.4 Hz, 1H), 6.98 (d, J=8.4 Hz, 1H), 6.76 (d, J=14.4 Hz, 1H), 6.36 (s, 2H), 3.35-3.83 (m, 1H), 3.86 (s, 3H), 2.52-2.44 (m, 2H), 2.35 (s, 6H), 1.93-1.79 (m, 6H), 1.69-1.58 (m, 2H); LC-MS m/z 340.2 [M+H]$^+$.

Example 63

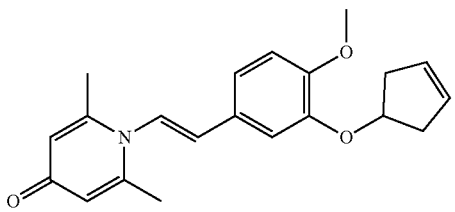 [SMILES: COc1ccc(/C=C/n2c(C)cc(=O)cc2C)cc1OC1CC=CC1]

(E)-1-(3-(cyclopent-3-en-1-yloxy)-4-methoxystyryl)-2,6-dimethylpyridin-4(1H)-one The specific reaction scheme is as shown below:

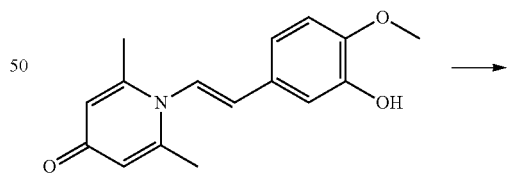

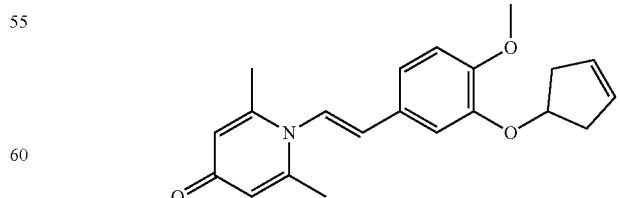

The compound (E)-1-(3-hydroxy-4-methoxystyryl)-2,6-dimethylpyridin-4(1H)-one (100 mg, 0.37 mmol) was dissolved in N,N-dimethylformamide (5 mL), and then cyclopent-3-en-1-yl methanesulfonate (110 mg, 0.74 mmol) and cesium carbonate (241 mg, 0.74 mmol) were added, and stirred overnight at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-(cyclopent-3-en-1-yloxy)-4-methoxystyryl)-2,6-dimethylpyridin-4(1H)-one (22 mg, yield 15%, white solid). $^1$H NMR (400 MHz, CDCl$_3$) δ 7.45 (s, 2H), 7.08 (d, J=8.0 Hz, 1H), 7.02-6.99 (m, 2H), 6.92 (d, J=8.0 Hz, 1H), 6.74 (d, J=14.4 Hz, 1H), 5.77 (s, 2H), 5.12-5.05 (m, 1H), 3.90 (s, 3H), 2.89-2.82 (m, 2H), 2.69-2.63 (m, 2H), 2.58 (s, 6H); LC-MS m/z 338.1 [M+H]$^+$.

Example 64

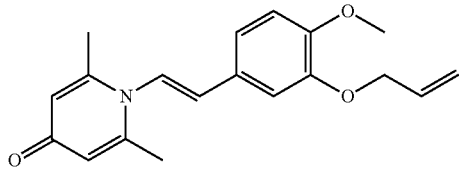 [SMILES: C=CCOc1cc(/C=C/n2c(C)cc(=O)cc2C)ccc1OC]

(E)-1-(3-allyloxy-4-methoxy-styryl)-2,6-dimethylpyridin-4(1H)-one

The specific reaction scheme is as shown below:

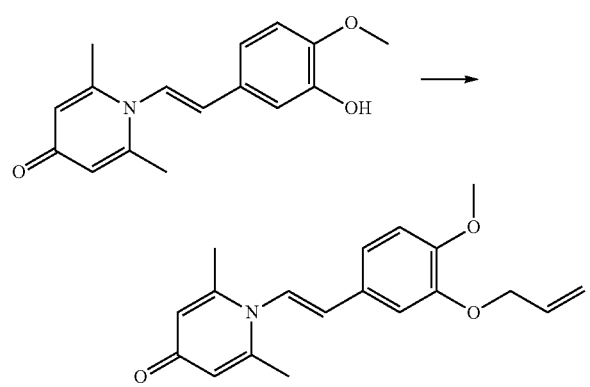

The compound (E)-1-(3-hydroxy-4-methoxystyryl)-2,6-dimethylpyridin-4(1H)-one (50 mg, 0.18 mmol) was dissolved in N,N-dimethylformamide (5 mL), and then 3-bromopropene (44 mg, 0.36 mmol) and cesium carbonate (117 mg, 0.36 mmol) were added, and stirred for 2 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-allyloxy-4-methoxy-styryl)-2,6-dimethylpyridin-4(1H)-one (12 mg, yield 20%, pale yellow oil). $^1$H NMR (400 MHz, CDCl$_3$) δ 7.23 (s, 2H), 7.09-6.92 (m, 4H), 6.73-6.69 (m, 1H), 6.16-6.05 (m, 1H), 5.45 (d, J=17.2 Hz, 1H), 5.34 (d, J=10.4 Hz, 1H), 4.67 (d, J=4.0 Hz, 2H), 3.94 (s, 3H), 2.54 (s, 6H); LC-MS m/z 312.2 [M+H]$^+$.

Example 65

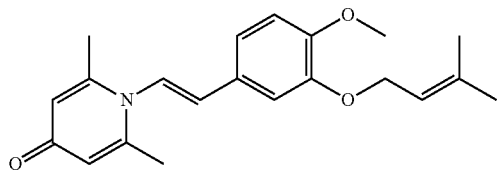 [SMILES: COc1ccc(/C=C/n2c(C)cc(=O)cc2C)cc1OCC=C(C)C]

(E)-1-((3-(3-methylbut-2-en-1-yl)oxy-4-methoxy)-styryl)-2,6-dimethylpyridin-4(1H)-one The specific reaction scheme is as shown below:

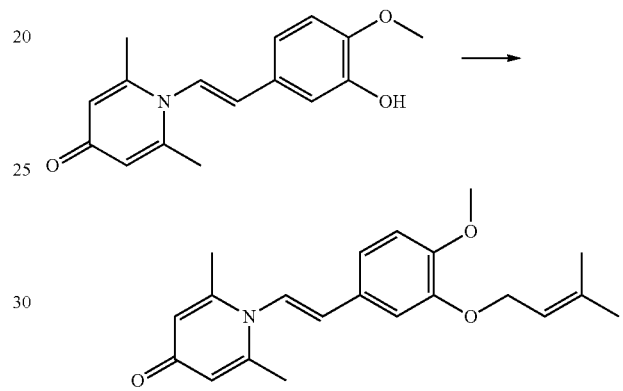

The compound (E)-1-(3-hydroxy-4-methoxystyryl)-2,6-dimethylpyridin-4(1H)-one (50 mg, 0.18 mmol) was dissolved in N,N-dimethylformamide (5 mL), and then 1-bromo-3-methyl-2-butene (55 mg, 0.36 mmol) and cesium carbonate (117 mg, 0.36 mmol) were added, and stirred for 1 hr at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-((3-(3-methylbut-2-en-1-yl)oxy-4-methoxy)-styryl)-2,6-dimethylpyridin-4(1H)-one (15 mg, yield 18%, yellow solid). $^1$H NMR (400 MHz, CDCl$_3$) δ 7.08 (s, 2H), 7.08-7.04 (m, 2H), 6.92-6.90 (m, 1H), 6.91 (d, J=14.4 Hz, 1H), 6.69 (d, J=14.4 Hz, 1H), 5.54 (t, J=6.0 Hz, 1H), 4.62 (d, J=6.0 Hz, 2H), 3.92 (s, 3H), 2.51 (s, 6H), 1.80 (s, 3H), 1.72 (s, 3H); LC-MS m/z 340.0 [M+H]$^+$.

Example 66

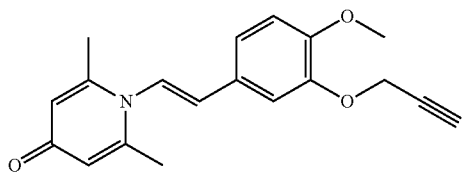 [SMILES: C#CCOc1cc(/C=C/n2c(C)cc(=O)cc2C)ccc1OC]

(E)-1-(3-(prop-2-yn-1-yloxy)-4-methoxy)styryl)-2,6-dimethylpyridin-4(1H)-one

The specific reaction scheme is as shown below:

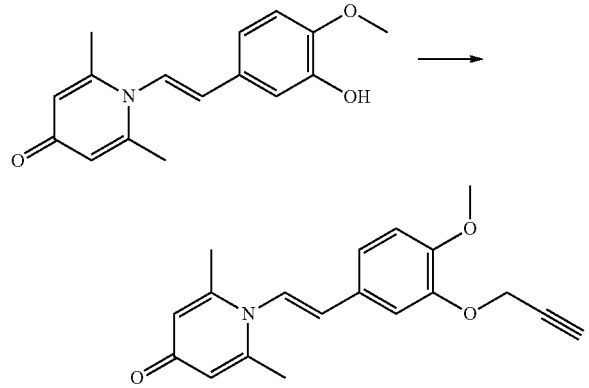

The compound (E)-1-(3-hydroxy-4-methoxystyryl)-2,6-dimethylpyridin-4(1H)-one (50 mg, 0.18 mmol) was dissolved in N,N-dimethylformamide (5 mL), and then 3-bromo-propyne (44 mg, 0.36 mmol) and cesium carbonate (117 mg, 0.36 mmol) were added, and stirred for 3 hours at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-(prop-2-yn-1-yloxy)-4-methoxy)styryl)-2,6-dimethylpyridin-4(1H)-one (10 mg, yield 15%, white solid). $^1$H NMR (400 MHz, CDCl$_3$) δ 7.26-7.14 (m, 3H), 7.13 (s, 2H), 6.96 (d, J=8.4 Hz, 1H), 6.73 (d, J=14.4 Hz, 1H), 4.83 (s, 2H), 3.94 (s, 3H), 2.56 (s, 1H), 2.52 (s, 6H); LC-MS m/z 310.1 [M+H]$^+$.

Example 67

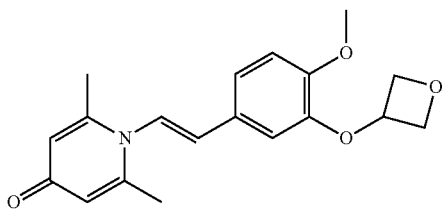

(E)-1-(3-(but-2-yn-1-yloxy)-4-methoxystyryl)-2,6-dimethylpyridin-4(1H)-one

The specific reaction scheme is as shown below:

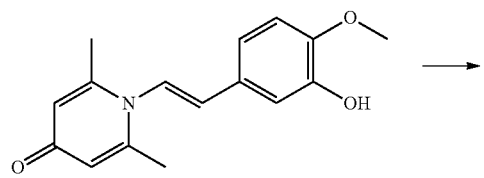

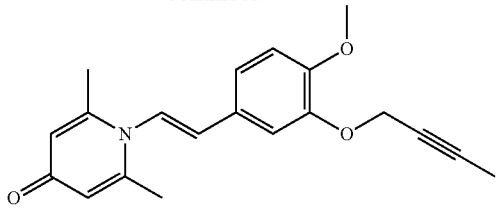

The compound (E)-1-(3-hydroxy-4-methoxystyryl)-2,6-dimethylpyridin-4(1H)-one (50 mg, 0.18 mmol) was dissolved in N,N-dimethylformamide (5 mL), and then 1-bromo-2-butyne (49 mg, 0.36 mmol) and cesium carbonate (117 mg, 0.36 mmol) were added, and stirred for 1 hr at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-(but-2-yn-1-yloxy)-4-methoxystyryl)-2,6-dimethylpyridin-4(1H)-one (15 mg, yield 25%, yellow solid). $^1$H NMR (400 MHz, CDCl$_3$) δ 7.17 (s, 1H), 7.13 (d, J=8.4 Hz, 1H), 6.09 (s, 2H), 6.98 (d, J=14.4 Hz, 1H), 6.94 (d, J=8.4 Hz, 1H), 6.74 (d, J=14.4 Hz, 1H), 4.78 (s, 2H), 3.93 (s, 3H), 2.52 (s, 6H), 1.86 (s, 3H); LC-MS m/z 324.1 [M+H]$^+$.

Example 68

(E)-1-((3-(oxacyclobutan-3-yl-oxy)-4-methoxy)-styryl)-2,6-dimethylpyridin-4(1H)-one The specific reaction scheme is as shown below:

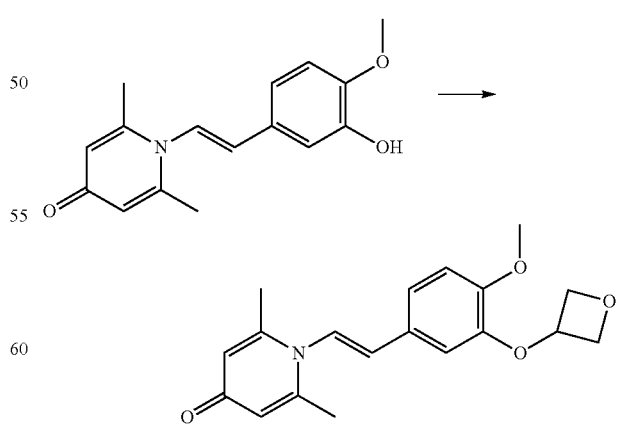

(E)-1-(3-hydroxy-4-methoxystyryl)-2,6-dimethylpyridin-4(1H)-one (150 mg, 0.55 mmol), oxacyclobutan-3-ol (81.4 mg, 1.1 mmol) and triphenylphosphine (288 mg, 1.1 mmol)

were dissolved in anhydrous tetrahydrofuran (10 mL), the reaction solution was cooled in an ice bath, diisopropyl azodicarboxylate (222 mg, 1.1 mmol) was added dropwise over 5 min under nitrogen atmosphere, and then reacted for 24 hours at room temperature. After the reaction was completed, saturated saline (20 mL) was added, and extracted with dichloromethane (3×10 mL). The organic phases were combined, and dried over anhydrous sodium sulfate. Filtration, rotary drying, and purification by reverse-phase HPLC gave (E)-1-((3-(oxacyclobutan-3-yl-oxy)-4-methoxy)-styryl)-2,6-dimethylpyridin-4(1H)-one (40 mg, yield 22%, white solid). $^1$H NMR (400 MHz, CDCl$_3$) δ 7.15 (d, J=8.4 Hz, 1H), 7.07 (s, 2H), 6.96 (d, J=8.4 Hz, 1H), 6.94 (d, J=13.2 Hz, 1H), 6.70 (s, 1H), 6.69 (d, J=13.2 Hz, 1H), 5.27 (m, 1H), 5.01 (m, 1H), 4.88 (m, 1H), 3.94 (s, 3H), 2.53 (s, 6H); LC-MS: m/z 328.2 [M+H]$^+$.

Example 69

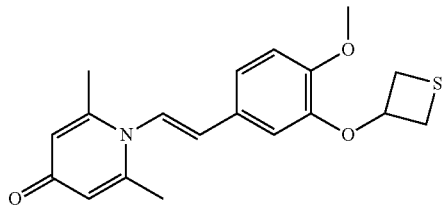 [SMILES: COc1ccc(/C=C/n2c(C)cc(=O)cc2C)cc1OC1COC1]

(E)-1-((3-(thiacyclobutan-3-yl-oxy)-4-methoxy)-styryl)-2,6-dimethylpyridin-4(1H)-one
The specific reaction scheme is as shown below:

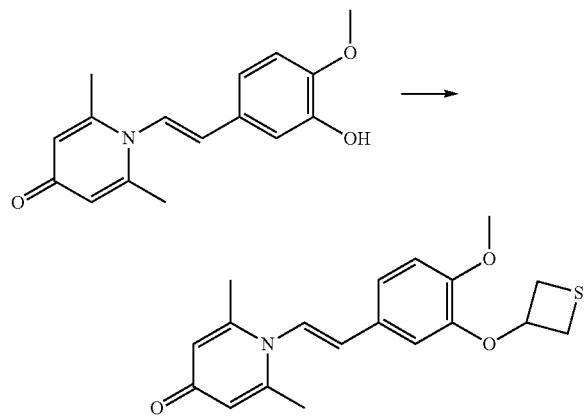

(E)-1-(3-hydroxy-4-methoxystyryl)-2,6-dimethylpyridin-4(1H)-one (150 mg, 0.55 mmol), thiacyclobutan-3-ol (99 mg, 1.1 mmol) and triphenylphosphine (288 mg, 1.1 mmol) were dissolved in anhydrous tetrahydrofuran (10 mL), the reaction solution was cooled in an ice bath, diisopropyl azodicarboxylate (222 mg, 1.1 mmol) was added dropwise over 5 min under nitrogen atmosphere, and then reacted for 24 hours at room temperature. After the reaction was completed, saturated saline (20 mL) was added, and extracted with dichloromethane (3×10 mL). The organic phases were combined, and dried over anhydrous sodium sulfate. Filtration, rotary drying, and purification by reverse-phase HPLC gave (E)-1-((3-(thiacyclobutan-3-yl-oxy)-4-methoxy)-styryl)-2,6-dimethylpyridin-4(1H)-one (30 mg, yield 16%, pale yellow solid). $^1$H NMR (400 MHz, CD$_3$OD) δ 7.37 (s, 2H), 7.19 (d, J=14.4 Hz, 1H), 7.13 (d, J=2.0 Hz, 1H), 7.05 (dd, J=8.4, 2.0 Hz, 1H), 6.98 (d, J=8.4 Hz, 1H), 6.88 (d, J=14.4 Hz, 1H), 5.77-5.69 (m, 1H), 3.90 (s, 3H), 3.65-3.61 (m, 2H), 3.57-3.53 (m, 2H), 2.66 (s, 6H); LC-MS: m/z 344.2 [M+H]$^+$.

Example 70

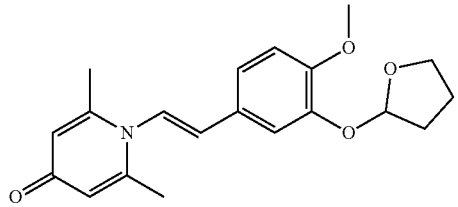 [SMILES: COc1ccc(/C=C/n2c(C)cc(=O)cc2C)cc1OC1CCCO1]

(E)-1-((3-(tetrahydrofuran-2-yl)oxy-4-methoxy)-styryl)-2,6-dimethylpyridin-4(1H)-one
The specific reaction scheme is as shown below:

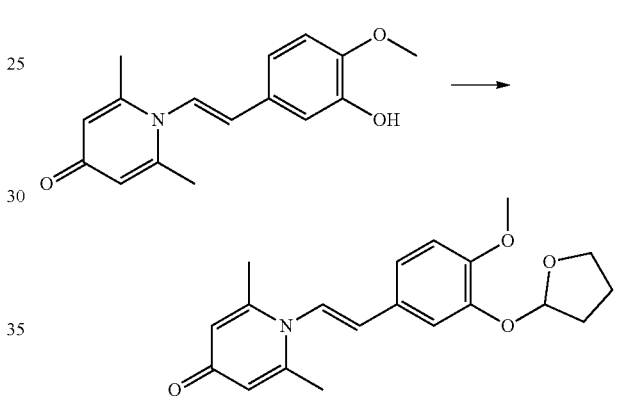

The compound (E)-1-(3-hydroxy-4-methoxystyryl)-2,6-dimethylpyridin-4(1H)-one (50 mg, 0.15 mmol) was dissolved in dichloromethane (5 mL), and then 2,3-dihydrofuran (68 mg, 0.42 mmol) and pyridinium toluene-4-sulphonate (4.6 mg, 0.018 mmol) were added, and stirred for 3 hours at room temperature. After the reaction was completed, the reaction solution was filtered, rotary dried, and purified by reverse-phase HPLC to obtain (E)-1-((3-(tetrahydrofuran-2-yl)oxy-4-methoxy)-styryl)-2,6-dimethylpyridin-4(1H)-one (16 mg, yield 24%, white solid). $^1$H NMR (400 MHz, CDCl$_3$) δ 7.31 (d, J=2.0 Hz, 1H), 7.26 (s, 2H), 7.09 (dd, J=8.4, 2.0 Hz, 1H), 6.91 (d, J=8.4 Hz, 1H), 7.05 (d, J=14.4 Hz, 1H), 6.75 (d, J=14.4 Hz, 1H), 5.82 (d, J=4.4 Hz, 1H), 5.70 (s, 2H), 4.13-4.08 (m, 1H), 4.01-3.95 (m, 1H), 3.90 (s, 3H), 2.35 (s, 6H), 2.24-2.14 (m, 2H), 2.02-1.95 (m, 2H); LC-MS m/z 342.3 [M+H]$^+$.

Example 71

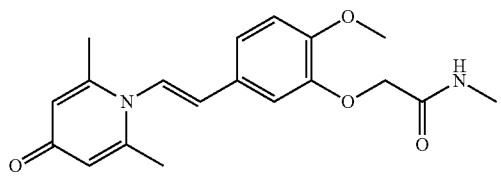 [SMILES: CNC(=O)COc1cc(/C=C/n2c(C)cc(=O)cc2C)ccc1OC]

(E)-2-(5-(2-(2,6-dimethyl-4-carbonylpyridin-1(4H)-yl)ethenyl)-2methoxyphenoxy)-N-methylacetamide The specific reaction scheme is as shown below:

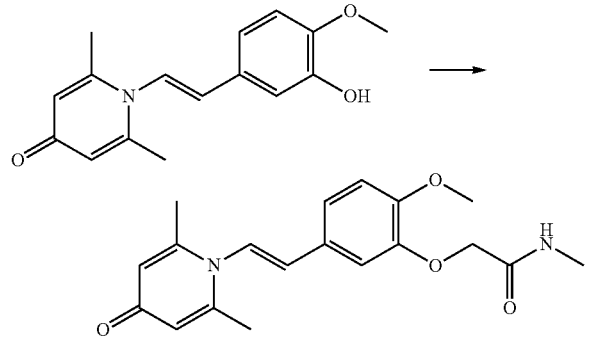

The compound (E)-1-(3-hydroxy-4-methoxystyryl)-2,6-dimethylpyridin-4(1H)-one (200 mg, 0.74 mmol) was dissolved in N,N-dimethylformamide (5 mL), and then 2-chloro-N-methylacetamide (119 mg, 1.11 mmol) and potassium carbonate (153 mg, 1.11 mmol) were added, and stirred overnight at 80° C. under nitrogen atmosphere. After the reaction was completed, saturated saline (10 mL) was added, and extracted with dichloromethane (3×10 mL). The organic phases were combined and dried over anhydrous sodium sulfate. Filtration, rotary drying, and purification by reverse-phase HPLC gave (E)-2-(5-(2-(2,6-dimethyl-4-carbonylpyridin-1(4H)-yl)ethenyl)-2methoxyphenoxy)-N-methylacetamide (100 mg, yield 40%, white solid). $^1$H NMR (400 MHz, CD$_3$OD) δ 7.28 (d, J=2.0 Hz, 1H), 7.23 (dd, J=8.4, 2.0 Hz, 1H), 7.08 (d, J=14.2 Hz, 1H), 7.07 (d, J=8.4 Hz, 1H), 6.76 (d, J=14.2 Hz, 1H), 6.35 (s, 2H), 4.55 (s, 2H), 3.92 (s, 3H), 2.84 (s, 3H), 2.34 (s, 6H); LC-MS m/z 343.1 [M+H]$^+$.

Example 72

(E)-1-((3-cyclopropylformyloxy-4-methoxy)-styryl)-2,6-dimethylpyridin-4(1H)-one

The specific reaction scheme is as shown below:

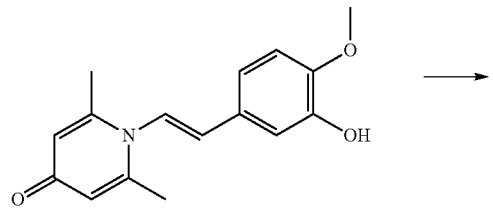

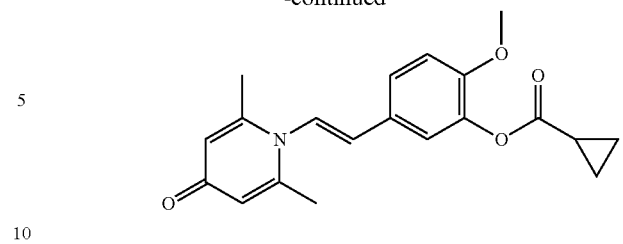

The compound (E)-1-(3-hydroxy-4-methoxystyryl)-2,6-dimethylpyridin-4(1H)-one (50 mg, 0.17 mmol) was dissolved in dichloromethane (5 mL), and then cyclopropanecarbonyl chloride (27 mg, 0.26 mmol) and potassium carbonate (36 mg, 0.26 mmol) were added and stirred for 2 hours at room temperature. After the reaction was completed, the reaction solution was filtered, rotary dried, and purified by reverse-phase HPLC to obtain (E)-1-((3-cyclopropylformyloxy-4-methoxy)-styryl)-2,6-dimethylpyridin-4(1H)-one (20 mg, yield 35%, white solid). $^1$H NMR (400 MHz, CDCl$_3$) δ 7.37 (dd, J=8.4, 2.0 Hz, 1H), 7.27 (d, J=2.0 Hz, 1H), 7.11 (s, 2H), 7.04 (d, J=8.4 Hz, 1H), 6.96 (d, J=14.4 Hz, 1H), 6.72 (d, J=14.4 Hz, 1H), 3.92 (s, 3H), 2.52 (s, 6H), 1.96-1.89 (m, 1H), 1.25-1.21 (m, 2H), 1.12-1.06 (m, 2H); LC-MS: m/z 340.2 [M+1-1]$^+$.

Example 73

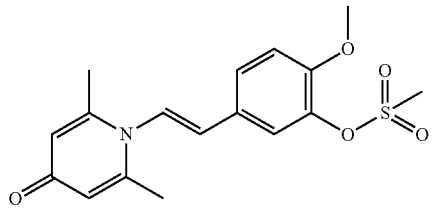 [SMILES: COc1ccc(/C=C/n2c(C)cc(=O)cc2C)cc1OS(C)(=O)=O]

(E)-5-(2-(2,6-dimethyl-4-carbonylpyridin-1(4H)-yl)ethenyl)-2-methoxyphenylmethyl sulfonate The specific reaction scheme is as shown below:

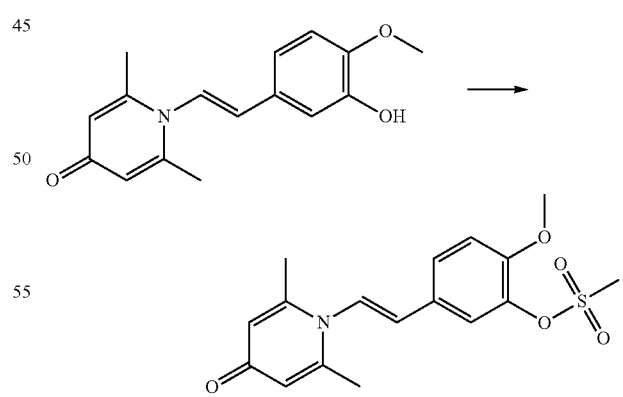

The compound (E)-1-(3-hydroxy-4-methoxystyryl)-2,6-dimethylpyridin-4(1H)-one (271 mg, 1.0 mmol) was dissolved in N, N-dimethylformamide (10 mL), and then triethyl amine (202 mg, 2.0 mmol), and methylsulfonyl chloride (172 mg, 1.5 mmol) were added, and stirred overnight at room temperature. After the reaction was completed, saturated saline (20 mL) was added, and extracted with dichloromethane (3×20 mL). The organic phases were combined, and dried over anhydrous sodium sulfate. Filtration, rotary drying, and purification by reverse-phase HPLC gave (E)-5-(2-(2,6-dimethyl-4-carbonylpyridin-1(4H)-yl)ethenyl)-2-methoxyphenylmethyl sulfonate (130 mg, yield 40%, white solid). $^1$H NMR (400 MHz, CD$_3$OD) δ 7.61 (d, J=2.4 Hz, 1H), 7.58 (dd, J=8.8, 2.4 Hz, 1H), 7.28 (d, J=14.4 Hz, 1H), 7.25 (d, J=8.8 Hz, 1H), 7.05 (s, 2H), 6.96 (d, J=14.4 Hz, 1H), 3.96 (s, 3H), 2.58 (s, 6H). LC-MS: m/z 350.1 [M+H]$^+$.

Example 74

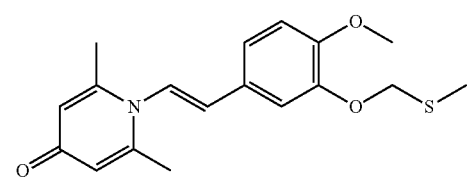

(E)-1-(3-methylthiomethoxy-4-methoxystyryl)-2,6-dimethylpyridin-4(1H)-one

The specific reaction scheme is as shown below:

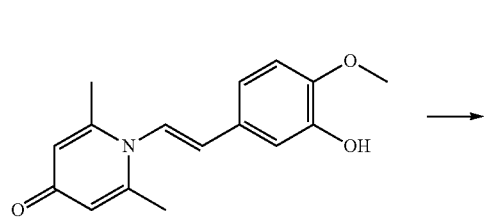

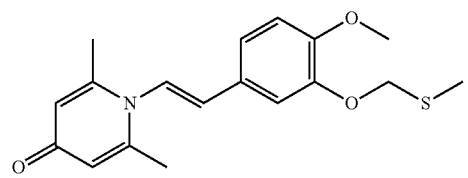 [SMILES: COc1ccc(/C=C/n2c(C)cc(=O)cc2C)cc1OCSC]

The compound (E)-1-(3-hydroxy-4-methoxystyryl)-2,6-dimethylpyridin-4(1H)-one (70 mg, 0.26 mmol) was dissolved in N,N-dimethylformamide (5 mL), and then chloromethylmethyl sulfide (50 mg, 0.52 mmol) and cesium carbonate (170 mg, 0.52 mmol) were added, and stirred overnight at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-methylthiomethoxy-4-methoxystyryl)-2,6-dimethylpyridin-4(1H)-one (50 mg, yield 58%, white solid). $^1$H NMR (400 MHz, CDCl$_3$) δ 7.31 (d, J=2.0 Hz, 1H), 7.25 (dd, J=8.4, 2.0 Hz, 1H), 7.08 (d, J=14.4 Hz, 1H), 7.05 (d, J=8.4 Hz, 1H), 6.78 (d, J=14.4 Hz, 1H), 6.77 (s, 2H), 5.03 (s, 2H), 3.90 (s, 3H), 2.36 (s, 6H), 2.26 (s, 3H); LC-MS: m/z 332.5 [M+H]$^+$.

Example 75

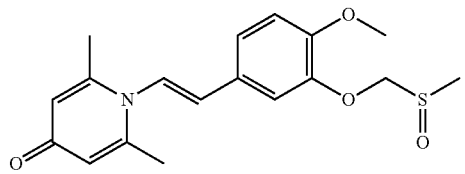 [SMILES: COc1ccc(/C=C/n2c(C)cc(=O)cc2C)cc1OCS(C)=O]

(E)-1-(3-methylsulfoxidemethoxy-4-methoxystyryl)-2,6-dimethylpyridin-4(1H)-one

The specific reaction scheme is as shown below:

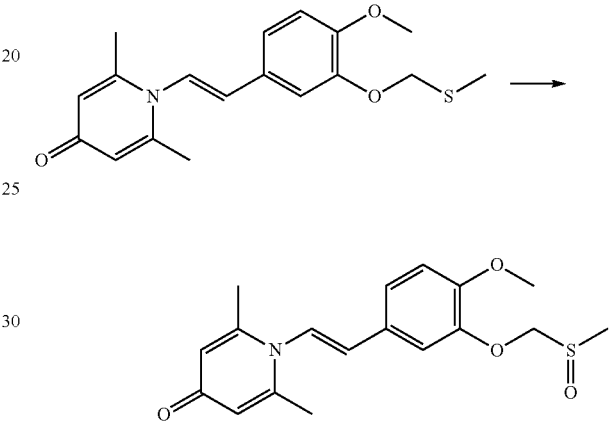

The compound (E)-1-(3-methylthiomethoxy-4-methoxystyryl)-2,6-dimethylpyridin-4(1H)-one (50 mg, 0.15 mmol) was dissolved in dichloromethane (5 mL), and then 85% m-chloroperoxybenzoic acid (28 mg, 0.14 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoxidemethoxy-4-methoxystyryl)-2,6-dimethylpyridin-4(1H)-one (36 mg, yield 69%, white solid). $^1$H NMR (400 MHz, CDCl$_3$) δ 7.41 (d, J=2.0 Hz, 1H), 7.28 (dd, J=8.4, 2.0 Hz, 1H), 7.09 (d, J=14.4 Hz, 1H), 7.05 (d, J=8.4 Hz, 1H), 7.03 (s, 2H), 6.68 (d, J=14.4 Hz, 1H), 5.26 (d, J=11.2 Hz, 1H), 5.11 (d, J=11.2 Hz, 1H), 3.96 (s, 3H), 2.36 (s, 6H), 2.26 (s, 3H); LC-MS: m/z 348.2 [M+H]$^+$.

Example 76

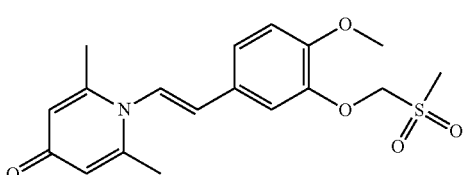

(E)-1-(3-methylsulfonemethoxy-4-methoxystyryl)-2,6-dimethylpyridin-4(1H)-one
The specific reaction scheme is as shown below:

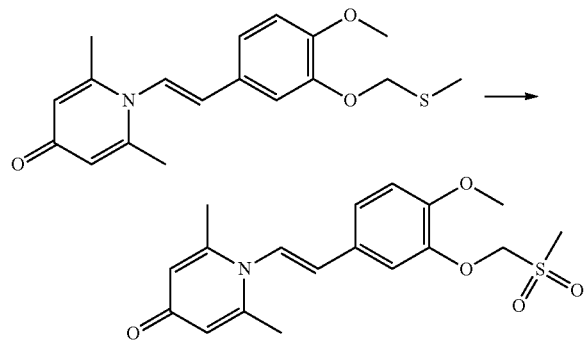

The compound (E)-1-(3-methylthiomethoxy-4-methoxystyryl)-2,6-dimethylpyridin-4(1H)-one (30 mg, 0.09 mmol) was dissolved in dichloromethane (5 mL), and then 85% m-chloroperoxybenzoic acid (54 mg, 0.27 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfonemethoxy-4-methoxystyryl)-2,6-dimethylpyridin-4(1H)-one (26 mg, yield 79%, white solid). $^1$H NMR (400 MHz, CD$_3$OD) δ 7.50 (d, J=2.0 Hz, 1H), 7.32 (dd, J=8.4, 2.0 Hz, 1H), 7.11 (d, J=8.4 Hz, 1H), 7.10 (d, J=14.0 Hz, 1H), 6.79 (d, J=14.0 Hz, 1H), 6.37 (s, 2H), 5.20 (s, 2H), 3.93 (s, 3H), 3.11 (s, 3H), 2.35 (s, 6H); LC-MS m/z 364.1 [M+H]$^+$.

Example 77

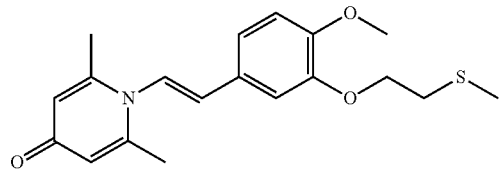 [SMILES: COc1ccc(/C=C/n2c(C)cc(=O)cc2C)cc1OCCSC]

(E)-1-(3-methylthioethoxy-4-methoxystyryl)-2,6-dimethylpyridin-4(1H)-one
The specific reaction scheme is as shown below:

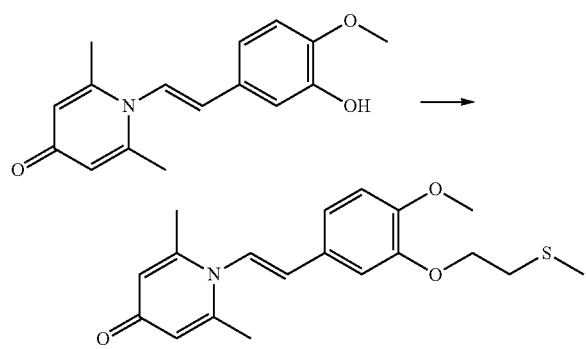

The compound (E)-1-(3-hydroxy-4-methoxystyryl)-2,6-dimethylpyridin-4(1H)-one (200 mg, 0.73 mmol) was dissolved in N,N-dimethylformamide (5 mL), and then chloroethyl methyl sulfide (165 mg, 1.5 mmol) and cesium carbonate (489 mg, 1.5 mmol) were added, and stirred overnight at room temperature. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-methylthioethoxy-4-methoxystyryl)-2,6-dimethylpyridin-4(1H)-one (220 mg, yield 87%, white solid). $^1$H NMR (400 MHz, CDCl$_3$) δ 7.05 (dd, J=8.4, 2.0 Hz, 1H), 7.01 (d, J=2.0 Hz, 1H), 6.91 (d, J=8.4 Hz, 1H), 6.77 (d, J=14.4 Hz, 1H), 6.59 (d, J=14.4 Hz, 1H), 6.26 (s, 2H), 4.24 (t, J=7.2 Hz, 2H), 3.91 (s, 3H), 2.96 (t, J=7.2 Hz, 2H), 2.26 (s, 6H), 2.24 (s, 3H); LC-MS: m/z 346.5 [M+H]$^+$.

Example 78

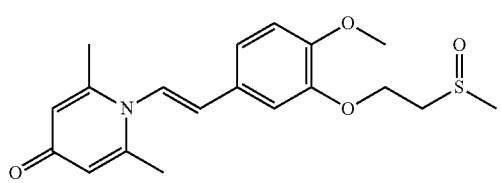 [SMILES: COc1ccc(/C=C/n2c(C)cc(=O)cc2C)cc1OCCS(C)=O]

(E)-1-(3-methylsulfoxideethoxy-4-methoxystyryl)-2,6-dimethylpyridin-4(1H)-one
The specific reaction scheme is as shown below:

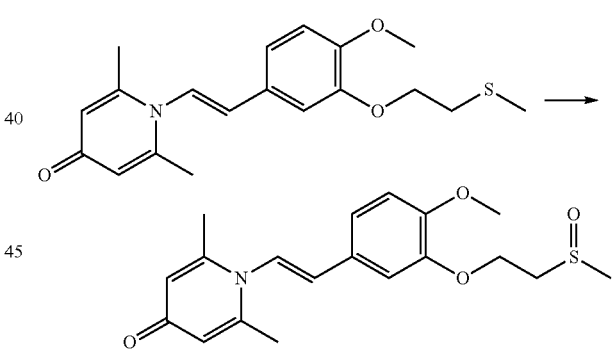

The compound (E)-1-(3-methylthioethoxy-4-methoxystyryl)-2,6-dimethylpyridin-4(1H)-one (50 mg, 0.15 mmol) was dissolved in dichloromethane (5 mL), and then 85% m-chloroperoxybenzoic acid (28 mg, 0.14 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoxideethoxy-4-methoxystyryl)-2,6-dimethylpyridin-4(1H)-one (30 mg, yield 53%, white solid). $^1$H NMR (400 MHz, CDCl$_3$) δ 7.07 (d, J=2.0 Hz, 1H), 6.99 (dd, J=8.4, 2.0 Hz, 1H), 6.84 (d, J=8.4 Hz, 1H), 6.72 (d, J=14.4 Hz, 1H), 6.51 (d, J=14.4 Hz, 1H), 6.17 (s, 2H), 4.50-4.41 (m, 2H), 3.83 (s, 3H), 3.27-3.20 (m, 1H), 3.07-3.01 (m, 1H), 2.68 (s, 3H), 2.17 (s, 6H); LC-MS: m/z 362.1 [M+H]$^+$.

Example 79

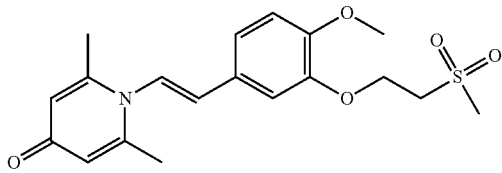 [SMILES: COc1ccc(/C=C/n2c(C)cc(=O)cc2C)cc1OCCS(C)(=O)=O]

(E)-1-(3-methylsulfoneethoxy-4-methoxystyryl)-2,6-dimethylpyridin-4(1H)-one

The specific reaction scheme is as shown below:

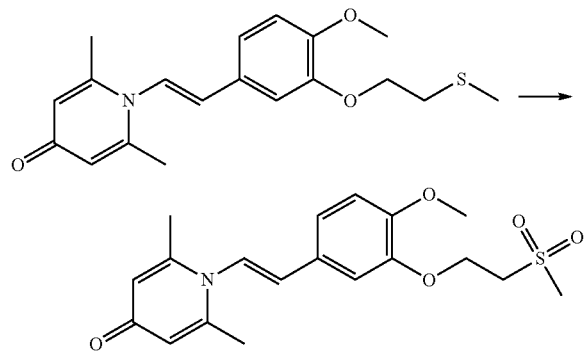

The compound (E)-1-(3-methylthioethoxy-4-methoxystyryl)-2,6-dimethylpyridin-4(1H)-one (30 mg, 0.09 mmol) was dissolved in dichloromethane (5 mL), and then 85% m-chloroperoxybenzoic acid (54 mg, 0.54 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoneethoxy-4-methoxystyryl)-2,6-dimethylpyridin-4(1H)-one (35 mg, yield 61%, white solid). $^1$H NMR (400 MHz, CDCl$_3$) δ 7.08 (dd, J=8.4, 2.0 Hz, 1H), 7.05 (d, J=2.0 Hz, 1H), 6.92 (d, J=8.4 Hz, 1H), 6.78 (d, J=14.4 Hz, 1H), 6.58 (d, J=14.4 Hz, 1H), 6.31 (s, 2H), 4.50 (t, J=4.2 Hz, 2H), 3.89 (s, 3H), 3.50 (t, J=4.2 Hz, 2H), 3.19 (s, 3H), 2.26 (s, 6H); LC-MS: m/z 378.1 [M+H]$^+$.

Example 80

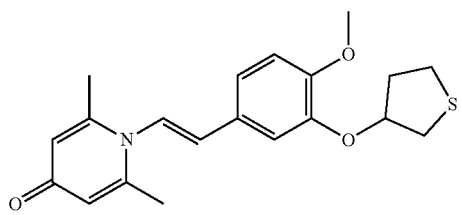 [SMILES: COc1ccc(/C=C/n2c(C)cc(=O)cc2C)cc1OC1CCSC1]

(E)-1-((3-(tetrahydrothiophen-3-yl)oxy-4-methoxy)-styryl)-2,6-dimethylpyridin-4(1H)-one The specific reaction scheme is as shown below:

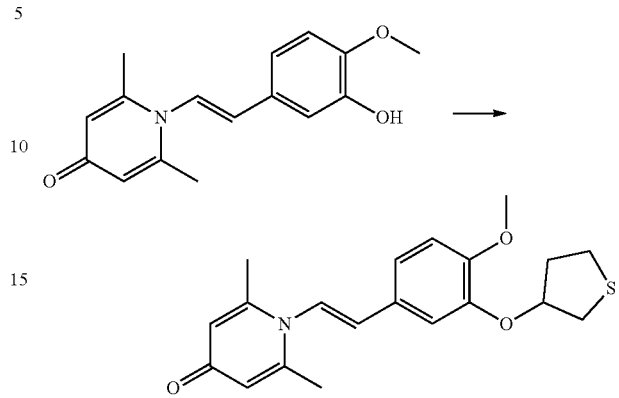

The compound (E)-1-(3-hydroxy-4-methoxystyryl)-2,6-dimethylpyridin-4(1H)-one (45 mg, 0.15 mmol) was dissolved in N,N-dimethylformamide (5 mL), and then tetrahydrothiophen-3-yl methanesulfonate (53 mg, 0.29 mmol) and cesium carbonate (95 mg, 0.29 mmol) were added, and stirred overnight at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-(tetrahydrothiophen-3-yl)oxy-4-methoxystyryl)-2,6-dimethylpyridin-4(1H)-one (35 mg, yield 65%, white solid). $^1$H NMR (400 MHz, CDCl$_3$) δ 7.10 (dd, J=8.4, 2.0 Hz, 1H), 7.08 (d, J=2.0 Hz, 1H), 6.93 (d, J=8.4 Hz, 1H), 6.77 (d, J=14.4 Hz, 1H), 6.58 (d, J=14.4 Hz, 1H), 6.31 (s, 2H), 5.16-5.13 (m, 1H), 3.90 (s, 3H), 3.18-3.08 (m, 1H), 3.09 (d, J=3.6 Hz, 2H), 2.98-2.93 (m, 1H), 2.49-2.42 (m, 1H), 2.27 (s, 6H), 2.08-1.99 (m, 1H); LC-MS: m/z 358.2 [M+H]$^+$.

Example 81

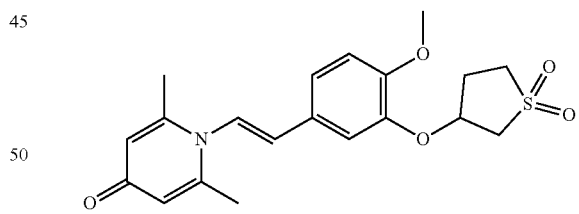

(E)-1-(3-((1,1,-dioxotetrahydrothiophen-3-yl)oxy)-4-methoxystyryl)-2,6-dimethylpyridin-4(1H)-one The specific reaction scheme is as shown below:

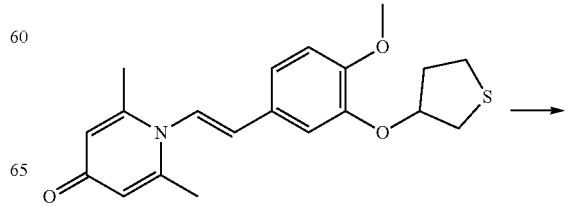

-continued

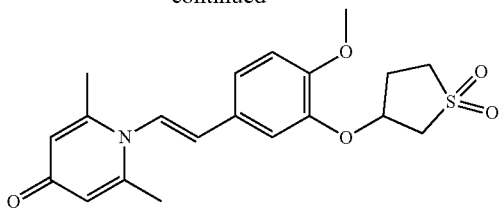

The compound (E)-1-((3-(tetrahydrothiophen-3-yl)oxy-4-methoxy)-styryl)-2,6-dimethylpyridin-4(1H)-one (68 mg, 0.19 mmol) was dissolved in dichloromethane (5 mL), and then 85% m-chloroperoxybenzoic acid (116 mg, 0.57 mmol) was added and stirred for 3 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-((1,1,-dioxotetrahydrothiophen-3-yl)oxy)-4-methoxystyryl)-2,6-dimethylpyridin-4(1H)-one (62 mg, yield 86%, white solid). $^1$H NMR (400 MHz, CDCl$_3$) δ 7.28 (s, 1H), 7.19 (d, J=8.4 Hz, 1H), 7.13 (d, J=14.4 Hz, 1H), 7.10 (s, 2H), 6.97 (d, J=14.4 Hz, 1H), 5.34-5.27 (m, 1H), 3.91 (s, 3H), 3.52-3.44 (m, 1H), 3.41-3.32 (m, 2H), 3.23-3.17 (m, 1H), 2.70-2.61 (m, 1H), 2.58-2.47 (m, 1H), 2.54 (s, 6H); LC-MS: m/z 390.1 [M+H]$^+$.

Example 82

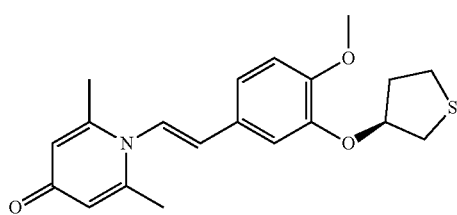 [SMILES: COc1ccc(/C=C/n2c(C)cc(=O)cc2C)cc1O[C@H]1CCSC1]

(S,E)-1-(3-(tetrahydrothiophen-3-yl)oxy-4-methoxystyryl)-2,6-dimethylpyridin-4(1H)-one The specific reaction scheme is as shown below:

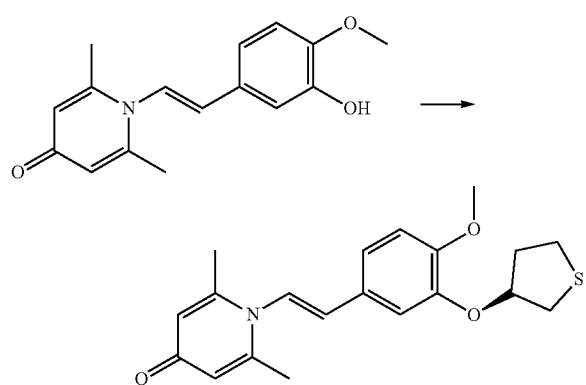

The compound (E)-1-(3-hydroxy-4-methoxystyryl)-2,6-dimethylpyridin-4(1H)-one (45 mg, 0.15 mmol) was dissolved in N,N-dimethylformamide (5 mL), and then (R)-tetrahydrothiophen-3-yl methanesulfonate (53 mg, 0.29 mmol) and cesium carbonate (95 mg, 0.29 mmol) were added, and stirred overnight at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (S,E)-1-(3-(tetrahydrothiophen-3-yl)oxy-4-methoxystyryl)-2,6-dimethylpyridin-4(1H)-one (30 mg, yield 56%, white solid). $^1$H NMR (400 MHz, CDCl$_3$) δ 7.10 (dd, J=8.4, 2.0 Hz, 1H), 7.08 (d, J=2.0 Hz, 1H), 6.93 (d, J=8.4 Hz, 1H), 6.77 (d, J=14.4 Hz, 1H), 6.58 (d, J=14.4 Hz, 1H), 6.31 (s, 2H), 5.16-5.13 (m, 1H), 3.90 (s, 3H), 3.18-3.08 (m, 1H), 3.09 (d, J=3.6 Hz, 2H), 2.98-2.93 (m, 1H), 2.49-2.42 (m, 1H), 2.27 (s, 6H), 2.08-1.99 (m, 1H); LC-MS: m/z 358.1 [M+H]$^+$.

Example 83

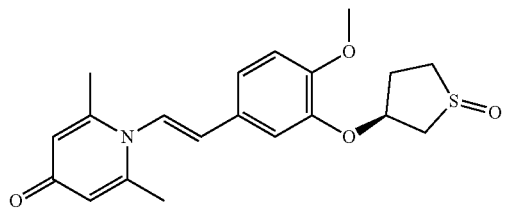 [SMILES: COc1ccc(/C=C/n2c(C)cc(=O)cc2C)cc1O[C@H]1CCS(=O)C1]

1-((E)-4-methoxy-3-(((3S)-1-oxotetrahydrothiophen-3-yl)oxy)styryl)-2,6-dimethylpyridin-4(1H)-one The specific reaction scheme is as shown below:

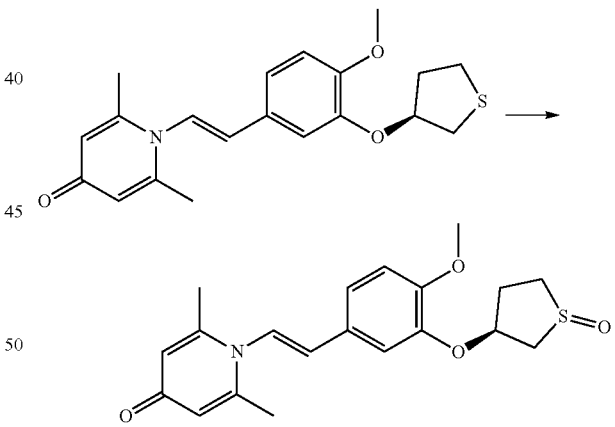

The compound (S,E)-1-(3-(tetrahydrothiophen-3-yl)oxy-4-methoxystyryl)-2,6-dimethylpyridin-4(1H)-one (81 mg, 0.23 mmol) was dissolved in dichloromethane (5 mL), and then 85% m-chloroperoxybenzoic acid (41 mg, 0.20 mmol) was added and stirred for 3 hours at 0° C. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave a diastereoisomer of 1-((E)-4-methoxy-3-(((3S)-1-oxotetrahydrothiophen-3-yl)oxy)styryl)-2,6-dimethylpyridin-4(1H)-one show below:

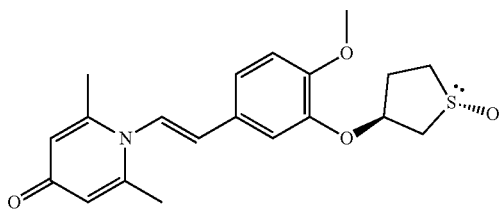

(25 mg, yield 29%, pale yellow oil). $^1$H NMR (400 MHz, CDCl$_3$) δ 7.35 (d, J=1.6 Hz, 1H), 7.12 (dd, J=8.4, 1.6 Hz, 1H), 7.07 (d, J=14.4 Hz, 1H), 7.01 (s, 2H), 6.94 (d, J=8.4 Hz, 1H), 6.68 (d, J=14.4 Hz, 1H), 5.28-5.24 (m, 1H), 3.91 (s, 3H), 3.34-3.14 (m, 4H), 2.93-2.85 (m, 1H), 2.51 (s, 6H), 2.34-2.25 (m, 1H); LC-MS: m/z 374.1 [M+H]$^+$.

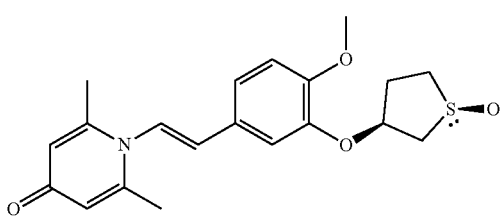

(20 mg, yield 23%, pale yellow oil)$^1$H NMR (400 MHz, CDCl$_3$) δ 7.17 (d, J=8.4 Hz, 1H), 7.15 (s, 1H), 7.07 (d, J=14.4 Hz, 1H), 7.03 (s, 2H), 6.95 (d, J=8.4 Hz, 1H), 6.71 (d, J=14.4 Hz, 1H), 5.48-5.43 (m, 1H), 3.89 (s, 3H), 3.64 (d, J=15.2 Hz, 1H), 3.21-3.07 (m, 3H), 2.83-2.74 (m, 1H), 2.65-2.59 (m, 1H), 2.51 (s, 6H); LC-MS: m/z 374.1 [M+H]$^+$.

Example 84

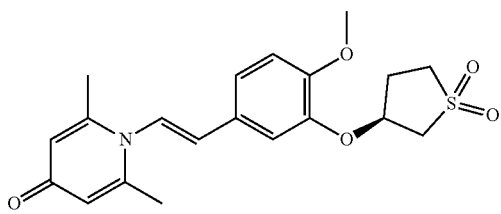 [SMILES: COc1ccc(/C=C/n2c(C)cc(=O)cc2C)cc1O[C@H]1CCS(=O)(=O)C1]

(S,E)-1-(3-((1,1-dioxotetrahydrothiophen-3-yl)oxy)-4-methoxy-styryl)-2,6-dimethylpyridin-4(1H)-one The specific reaction scheme is as shown below:

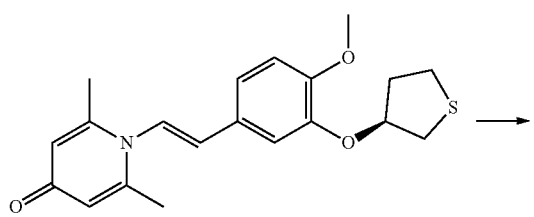

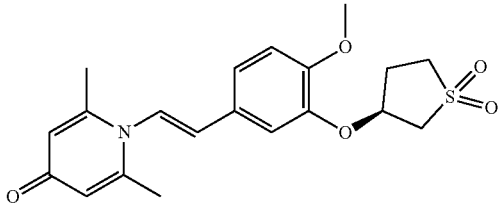

The compound (E)-1-(((3-(tetrahydrothiophen-3-yl)oxy-4-methoxy)-styryl)-2,6-dimethylpyridin-4(1H)-one (81 mg, 0.23 mmol) was dissolved in dichloromethane (5 mL), and then 85% m-chloroperoxybenzoic acid (140 mg, 0.69 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-((1,1,-dioxotetrahydrothiophen-3-yl)oxy)-4-methoxystyryl)-2,6-dimethylpyridin-4(1H)-one (58 mg, yield 66%, white solid). $^1$H NMR (400 MHz, CDCl$_3$) δ 7.26 (s, 1H), 7.19 (d, J=8.4 Hz, 1H), 7.08 (d, J=14.4 Hz, 1H), 7.05 (s, 2H), 6.97 (d, J=8.4 Hz, 1H), 6.71 (d, J=14.4 Hz, 1H), 5.32-5.27 (m, 1H), 3.91 (s, 3H), 3.52-3.43 (m, 1H), 3.41-3.31 (m, 2H), 3.22-3.16 (m, 1H), 2.69-2.62 (m, 1H), 2.57-2.47 (m, 1H), 2.52 (s, 6H); LC-MS m/z 390.2 [M+1-1]$^+$.

Example 85

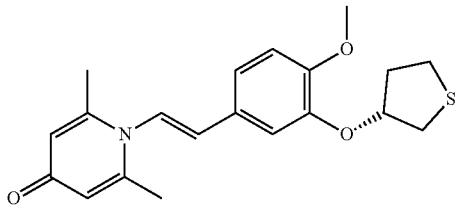

(R,E)-1-(3-(tetrahydrothiophen-3-yl)oxy-4-methoxystyryl)-2,6-dimethylpyridin-4(1H)-one The specific reaction scheme is as shown below:

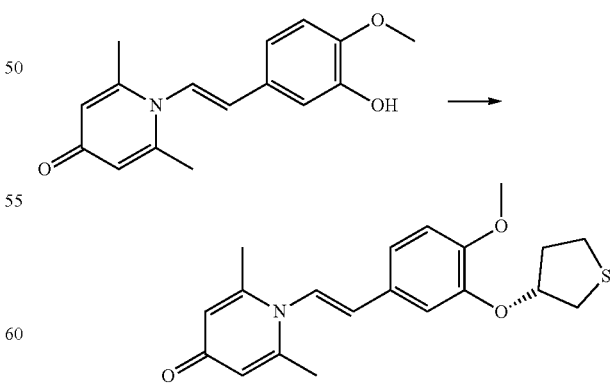

The compound (E)-1-(3-hydroxy-4-methoxystyryl)-2,6-dimethylpyridin-4(1H)-one (45 mg, 0.15 mmol) was dissolved in N,N-dimethylformamide (5 mL), and then (S)-tetrahydrothiophen-3-yl methanesulfonate (53 mg, 0.29 mmol) and cesium carbonate (95 mg, 0.29 mmol) were added, and stirred overnight at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (S,E)-1-(3-(tetrahydrothiophen-3-yl)oxy-4-methoxystyryl)-2,6-dimethylpyridin-4(1H)-one (30 mg, yield 56%, white solid). $^1$H NMR (400 MHz, CDCl$_3$) δ 7.10 (dd, J=8.4, 2.0 Hz, 1H), 7.08 (d, J=2.0 Hz, 1H), 6.93 (d, J=8.4 Hz, 1H), 6.77 (d, J=14.4 Hz, 1H), 6.58 (d, J=14.4 Hz, 1H), 6.31 (s, 2H), 5.16-5.13 (m, 1H), 3.90 (s, 3H), 3.18-3.08 (m, 1H), 3.09 (d, J=3.6 Hz, 2H), 2.98-2.93 (m, 1H), 2.49-2.42 (m, 1H), 2.27 (s, 6H), 2.08-1.99 (m, 1H); LC-MS: m/z 358.1 [M+H]$^+$.

Example 86

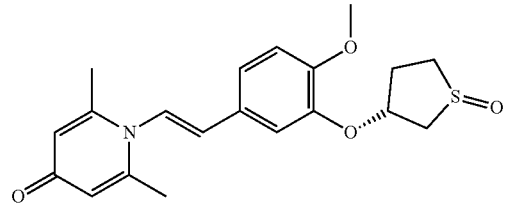

1-((E)-4-methoxy-3-(((3R)-1-oxotetrahydrothiophen-3-yl)oxy)styryl)-2,6-dimethylpyridin-4(1H)-one

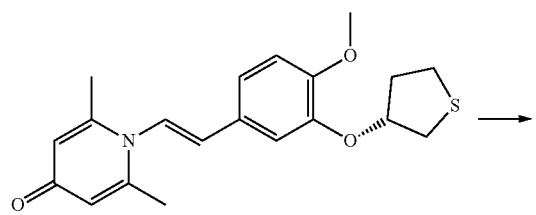

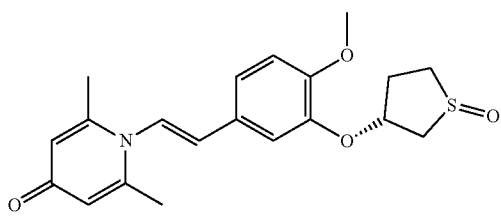

The compound (R,E)-1-(3-(tetrahydrothiophen-3-yl)oxy-4-methoxystyryl)-2,6-dimethylpyridin-4(1H)-one (57 mg, 0.16 mmol) was dissolved in dichloromethane (5 mL), and then 85% m-chloroperoxybenzoic acid (29 mg, 0.15 mmol) was added and stirred for 3 hours at 0° C. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave a diastereoisomer of 1-((E)-4-methoxy-3-(((3R)-1-oxotetrahydrothiophen-3-yl)oxy)styryl)-2,6-dimethylpyridin-4(1H)-one shown below:

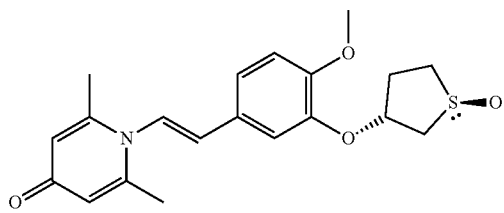

(15 mg, yield 25%, pale yellow oil). $^1$H NMR (400 MHz, CD$_3$OD) δ 7.26 (d, J=2.0 Hz, 1H), 7.20 (dd, J=8.4, 2.0 Hz, 1H), 7.12 (d, J=14.4 Hz, 1H), 6.99 (d, J=7.6 Hz, 1H), 6.96 (s, 2H), 6.80 (d, J=14.4, 1H), 5.18-5.13 (m, 1H), 3.80 (s, 3H), 3.36-3.25 (m, 2H), 3.09-3.00 (m, 2H), 2.69-2.61 (m, 1H), 2.49 (s, 6H), 2.27-2.19 (m, 1H); LC-MS: m/z 374.1 [M+H]$^+$.

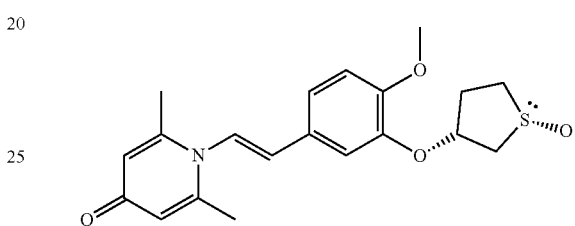

(10 mg, yield 17%, pale yellow oil)$^1$H NMR (400 MHz, CD$_3$OD) δ 7.33 (d, J=2.0 Hz, 1H), 7.30 (dd, J=8.4, 2.0 Hz, 1H), 7.26 (d, J=14.4 Hz, 1H), 7.10 (d, J=7.6 Hz, 1H), 7.09 (s, 2H), 6.93 (d, J=14.4 Hz, 1H), 5.52-5.49 (m, 1H), 3.89 (s, 3H), 3.76-3.71 (m, 1H), 3.30-3.22 (m, 2H), 3.76-3.71 (m, 1H), 2.77-2.67 (m, 1H), 2.65-2.63 (m, 1H), 2.61 (s, 6H); LC-MS: m/z 374.1 [M+H]$^+$.

Example 87

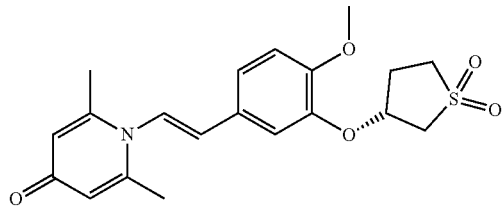

(R,E)-1-(3-((1,1-dioxotetrahydrothiophen-3-yl)oxy)-4-methoxy-styryl)-2,6-dimethylpyridin-4(1H)-one The specific reaction scheme is as shown below:

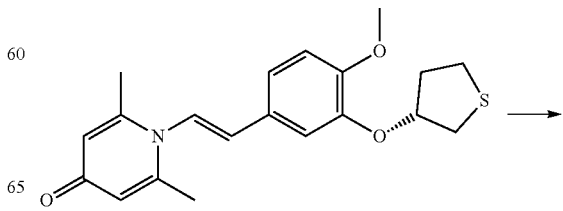

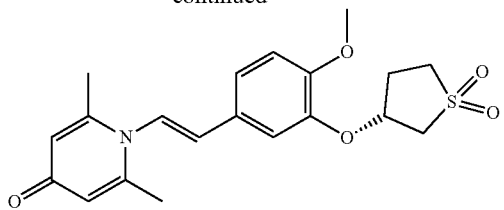

The compound (E)-1-((3-(tetrahydrothiophen-3-yl)oxy-4-methoxy)-styryl)-2,6-dimethylpyridin-4(1H)-one (30 mg, 0.08 mmol) was dissolved in dichloromethane (5 mL), and then 85% m-chloroperoxybenzoic acid (49 mg, 0.24 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-((1,1,-dioxotetrahydrothiophen-3-yl)oxy)-4-methoxystyryl)-2,6-dimethylpyridin-4(1H)-one (12 mg, yield 40%, white solid). $^1$H NMR (400 MHz, CD$_3$OD) δ 7.23 (s, 1H), 7.22 (dd, J=8.4, 2.0 Hz, 1H), 7.12 (d, J=14.4 Hz, 1H), 7.10 (dd, J=8.4, 2.0 Hz, 1H), 6.96 (s, 2H), 6.81 (d, J=14.4 Hz, 1H), 5.20-5.16 (m, 1H), 3.80 (s, 3H), 3.38-3.28 (m, 2H), 3.25-3.24 (m, 1H), 3.13-3.07 (m, 1H), 2.49 (s, 6H), 2.47-2.34 (m, 2H); LC-MS: m/z 390.0 [M+H]$^+$.

Step A:

The compound 1-(2-(3-cyclopropylmethoxy-4-difluoromethoxyphenyl)-2-hydroxyethyl)-2,6-dimethylpyridin-4(1H)-one (80 mg, 0.21 mmol) was dissolved in trichloromethane (10 mL), and heated to 80° C. Then thionyl chloride (0.5 mL) was added and stirred at 80° C. for 15 min. After the reaction was completed, the reaction solution was directly rotary dried to obtain a crude product of 1-(2-chloro-2-(3-cyclopropylmethoxy-4-difluoromethoxyphenyl)ethyl)-2,6-dimethylpyridin-4(1H)-one (85 mg, 100%). LC-MS: m/z 398.2 [M+H]$^+$.

Step B:

The compound 1-(2-chloro-2-(3-cyclopropylmethoxy-4-difluoromethoxyphenyl)ethyl)-2,6-dimethylpyridin-4(1H)-one (85 mg, 0.21 mmol) was dissolved in ethanol (10 mL), and then sodium hydroxide (64 mg, 1.60 mmol) and water (2 mL) were added in sequence, heated to 100° C., and stirred for 16 hours under nitrogen atmosphere. After the reaction was completed, the reaction solution was rotary dried, and purified to obtain (E)-1-(3-(cyclopropylmethoxy)-4-(difluoromethoxy)styryl)-2,6-dimethylpyridin-4(1H)-one (20 mg, 26%, white solid). $^1$H NMR (400 MHz, DMSO-d$_6$) δ 7.41 (d, J=2.0 Hz, 1H), 7.34 (d, J=14.4 Hz, 1H), 7.23 (d, J=8.4 Hz, 1H), 7.17 (dd, J=8.4, 2.0 Hz, 1H), 7.12 (t, J$_{H-F}$=74.4 Hz, 1H), 6.91 (d, J=14.4 Hz, 1H), 6.49 (s, 2H), 3.95 (d, J=7.2 Hz, 2H), 2.34 (s, 6H), 1.31-1.21 (m, 1H), 0.62-0.57 (m, 2H), 0.37-0.33 (m, 2H); LC-MS: m/z 362.2 [M+H]$^+$.

Example 88

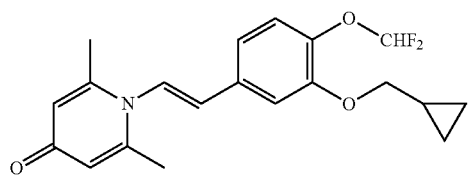 [SMILES: Cc1cc(=O)cc(C)n1/C=C/c1ccc(OC(F)F)c(OCC2CC2)c1]

(E)-1-(3-(cyclopropylmethoxy)-4-(difluoromethoxy)styryl)-2,6-dimethylpyridin-4(1H)-one The specific reaction scheme is as shown below:

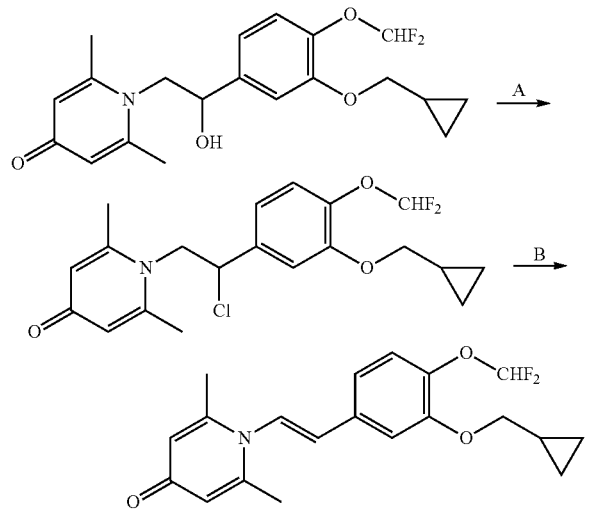

Example 89

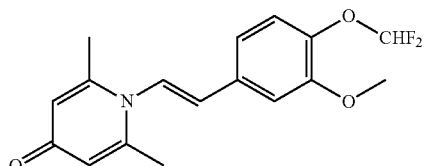

(E)-1-(3-methoxy-4-difluoromethoxy-styryl)-2,6-dimethylpyridin-4(1H)-one

The specific reaction scheme is as shown below:

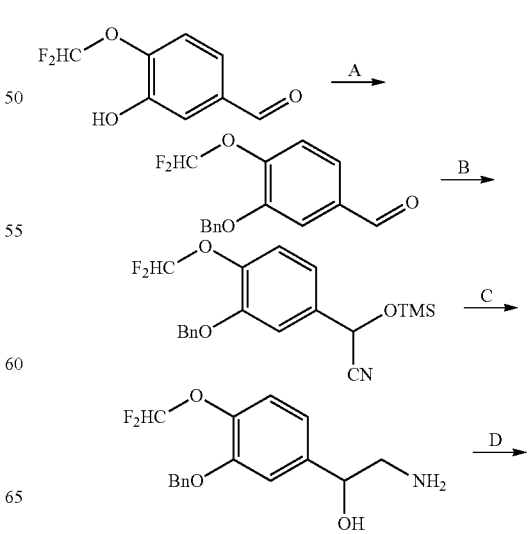

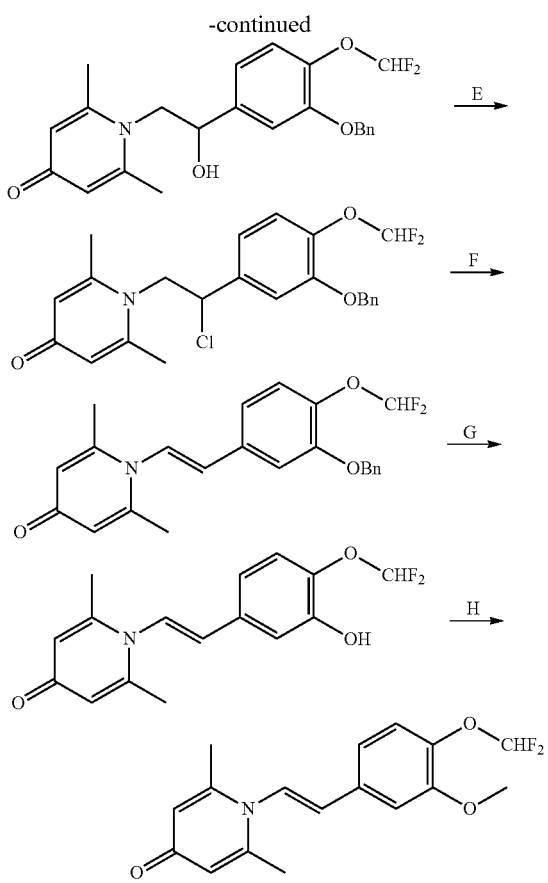

Step A:

At room temperature, 3-hydroxy-4-difluoromethoxybenzaldehyde (2.36 g, 12.5 mmol) was dissolved in acetonitrile (40 mL), and then potassium carbonate (3.46 g, 25.1 mmol) and benzyl bromide (2.79 g, 16.3 mmol) were added in sequence, and heated to 80° C. for 3 hours with stirring under nitrogen atmosphere. After the reaction was completed, a saturated aqueous sodium chloride solution (30 mL) was added, and extracted with dichloromethane (3×120 mL). The organic phases were combined, dried over anhydrous sodium sulfate, filtered, rotary dried, and purified by column chromatography to obtain 3-benzoxy-4-difluoromethoxybenzaldehyde (3.30 g, 95%).

Step B:

3-benzoxy-4-difluoromethoxybenzaldehyde (3.30 g, 11.9 mmol) was dissolved in dichloromethane (30 mL), and then triethyl amine (2.40 g, 23.7 mmol) and trimethylsilyl cyanide (3.53 g, 35.6 mmol) were added in sequence in an ice bath and stirred for 16 hours under nitrogen atmosphere at room temperature. After the reaction was completed, the reaction solution was directly rotary dried to obtain 2-(3-benzoxy-4-difluoromethoxyphenyl)-2-trimethylsiloxyacetonitrile, which was directly used in the next reaction.

Step C:

The compound 2-(3-benzoxy-4-difluoromethoxyphenyl)-2-trimethylsiloxyacetonitrile (4.47 g, 11.9 mmol) was dissolved in anhydrous tetrahydrofuran (40 mL), and then lithium aluminum hydride (1.35 g, 35.6 mmol) was added portion-wise in an ice bath, and stirred overnight at room temperature. After the reaction was completed, the reaction was diluted with anhydrous tetrahydrofuran (200 mL), and then water (1.35 mL), an aqueous sodium hydroxide solution (1.35 mL, 15%), and water (4.05 mL) were added in sequence, stirred for half an hour, dried over anhydrous sodium sulfate, filtered, and rotary dried to obtain a crude product of 2-amino-1-(3-benzoxy-4-difluoromethoxyphenyl)ethanol, which was directly used in the next reaction.

Step D:

The compound 2-amino-1-(3-benzoxy-4-difluoromethoxyphenyl)ethanol (3.67 g, 11.9 mmol) was dissolved in ethanol (60 mL), and then 2,6-dimethyl-4H-pyran-4-one (2.19 g, 17.7 mmol), sodium hydroxide (708 mg, 17.7 mmol) and water (10 mL) were added in sequence, heated to 60° C., and stirred for 16 hours under nitrogen atmosphere. After the reaction was completed, the reaction solution was rotary dried, and purified by column chromatography to obtain 1-(2-(3-benzoxy-4-difluoromethoxyphenyl)-2-hydroxyethyl)-2,6-dimethylpyridin-4(1H)-one (2.3 g, 47%). LC-MS m/z 416.2 [M+H]$^+$.

Step E:

The compound 1-(2-(3-benzoxy-4-difluoromethoxyphenyl)-2-hydroxyethyl)-2,6-dimethylpyridin-4(1H)-one (2.3 g, 5.3 mmol) was dissolved in trichloromethane (80 mL), and then heated to 90° C. Thionyl chloride (3 mL) was added and stirred at 90° C. for 15 min. After the reaction was completed, the reaction solution was directly rotary dried to obtain a crude product of 1-(2-(3-benzoxy-4-difluoromethoxyphenyl)-2-chloroethyl)-2,6-dimethylpyridin-4(1H)-one (2.15 g, 93%). LC-MS m/z 434.2 [M+H]$^+$.

Step F:

The compound 1-(2-(3-benzoxy-4-difluoromethoxyphenyl)-2-chloroethyl)-2,6-dimethylpyridin-4(1H)-one (2.15 g, 5.0 mmol) was dissolved in ethanol (40 mL), and then sodium hydroxide (1.2 g, 30 mmol) and water (15 mL) were added in sequence, heated to 90° C., and stirred for 16 hours under nitrogen atmosphere. After the reaction was completed, the reaction solution was rotary dried, and purified to obtain (E)-1-(3-benzoxy-4-difluoromethoxystyryl)-2,6-dimethylpyridin-4(1H)-one (1.5 g, 75%). LC-MS: m/z 398.2 [M+H]$^+$.

Step G:

The compound (E)-1-(3-benzoxy-4-difluoromethoxystyryl)-2,6-dimethylpyridin-4(1H)-one (400 mg, 1.0 mmol) was dissolved in anhydrous dichloromethane (100 mL), and titanium tetrachloride (1 M, 2 mL, 2.0 mmol) was slowly added dropwise in an ice bath, and stirred overnight at room temperature. After the reaction was completed, the reaction solution was rotary dried, and purified to obtain (E)-1-(3-hydroxy-4-difluoromethoxystyryl)-2,6-dimethylpyridin-4(1H)-one (50 mg, 16%). LC-MS: m/z 308.2 [M+H]$^+$.

Step H:

The compound (E)-1-(3-hydroxy-4-difluoromethoxystyryl)-2,6-dimethylpyridin-4(1H)-one (50 mg, 0.16 mmol) was dissolved in acetonitrile (5 mL), and then iodomethane (30 mg, 0.21 mmol) and potassium carbonate (90 mg, 0.65 mmol) were added, and stirred for 2 hours at 80° C. under nitrogen atmosphere. After the reaction was completed, the reaction solution was filtered, rotary dried, and purified by reverse-phase HPLC to obtain (E)-1-(3-methoxy-4-difluoromethoxy-styryl)-2,6-dimethylpyridin-4(1H)-one (38 mg, yield 71%, white solid). $^1$H NMR (400 MHz, CDCl$_3$) δ 7.21 (d, J=8.0 Hz, 1H), 7.08-7.05 (m, 2H), 6.96 (d, J=14.0 Hz, 1H), 6.69 (d, J=14.0 Hz, 1H), 6.59 (t, J$_{H-F}$=74.8 Hz, 1H), 6.41 (s, 2H), 3.95 (s, 3H), 2.31 (s, 6H); LC-MS: m/z 322.2 [M+H]$^+$.

Example 90

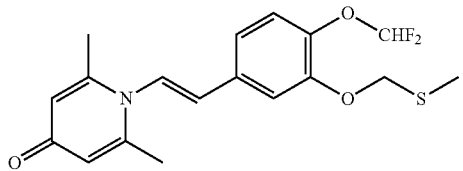 [SMILES: CSCOc1cc(/C=C/n2c(C)cc(=O)cc2C)ccc1OC(F)F]

(E)-1-(3-methylthiomethoxy-4-difluoromethoxy-styryl)-2,6-dimethylpyridin-4(1H)-one The specific reaction scheme is as shown below:

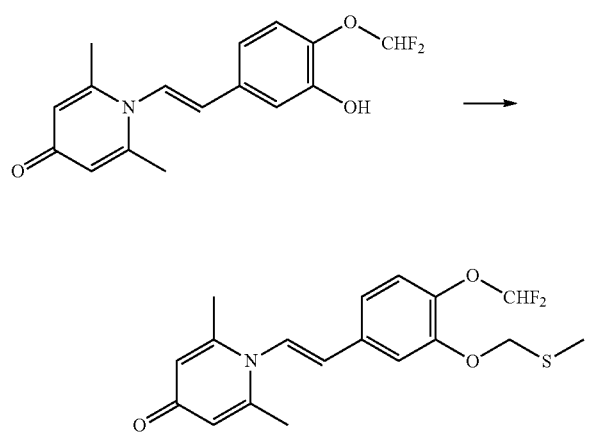

The compound (E)-1-(3-hydroxy-4-difluoromethoxystyryl)-2,6-dimethylpyridin-4(1H)-one (35 mg, 0.11 mmol) was dissolved in N,N-dimethylformamide (5 mL), and then chloromethylmethyl sulfide (22 mg, 0.23 mmol) and cesium carbonate (150 mg, 0.46 mmol) were added, and stirred for 1 hr at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-methylthiomethoxy-4-difluoromethoxy-styryl)-2,6-dimethylpyridin-4(1H)-one (30 mg, yield 71%, white solid). $^1$H NMR (400 MHz, CDCl$_3$) δ 7.24-7.22 (m, 2H), 7.16 (dd, J=8.4, 2.0 Hz, 1H), 7.08 (d, J=14.4 Hz, 1H), 6.77 (s, 2H), 6.76 (d, J=14.4 Hz, 1H), 6.59 (t, J$_{H-F}$=74.0 Hz, 1H), 5.29 (s, 2H), 2.41 (s, 6H), 2.29 (s, 3H); LC-MS: m/z 368.4 [M+H]$^+$.

Example 91

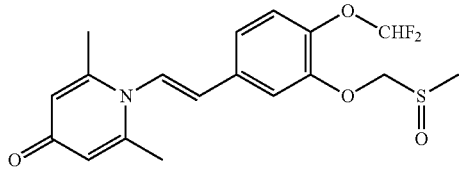 [SMILES: Cc1cc(=O)cc(C)n1/C=C/c1ccc(OC(F)F)c(OCS(C)=O)c1]

(E)-1-(3-methylsulfoxidemethoxy-4-difluoromethoxystyryl)-2,6-dimethylpyridin-4(1H)-one The specific reaction scheme is as shown below:

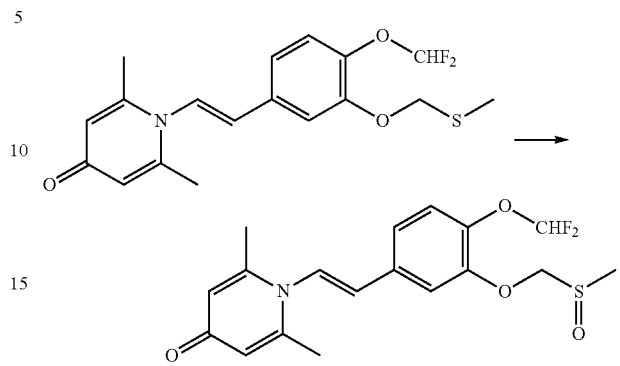

The compound (E)-1-(3-methylthiomethoxy-4-difluoromethoxystyryl)-2,6-dimethylpyridin-4(1H)-one (78 mg, 0.21 mmol) was dissolved in dichloromethane (5 mL), and then 85% m-chloroperoxybenzoic acid (39 mg, 0.19 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoxidemethoxy-4-difluoromethoxystyryl)-2,6-dimethylpyridin-4(1H)-one (64 mg, yield 78%, white solid). $^1$H NMR (400 MHz, CDCl$_3$) δ 7.72 (s, 1H), 7.27 (d, J=14.8 Hz, 1H), 7.26 (d, J=8.4 Hz, 1H), 7.18 (d, J=8.4 Hz, 1H), 7.03 (s, 2H), 6.80 (d, J=14.8 Hz, 1H), 6.64 (t, J$_{H-F}$=73.6 Hz, 1H), 5.26 (d, J=11.2 Hz, 1H), 5.11 (d, J=11.2 Hz, 1H), 2.77 (s, 3H), 2.52 (s, 6H); LC-MS: m/z 384.0 [M+H]$^+$.

Example 92

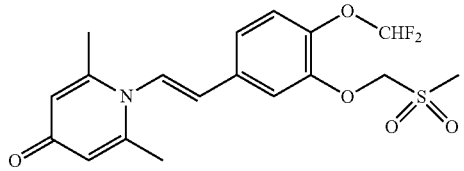 [SMILES: Cc1cc(=O)cc(C)n1/C=C/c1ccc(OC(F)F)c(OCS(C)(=O)=O)c1]

(E)-1-(3-methylsulfonemethoxy-4-difluoromethoxystyryl)-2,6-dimethylpyridin-4(1H)-one The specific reaction scheme is as shown below:

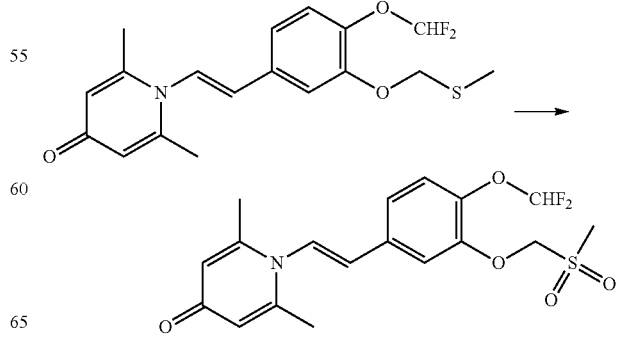

The compound (E)-1-(3-methylthiomethoxy-4-difluoromethoxystyryl)-2,6-dimethylpyridin-4(1H)-one (78 mg, 0.21 mmol) was dissolved in dichloromethane (5 mL), and then 85% m-chloroperoxybenzoic acid (128 mg, 0.63 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfonemethoxy-4-difluoromethoxystyryl)-2,6-dimethylpyridin-4(1H)-one (35 mg, yield 41%, white solid). $^1$H NMR (400 MHz, CD$_3$OD) δ 7.56 (d, J=2.0 Hz, 1H), 7.27 (d, J=8.4, 2.0 Hz, 1H), 7.26 (d, J=14.4 Hz, 1H), 7.21 (d, J=8.4 Hz, 1H), 6.97 (s, 2H), 6.91 (d, J=14.4 Hz, 1H), 6.79 (t, $J_{H-F}$=73.6 Hz, 1H), 5.23 (s, 2H), 3.01 (s, 3H), 2.49 (s, 6H); LC-MS: m/z 399.9 [M+H]$^+$.

Example 93

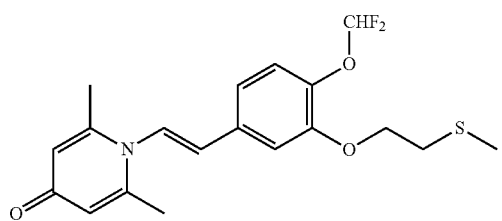 [SMILES: CSCCOc1cc(/C=C/n2c(C)cc(=O)cc2C)ccc1OC(F)F]

(E)-1-(3-methylthioethoxy-4-difluoromethoxystyryl)-2,6-dimethylpyridin-4(1H)-one The specific reaction scheme is as shown below:

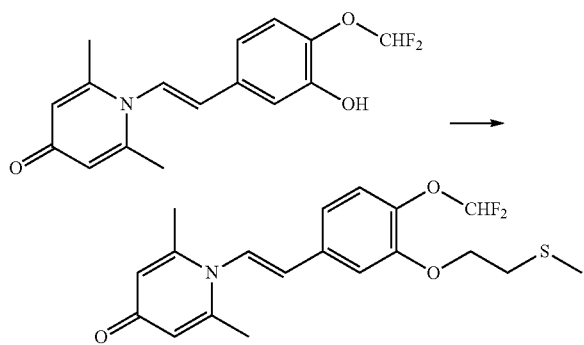

At room temperature, (E)-1-(4-(difluoromethoxy)-3-hydroxystyryl)-2,6-dimethylpyridin-4(1H)-one (50 mg, 0.16 mmol) was dissolved in N,N-dimethylformamide (2 mL), and then potassium carbonate (34 mg, 0.24 mmol) and chloroethyl methyl sulfide (36 mg, 0.33 mmol) were added in sequence, and heated to 80° C. for 16 hours with stirring under nitrogen atmosphere. After the reaction was completed, the reaction solution was filtered, rotary dried, and purified by reverse-phase HPLC to obtain (E)-1-(3-methylthioethoxy-4-difluoromethoxystyryl)-2,6-dimethylpyridin-4(1H)-one (8 mg, 14%). $^1$H NMR (400 MHz, CDCl$_3$) δ 7.18 (d, J=8.4 Hz, 1H), 7.06-6.99 (m, 2H), 6.84 (d, J=14.0 Hz, 1H), 6.59 (t, J=14.0 Hz, 1H), 6.58 (d, $J_{H-F}$=75.2 Hz, 1H), 6.19 (s, 2H), 4.20 (t, J=6.4 Hz, 2H), 2.87 (t, J=6.4 Hz, 2H), 2.19 (s, 6H), 2.16 (s, 3H); LC-MS: m/z 382.2 [M+H]$^+$.

Example 94

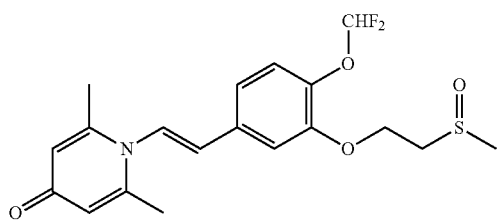 [SMILES: Cc1cc(=O)cc(C)n1/C=C/c1ccc(OC(F)F)c(OCCS(C)=O)c1]

(E)-1-(3-methylsulfoxideethoxy-4-difluoromethoxystyryl)-2,6-dimethylpyridin-4(1H)-one The specific reaction scheme is as shown below:

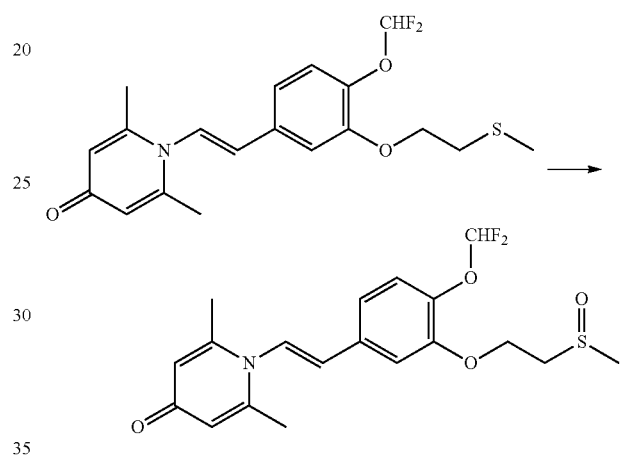

The compound (E)-1-(3-methylthioethoxy-4-difluoromethoxystyryl)-2,6-dimethylpyridin-4(1H)-one (55 mg, 0.14 mmol) was dissolved in dichloromethane (5 mL), and then 85% m-chloroperoxybenzoic acid (27 mg, 0.13 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoxideethoxy-4-difluoromethoxystyryl)-2,6-dimethylpyridin-4(1H)-one (16 mg, yield 28%, white solid). $^1$H NMR (400 MHz, CDCl$_3$) δ 7.38 (s, 1H), 7.26 (d, J=14.4 Hz, 1H), 7.22 (d, J=8.4 Hz, 1H), 7.10 (d, J=8.4 Hz, 1H), 6.97 (s, 2H), 6.79 (d, J=14.4 Hz, 1H), 6.58 (t, $J_{H-F}$=74.0 Hz, 1H), 4.60 (t, J=8.8 Hz, 1H), 3.33-3.26 (m, 1H), 3.16-3.10 (m, 1H), 2.75 (s, 3H), 2.51 (s, 6H); LC-MS: m/z 398.0 [M+H]$^+$.

Example 95

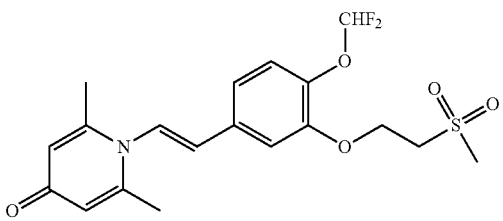 [SMILES: Cc1cc(=O)cc(C)n1/C=C/c1ccc(OC(F)F)c(OCCS(C)(=O)=O)c1]

(E)-1-(3-methylsulfoneethoxy-4-difluoromethoxystyryl)-2,6-dimethylpyridin-4(1H)-one
The specific reaction scheme is as shown below:

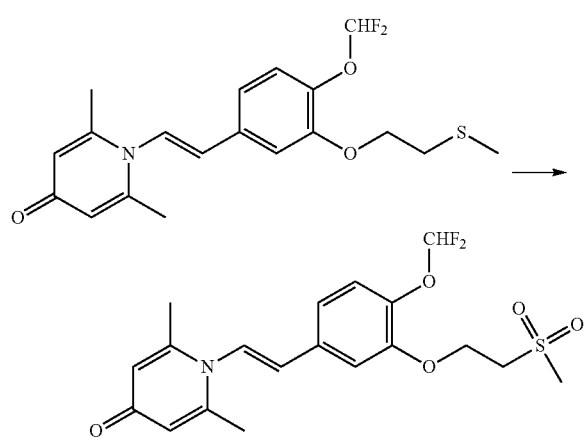

The compound (E)-1-(3-methylthioethoxy-4-difluoromethoxystyryl)-2,6-dimethylpyridin-4(1H)-one (55 mg, 0.14 mmol) was dissolved in dichloromethane (5 mL), and then m-chloroperoxybenzoic acid (85 mg, 0.42 mmol) was added and stirred for 2 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (E)-1-(3-methylsulfoneethoxy-4-difluoromethoxystyryl)-2,6-dimethylpyridin-4(1H)-one (33 mg, yield 75%, white solid). $^1$H NMR (400 MHz, CD$_3$OD) δ 7.45 (s, 1H), 7.36 (d, J=14.4 Hz, 1H), 7.30-7.25 (m, 2H), 7.04 (s, 2H), 7.00 (d, J=14.4 Hz, 1H), 6.58 (t, J$_{H-F}$=74.4 Hz, 1H), 4.55 (t, J=5.2 Hz, 1H), 3.66 (t, J=5.2 Hz, 1H), 3.15 (s, 3H), 2.59 (s, 6H); LC-MS: m/z 414.0 [M+H]$^+$.

Example 96

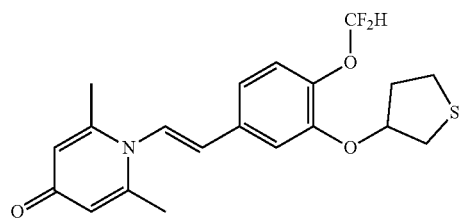 [SMILES: Cc1cc(=O)cc(C)n1/C=C/c1ccc(OC(F)F)c(OC2CCSC2)c1]

(E)-1-((3-(tetrahydrothiophen-3-yl)oxy-4-difluoromethoxy)-styryl)-2,6-dimethylpyridin-4(1H)-one
The specific reaction scheme is as shown below:

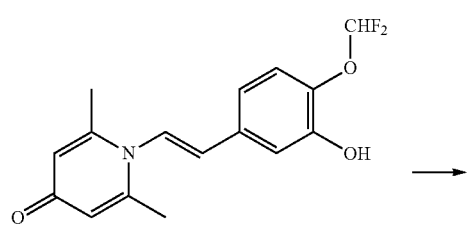

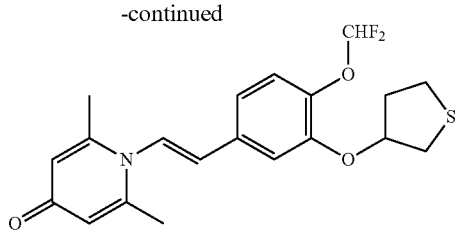

The compound (E)-1-(3-hydroxy-4-methoxystyryl)-2,6-dimethylpyridin-4(1H)-one (42 mg, 0.14 mmol) was dissolved in N,N-dimethylformamide (5 mL), and then tetrahydrothiophen-3-yl methanesulfonate (53 mg, 0.29 mmol) and cesium carbonate (95 mg, 0.29 mmol) were added, and stirred for 1 hr at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-1-(3-(tetrahydrothiophen-3-yl)oxy-4-difluoromethoxystyryl)-2,6-dimethylpyridin-4(1H)-one (30 mg, yield 54%, white solid). $^1$H NMR (400 MHz, CD$_3$OD) δ 7.41 (d, J=2.0 Hz, 1H), 7.27 (d, J=14.4 Hz, 1H), 7.26 (dd, J=8.4, 2.0 Hz, 1H), 7.21 (d, J=8.4 Hz, 1H), 6.91 (d, J=14.4 Hz, 1H), 6.79 (t, J$_{H-F}$=75.0 Hz, 1H), 6.65 (s, 2H), 5.36-5.32 (m, 1H), 3.16 (dd, J=12.0, 4.4 Hz, 1H), 3.11-3.02 (m, 2H), 2.99-2.94 (m, 1H), 2.49-2.41 (m, 1H), 2.45 (s, 6H), 2.10-2.01 (m, 1H); LC-MS: m/z 394.2 [M+H]$^+$.

Example 97

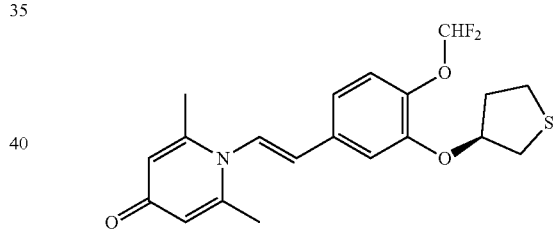

(S,E)-1-(3-(tetrahydrothiophen-3-yl)oxy-4-difluoromethoxystyryl)-2,6-dimethylpyridin-4(1H)-one
The specific reaction scheme is as shown below:

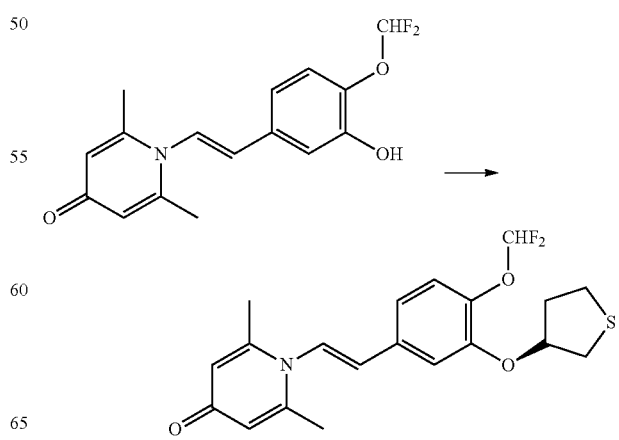

The compound (E)-1-(3-hydroxy-4-difluoromethoxystyryl)-2,6-dimethylpyridin-4(1H)-one (50 mg, 0.15 mmol) was dissolved in N,N-dimethylformamide (5 mL), and then (R)-tetrahydrothiophen-3-yl methanesulfonate (53 mg, 0.29 mmol) and cesium carbonate (95 mg, 0.29 mmol) were added, and stirred overnight at 80° C. under nitrogen atmosphere. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (S,E)-1-(3-(tetrahydrothiophen-3-yl)oxy-4-difluoromethoxystyryl)-2,6-dimethylpyridin-4(1H)-one (10 mg, yield 17%, pale yellow solid). $^1$H NMR (400 MHz, CDCl$_3$) δ 7.23 (d, J=8.4 Hz, 1H), 7.11 (dd, J=8.4, 2.0 Hz, 1H), 7.08 (d, J=2.0 Hz, 1H), 6.87 (d, J=14.4 Hz, 1H), 6.77 (d, J=14.4 Hz, 1H), 6.64 (d, J=14.4 Hz, 1H), 6.61 (t, J$_{H-F}$=74.8 Hz, 1H), 6.29 (s, 2H), 5.21-5.16 (m, 1H), 3.16-3.09 (m, 3H), 3.03-2.97 (m, 1H), 2.52-2.47 (m, 1H), 2.26 (s, 6H), 2.11-2.02 (m, 1H); LC-MS: m/z 394.2 [M+H]$^+$.

Example 98

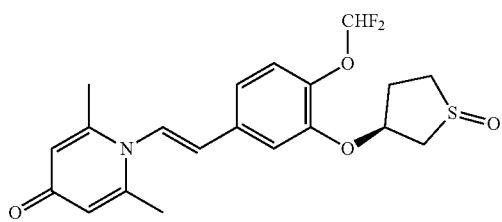 [SMILES: Cc1cc(=O)cc(C)n1/C=C/c1ccc(OC(F)F)c(O[C@H]2CCS(=O)C2)c1]

The specific reaction scheme is as shown below:

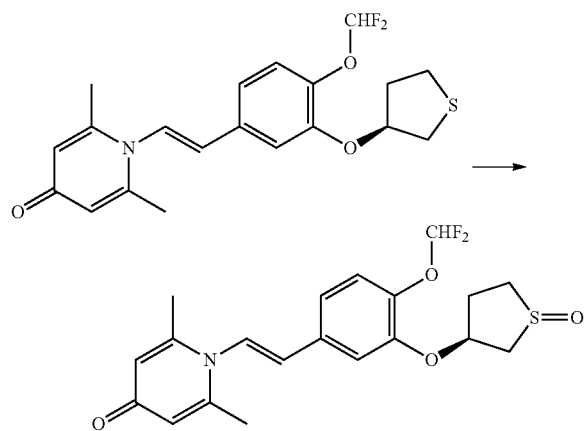

The compound (E)-1-((3-(tetrahydrothiophen-3-yl)oxy-4-difluoromethoxy)-styryl)-2,6-dimethylpyridin-4(1H)-one (103 mg, 0.26 mmol) was dissolved in dichloromethane (5 mL), and then 85% m-chloroperoxybenzoic acid (48 mg, 0.24 mmol) was added and stirred for 2 hours at 0° C. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave a diastereoisomer of 1-((E)-4-difluoromethoxy-3-(((3S)-1-oxotetrahydrothiophen-3-yl)oxy)styryl)-2,6-dimethylpyridin-4(1H)-one shown below:

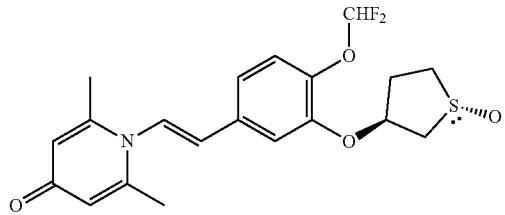

(42 mg, yield 39%, pale yellow oil). $^1$H NMR (400 MHz, CDCl$_3$) δ 7.48 (s, 1H), 7.37 (d, J=14.4 Hz, 1H), 7.24 (d, J=8.4 Hz, 1H), 7.08 (d, J=8.4 Hz, 1H), 6.94 (s, 2H), 6.81 (d, J=14.4 Hz, 1H), 6.80 (t, J$_{H-F}$=72.4 Hz, 1H), 5.46-5.38 (m, 1H), 3.46-3.38 (m, 1H), 3.33-3.17 (m, 3H), 2.94-2.85 (m, 1H), 2.54 (s, 6H), 2.41-2.32 (m, 1H); LC-MS: m/z 410.1 [M+H]$^+$.

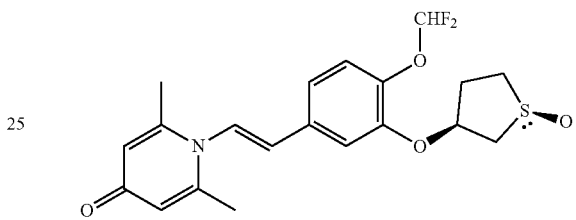

(30 mg, yield 28%, pale yellow oil). $^1$H NMR (400 MHz, CDCl$_3$) δ 7.35 (s, 1H), 7.30 (d, J=14.4 Hz, 1H), 7.23 (d, J=8.4 Hz, 1H), 7.16 (dd, J=8.4, 1.2 Hz, 1H), 6.95 (s, 2H), 6.82 (d, J=14.4 Hz, 1H), 6.48 (t, J$_{H-F}$=73.6 Hz, 1H), 5.58-5.53 (m, 1H), 3.60 (d, J=15.2 Hz, 1H), 3.17 (dd, J=15.2, 4.8 Hz, 1H), 3.11-3.07 (m, 2H), 2.90-2.80 (m, 1H), 2.65-2.61 (m, 1H), 2.51 (s, 6H); LC-MS: m/z 410.1 [M+H]$^+$.

Example 99

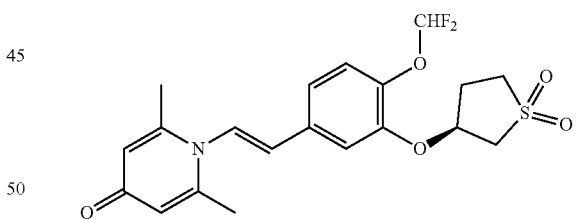

(S,E)-1-(3-(1,1-dioxotetrahydrothiophen-3-yl)oxy-4-difluoromethoxystyryl)-2,6-dimethylpyridin-4(1H)-one The specific reaction scheme is as shown below:

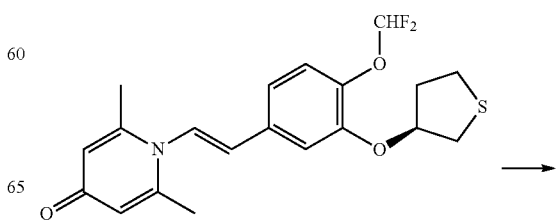

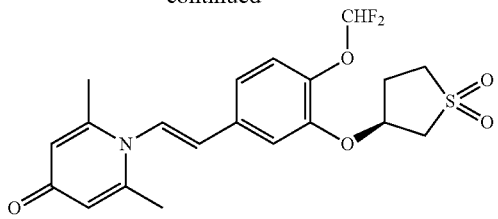

The compound (E)-1-((3-(tetrahydrothiophen-3-yl)oxy-4-methoxy)-styryl)-2,6-dimethylpyridin-4(1H)-one (55 mg, 0.14 mmol) was dissolved in dichloromethane (5 mL), and then 85% m-chloroperoxybenzoic acid (85 mg, 0.42 mmol) was added and stirred for 3 hours at room temperature. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (S,E)-1-(3-(1,1-dioxotetrahydrothiophen-3-yl)oxy-4-difluoromethoxystyryl)-2,6-dimethylpyridin-4(1H)-one (52 mg, yield 86%, white solid). $^1$H NMR (400 MHz, CDCl$_3$) δ 7.44 (s, 1H), 7.36 (d, J=14.0, Hz, 1H), 7.27 (d, J=8.4 Hz, 1H), 7.14 (d, J=8.4 Hz, 1H), 6.96 (s, 2H), 6.81 (d, J=14.0 Hz, 1H), 6.60 (t, J$_{H-F}$=73.6 Hz, 1H), 5.45-5.40 (m, 1H), 3.50-3.35 (m, 3H), 3.27-2.21 (m, 1H), 2.70-2.58 (m, 2H), 2.53 (s, 6H); LC-MS m/z 426.0 [M+H]$^+$.

Example 100

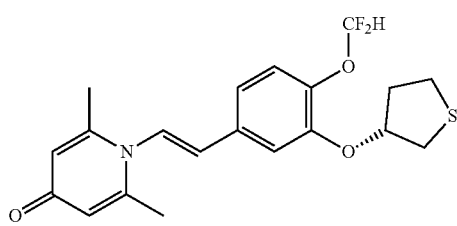

(R,E)-1-(3-(tetrahydrothiophen-3-yl)oxy-4-difluoromethoxystyryl)-2,6-dimethylpyridin-4(1H)-one The specific reaction scheme is as shown below:

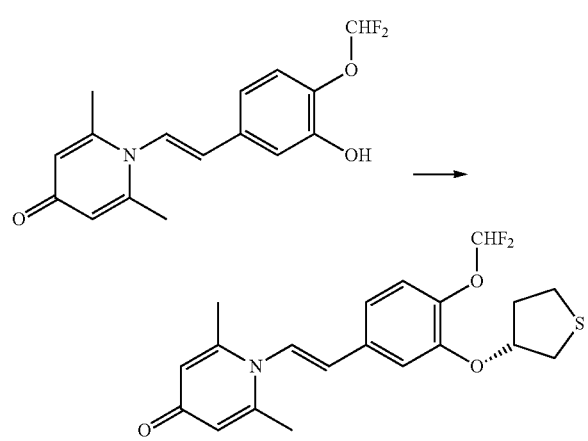

The compound (E)-1-(3-hydroxy-4-difluoromethoxystyryl)-2,6-dimethylpyridin-4(1H)-one (200 mg, 0.58 mmol) was dissolved in N,N-dimethylformamide (10 mL), and then (S)-tetrahydrothiophen-3-yl methanesulfonate (212 mg, 1.16 mmol) and cesium carbonate (758 mg, 2.3 mmol) were added, and stirred overnight at 80° C. under nitrogen atmosphere. After the reaction was completed, saturated saline (20 mL) was added, and extracted with dichloromethane (3×20 mL). The organic phases were combined, and dried over anhydrous sodium sulfate. Filtration, rotary drying, and purification by reverse-phase HPLC gave (R,E)-1-(3-(tetrahydrothiophen-3-yl)oxy-4-difluoromethoxystyryl)-2,6-dimethylpyridin-4(1H)-one (30 mg, yield 13%, white solid). $^1$H NMR (400 MHz, CDCl$_3$) δ 7.23 (d, J=8.4 Hz, 1H), 7.11 (dd, J=8.4 2.0 Hz, 1H), 7.08 (d, J=2.0 Hz, 1H), 6.89 (d, J=14.4 Hz, 1H), 6.65 (d, J=14 Hz, 1H), 6.60 (m, J=14.4 Hz, 1H), 6.63 (t, J=74.8 Hz, 1H), 6.31 (s, 2H), 5.21-5.16 (m, 1H), 3.16-3.09 (m, 3H), 3.03-2.97 (m, 1H), 2.52-2.47 (m, 1H), 2.26 (s, 6H), 2.11-2.02 (m, 1H); LC-MS m/z 394.0 [M+H]$^+$.

Example 101

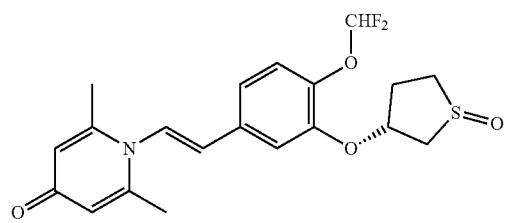

1-((E)-4-difluoromethoxy-3-(((3R)-1-oxotetrahydrothiophen-3-yl)oxy)styryl)-2,6-dimethylpyridin-4(1H)-one The specific reaction scheme is as shown below:

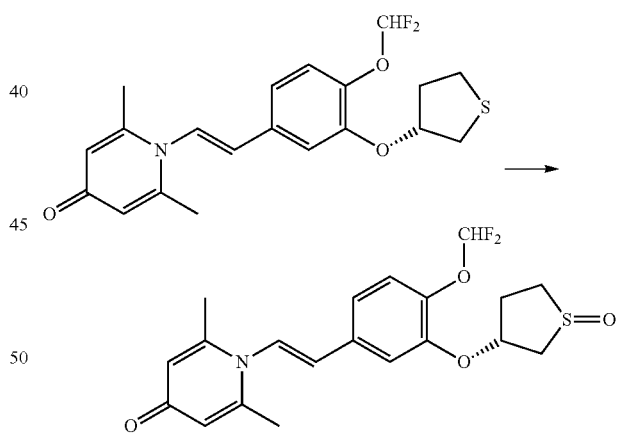

The compound (R,E)-1-(3-(tetrahydrothiophen-3-yl)oxy-4-difluoromethoxystyryl)-2,6-dimethylpyridin-4(1H)-one (55 mg, 0.14 mmol) was dissolved in dichloromethane (5 mL), and then 85% m-chloroperoxybenzoic acid (26 mg, 0.13 mmol) was added and stirred for 3 hours at 0° C. Then, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave a diastereoisomer of 1-((E)-4-difluoromethoxy-3-(((3R)-1-oxotetrahydrothiophen-3-yl)oxy)styryl)-2,6-dimethylpyridin-4(1H)-one shown below:

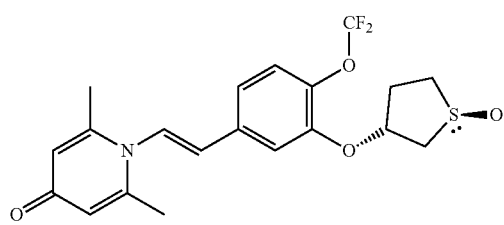

(20 mg, yield 35%, pale yellow oil). $^1$H NMR (400 MHz, CD$_3$Cl) δ 7.50 (s, 1H), 7.20 (d, J=12.8 Hz, 1H), 7.24 (d, J=8.4 Hz, 1H), 7.07 (d, J=8.4 Hz, 1H), 6.95 (s, 2H), 6.82 (s, 1H), 6.80 (m, J=76.4 Hz, 1H), 5.43 (m, 1H), 3.44-3.38 (m, 2H), 3.29-3.16 (m, 2H), 2.92-2.89 (m, 1H), 2.54 (s, 6H), 2.41-2.33 (m, 1H); LC-MS: m/z 410.0 [M+H]$^+$.

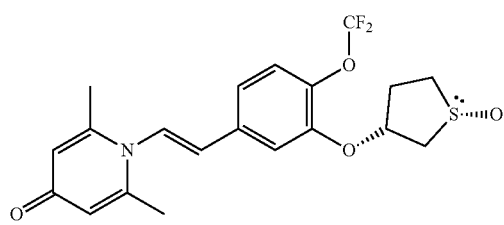

(10 mg, yield 17%, pale yellow oil)$^1$H NMR (400 MHz, CD$_3$Cl) δ 7.34 (s, 1H), 7.30 (d, J=14.4 Hz, 1H), 7.23 (d, J=8.4 Hz, 1H), 7.15 (d, J=8.4 Hz, 1H), 6.94 (s, 2H), 6.82 (d, J=14.4 Hz, 1H), 6.48 (t, J=73.6 Hz, 1H), 5.55 (m, 1H), 3.59 (d, J=14.8 Hz, 1H), 3.19-3.14 (m, 1H), 3.11-3.08 (m, 2H), 2.90-2.81 (m, 1H), 2.64-2.61 (m, 1H), 2.54 (s, 6H); LC-MS: m/z 410.0 [M+H]$^+$.

Example 102

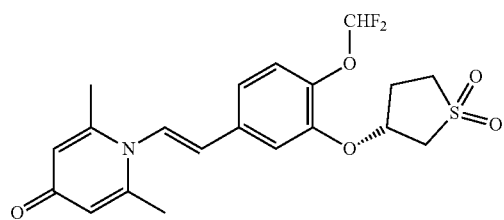

(R,E)-1-(3-(1,1-dioxotetrahydrothiophen-3-yl)oxy-4-difluoromethoxystyryl)-2,6-dimethylpyridin-4(1H)-one The specific reaction scheme is as shown below:

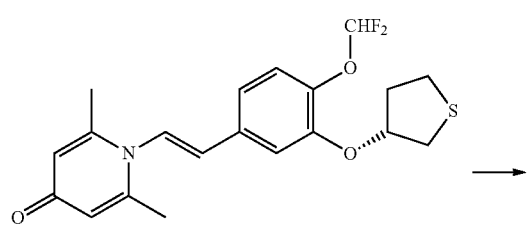

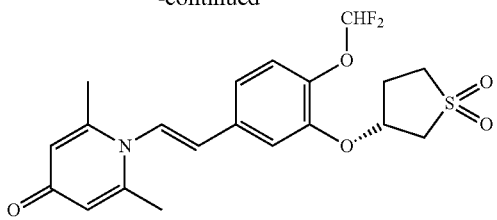

The compound (R,E)-1-(3-(tetrahydrothiophen-3-yl)oxy-4-difluoromethoxystyryl)-2,6-dimethylpyridin-4(1H)-one (40 mg, 0.1 mmol) was dissolved in dichloromethane (5 mL), and then 85% m-chloroperoxybenzoic acid (61 mg, 0.3 mmol) was added and stirred for 2 hours at room temperature. After the reaction was completed, a saturated aqueous sodium sulfite solution (10 mL) was added, stirred for 10 min, and extracted with dichloromethane (3×10 mL). The organic phases were combined, and dried over anhydrous sodium sulfate. Filtration, rotary drying, and purification by reverse-phase HPLC gave (R,E)-1-(3-(1,1-dioxotetrahydrothiophen-3-yl)oxy-4-difluoromethoxystyryl)-2,6-dimethylpyridin-4(1H)-one (33 mg, yield 75%, white solid). $^1$H NMR (400 MHz, CD$_3$OD) δ 7.43 (d, J=1.6 Hz, 1H), 7.38 (dd, J=8.4, 2.0 Hz, 1H), 7.36 (d, J=2.0 Hz, 1H), 7.31 (d, J=8.4 Hz, 1H), 7.06 (s, 2H), 7.01 (d, J=14.4 Hz, 1H), 6.87 (t, J=75.2 Hz, 1H), 5.43-5.39 (m, 1H), 3.56-8.51 (m, 1H), 3.44-3.36 (m, 2H), 3.31-3.25 (m, 1H), 2.66-2.62 (m, 2H), 2.61 (s, 6H); LC-MS: m/z 426.0 [M+H]$^+$.

Example 103

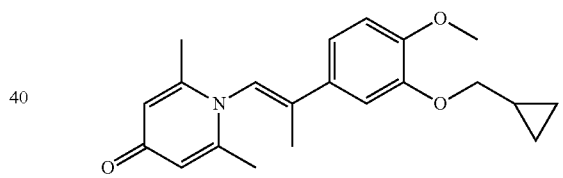

(E)-1-(2-(3-cyclopropylmethoxy-4-methoxyphenyl)-2-methylethenyl)-2,6-dimethylpyridin-4(1H)-one The specific reaction scheme is as shown below:

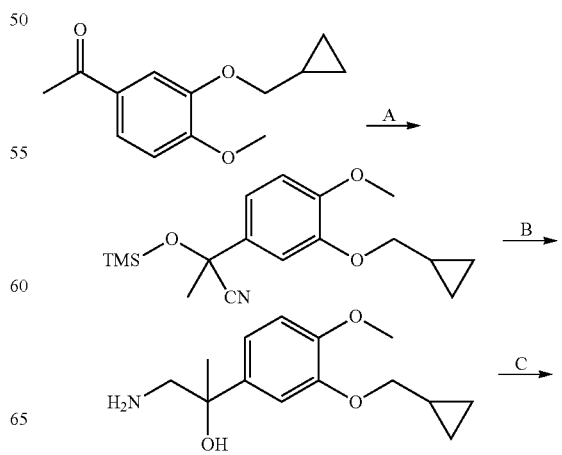

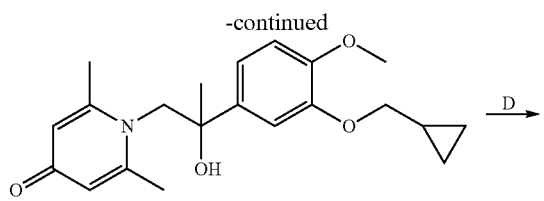

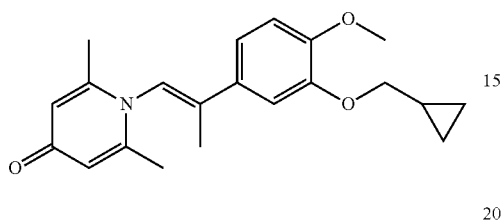

Step A:
3-Cyclopropylmethoxy-4-methoxyphenylacetophenone (220 mg, 1.0 mmol) was dissolved in acetonitrile (2 mL); and under nitrogen atmosphere, cesium fluoride (76 mg, 0.50 mmol) was added, trimethylsilyl cyanide (149 mg, 1.50 mmol) was slowly added dropwise at 0° C., and stirred for 5 hours. The reaction solution was filtered, and rotary dried to obtain a crude product of 2-(3-cyclopropylmethoxy-4-methoxyphenyl)-2-trimethylsiloxy-propionitrile. LC-MS: m/z 320.2 [M+H]$^+$.

Step B:
The compound 2-(3-cyclopropylmethoxy-4-methoxyphenyl)-2-trimethylsiloxy-propionitrile (319 mg, 1.0 mmol) was dissolved in anhydrous tetrahydrofuran (3 mL); and under nitrogen atmosphere, lithium aluminum hydride (96 mg, 2.0 mmol) was slowly added dropwise at 0° C., and the solution was stirred at room temperature for 1 hr. After the reaction was completed, sodium sulfate decahydrate was added to quench the reaction. Then, the reaction solution was filtered, and the filtrate was rotary dried to obtain a crude product of 1-amino-2-(3-(cyclopropylmethoxy)-4-methoxyphenyl)-2-propanol. LC-MS: m/z 252.2 [M+H]$^+$.

Step C:
The compound 1-amino-2-(3-(cyclopropylmethoxy)-4-methoxyphenyl)-2-propanol (251 mg, 1.0 mmol) was dissolved in ethanol (3 mL), and then 2,6-dimethyl-4H-pyran-4-one (186 mg, 1.5 mmol) and sodium hydroxide (80 mg, 2.0 mmol) were added, and stirred overnight at 60° C. The reaction was complete as indicated by LCMS. The reaction solution was rotary dried, and purified to obtain 1-(2-(3-(cyclopropylmethoxy)-4-methoxyphenyl)-2-hydroxypropyl)-2,6-dimethylpyridin-4(1H)-one (40 mg, yield 11%). LC-MS: m/z 358.0 [M+H]$^+$.

Step D:
The compound 1-(2-(3-cyclopropylmethoxy-4-methoxyphenyl)-2-hydroxypropyl)-2,6-dimethylpyridin-4(1H)-one (36 mg, 0.1 mmol) was dissolved in toluene (3 mL), and then p-toluenesulfonic acid (29 mg, 0.15 mmol) was added and stirred overnight at 110° C. The reaction was complete as indicated by TLC. The reaction solution was rotary dried, and purified by reverse-phase HPLC to obtain (E)-1-(2-(3-cyclopropylmethoxy-4-methoxyphenyl)-2-methylethenyl)-2,6-dimethylpyridin-4(1H)-one (27 mg, yield 80%, white solid). $^1$H NMR (400 MHz, CDCl$_3$) δ 7.05-7.03 (m, 1H), 6.92-6.90 (m, 2H), 6.68 (s, 2H), 6.10 (s, 1H), 3.92 (s, 3H), 3.88 (d, J=6.8 Hz, 2H), 2.42 (s, 3H), 2.52 (s, 6H), 1.12-1.06 (m, 1H), 0.72-0.68 (m, 2H), 0.40-0.36 (m, 2H); LC-MS: m/z 340.2 [M+H]$^+$.

Example 104

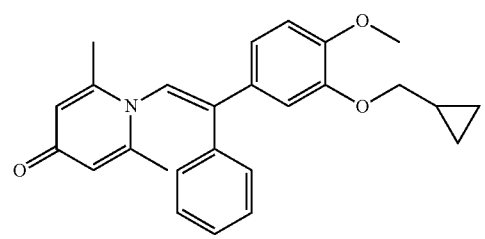 [SMILES: COc1ccc(/C(=C/n2c(C)cc(=O)cc2C)c2ccccc2)cc1OCC1CC1]

(E)-1-(2-(3-cyclopropylmethoxy-4-methoxyphenyl)-2-phenylethenyl)-2,6-dimethylpyridin-4(1H)-one

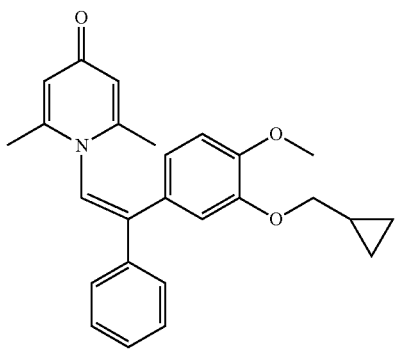 [SMILES: COc1ccc(/C(=C\n2c(C)cc(=O)cc2C)c2ccccc2)cc1OCC1CC1]

(Z)-1-(2-(3-cyclopropylmethoxy-4-methoxyphenyl)-2-phenylethenyl)-2,6-dimethylpyridin-4(1H)-one

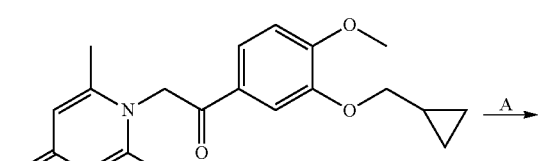

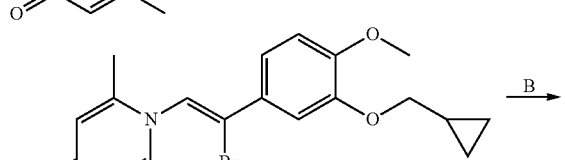

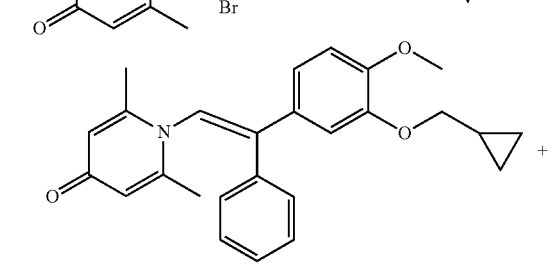

115
-continued

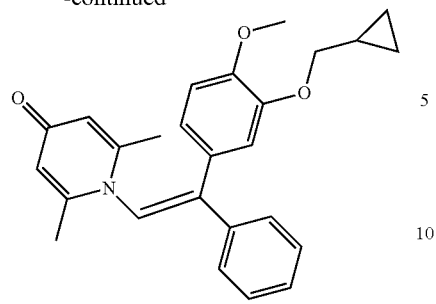

116
Example 105

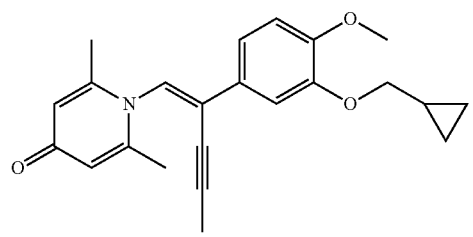 [SMILES: CC#C/C(=C\n1c(C)cc(=O)cc1C)c1ccc(OC)c(OCC2CC2)c1]

(Z)-1-(2-(3-cyclopropylmethoxy-4-methoxyphenyl)pent-1-en-3-yn-1-yl)-2,6-dimethylpyridin-4(1H)-one The specific reaction scheme is as shown below:

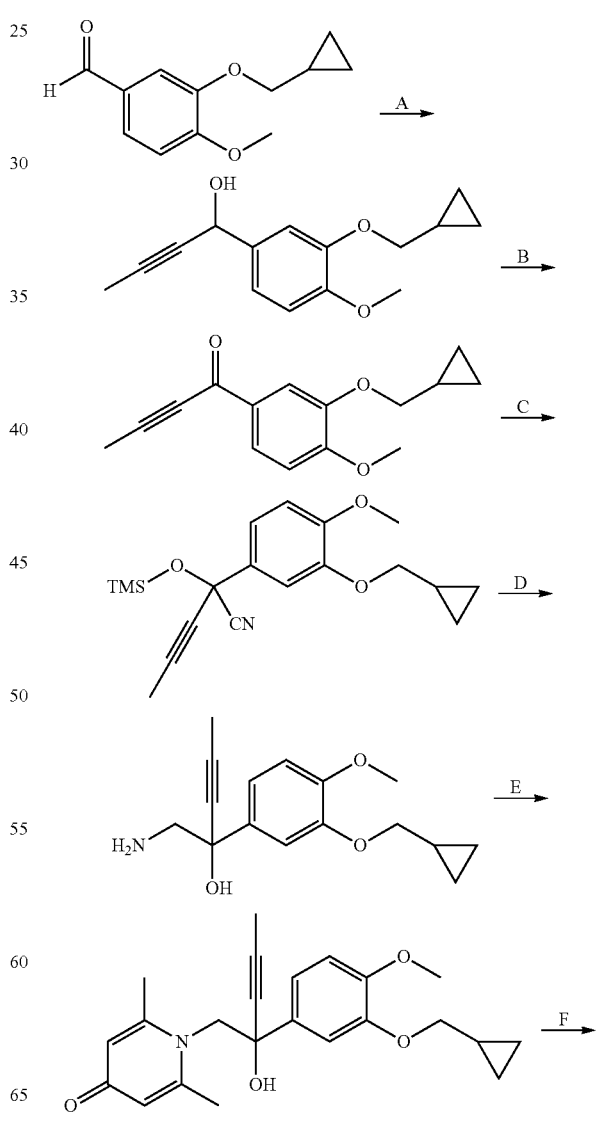

Step A:

Trisphenyl phosphite (1.49 g, 4.80 mmol) was dissolved in anhydrous tetrahydrofuran (15 mL), and then triethyl amine (0.53 mg, 5.20 mmol) and the compound 1-(2-(3-cyclopropylmethoxy-4-methoxyphenyl)-2-oxoethyl)pyridin-2,6-dimethyl-4(1H)-one (1.36 mg, 4.00 mmol) was slowly added to the reaction solution at −60° C. and stirred for 15 min. Then, bromine (0.77 mg, 4.80 mmol) was slowly added to the reaction solution. After the reaction was completed, the reaction was quenched with a saturated aqueous ammonium chloride solution, and the reaction solution was directly rotary dried, and purified by column chromatography to obtain 1-(2-(3-cyclopropylmethoxy-4-methoxyphenyl)-2-bromoethenyl)-2,6-dimethylpyridin-4(1H)-one (708 mg, yield 44%). LC-MS: m/z 403.9 [M+H]+.

Step B:

The compound 1-(2-(3-cyclopropylmethoxy-4-methoxyphenyl)-2-bromoethenyl)-2,6-dimethylpyridin-4(1H)-one (200 mg, 0.50 mmol) was dissolved in tetrahydrofuran (2 mL) and water (1 mL). Under nitrogen atmosphere, palladium acetate (5.5 mg, 5 mol %), sodium carbonate (5 mg, 0.50 mmol) and phenylboronic acid (73.0 mg, 0.60 mmol) were added to the reaction solution, and stirred at 80° C. for 1 hr. After the reaction was completed, a saturated ammonium chloride solution (10 mL) was added, and extracted with dichloromethane (3×10 mL). The organic phases were combined, and dried over anhydrous sodium sulfate. The reaction solution was filtered, rotary dried, and purified by reverse-phase HPLC to obtain (E)-1-(2-(3-cyclopropylmethoxy-4-methoxyphenyl)-2-phenylethenyl)-2,6-dimethylpyridin-4(1H)-one (69 mg, yield 34%, white solid) and (Z)-1-(2-(3-cyclopropylmethoxy-4-methoxyphenyl)-2-phenylethenyl)-2,6-dimethylpyridin-4(1H)-one (30.4 mg, yield 15%, white solid).

(E)-1-(2-(3-cyclopropylmethoxy-4-methoxyphenyl)-2-phenylethenyl)-2,6-dimethylpyridin-4(1H)-one: $^1$H NMR (400 MHz, CDCl$_3$) δ 8.40 (s, 1H), 8.35 (s, 1H), 8.06-8.04 (m, 2H), 7.68-7.66 (m, 3H), 7.26-7.20 (m, 2H), 7.04 (d, J=8.4 Hz, 1H), 6.33 (m, 1H), 3.85 (d, J=6.8 Hz, 2H), 3.81 (s, 3H), 2.83 (s, 6H), 0.89-0.82 (m, 1H), 0.62-0.58 (m, 2H), 0.34-0.30 (m, 2H); LC-MS: m/z 401.9 [M+H]+.

(Z)-1-(2-(3-cyclopropylmethoxy-4-methoxyphenyl)-2-phenylethenyl)-2,6-dimethylpyridin-4(1H)-one: $^1$H NMR (400 MHz, CDCl$_3$) δ 8.50 (s, 1H), 8.39 (s, 1H), 8.12-8.08 (m, 2H), 7.65-7.62 (m, 3H), 7.32 (J=8.4 Hz, 1H), 7.10-7.00 (m, 2H), 6.13 (m, 1H), 3.86 (d, J=6.8 Hz, 2H), 3.81 (s, 3H), 2.83 (s, 6H), 0.89-0.82 (m, 1H), 0.62-0.58 (m, 2H), 0.34-0.30 (m, 2H); LC-MS: m/z 401.9 [M+H]+.

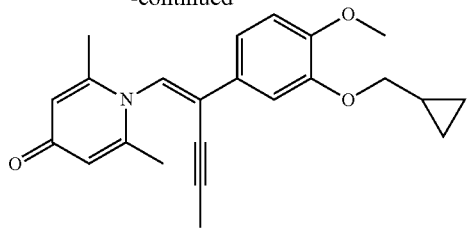

Step A:

3-(cyclopropylmethoxy)-4-methoxybenzaldehyde (1.03 g, 5 mmol) was dissolved in anhydrous tetrahydrofuran (5 mL); and under nitrogen atmosphere, 1-ethynylmagnesium bromide (0.5 M, 12 mL, 6 mmol) was added dropwise at 0° C., warmed to room temperature, and stirred for 3 hours at room temperature. The reaction was quenched with a saturated aqueous ammonium chloride solution, and extracted with dichloromethane (3×30 mL). The organic phases were combined, dried over anhydrous sodium sulfate, filtered, and rotary dried to obtain a crude product of 1-(3-cyclopropylmethoxy-4-methoxyphenyl)-2-alkynyl-1-butanol (1.50 g). LC-MS: m/z 228.9 [M−17]$^+$.

Step B:

The compound 1-(3-cyclopropylmethoxy-4-methoxyphenyl)-2-alkynyl-1-butanol (1.50 g, 5 mmol) was dissolved in dichloromethane (20 mL); and Dess-Martin Periodinane (3.18 g, 7.5 mmol) and solid sodium bicarbonate (6.30 g, 75 mmol) were added at 35° C., and stirred for 1 hr. After the reaction was completed, a saturated sodium bicarbonate solution was added, and extracted with dichloromethane (3×30 mL). The organic phases were combined, and dried over anhydrous sodium sulfate, filtered, rotary dried, and purified to obtain a crude product of 1-(3-cyclopropylmethoxy-4-methoxyphenyl)-2-alkynyl-1-butanol, which was directly used in the next reaction. LC-MS: m/z 249.9 [M+H]$^+$.

Step C:

The compound 1-(3-cyclopropylmethoxy-4-methoxyphenyl)-2-alkynyl-1-butanone (336 mg, 1.5 mmol) was dissolved in acetonitrile (5 mL); and under nitrogen atmosphere, cesium fluoride (114 mg, 0.75 mmol) was added, trimethylsilyl cyanide (225 mg, 2.25 mmol) was slowly added dropwise at 0° C., and stirred for 1.5 hours. After the reaction was completed, the reaction solution was filtered, and rotary dried to obtain a crude product of 2-(3-cyclopropylmethoxy-4-methoxyphenyl)-2-(trimethylsiloxy)pent-3-ynyl nitrile. LC-MS: m/z 344.2 [M+H]$^+$.

Step D:

The compound 2-(3-cyclopropylmethoxy-4-methoxyphenyl)-2-(trimethylsiloxy)-3-alkynylpentyl nitrile (413 mg, 1.5 mmol) was dissolved in anhydrous tetrahydrofuran (4 mL); and under nitrogen atmosphere, lithium aluminum hydride (114 mg, 3.0 mmol) was slowly added dropwise at 0° C., and the solution was stirred at room temperature for 1 hr. After the reaction was completed, sodium sulfate decahydrate was added to quench the reaction. The reaction solution was filtered, and the filtrate was rotary dried to obtain a crude product of 1-amino-2-(3-cyclopropylmethoxy)4-methoxyphenyl)-3-alkynyl-2-pentanol. LC-MS: m/z 276.2 [M+H]$^+$.

Step E:

The compound 1-amino-2-(3-(cyclopropylmethoxy)-4-methoxyphenyl)-3-alkynyl-2-pentanol (413 mg, 1.5 mmol) was dissolved in ethanol (5 mL), and then 2,6-dimethylpyran-4-one (279 mg, 2.25 mmol) and sodium hydroxide (120 mg, 3.0 mmol) were added, and stirred overnight at 60° C. The reaction was complete as indicated by LCMS. The reaction solution was rotary dried, and purified to obtain 1-(2-(3-cyclopropylmethoxy-4-methoxyphenyl)-2-hydroxypent-3-yn-1-yl)-2,6-dimethylpyridin-4(1H)-one (20 mg, yield 3%). $^1$H NMR (400 MHz, CDCl$_3$) δ 7.12-7.07 (m, 2H), 6.86 (d, J=8.4 Hz, 1H), 6.20 (s, 1H), 6.10 (s, 1H), 4.22-4.12 (m, 2H), 3.88 (s, 3H), 3.83 (d, J=7.2 Hz, 2H), 2.42 (s, 3H), 2.20 (s, 3H), 1.88 (s, 3H), 1.34-1.28 (m, 1H), 0.67-0.62 (m, 2H), 0.39-0.35 (m, 2H); LC-MS: m/z 381.9 [M+H]$^+$.

Step F:

The compound 1-(2-(3-cyclopropylmethoxy-4-methoxyphenyl)-2-hydroxypent-3-yn-1-yl)-2,6-dimethylpyridin-4(1H)-one (20 mg, 0.05 mmol) was dissolved in toluene (3 mL), and then p-toluenesulfonic acid (15 mg, 0.08 mmol) was added and stirred overnight at 60° C. The reaction was complete as indicated by TLC. The reaction solution was rotary dried, and purified to obtain (Z)-1-(2-(3-cyclopropylmethoxy-4-methoxyphenyl)pent-1-en-3-yn-1-yl)-2,6-dimethylpyridin-4(1H)-one (18 mg, yield 90%, white solid). $^1$H NMR (400 MHz, CDCl$_3$) δ 7.27 (dd, J=8.4, 2.0 Hz, 1H), 7.16 (J=8.4 Hz, 1H), 6.92-6.90 (m, 2H), 6.31 (s, 2H), 3.92-3.90 (m, 5H), 2.25 (s, 6H), 1.98 (s, 3H), 1.40-1.31 (m, 1H), 0.70-0.65 (m, 2H), 0.41-0.37 (m, 2H). LC-MS: m/z 363.9 [M+H]$^+$.

Example 106

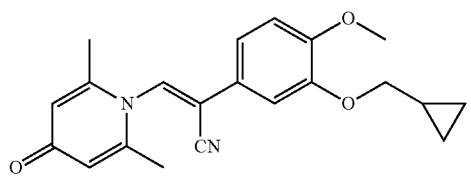 [SMILES: COc1ccc(/C(C#N)=C/n2c(C)cc(=O)cc2C)cc1OCC1CC1]

(E)-1-(2-(3-cyclopropylmethoxy-4-methoxyphenyl)-2-cyanoethenyl)-2,6-dimethylpyridin-4(1H)-one The specific reaction scheme is as shown below:

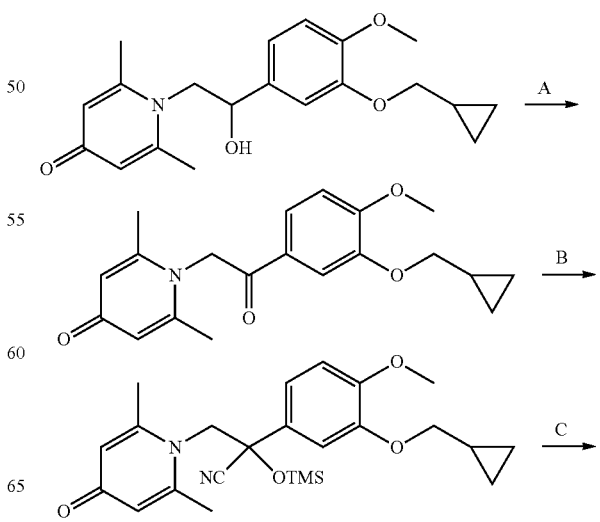

119

-continued

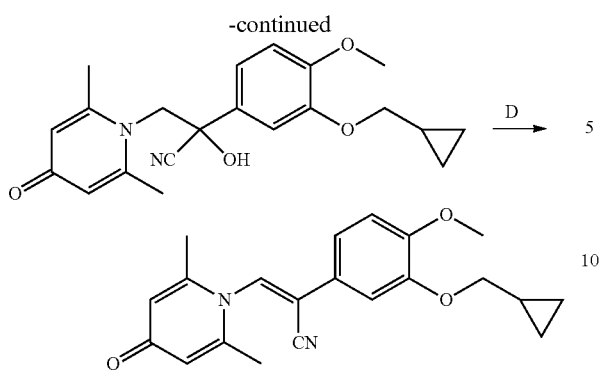

Step A:

The compound 1-(2-(3-cyclopropylmethoxy-4-methoxyphenyl)-2-hydroxyethyl)-2,6-dimethylpyridin-4(1H)-one (2.50 g, 7.3 mmol) was dissolved in dichloromethane (50 mL); and Dess-Martin Periodinane (4.80 g, 11.0 mmol) and sodium bicarbonate (9.00 g, 110 mmol) were slowly added at 35° C., and stirred for 1 hr. After the reaction was completed, a saturated sodium bicarbonate solution (50 mL) was added, and extracted with dichloroethane (3×30 mL). The organic phases were combined and dried over anhydrous sodium sulfate. Filtration, rotary drying, and purification gave 1-(2-(3-cyclopropylmethoxy-4-methoxyphenyl)-2-oxoethyl)-2, 6-dimethylpyridin-4(1H)-one (1.98 g, yield 80%, white solid). LC-MS: m/z 342.4 [M+H]⁺.

Step B:

The compound 1-(2-(3-cyclopropylmethoxy-4-methoxyphenyl)-2-oxoethyl)-2,6-dimethylpyridin-4(1H)-one (500 mg, 1.5 mmol) was dissolved in acetonitrile (25 mL); and under nitrogen atmosphere, triethyl amine (456 mg, 4.5 mmol) was added, trimethylsilyl cyanide (600 mg, 6.0 mmol) was slowly added dropwise at 0° C., and stirred for 4 hours. The reaction solution was rotary dried to obtain a crude product of 1-(2-(3-cyclopropylmethoxy-4-methoxyphenyl)-2-cyano-2-(trimethylsilyloxy)ethyl)-2,6-dimethylpyridin-4(1H)-one. LC-MS: m/z 441.4 [M+H]⁺.

Step C:

The compound 1-(2-(3-cyclopropylmethoxy-4-methoxyphenyl)-2-cyano-2-(trimethylsilyloxy)ethyl)-2,6-dimethylpyridin-4(1H)-one (660 mg, 1.5 mmol) was dissolved in acetonitrile (25 mL), and aqueous hydrochloric acid (3M, 1.5 mL) was added and stirred at 80° C. for 0.5 hours. The reaction was complete as indicated by TLC. The reaction solution was rotary dried to obtain a crude product of 1-(2-(3-cyclopropylmethoxy-4-methoxyphenyl)-2-cyano-2-hydroxyethyl)-2,6-dimethylpyridin-4(1H)-one. LC-MS: m/z 369.4 [M+H]⁺.

Step D:

The compound 1-(2-(3-cyclopropylmethoxy-4-methoxyphenyl)-2-cyano-2-hydroxyethyl)-2,6-dimethylpyridin-4 (1H)-one (552 mg, 1.5 mmol) was dissolved in chloroform (25 mL), and then thionyl chloride (1.0 mL) was added and stirred for 0.5 hours at 80° C. The reaction was complete as indicated by TLC. The reaction solution was rotary dried, and purified to obtain (E)-1-(2-(3-cyclopropylmethoxy-4-methoxyphenyl)-2-cyanoethenyl)-2,6-dimethylpyridin-4 (1H)-one (283 mg, 54%, white solid). ¹H NMR (400 MHz, CDCl₃) δ 7.44 (s, 1H), 7.29 (d, J=2.0 Hz, 1H), 7.14 (d, J=1.2 Hz, 1H), 6.97 (d, J=8.4 Hz, 1H), 6.36 (s, 2H), 3.95-3.92 (m, 5H), 2.30 (s, 6H), 1.38-1.30 (m, 1H), 0.71-0.67 (m, 2H), 0.42-0.38 (m, 2H). LC-MS: m/z 351.4 [M+H]⁺.

120

Example 107

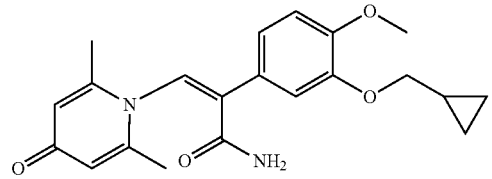

(Z)-2-(3-cyclopropylmethoxy-4-methoxyphenyl)-3-(2,6-dimethyl-4-carbonylpyridin-1(4H)-yl)-acrylamide The specific reaction scheme is as shown below:

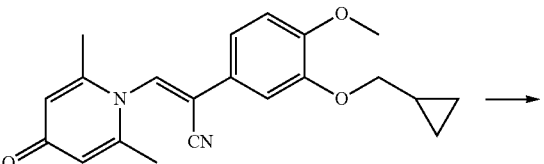

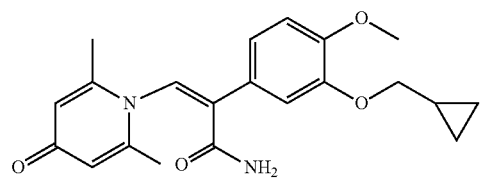

(E)-1-(2-(3-cyclopropylmethoxy-4-methoxyphenyl)-2-cyanoethenyl)-2,6-dimethylpyridin-4(1H)-one (500 mg, 1.4 mmol) was dissolved in acetonitrile (10 mL), and then potassium hydroxide (10 wt %, 10 mL) was added at room temperature and stirred at 80° C. for 2 hours. The reaction was complete as indicated by TLC. The reaction solution was directly rotary dried, and purified by column chromatography to obtain (Z)-2-(3-cyclopropylmethoxy-4-methoxyphenyl)-3-(2,6-dimethyl-4-carbonylpyridin-1(4H)-yl)-acrylamide (140 mg, 27%, white solid). ¹H NMR (400 MHz, DMSO-d₆) δ 7.73 (s, 1H), 7.56 (s, 1H), 7.13 (s, 1H), 7.04 (s, 2H), 6.99 (s, 1H), 5.96 (s, 2H), 3.85 (d, J=7.2 Hz, 2H), 3.80 (s, 3H), 2.27 (m, 6H), 0.87-0.84 (m, 1H), 0.61-0.56 (m, 2H), 0.35-0.31 (m, 2H); LC-MS: m/z 369.1 [M+H]⁺.

Example 108

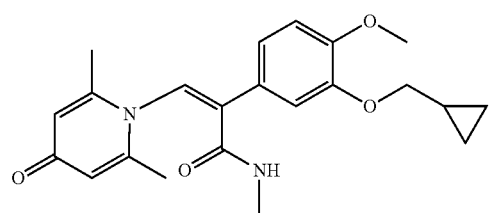 [SMILES: CNC(=O)/C(=C\n1c(C)cc(=O)cc1C)c1ccc(OC)c(OCC2CC2)c1]

(Z)-2-(3-cyclopropylmethoxy-4-methoxyphenyl)-3-(2,6-dimethyl-4-carbonylpyridin-1(4H)-yl)-N-methylacrylamide
The specific reaction scheme is as shown below:

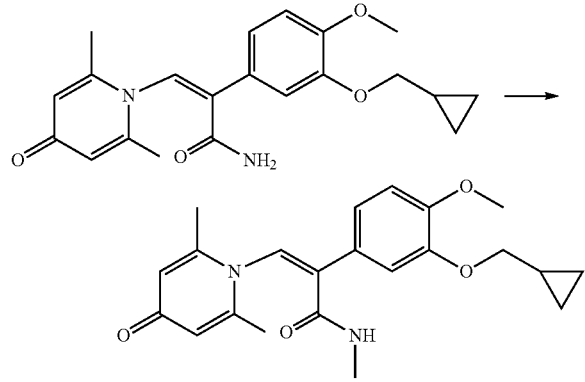

The compound (Z)-2-(3-cyclopropylmethoxy-4-methoxyphenyl)-3-(2,6-dimethyl-4-carbonylpyridin-1(4H)-yl)-acrylamide (30 mg, 0.08 mmol) was dissolved in N,N-dimethylformamide (0.5 mL), and then 60% sodium hydride (16 mg, 0.4 mmol) was added, and stirred at 70° C. for 0.5 hours. Iodomethane (12 mg, 0.08 mmol) was added to the reaction solution, and stirred at 70° C. for another 1 hr. The reaction solution was quenched with a saturated aqueous ammonium chloride solution, and the reaction solution was directly rotary dried, and purified by column chromatography to obtain (Z)-2-(3-cyclopropylmethoxy-4-methoxyphenyl)-3-(2,6-dimethyl-4-carbonylpyridin-1(4H)-yl)-N-methylacrylamide (5 mg, 17%, white solid). $^1$H NMR (400 MHz, CDCl$_3$) δ 7.04-7.02 (m, 1H), 6.93-6.91 (m, 2H), 6.63 (s, 1H), 6.28 (s, 2H), 6.02 (s, 1H), 3.92 (s, 3H), 3.88 (d, J=6.8 Hz, 2H), 2.81 (t, J=4.8 Hz, 3H), 2.34 (s, 6H), 0.97-0.83 (m, 1H), 0.76-0.62 (m, 2H), 0.40-0.36 (m, 2H); LC-MS: m/z 383.1 [M+H]$^+$.

Example 109

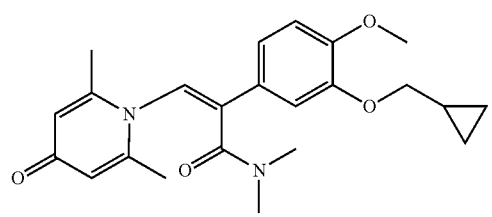 [SMILES: COc1ccc(/C(=C/n2c(C)cc(=O)cc2C)C(=O)N(C)C)cc1OCC1CC1]

(Z)-2-(3-cyclopropylmethoxy-4-methoxyphenyl)-3-(2,6-dimethyl-4-carbonylpyridin-1(4H)-yl)-N,N-dimethylacrylamide
The specific reaction scheme is as shown below:

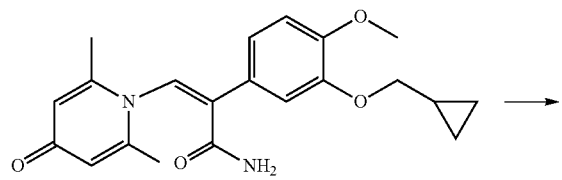

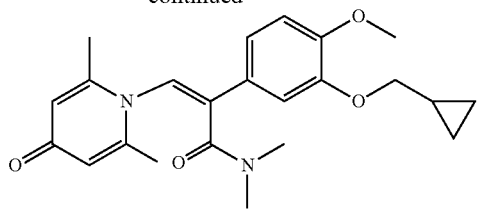

The compound (Z)-2-(3-cyclopropylmethoxy-4-methoxyphenyl)-3-(2,6-dimethyl-4-carbonylpyridin-1(4H)-yl)-acrylamide (30 mg, 0.08 mmol) was dissolved in N,N-dimethylformamide (0.5 mL), and then 60% sodium hydride (16 mg, 0.4 mmol) was added, and stirred at 70° C. for 0.5 hours. Iodomethane (24 mg, 0.16 mmol) was added to the reaction solution, and stirred at 70° C. for another 1 hr. The reaction was quenched with a saturated aqueous ammonium chloride solution, and the reaction solution was directly rotary dried and purified by column chromatography to obtain (Z)-2-(3-cyclopropylmethoxy-4-methoxyphenyl)-3-(2,6-dimethyl-4-carbonylpyridin-1(4H)-yl)-N,N-dimethylacrylamide (10 mg, 50%, white solid). $^1$H NMR (400 MHz, CDCl$_3$) δ 6.70-6.97 (m, 1H), 6.93-6.91 (m, 2H), 6.70 (s, 1H), 6.27 (s, 2H), 3.92 (s, 3H), 3.88 (d, J=6.8 Hz, 2H), 2.92 (s, 3H), 2.78 (s, 3H), 2.37 (s, 6H), 1.37-1.29 (m, 1H), 0.69-0.65 (m, 2H), 0.40-0.36 (m, 2H). LC-MS: m/z 397.1 [M+H]$^+$.

Example 110

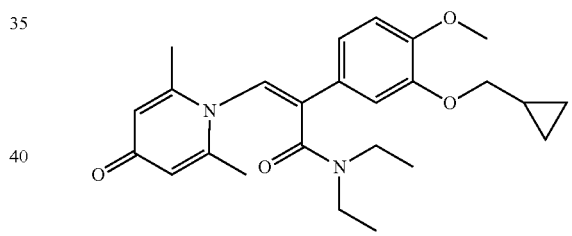

(Z)-2-(3-cyclopropylmethoxy-4-methoxyphenyl)-3-(2,6-dimethyl-4-carbonylpyridin-1(4H)-yl)-N,N-diethylacrylamide
The specific reaction scheme is as shown below:

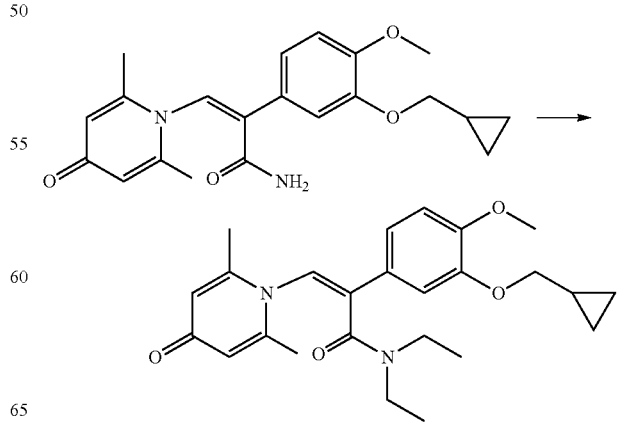

The compound (Z)-2-(3-cyclopropylmethoxy-4-methoxyphenyl)-3-(2,6-dimethyl-4-carbonylpyridin-1(4H)-yl)-acrylamide (20 mg, 0.06 mmol) was dissolved in N,N-dimethylformamide (0.5 mL), and then 60% sodium hydride (12 mg, 0.3 mmol) was added, and stirred at 70° C. for 0.5 hours. Iodoethane (19 mg, 0.12 mmol) was added to the reaction solution, and stirred at 70° C. for another 1 hr. The reaction was quenched with a saturated aqueous ammonium chloride solution, and the reaction solution was directly rotary dried and purified by column chromatography to obtain (Z)-2-(3-cyclopropylmethoxy-4-methoxyphenyl)-3-(2,6-dimethyl-4-carbonylpyridin-1(4H)-yl)-N,N-diethylacrylamide (6 mg, 30%, white solid). $^1$H NMR (400 MHz, CDCl$_3$) δ 7.04-7.01 (m, 1H), 6.95-6.91 (m, 2H), 6.72 (s, 1H), 6.41 (s, 2H), 3.92 (s, 3H), 3.88 (d, J=7.2 Hz, 2H), 3.34-3.31 (m, 2H), 3.18 (q, J=6.8 Hz, 2H), 1.01 (t, J=7.2 Hz, 3H), 0.90-0.82 (m, 1H), 0.81 (t, J=7.2 Hz, 3H), 0.69-0.65 (m, 2H), 0.40-0.36 (m, 2H); LC-MS: m/z 425.1 [M+H]$^+$.

Example 111

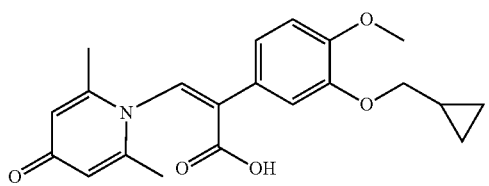 [SMILES: COc1ccc(/C(=C/n2c(C)cc(=O)cc2C)C(=O)O)cc1OCC1CC1]

(Z)-2-(3-cyclopropylmethoxy-4-methoxyphenyl)-3-(2,6-dimethyl-4-carbonylpyridin-1(4H)-yl)-acrylic acid The specific reaction scheme is as shown below:

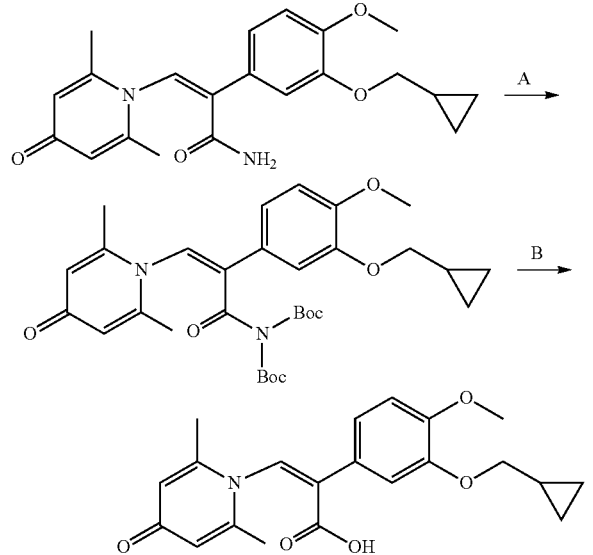

Step A:

The compound (Z)-2-(3-cyclopropylmethoxy-4-methoxyphenyl)-3-(2,6-dimethyl-4-carbonylpyridin-1(4H)-yl)-N,N-diethylacrylamide (60.0 mg, 0.16 mmol) was dissolved in N,N-dimethylformamide (5 mL). 4-dimethylaminopyridine (4.0 mg, 0.03 mmol) and triethylamine (36 mg, 0.36 mmol) were added at 35° C., and then di-tert butyl dicarbonate (71 mg, 0.33 mmol) was slowly added to the reaction solution and stirred for 2 hours. After the reaction was completed, the reaction solution was rotary dried to obtain a crude product of (Z)-2-(3-cyclopropylmethoxy-4-methoxyphenyl)-3-(2,6-dimethyl-4-carbonylpyridin-1(4H)-yl)-N,N-di-tert butyloxycarbonylacrylamide. LC-MS: m/z 569.2 [M+H]$^+$.

Step B:

The compound (Z)-2-(3-cyclopropylmethoxy-4-methoxyphenyl)-3-(2,6-dimethyl-4-carbonylpyridin-1(4H)-yl)-N,N-di-tert butyloxycarbonylacrylamide (90 mg, 0.16 mmol) was dissolved in methanol (2 mL), and a sodium hydroxide solution (2N, 1 mL) was added to the reaction solution at 35° C. and stirred for 2 hours. After the reaction was completed, water (10 mL) was added, and extracted with dichloromethane (3×10 mL). The organic phases were combined, dried over anhydrous sodium sulfate, filtered, rotary dried, and purified to obtain (Z)-2-(3-cyclopropylmethoxy-4-methoxyphenyl)-3-(2,6-dimethyl-4-carbonylpyridin-1(4H)-yl)-acrylic acid (23.1 mg, yield 39%, white solid). $^1$H NMR (400 MHz, CDCl$_3$) δ 7.18-7.16 (d, J=8.0 Hz, 1H), 7.11 (s, 2H), 6.94 (d, J=8.0 Hz, 1H), 6.82 (s, 1H), 3.92 (s, 3H), 3.90 (d, J=6.4 Hz, 2H), 2.6 (s, 6H), 1.33-1.27 (m, 1H), 0.68-0.63 (m, 2H), 0.41-0.35 (m, 2H). LC-MS: m/z 370.1 [M+H]$^+$.

Example 112

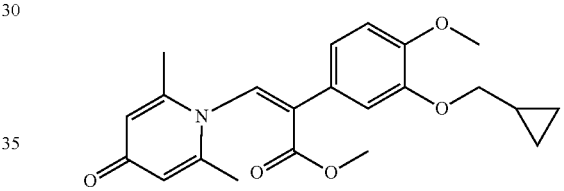

(Z)-methyl 2-(3-cyclopropylmethoxy-4-methoxyphenyl)-3-(2,6-dimethyl-4-carbonylpyridin-1(4H)-yl)-acrylate The specific reaction scheme is as shown below:

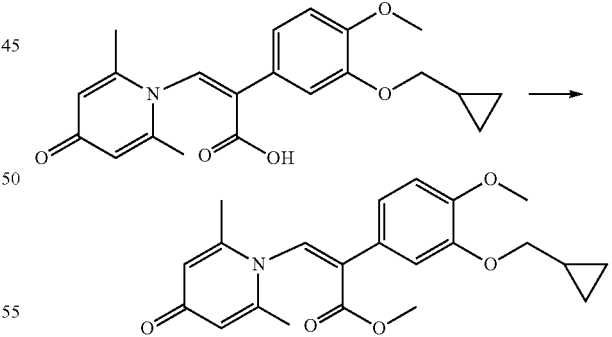

The compound (Z)-2-(3-cyclopropylmethoxy-4-methoxyphenyl)-3-(2,6-dimethyl-4-carbonylpyridin-1(4H)-yl)-acrylic acid (10 mg, 0.03 mmol) was dissolved in dichloromethane (0.5 mL), and one drop of N,N-dimethylformamide was added to the reaction solution. Oxalyl chloride (8 mg, 0.03 mmol) was slowly added to the reaction solution, and stirred for 1 hr. Then, methanol (0.5 mL) was added to the reaction solution. After the reaction was completed, the reaction was quenched with a saturated aqueous ammonium chloride solution, and the reaction solution was directly rotary dried and purified by column chromatography to obtain (Z)-methyl 2-(3-cyclopropylmethoxy-4-methoxyphenyl)-3-(2,6-dimethyl-4-carbonylpyridin-1(4H)-yl)-acrylate (3 mg, yield 26%, white solid). $^1$H NMR (400 MHz, CDCl$_3$) δ 8.02 (s, 1H), 7.95 (s, 2H), 7.15 (s, 1H), 7.09 (d, J=8.4 Hz, 1H), 6.94 (d, J=8.4 Hz, 1H), 3.94-3.93 (m, 5H), 3.70 (s, 3H), 2.83 (s, 6H), 1.70-1.59 (m, 1H), 0.68-0.63 (m, 2H), 0.40-0.39 (m, 2H); LC-MS: m/z 384.3 [M+H]$^+$.

Example 113

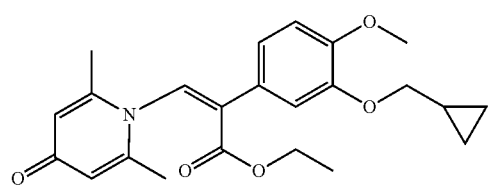 [SMILES: CCOC(=O)/C(=C\n1c(C)cc(=O)cc1C)c1ccc(OC)c(OCC2CC2)c1]

(Z)-ethyl 2-(3-cyclopropylmethoxy-4-methoxyphenyl)-3-(2,6-dimethyl-4-carbonylpyridin-1(4H)-yl)-acrylate The specific reaction scheme is as shown below:

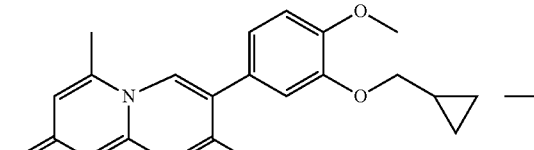

(Z)-2-(3-cyclopropylmethoxy-4-methoxyphenyl)-3-(2,6-dimethyl-4-carbonylpyridin-1(4H)-yl)-acrylic acid (10 mg, 0.03 mmol) was dissolved in dichloromethane (0.5 mL), and one drop of N,N-dimethylformamide was added to the reaction solution. Oxalyl chloride (8 mg, 0.03 mmol) was slowly added to the reaction solution, and stirred for 1 hr. Then, ethanol (0.5 mL) was added to the reaction solution. After the reaction was completed, the reaction was quenched with a saturated aqueous ammonium chloride solution, and the reaction solution was directly rotary dried and purified by column chromatography to obtain (Z)-ethyl 2-(3-cyclopropylmethoxy-4-methoxyphenyl)-3-(2,6-dimethyl-4-carbonylpyridin-1(4H)-yl)-acrylate (4 mg, yield 34%, white solid). $^1$H NMR (400 MHz, CDCl$_3$) δ 8.64 (s, 1H), 7.65 (s, 2H), 7.28 (s, 1H), 7.16 (d, J=8.0 Hz, 1H), 6.92 (d, J=8.4 Hz, 1H), 4.18 (q, J=7.2 Hz, 2H), 4.00 (d, J=6.8 Hz, 2H), 3.92 (m, 3H), 2.92 (s, 6H), 1.45-1.32 (m, 1H), 1.15 (t, J=14.4 Hz, 3H), 0.67-0.63 (m, 2H), 0.44-0.40 (m, 2H); LC-MS: m/z 398.3 [M+H]$^+$.

Example 114

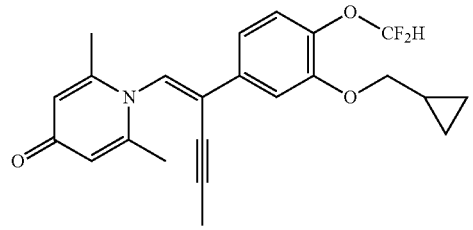 [SMILES: CC#C/C(=C\n1c(C)cc(=O)cc1C)c1ccc(OC(F)F)c(OCC2CC2)c1]

(Z)-1-(2-(3-cyclopropylmethoxy-4-difluoromethoxyphenyl)pent-1-en-3-yn-1-yl)-2,6-dimethylpyridin-4(1H)-one The specific reaction scheme is as shown below:

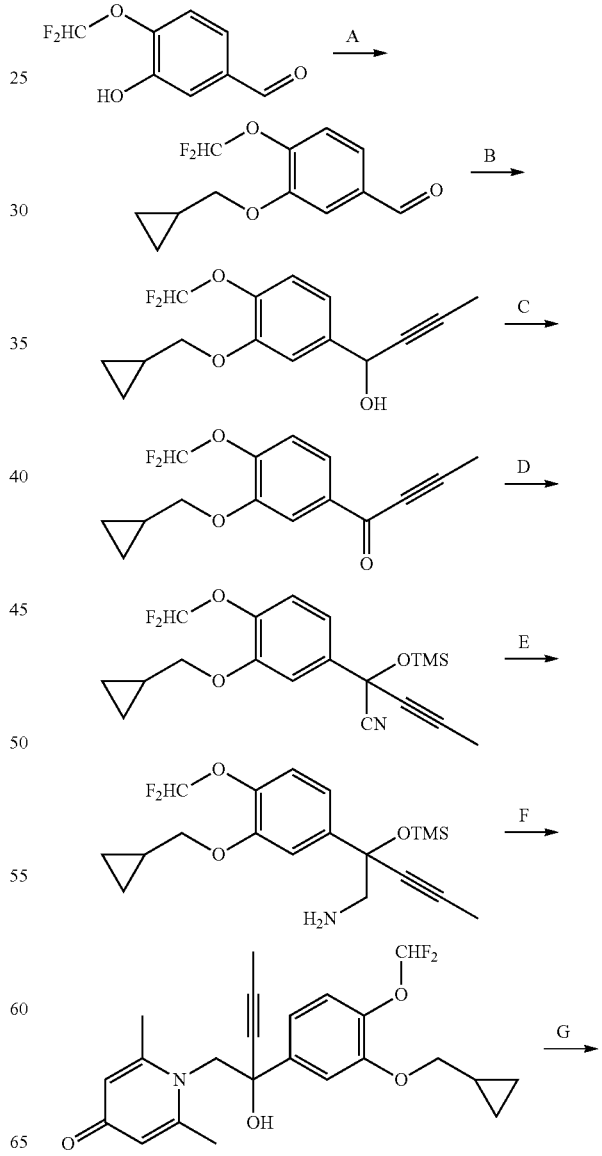

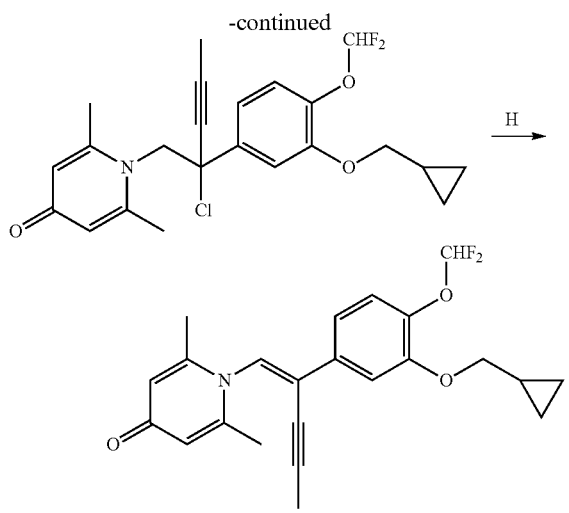

Step A:
At room temperature, 4-(difluoromethoxy)-3-hydroxybenzaldehyde (0.964 g, 5.13 mmol) was dissolved in acetonitrile (10 mL), and then potassium carbonate (1.06 g, 7.69 mmol) and bromomethylcyclopropane (0.9 g, 6.67 mmol) were added in sequence, and heated to 80° C. for 3 hours with stirring under nitrogen atmosphere. After the reaction was completed, water (30 mL) was added, and extracted with dichloromethane (3×30 mL). The organic phases were combined, dried over anhydrous sodium sulfate, filtered, rotary dried, and purified to obtain 3-cyclopropylmethoxy-4-difluoromethoxybenzaldehyde (1.16 g, yield 93%). LC-MS: m/z 343.2 [M+H]$^+$.

Step B:
The compound 3-cyclopropylmethoxy-4-difluoromethoxybenzaldehyde (1.16 g, 4.79 mmol) was dissolved in anhydrous tetrahydrofuran (30 mL), and then prop-1-yn-1-ylmagnesium bromide (0.5 N, 19.2 mL, 9.6 mmol) was slowly added in an ice bath, and stirred for 16 hours at room temperature under nitrogen atmosphere. After the reaction was completed, the reaction solution was quenched with water (30 mL), and extracted with ethyl acetate (3×60 mL). The organic phases were combined, dried over anhydrous sodium sulfate, filtered, rotary dried, and purified to obtain 1-(3-cyclopropylmethoxy-4-difluoromethoxyphenyl)but-2-yn-1-ol (1.01 g, 74%).

Step C:
The compound 1-(3-cyclopropylmethoxy-4-difluoromethoxyphenyl)but-2-yn-1-ol (1.01 g, 3.58 mmol) was dissolved in dichloromethane (50 mL), and then Dess-Martin periodinane (3.04 g, 7.16 mmol) were added and stirred overnight at room temperature. After the reaction was completed, the reaction solution was filtered, rotary dried, and purified to obtain 1-(3-cyclopropylmethoxy-4-difluoromethoxyphenyl)but-2-yn-1-one (0.96 g, yield 96%).

Step D:
The compound 1-(3-cyclopropylmethoxy-4-difluoromethoxyphenyl)but-2-yn-1-one (0.96 g, 3.43 mmol) was dissolved in dichloromethane (10 mL), and then triethyl amine (0.693 g, 6.86 mmol) and trimethylsilyl cyanide (1.02 g, 10.29 mmol) were added in sequence in an ice bath and stirred for 16 hours under nitrogen atmosphere at room temperature. After the reaction was completed, the reaction solution was directly rotary dried to obtain a crude product of 2-(3-cyclopropylmethoxy-4-difluoromethoxyphenyl)-2-(trimethylsiloxy)pent-3-ynyl nitrile, which was directly used in the next reaction.

Step E:
The compound 2-(3-cyclopropylmethoxy-4-difluoromethoxyphenyl)-2-(trimethylsiloxy)pent-3-ynyl nitrile (1.30 g, 3.43 mmol) was dissolved in anhydrous tetrahydrofuran (40 mL); and then lithium aluminum hydride (0.391 g, 10.29 mmol) was added portion-wise in an ice bath, and stirred overnight at room temperature. After the reaction was completed, water (0.4 mL), a 15% aqueous sodium hydroxide solution (0.4 mL), and water (1.2 mL) were added in sequence, stirred for half an hour, dried over anhydrous sodium sulfate, filtered, and rotary dried to obtain a crude product of 1-amino-2-(3-cyclopropylmethoxy-4-difluoromethoxyphenyl)pent-3-yn-2-ol, which was directly used in the next reaction.

Step F:
The compound 1-amino-2-(3-cyclopropylmethoxy-4-difluoromethoxyphenyl)pent-3-yn-2-ol (1.07 g, 3.43 mmol) was dissolved in ethanol (40 mL), and then 2,6-dimethyl-4H-pyran-4-one (0.553 g, 4.46 mmol), sodium hydroxide (206 mg, 5.15 mmol) and water (6 mL) were added in sequence, heated to 60° C., and stirred for 72 hours under nitrogen atmosphere. After the reaction was completed, the reaction solution was rotary dried, and purified by column chromatography to obtain 1-(2-(3-cyclopropylmethoxy-4-difluoromethoxyphenyl)-2-hydroxypent-3-yn-1-yl)-2,6-dimethylpyridin-4(1H)-one (120 mg, yield 8%). LC-MS: m/z 418.2 [M+H]$^+$.

Step G:
The compound 1-(2-(3-cyclopropylmethoxy-4-difluoromethoxyphenyl)-2-hydroxypent-3-yn-1-yl)-2,6-dimethylpyridin-4(1H)-one (120 mg, 0.29 mmol) was dissolved in trichloromethane (10 mL), and heated to 90° C. Then thionyl chloride (0.5 mL) was added and stirred at 90° C. for 15 min. After the reaction was completed, the reaction solution was directly rotary dried to obtain a crude product of 1-(2-chloro-2-(3-(cyclopropylmethoxy)-4-(difluoromethoxy)phenyl)pent-3-yn-1-yl)-2,6-dimethylpyridin-4(1H)-one. LC-MS: m/z 436.2 [M+H]$^+$.

Step H:
The compound 1-(2-chloro-2-(3-(cyclopropylmethoxy)-4-(difluoromethoxy)phenyl)pent-3-yn-1-yl)-2,6-dimethylpyridin-4(1H)-one (125 mg, 0.29 mmol) was dissolved in ethanol (10 mL), and then sodium hydroxide (72 mg, 1.8 mmol) and water (2 mL) were added in sequence, heated to 90° C., and stirred for 16 hours under nitrogen atmosphere. After the reaction was completed, the reaction solution was rotary dried, and purified by reverse-phase HPLC to obtain the product (Z)-1-(2-(3-cyclopropylmethoxy-4-difluoromethoxyphenyl)pent-1-en-3-yn-1-yl)-2,6-dimethylpyridin-4(1H)-one (2.3 mg, yield 2%, white solid). $^1$H NMR (400 MHz, CDCl$_3$) δ 7.38-7.28 (m, 3H), 7.21 (d, J=8.0 Hz, 1H), 7.01 (s, 2H), 6.69 (t, J=75.2 Hz, 1H), 3.97 (d, J=6.4 Hz, 2H), 2.48 (s, 6H), 1.95 (s, 3H), 1.35-1.25 (m, 1H), 0.70-0.65 (m, 2H), 0.42-0.36 (m, 2H); LC-MS: m/z 400.1 [M+H]$^+$.

Example 115

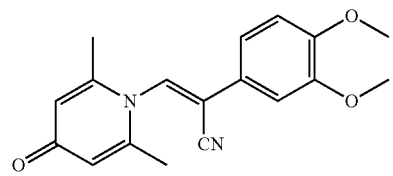 [SMILES: COc1ccc(/C(C#N)=C/n2c(C)cc(=O)cc2C)cc1OC]

(Z)-2-(3,4-dimethoxyphenyl)-3-(2,6dimethyl-4-carbonylpyridine)-1(4H)-yl)acrylonitrile The specific reaction scheme is as shown below:

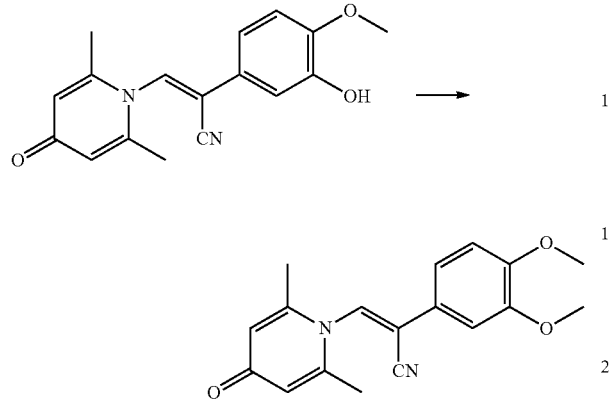

The compound (Z)-3-(2,6dimethyl-4-carbonylpyridine)-1(4H)-yl)-2-(3-hydroxy4-methoxyphenyl)acrylonitrile (100 mg, 0.34 mmol) was dissolved in acetonitrile (10 mL), and then iodomethane (96 mg, 0.68 mmol) and potassium carbonate (187 mg, 1.35 mmol) were added and stirred for 5 hours at 85° C. under nitrogen atmosphere. After the reaction was completed, the reaction solution was filtered, and the filtrate was rotary dried, and purified by reverse-phase HPLC to obtain (Z)-2-(3,4-dimethoxyphenyl)-3-(2,6dimethyl-4-carbonylpyridine)-1(4H)-yl)acrylonitrile (21 mg, yield 33%, white solid). $^1$H NMR (400 MHz, CDCl$_3$) δ 7.65 (s, 1H), 7.29 (dd, J=8.4, 2.0 Hz, 1H), 7.18 (d, J=2.0 Hz, 1H), 6.97 (d, J=8.4 Hz, 1H), 6.51 (s, 2H), 3.98 (s, 3H), 3.96 (s, 3H), 2.37 (s, 6H); LC-MS m/z 311.2 [M+H]$^+$.

Example 116

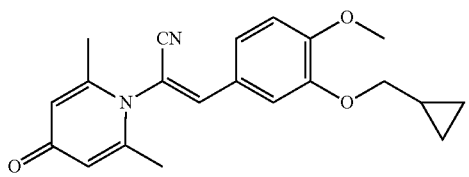 [SMILES: COc1ccc(/C=C(\C#N)n2c(C)cc(=O)cc2C)cc1OCC1CC1]

(E)-3-(3-cyclopropylmethoxy-4methoxyphenyl)-2(2,6-dimethyl-4-carbonylpyridin-1(4H)-yl)acrylonitrile

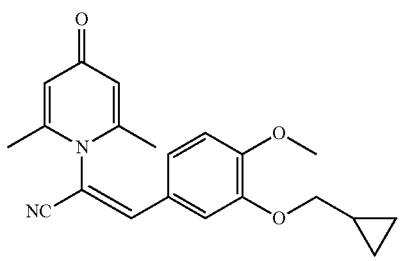 [SMILES: COc1ccc(/C=C(/C#N)n2c(C)cc(=O)cc2C)cc1OCC1CC1]

(Z)-3-(3-cyclopropylmethoxy-4methoxyphenyl)-2(2,6-dimethyl-4-carbonylpyridin-1(4H)-yl)acrylonitrile The specific reaction scheme is as shown below:

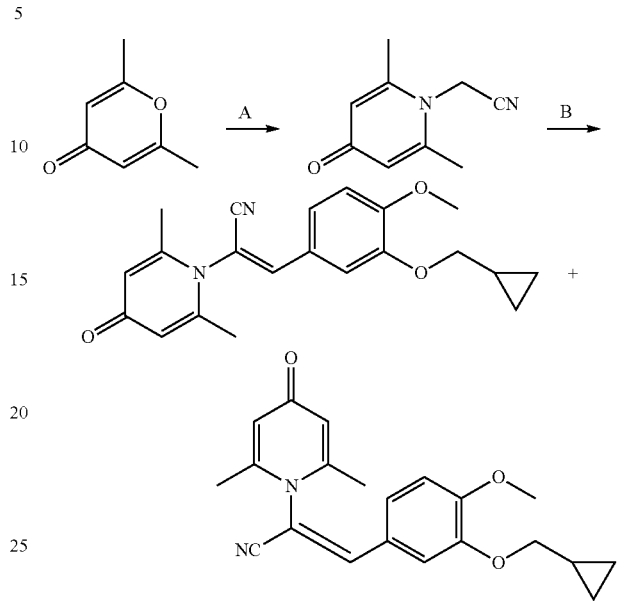

Step A 2,6-dimethyl-4H-pyran-4-one (620 mg, 5 mmol) and aminoacetonitrile hydrochloride (463 mg, 6 mmol) were dissolved in pyridine (10 mL), and stirred for 46 hours at 80° C. under nitrogen atmosphere. After the reaction was completed, the reaction solution was rotary dried, and purified by column chromatography to obtain 2-(2,6-dimethyl-4-carbonylpyridin-1(4H)-yl)acetonitrile (583 mg, yield 72%, white solid). LC-MS: m/z 163.1 [M+H]$^+$.

Step B 2-(2,6-dimethyl-4-carbonylpyridin-1(4H)-yl)acetonitrile (162 mg, 1 mmol) and 3-cyclopropylmethoxy-4-methoxybenzaldehyde (206 mg, 1 mmol) were dissolved in pyridine (10 mL), and stirred overnight at 100° C. under nitrogen atmosphere. After the reaction was completed, the reaction solution was rotary dried to remove pyridine, and purified by reverse-phase HPLC to obtain (E)-3-(3-cyclopropylmethoxy-4methoxyphenyl)-2(2,6-dimethyl-4-carbonylpyridin-1(4H)-yl)acrylonitrile (126 mg, yield 36%, white solid) and (Z)-3-(3-cyclopropylmethoxy-4methoxyphenyl)-2(2,6-dimethyl-4-carbonylpyridin-1(4H)-yl)acrylonitrile (20 mg, yield 6%, white solid).

(E)-3-(3-cyclopropylmethoxy-4-methoxyphenyl)-2(2,6-dimethyl-4-carbonylpyridin-1(4H)-yl)acrylonitrile. $^1$H NMR (400 MHz, DMSO-d$_6$) δ 8.85 (s, 1H), 7.24 (d, J=8.4 Hz, 1H), 7.07 (dd, J=8.4, 2.0 Hz, 1H), 6.65 (d, J=2.0 Hz, 1H), 6.38 (s, 2H), 3.92 (s, 3H), 3.88 (d, J=6.8 Hz, 2H), 2.22 (s, 6H), 1.26-1.17 (m, 1H), 0.65-0.58 (m, 2H), 0.32-0.26 (m, 2H); LC-MS: m/z 351.2 [M+H]$^+$.

(Z)-3-(3-cyclopropylmethoxy-4methoxyphenyl)-2(2,6-dimethyl-4-carbonylpyridin-1(4H)-yl)acrylonitrile. $^1$H NMR (400 MHz, DMSO-d$_6$) δ 7.58 (s, 1H), 7.23 (d, J=8.4 Hz, 1H), 6.97 (dd, J=8.4, 1.6 Hz, 1H), 6.69 (d, J=1.6 Hz, 1H), 6.09 (s, 2H), 3.80 (s, 3H), 3.53 (d, J=6.8 Hz, 2H), 3.34 (s, 6H), 2.02 (s, 6H), 1.16-1.11 (m, 1H), 0.56-0.52 (m, 2H), 0.27-0.23 (m, 2H); LC-MS: m/z 351.2 [M+H]$^+$.

Example 117

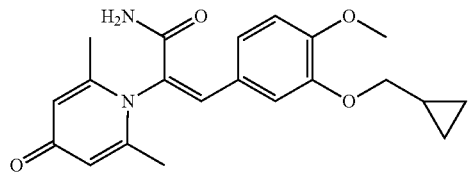

(E)-3-(3-propylmethoxy-4-methoxyphenyl)-2-(2,6-dimethyl-4-carbonylpyridin-1(4H)-yl)acrylamide

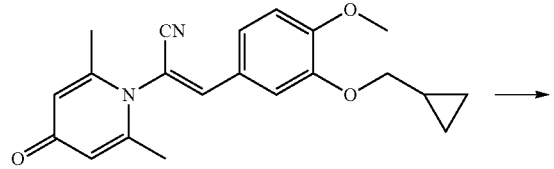

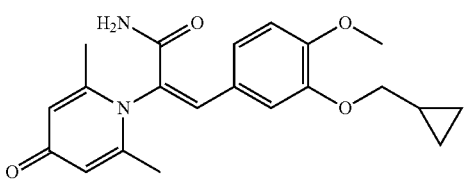 [SMILES: COc1ccc(/C=C(\C(N)=O)n2c(C)cc(=O)cc2C)cc1OCC1CC1]

(E)-3-(3-cyclopropylmethoxy-4methoxyphenyl)-2(2,6-dimethyl-4-carbonylpyridin-1(4H)-yl)acrylonitrile (350 mg, 1 mmol) was dissolved in acetonitrile (10 mL), and then potassium hydroxide (10 wt %, 10 mL) was added at room temperature and stirred at 80° C. for 2 hours. After the reaction was completed, the reaction solution was directly rotary dried, and purified by reverse-phase HPLC to obtain (Z)-2-(3-cyclopropylmethoxy-4-methoxyphenyl)-3-(2,6-dimethyl-4-carbonylpyridin-1(4H)-yl)-acrylamide (247 mg, 67%, white solid). $^1$H NMR (400 MHz, DMSO-d$_6$) δ 7.82 (s, 1H), 7.75 (s, 1H), 7.54 (s, 1H), 7.04 (d, J=8.4 Hz, 1H), 6.87 (dd, J=8.4, 2.0 Hz, 1H), 6.38 (d, J=2.0 Hz, 1H), 6.14 (s, 2H), 3.80 (s, 3H), 3.51 (d, J=6.8 Hz, 2H), 1.94 (s, 6H), 1.16-1.07 (m, 1H), 0.56-0.51 (m, 2H), 0.27-0.24 (m, 2H); LC-MS: m/z 369.4 [M+H]$^+$.

Example 118

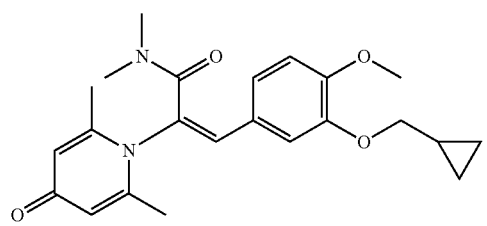 [SMILES: COc1ccc(/C=C(\C(=O)N(C)C)n2c(C)cc(=O)cc2C)cc1OCC1CC1]

(E)-3-(3-cyclopropylmethoxy-4-methoxyphenyl)-2-(2,6-dimethyl-4-carbonylpyridine)-1(4H)-yl)-N,N-dimethylacrylamide The specific reaction scheme is as shown below:

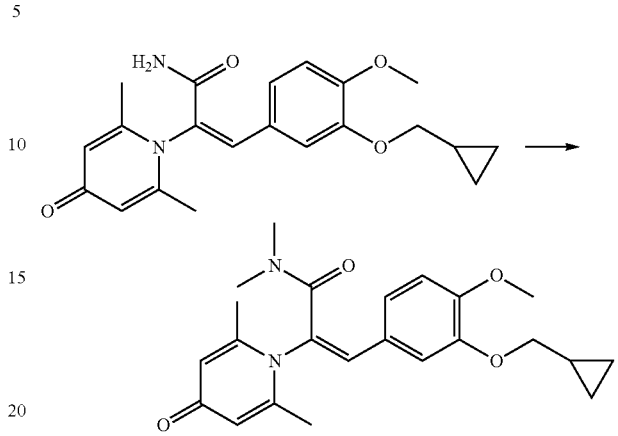

The compound (E)-3-(3-(cyclopropylmethoxy)-4-methoxyphenyl)-2-(2,6-dimethyl-4-carbonylpyridine)-1(4H)acrylamide (37 mg, 0.1 mmol) was dissolved in N,N-dimethylformamide (2 mL), and then 60% sodium hydride (24 mg, 0.6 mmol) was added at 0° C., and stirred for half an hour. Then, iodomethane (43 mg, 0.3 mmol) was added, and stirred at room temperature for 4 hours. After the reaction was completed, saturated saline (10 mL) was added, and extracted with dichloromethane (3×10 mL). The organic phases were combined, and dried over anhydrous sodium sulfate. Filtration, rotary drying, and purification by reverse-phase HPLC gave (E)-3-(3-cyclopropylmethoxy-4-methoxyphenyl)-2-(2,6-dimethyl-4-carbonylpyridine)-1(4H)-yl)-N, N-dimethylacrylamide (22 mg, yield 55%, white solid). $^1$H NMR (400 MHz, DMSO-d$_6$) δ 7.28 (s, 1H), 7.03 (d, J=8.4 Hz, 1H), 6.87 (dd, J=8.4, 1.6 Hz, 1H), 6.49 (d, J=1.6 Hz, 1H), 6.09 (s, 2H), 3.80 (s, 3H), 3.53 (d, J=6.8 Hz, 2H), 3.34 (s, 6H), 2.02 (s, 6H), 1.16-1.11 (m, 1H), 0.56-0.52 (m, 2H), 0.27-0.23 (m, 2H); LC-MS: m/z 397.2 [M+H]$^+$.

Example 119

Determination of the inhibition of the compounds on PDE4B1 activity by using cAMP HTRF® assay The inhibitory effect of the compounds on human PDE4B1 enzyme activity was determined by quantifying the 5'-adenosine monophosphate (5'-AMP) formed from 3',5'-cyclic adenosine monophosphate (cAMP).

The test compound or water (control) and human recombinant PDE4B1 enzyme (4.8 U) were mixed in a buffer solution (pH 7.4) consisting of 1× Hanks' balanced salt solution (HBSS), 5 mM HEPES, 3 mM MgCl2, and 0.1% BSA and incubated for 10 min. A cAMP enzyme substrate (final concentration 40 nM) was added, and the mixture was incubated at room temperature for 60 min. Then a fluorescent acceptor (Dye2 labeled with cAMP), a fluorescent donor (anti-cAMP antibody labeled with europium cryptate) and a non-specific phosphodiesterase inhibitor IBMX (3-isobutyl-1-methyl xanthine; final concentration 1 mM) were added. After 60 min, the fluorescence transfer related to the amount of remaining cAMP was measured on a microplate reader (Rubystar, BMG) at λex=337 nm, λem=620 nm and λem=665 nm. The enzyme activity is calculated from the ratio of the signals measured at 665 nm and 620 nm. The results are expressed as percent inhibition of the enzyme activity of the control (without PDE4 inhibitor). The enzyme was omitted for measurement of the basic control. The IC50 value (IC50=the concentration that caused the half-maximum inhibition of the specific activity of the control) is derived from dose-response measurements with eight different concentrations (n=2; repeated 2 times)

The experimental results obtained are listed in Table 1.

| Example | IC$_{50}$ (nM) |
|---|---|
| 1 | 760 |
| 2 | 125 |
| 3 | 39 |
| 4 | 36 |
| 5 | 5 |
| 6 | 19 |
| 7 | 5.7 |
| 8 | 23 |
| 9 | 25 |
| 10 | 3300 |
| 11 | 44 |
| 12 | N.A. |
| 13 | 4.9 |
| 14 | 21 |
| 15 | 33 |
| 16 | 10.3 |
| 17 | 16 |
| 18 | 4.5 |
| 19 | 4.6 |
| 20 | 13 |
| 21 | 4.6 |
| 22 | 20 |
| 23 | 5 |
| 24 | 23 |
| 25 | 11.5 |
| 26 | 39 |
| 27 | 65 |
| 28 | 92 |
| 29 | 93 |
| 30 | 116 |
| 31 | 26 |
| 32 | 13.9 |
| 33 | 830 |
| 34 | 420 |
| 35 | 32 |
| 36 | 1250 |
| 37 | 510 |
| 38-1 | 1090 |
| 38-2 | 71 |
| 39 | 1070 |
| 40 | 6.8 |
| 41 | 1.22 |
| 42 | 8.2 |
| 43 | 4.9 |
| 44 | 30 |
| 45 | 170 |
| 46 | 25 |
| 47 | 7.1 |
| 48 | 420 |
| 49 | 2.9 |
| 50 | 180 |
| 51 | 57 |
| 52 | N.A. |
| 53 | 15 |
| 54 | 26 |
| 55 | 54 |
| 56 | 16 |
| 57 | 100 |
| 58 | 5.5 |
| 59 | 5.1 |
| 60 | 1200 |
| 61 | 6.2 |
| 62 | 10.2 |
| 63 | 11.1 |
| 64 | 43 |
| 65 | 520 |
| 66 | 270 |
| 67 | 170 |
| 68 | 27 |
| 69 | 5200 |
| 70 | 8.1 |
| 71 | 1420 |
| 72 | 3900 |
| 73 | 2000 |
| 74 | 38 |
| 75 | 290 |
| 76 | 105 |
| 77 | 26.4 |
| 78 | 36 |
| 79 | 160 |
| 80 | 7 |
| 81 | 1.15 |
| 82 | 7.5 |
| 83-1 | 550 |
| 83-2 | 106 |
| 84 | 230 |
| 85 | 3.8 |
| 86-1 | 310 |
| 86-2 | 81 |
| 87 | 78 |
| 88 | 2.8 |
| 89 | 6.9 |
| 90 | 3.8 |
| 91 | 75 |
| 92 | 94 |
| 93 | 12.9 |
| 94 | 137 |
| 95 | 260 |
| 96 | 2.4 |
| 97 | 3.7 |
| 98-1 | 97 |
| 98-2 | 12.5 |
| 99 | 59 |
| 100 | 1.5 |
| 101-1 | 99 |
| 101-2 | 26 |
| 102 | 50 |
| 103 | 14 |
| 104-1 | 1700 |
| 104-2 | 8400 |
| 105 | 3 |
| 106 | 2.7 |
| 107 | 450 |
| 108 | 760 |
| 109 | 180 |
| 110 | 460 |
| 111 | 6600 |
| 112 | 138 |
| 113 | 170 |
| 114 | 1.6 |
| 115 | 9.9 |
| 116-1 | 460 |
| 116-2 | 35 |
| 117 | 3600 |
| 118 | 320 |

Example 120

Inhibition of the compounds on proinflammatory cytokine release by peripheral blood mononuclear cells (PBMCs)

The effect of the compounds on the release characteristics of TNFa cytokines in frozen human peripheral blood mononuclear cells (PBMCs) was determined.

Fresh human PBMCs were isolated, and suspended in a fresh medium. The PBMC medium (CM) is RPMI1640 containing 10% FBS, 1% PBS, and 2 mM L-glutamine. The cells were plated at a density of 2*10^5 cells/well (100 ul). The test compound was dissolved in DMSO to form a 10 mM sample (DMSO, 100%). The compound was diluted with PBMC medium to the required concentrations. The sample (50 uL) was incubated for 1 hr with cells at 37° C., 5% CO2, after which the inducer (LPS, 1 ug/mL) was added.

The inducer+vehicle (LPS+0.05% DMSO) was used as a control in this experiment. The vehicle without inducer was used as a negative control. Crisaborole was used as a positive control. After 24 hours of incubation, the supernatant was extracted and stored at −80° C. The supernatant was thawed and the TNFα level in the supernatant was measured by Luminex4-plex assay.

Result:

Using this experimental method, it is determined that the EC50 of Example 77 is =11 nM, the EC50 of Example 80 is <5 nM; and the EC50 of Example 88 is <5 nM.

Example 121

Test of Inhibition on allergic dermatitis on mouse ear induced by topically administered phorbol ester The test compounds are used to treat various skin diseases such as itching, redness, dryness, crusting, desquamation, inflammation and discomfort.

The test compound was topically applied to the right ear of the test animal 30 minutes before and 15 minutes after the administration of (12-) phorbol myristate(-13-)acetate (PMA). The dosing volume was 20 ul/ear for a solvent vehicle or 20 mg/ear for a cream.

Male CD-1 mice weighing 24±2 g were used. All animals were maintained in an environment at a controlled temperature (22° C.-23° C.) and humidity (70%-80%), with a 12-h-light and 12-h-dark photoperiod. The animals were raised in the animal room for at least 1 week before they are used for experimental test. The mice were allowed to access food and drinking water freely. Generally, all aspects of this work were carried out in accordance with the guidelines of Care and Use of Laboratory Animals (National Academy Press, Washington, D.C., 1996), including animal breeding, experimentation, and handling.

Each group had 5 mice. PMA (4 pg in 20 uL acetone) was applied topically to the front and back surfaces of the right ear of each animal. The vehicle (ethanol:acetone/1:1, 20 μL/ear) or test compound (specified dose in 20 uL of 1:1 acetone:ethanol, for each ear) was applied 30 minutes before and 15 minutes after PMA administration, and crisaborole was administered as a positive control. Then, 6 hours after PMA administration, ear swelling was measured as an indicator of inflammation using a staining micrometer. The percentage of inhibition is calculated according to the following formula: ([IC−IT]/IC)×100%, where IC and IT means the increase in ear thickness (mm) of mice in the control and treatment groups, respectively. 30% or more inhibition is considered to have significant anti-inflammatory activity.

Example 123

Formulation of Topical Preparations.

Compounds of the present invention, such as compound 88, can be administered as a gel, lotion, ointment and solution, and the route of administration includes, but is not limited to, topical administration, instillation, aerosol, transdermal patch, via insertion, or oral administration.

The following is a preparation method of 1% ointment preparation (weight percentage):

1% compound, 15% PEG400, 0.02% butylated hydroxytoluene, 2% span 80, 10% white wax, and 71.98% white petrolatum were mechanically stirred until an ointment was formed.

What is claimed is:

1. An anti-inflammatory compound, which is a compound having a structure shown below:

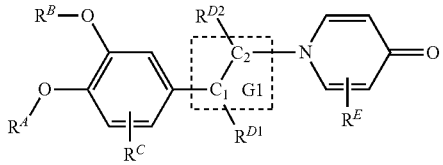

wherein $R^A$ is hydrogen, alkyl, or aryl, and in the above groups one or more hydrogen atom(s) attached to carbon in the groups is/are optionally substituted with alkyl, cycloalkyl, aryl, or halogen;

$R^B$ is hydrogen, alkyl, cycloalkyl, heterocycloalkyl, aryl, alkenyl, or alkynyl, and in the above groups one or more hydrogen atom(s) attached to carbon in the groups is/are optionally substituted with alkyl, cycloalkyl, heterocycloalkyl, aryl, or halogen, and one or more carbon atom(s) in the groups is/are optionally replaced with sulfur, sulfoxide, sulfone, or sulfonyl;

$R^C$ is hydrogen, alkyl, halogen, or alkoxy;

$R^{D1}$ is hydrogen, oxo, imino, hydroxy, cyano, amino, amido, alkyl, aryl, an ester group, carboxyl, alkenyl, or alkynyl, and in the above groups one or more hydrogen atom(s) attached to carbon/oxygen/nitrogen in the groups is/are optionally substituted with alkyl, cycloalkyl, alkynyl, alkenyl, aryl, halogen, sulfonyl, a sulfoxide group, or an ether group, and one or more carbon atom(s) in the groups is/are replaced optionally with sulfur, sulfoxide, sulfone, or sulfonyl;

$C_1$-$R^{D1}$ bond is a single bond or a double bond;

$R^{D2}$ is hydrogen, cyano, alkyl, cycloalkyl, aryl, or carboxyl, and in the above groups one or more hydrogen atom(s) attached to carbon/oxygen/nitrogen in the group is/are optionally substituted with alkyl, cycloalkyl, alkynyl, alkenyl, aryl, halogen, sulfonyl, or a sulfoxide group;

G1 is a single bond, a double bond or a ring, that comprises $C_1$ and $C_2$; and $R^E$ is hydrogen, alkyl, or halogen, wherein when $R^{D1}$ is aryl, it is unsubstituted aryl, and when $R^{D2}$ is aryl, it is unsubstituted aryl.

2. The anti-inflammatory compound according to claim 1, wherein G1 is a three-membered ring having a specific structure shown below:

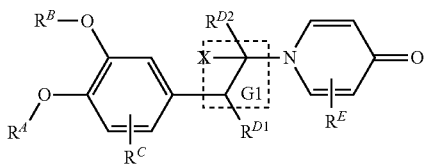

in which X is carbon.

3. A method for preparing the anti-inflammatory compound according to claim 1, comprising:

using a 3-hydroxybenzaldehyde derivative A as a starting material, and substituting the hydrogen in the hydroxyl group of the 3-hydroxybenzaldehyde derivative A with RB to obtain an intermediate product B;

reacting the intermediate product B with trimethylsilyl cyanide to obtain an intermediate product C;

reducing the intermediate product C to obtain an intermediate product D having an amino group; and
reacting the amino group in the intermediate product D with a six-membered oxygen-containing cyclic compound to obtain a type-A target product,
wherein the 3-hydroxybenzaldehyde derivative A is a compound having a structure shown below:

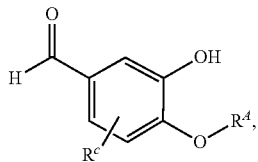

the intermediate product B is a compound having a structure shown below:

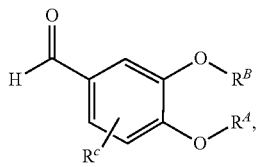

the intermediate product C is a compound having a structure shown below:

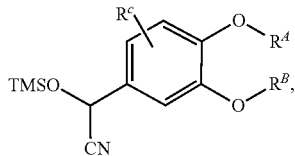

the intermediate product D is a compound having a structure shown below:

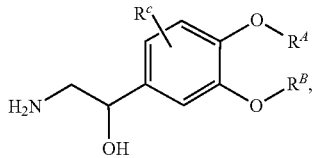

and
the type-A target product is a compound having a structure shown below:

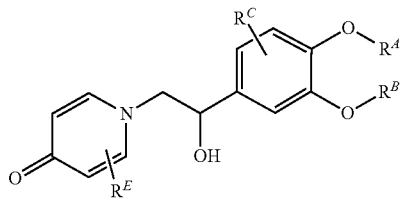

subjecting the hydroxyl group on the middle bridge of the type-A target product to an addition/substitution reaction to obtain a type-A-1 target product, wherein the type-A-1 target product is a compound having a structure shown below:

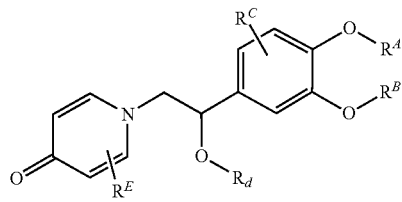

in which Rd is alkyl, cycloalkyl, or an ester group, and in the above groups one or more hydrogen atom(s) attached to carbon in the groups is/are optionally substituted with alkyl, alkynyl, alkenyl, cycloalkyl, aryl, halogen, hydroxy, thio, cyano, or thioalkyl, or
oxidizing the hydroxyl group on the middle bridge of the type-A target product to obtain a type-B target product,
wherein the type-B target product is a compound having a structure shown below:

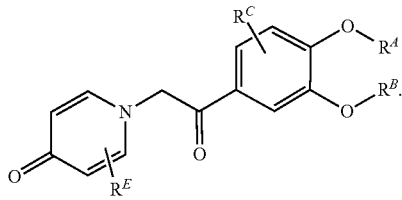

4. The method for preparing an anti-inflammatory compound according to claim 3, comprising:
oximating the carbonyl group on the middle bridge of the type-B target product to obtain a type-B-3 target product,
wherein the type-B-3 target product is a compound having a structure shown below:

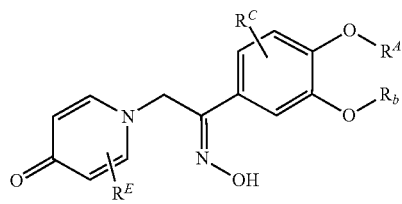

subjecting the hydroxyl group on the oxime of the type-B-3 target product to an addition/substitution reaction to obtain a type-B-4 target product,
wherein the type-B-4 target product is a compound having a structure shown below:

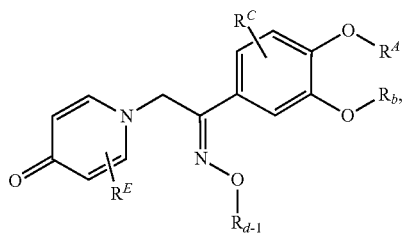

in which Rd-1 is alkyl, cycloalkyl, or an ester group, and in the above groups one or more hydrogen atom(s) attached to carbon in the groups is/are optionally substituted with alkyl, alkynyl, alkenyl, cycloalkyl, aryl, halogen, hydroxy, thio, cyano, or thioalkyl.

5. The method for preparing the anti-inflammatory compound according to claim 3, comprising:
removing the hydroxyl group on the middle bridge of the type-A target product to obtain a type-C target product, wherein the type-C target product is a compound having a structure shown below:

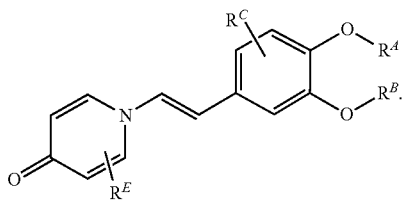

6. The method for preparing the anti-inflammatory compound according to claim 3, comprising:
reacting the carbonyl group on the middle bridge of the type-B target product with a halogenating reagent to obtain an intermediate product X1, and
replacing the halogen in the intermediate product X1 to obtain a type-C-3 target product,
wherein the intermediate product X1 is a compound having a structure shown below:

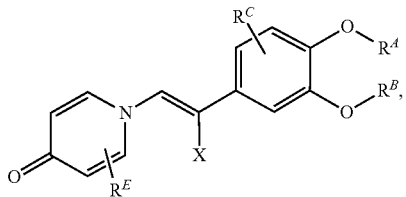

in which X is halogen; and
the type-C-3 target product is a compound having a structure shown below:

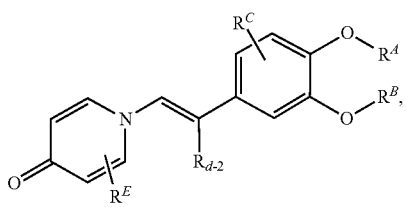

in which Rd-2 is aryl, alkyl, cycloalkyl, an ether group, or an ester group, and in the above groups one or more hydrogen atom(s) attached to carbon in the group is/are optionally substituted with alkyl, alkynyl, alkenyl, cycloalkyl, aryl, halogen, hydroxy, thio, cyano, or thioalkyl.

7. A method for preparing the anti-inflammatory compound according to claim 1, comprising:
reacting an acetophenone derivative 1 as a starting material with trimethylsilyl cyanide, to obtain an intermediate product 2;
reducing the intermediate product 2 to obtain an intermediate product 3; and
reacting the amino group in the intermediate product 3 with a six-membered oxygen-containing cyclic compound to obtain a type-A' target product,
wherein the acetophenone derivative 1 is a compound having a structure shown below:

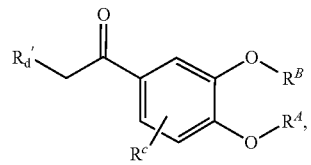

in which Rd' is hydrogen, alkyl, aryl, alkynyl, or alkenyl, and in the above groups one or more hydrogen atom(s) attached to carbon in the groups is/are optionally substituted with alkyl, alkynyl, alkenyl, cycloalkyl, aryl, halogen, hydroxy, thio, cyano, or thioalkyl;

the intermediate product 2 is a compound having a structure shown below:

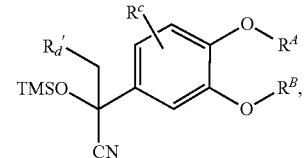

the intermediate product 3 is a compound having a structure shown below:

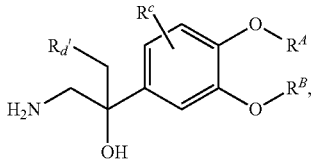

and
the type-A' target product is a compound having a structure shown below:

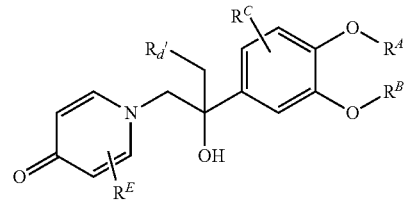

removing the hydroxyl group on the middle bridge of the type-A' target product to obtain a type-C' target product,
wherein the type-C' target product is a compound having a structure shown below:

141

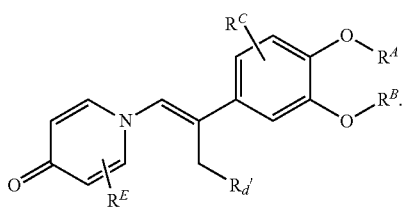

8. The method for preparing the anti-inflammatory compound according to claim 3, comprising:
reacting the carbonyl group on the middle bridge of the type-B target product with trimethylsilyl cyanide to obtain an intermediate product Y1, and
subjecting the intermediate product Y1 to reduction and elimination to obtain a type-C" target product,
wherein the intermediate product Y1 is a compound having a structure shown below:

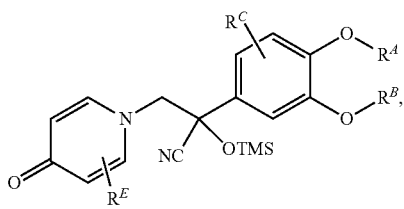

the type-C" target product is a compound having a structure shown below:

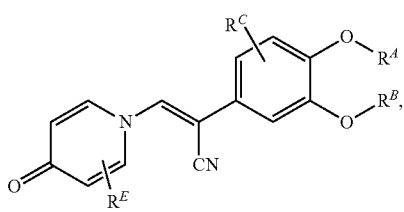

or
reacting a six-membered N-acetonitrile compound Z1 with a benzaldehyde derivative Z2 to obtain a type-C2" target product,
wherein the six-membered N-acetonitrile compound Z1 is a compound having a structure shown below:

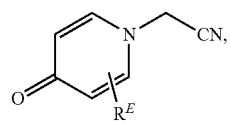

the benzaldehyde derivative Z2 is a compound having a structure shown below:

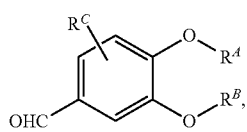

142 and
the type-CT' target product is a compound having a structure shown below:

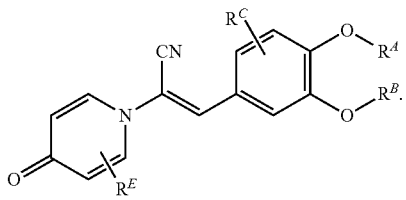

9. A method for preparing an anti-inflammatory compound according to claim 1, comprising:
using a cinnamic acid derivative 1 as a starting material, and esterifying the cinnamic acid derivative 1 to obtain an intermediate product 2;
forming a ring from the double bond on the intermediate product 2 to obtain an intermediate product 3;
hydrolyzing the terminal ester group on the intermediate product 3 to give an intermediate product 4 having a carboxyl group;
aminating the terminal carboxyl group of the intermediate product 4 to obtain an intermediate product 5; and
reacting the intermediate product 5 with a six-membered oxygen-containing cyclic compound to obtain a type-D target product,
wherein the cinnamic acid derivative 1 is a compound having a structure shown below:

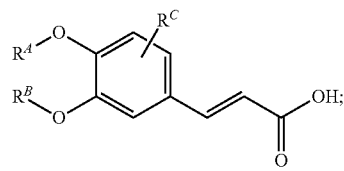

the intermediate product 2 is a compound having a structure shown below:

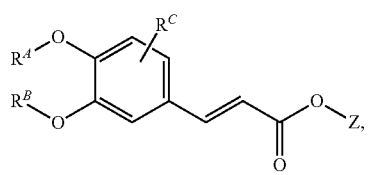

in which Z is alkyl;
the intermediate product 3 is a compound having a structure shown below:

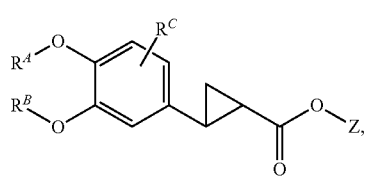

the intermediate product 4 is a compound having a structure shown below:

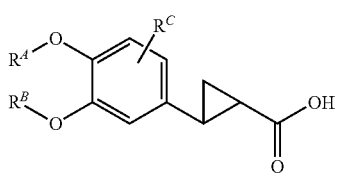

the intermediate product 5 is a compound having a structure shown below:

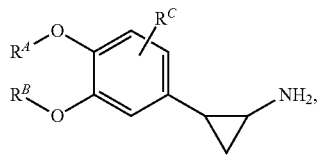

and the type-D target product is a compound having a structure shown below:

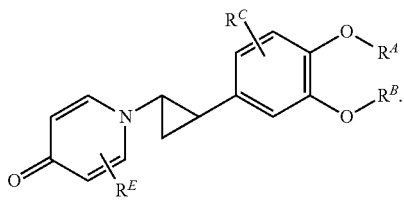

10. A method of inhibiting PDE4, comprising:
administering the anti-inflammatory compound according to claim 1 as a PDE4 inhibitor.

11. A method of treating inflammatory skin diseases, comprising:
administering the anti-inflammatory compound according to claim 1.

12. A drug for treating the inflammatory skin diseases, comprising
0.01-10% of the anti-inflammatory compound according to claim 1; and
other components selected from a surfactant, a lipid compound, and an auxiliary agent;
wherein the amount of the surfactant accounts for 10-30% of the total weight of the drug;
the amount of the lipid compound accounts for 50-85% of the total weight of the drug; and
the amount of the auxiliary agent accounts for 10-30% of the total weight of the drug.

13. The anti-inflammatory compound according to claim 1, wherein the compound having a structure shown below:

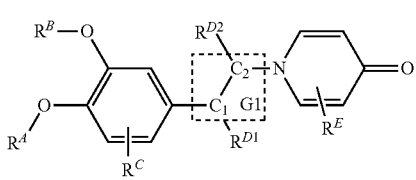

wherein $R^A$ is hydrogen, alkyl comprising from 1 to 6 carbon atoms, and in the above groups one or more hydrogen atom(s) attached to carbon in the groups is/are optionally substituted with alkyl comprising from 1 to 6 carbon atoms, cycloalkyl which is three-membered, four-membered, five-membered or six-membered cycle, or halogen;

$R^B$ is hydrogen, alkyl comprising from 1 to 6 carbon atoms, cycloalkyl which is a three-membered, four-membered, five-membered or six-membered cycle, heterocycloalkyl which is an oxo/thia three-membered, four-membered, five-membered or six-membered cycle, alkenyl comprising from 2 to 4 carbon atoms, or alkynyl comprising from 2 to 4 carbon atoms, and in the above groups one or more hydrogen atom(s) attached to carbon in the groups is/are optionally substituted with alkyl comprising from 1 to 6 carbon atoms, cycloalkyl which is a three-membered, four-membered, five-membered or six-membered cycle, or halogen, and one or more carbon atom(s) in the groups is/are optionally replaced with a sulfur atom, sulfoxide, sulfone, or sulfonyl;

$R^C$ is hydrogen;

$R^{D1}$ is hydrogen, oxo, imino, hydroxy, cyano, alkyl comprising from 1 to 6 carbon atoms, phenyl, an ester group, carboxyl, or alkynyl comprising from 2 to 4 carbon atoms, and in the above groups one or more hydrogen atom(s) attached to carbon/oxygen in the groups is/are optionally substituted with alkyl comprising 1 to 6 carbon atoms, cycloalkyl which is a three-membered, a four-membered, five-membered or six-membered ring, alkynyl comprising from 2 to 4 carbon atoms, alkenyl comprising from 2 to 4 carbon atoms, or phenyl, and one or more carbon atom(s) in the groups is/are optionally replaced with a sulfur atom;

$C_1$-$R^{D1}$ bond is a single bond or a double bond;

$R^{D2}$ is hydrogen or cyano;

G1 is a single bond, a double bond or cyclopropane comprising $C_1$ and $C_2$; and $R^E$ is alkyl comprising from 1 to 6 carbon atoms or halogen.

14. The anti-inflammatory compound according to claim 1, wherein the compound is selected from the group consisting of:

1-(2-(3-cyclopropylmethoxy-4-methoxyphenyl)-2-hydroxyethyl)-2,6, dimethylpyridin-4(1H)-one;

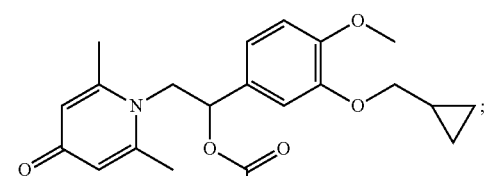

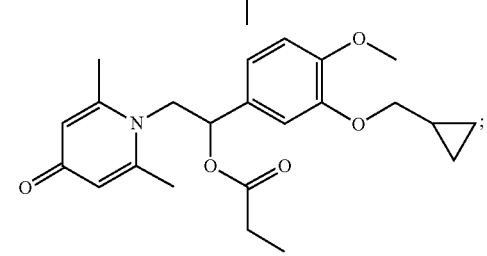

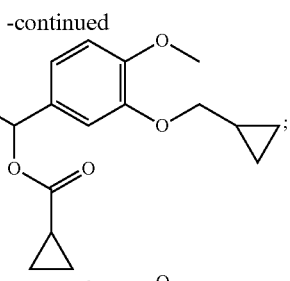

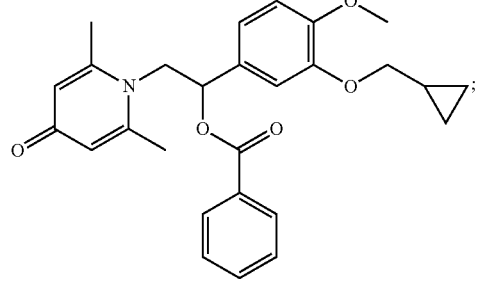

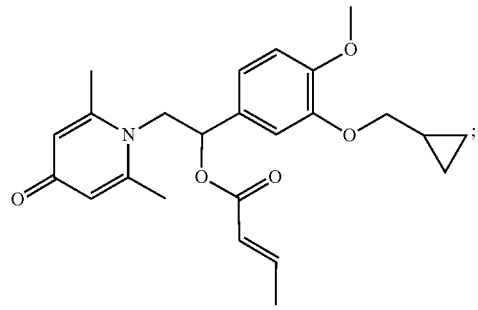

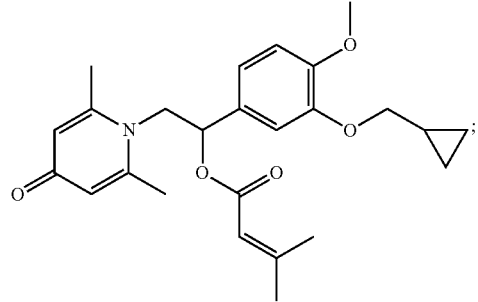

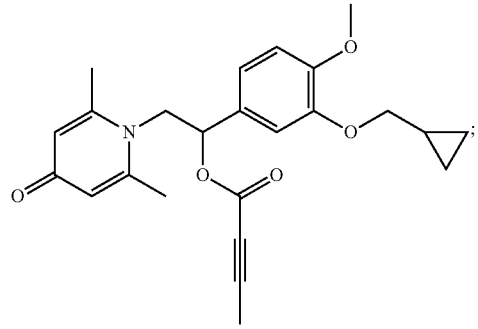 [SMILES: CC#CC(=O)OC(Cn1c(C)cc(=O)cc1C)c1ccc(OC)c(OCC2CC2)c1]

1-(2-(but-2-yn-1-yloxy)-2-(3-cyclopropylmethoxy-4-methoxyphenyl)ethyl)-2,6-dimethylpyridin-4-(1H)-one;
1-(2-(3-hydroxy-4-methoxyphenyl)-2-oxoethyl)-2, 6-dimethylpyridin-4(1H)-one;
1-(2-(3,4-dimethoxyphenyl)-2-oxoethyl)-2, 6-dimethylpyridin-4(1H)-one;
1-(2-(3-ethoxy-4-methoxyphenyl)-2-oxoethyl)-2, 6-dimethylpyridin-4(1H)-one;
1-(2-(3-propoxy-4-methoxyphenyl)-2-oxoethyl)-2, 6-dimethylpyridin-4(1H)-one;
1-(2-(3-isopropoxy-4-methoxyphenyl)-2-oxoethyl)-2,6-dimethylpyridin-4(1H)-one;
1-(2-(3-n-butoxy-4-methoxyphenyl)-2-oxoethyl)-2,6-dimethylpyridin-4(1H)-one;
1-(2-(3-iso-butoxy-4-methoxyphenyl)-2-oxoethyl)-2,6-dimethylpyridin-4(1H)-one;
1-(2-(3-n-pentyloxy-4-methoxyphenyl)-2-oxoethyl)-2,6-dimethylpyridin-4(1H)-one;
1-(2-(3-n-hexyloxy-4-methoxyphenyl)-2-oxoethyl)-2,6-dimethylpyridin-4(1H)-one;
1-(2-(3-cyclopropyloxy-4-methoxyphenyl)-2-oxoethyl)-2,6-dimethylpyridin-4(1H)-one;
1-(2-(3-cyclopropylmethoxy-4-methoxyphenyl)-2-oxo)ethyl-2,6-dimethylpyridin-4(1H)-one;
1-(2-(3-cyclobutyloxy-4-methoxyphenyl)-2-oxoethyl)-2, 6-dimethylpyridin-4(1H)-one;
1-(2-(3-cyclobutylmethoxy-4-methoxyphenyl)-2-oxo)ethyl-2,6-dimethylpyridin-4(1H)-one;
1-(2-(3-cyclopentyloxy-4-methoxyphenyl)-2-oxoethyl)-2,6-dimethylpyridin-4(1H)-one;
1-(2-(3-cyclohexyloxy-4-methoxyphenyl)-2-oxoethyl)-2, 6-dimethylpyridin-4(1H)-one;
1-(2-(3-(cyclopent-3-en-1-yloxy)-4-methoxyphenyl)-2-oxoethyl)-2, 6-dimethylpyridin-4(1H)-one;
1-(2-(3-allyloxy-4-methoxyphenyl)-2-oxoethyl)-2,6-dimethylpyridin-4(1H)-one;
1-(2-(3-((3-methylbut-2-en-1-yl)oxy)-4-methoxyphenyl)-2-oxoethyl)-2,6-dimethylpyridin-4(1H)-one;
1-(2-(3-propargyloxy-4-methoxyphenyl)-2-oxoethyl)-2, 6-dimethylpyridin-4(1H)-one;
1-(2-(3-(but-2-yn-1-yloxy)-4-methoxyphenyl)-2-oxoethyl)-2,6-dimethylpyridin-4(1H)-one;
1-(2-(3-(oxacyclobutan-3-yl-oxy)-4-methoxyphenyl)-2-oxoethyl)-2,6-dimethylpyridin-4(1H)-one;
1-(2-(3-(tetrahydrofuran-2-yl)oxy-4-methoxyphenyl)-2-oxoethyl)-2,6-dimethylpyridin-4(1H)-one;
1-(2-(3-methylthiomethoxy-4-methoxyphenyl)-2-oxoethyl)-2,6-dimethylpyridin-4(1H)-one;
1-(2-(3-methylsulfinylmethoxy-4-methoxyphenyl)-2-oxoethyl)-2,6-dimethylpyridin-4(1H)-one;
1-(2-(3-methylsulfonylmethoxy-4-methoxyphenyl)-2-oxoethyl)-2,6-dimethylpyridin-4(1H)-one;
1-(2-(3-methylthioethoxy-4-methoxyphenyl)-2-oxoethyl)-2,6-dimethylpyridin-4(1H)-one;
1-(2-(3-methylsulfinylethoxy-4-methoxyphenyl)-2-oxoethyl)-2,6-dimethylpyridin-4(1H)-one;
1-(2-(3-methylsulfonylethoxy-4-methoxyphenyl)-2-oxoethyl)-2,6-dimethylpyridin-4(1H)-one;
(Z)-1-(2-(3-cyclopropylmethoxy-4-methoxyphenyl)-2-(hydroxyimido)ethyl)-2,6-dimethylpyridin-4(1H)-one;
(Z)-1-(2-(3-cyclopropylmethoxy-4-methoxyphenyl)-2-(methoxyimido)ethyl)-2,6-dimethylpyridin-4(1H)-one;
(E)-1-(2-(3-cyclopropylmethoxy-4-methoxyphenyl)-2-(methoxyimido)ethyl)-2,6-dimethylpyridin-4(1H)-one;
(Z)-1-(2-(3-cyclopropylmethoxy-4-methoxyphenyl)-2-(methylthiomethoxyimido)ethyl)-2,6-dimethylpyridin-4(1H)-one;
(E)-1-(2-(3-cyclopropylmethoxy-4-methoxyphenyl)-2-(methylthiomethoxyimido)ethyl)-2,6-dimethylpyridin-4(1H)-one;
(Z)-1-(2-(3-cyclopropylmethoxy-4-methoxyphenyl)-2-(methylsulfinylmethoxyimido)ethyl)-2,6-dimethylpyridin-4(1H)-one;

(Z)-1-(2-(3-cyclopropylmethoxy-4-methoxyphenyl)-2-(methylsulfonylmethoxyimido)ethyl)-2,6-dimethylpyridin-4(1H)-one;
1-(2-(3-cyclopropylmethoxy-4-methoxyphenyl)-2-oxoethyl)pyridin-4(1H)-one;
1-(2-(3-cyclopropylmethoxy-4-methoxyphenyl)-2-oxoethyl)-2-methylpyridin-4(1H)-one;
1-(2-(3-cyclopropylmethoxy-4-methoxyphenyl)-2-oxoethyl)-2-chloropyridin-4(1H)-one;
1-(2-(3-cyclopropylmethoxy-4-methoxyphenyl)cyclopropyl)-2,6-dimethylpyridin-4(1H)-one;
1-(2-(3-cyclopropylmethoxy-4-difluoromethoxyphenyl)-2-oxoethyl)-2,6-dimethylpyridin-4(1H)-one;
(E)-1-(3-cyclopropylmethoxy-4-methoxystyryl)pyridin-4(1H)-one;
(E)-1-(3-cyclopropylmethoxy-4-methoxystyryl)-2-methylpyridin-4(1H)-one;
(E)-1-(3-hydroxy-4-methoxystyryl)-2,6-dimethylpyridin-4(1H)-one;
(E)-1-(3-propoxy-4-methoxystyryl)-2,6-dimethylpyridin-4(1H)-one;
(E)-1-(3-isopropoxy-4-methoxystyryl)-2,6-dimethylpyridin-4(1H)-one;
(E)-1-((3-n-butoxy-4-methoxy)-styryl)-2,6-dimethylpyridin-4(1H)-one;
(E)-1-(3-iso-butoxy-4-methoxystyryl)-2,6-dimethylpyridin-4(1H)-one;
(E)-1-((3-neopentyloxy-4-methoxy)-styryl)-2,6-dimethylpyridin-4(1H)-one;
(E)-1-(3-cyclopropyloxy-4-methoxystyryl)-2,6-dimethylpyridin-4(1H)-one;
(E)-1-(3-cyclopropylmethoxy-4-methoxystyryl)-2,6-dimethylpyridin-4(1H)-one;
(E)-1-(3-cyclopropylmethoxy-4-methoxyphenethyl)-2,6-dimethylpyridin-4(1H)-one;
(E)-1-(3-cyclobutyloxy-4-methoxy-styryl)-2,6-dimethylpyridin-4(1H)-one;
(E)-1-((3-cyclopentyloxy-4-methoxy)-styryl)-2,6-dimethylpyridin-4(1H)-one;
(E)-1-(3-(cyclopent-3-en-1-yloxy)-4-methoxystyryl)-2,6-dimethylpyridin-4(1H)-one;
(E)-1-(3-allyloxy-4-methoxy-styryl)-2,6-dimethylpyridin-4(1H)-one;
(E)-1-((3-(3-methylbut-2-en-1-yl)oxy-4-methoxy)-styryl)-2,6-dimethylpyridin-4(1H)-one;
(E)-1-(3-(prop-2-yn-1-yloxy)-4-methoxy)styryl)-2,6-dimethylpyridin-4(1H)-one;
(E)-1-(3-(but-2-yn-1-yloxy)-4-methoxystyryl)-2,6-dimethylpyridin-4(1H)-one;
(E)-1-((3-(oxacyclobutan-3-yl-oxy)-4-methoxy)-styryl)-2,6-dimethylpyridin-4(1H)-one;
(E)-1-((3-(thiacyclobutan-3-yl-oxy)-4-methoxy)-styryl)-2,6-dimethylpyridin-4(1H)-one;
(E)-1-((3-(tetrahydrofuran-2-yl)oxy-4-methoxy)-styryl)-2,6-dimethylpyridin-4(1H)-one;
(E)-2-(5-(2-(2,6-dimethyl-4-carbonylpyridin-1(4H)-yl)ethenyl)-2-methoxyphenoxy)-N-methylacetamide;
(E)-1-((3-cyclopropylformyloxy-4-methoxy)-styryl)-2,6-dimethylpyridin-4(1H)-one;
(E)-5-(2-(2,6-dimethyl-4-carbonylpyridin-1(4H)-yl)ethenyl)-2-methoxyphenylmethyl sulfonate;
(E)-1-(3-methylthiomethoxy-4-methoxystyryl)-2,6-dimethylpyridin-4(1H)-one;
(E)-1-(3-methylsulfinylmethoxy-4-methoxystyryl)-2,6-dimethylpyridin-4(1H)-one;
(E)-1-(3-methylsulfonylmethoxy-4-methoxystyryl)-2,6-dimethylpyridin-4(1H)-one;
(E)-1-(3-methylthioethoxy-4-methoxystyryl)-2,6-dimethylpyridin-4(1H)-one;
(E)-1-(3-methylsulfinylethoxy-4-methoxystyryl)-2,6-dimethylpyridin-4(1H)-one;
(E)-1-(3-methylsulfonylethoxy-4-methoxystyryl)-2,6-dimethylpyridin-4(1H)-one;
(E)-1-((3-(tetrahydrothiophen-3-yl)oxy-4-methoxy)-styryl)-2,6-dimethylpyridin-4(1H)-one;
(E)-1-(3-((1,1,-dioxotetrahydrothiophen-3-yl)oxy)-4-methoxystyryl)-2,6-dimethylpyridin-4(1H)-one;
(S,E)-1-(3-(tetrahydrothiophen-3-yl)oxy-4-methoxystyryl)-2,6-dimethylpyridin-4(1H)-one;
1-((E)-4-methoxy-3-(((3S)-1-oxotetrahydrothiophen-3-yl)oxy)styryl)-2,6-dimethylpyridin-4(1H)-one;
(S,E)-1-(3-((1,1-dioxotetrahydrothiophen-3-yl)oxy)-4-methoxy-styryl)-2,6-dimethylpyridin-4(1H)-one;
(R,E)-1-(3-(tetrahydrothiophen-3-yl)oxy-4-methoxystyryl)-2,6-dimethylpyridin-4(1H)-one;
1-((E)-4-methoxy-3-(((3R)-1-oxotetrahydrothiophen-3-yl)oxy)styryl)-2,6-dimethylpyridin-4(1H)-one;
(R,E)-1-(3-((1,1-dioxotetrahydrothiophen-3-yl)oxy)-4-methoxy-styryl)-2,6-dimethylpyridin-4(1H)-one;
(E)-1-(3-(cyclopropylmethoxy)-4-(difluoromethoxy)styryl)-2,6-dimethylpyridin-4(1H)-one;
(E)-1-(3-methoxy-4-difluoromethoxy-styryl)-2,6-dimethylpyridin-4(1H)-one;
(E)-1-(3-methylthiomethoxy-4-difluoromethoxy-styryl)-2,6-dimethylpyridin-4(1H)-one;
(E)-1-(3-methylsulfinylmethoxy-4-difluoromethoxystyryl)-2,6-dimethylpyridin-4(1H)-one;
(E)-1-(3-methylsulfonylmethoxy-4-difluoromethoxystyryl)-2,6-dimethylpyridin-4(1H)-one;
(E)-1-(3-methylthioethoxy-4-difluoromethoxystyryl)-2,6-dimethylpyridin-4(1H)-one;
(E)-1-(3-methylsulfinylethoxy-4-difluoromethoxystyryl)-2,6-dimethylpyridin-4(1H)-one;
(E)-1-(3-methylsulfonylethoxy-4-difluoromethoxystyryl)-2,6-dimethylpyridin-4(1H)-one;
(E)-1-((3-(tetrahydrothiophen-3-yl)oxy-4-difluoromethoxy)-styryl)-2,6-dimethylpyridin-4(1H)-one;
(S,E)-1-(3-(tetrahydrothiophen-3-yl)oxy-4-difluoromethoxystyryl)-2,6-dimethylpyridin-4(1H)-one;

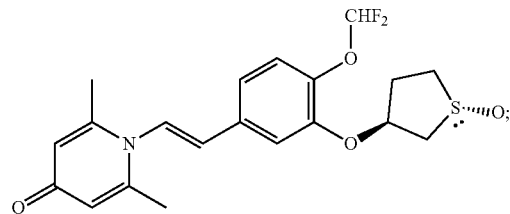

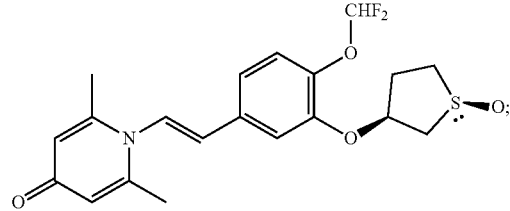

(S,E)-1-(3-(1,1-dioxotetrahydrothiophen-3-yl)oxy-4-difluoromethoxystyryl)-2,6-dimethylpyridin-4(1H)-one;
(R,E)-1-(3-(tetrahydrothiophen-3-yl)oxy-4-difluoromethoxystyryl)-2,6-dimethylpyridin-4(1H)-one;

1-((E)-4-difluoromethoxy-3-(((3R)-1-oxotetrahydrothiophen-3-yl)oxy)styryl)-2,6-dimethylpyridin-4(1H)-one;

(R,E)-1-(3-(1,1-dioxotetrahydrothiophen-3-yl)oxy-4-difluoromethoxystyryl)-2,6-dimethylpyridin-4(1H)-one;

(E)-1-(2-(3-cyclopropylmethoxy-4-methoxyphenyl)-2-methylethenyl)-2,6-dimethylpyridin-4(1H)-one;

(E)-1-(2-(3-cyclopropylmethoxy-4-methoxyphenyl)-2-phenylethenyl)-2,6-dimethylpyridin-4(1H)-one;

(Z)-1-(2-(3-cyclpropylmethoxy-4-methoxyphenyl)pent-1-en-3-yn-1-yl)-2,6-dimethylpyridin-4(1H)-one;

(E)-1-(2-(3-cyclopropylmethoxy-4-methoxyphenyl)-2-cyanoethenyl)-2,6-dimethylpyridin-4(1H)-one;

(Z)-2-(3-cyclopropylmethoxy-4-methoxyphenyl)-3-(2,6-dimethyl-4-carbonylpyridin-1 (4H)-yl)-acrylamide;

(Z)-2-(3-cyclopropylmethoxy-4-methoxyphenyl)-3-(2,6-dimethyl-4-carbonylpyridin-1 (4H)-yl)-N-methylacrylamide;

(Z)-2-(3-cyclopropylmethoxy-4-methoxyphenyl)-3-(2,6-dimethyl-4-carbonylpyridin-1 (4H)-yl)-N,N-dimethylacrylamide;

(Z)-2-(3-cyclopropylmethoxy-4-methoxyphenyl)-3-(2,6-dimethyl-4-carbonylpyridin-1 (4H)-yl)-N,N-diethylacrylamide;

(Z)-2-(3-cyclopropylmethoxy-4-methoxyphenyl)-3-(2,6-dimethyl-4-carbonylpyridin-1 (4H)-yl)-acrylic acid;

(Z)-methyl-2-(3-cyclopropylmethoxy-4-methoxyphenyl)-3-(2,6-dimethyl-4-carbonylpyridin-1 (4H)-yl)-acrylate;

(Z)-ethyl-2-(3-cyclopropylmethoxy-4-methoxyphenyl)-3-(2,6-dimethyl-4-carbonylpyridin-1 (4H)-yl)-acrylate;

(Z)-1-(2-(3-cyclopropylmethoxy-4-difluoromethoxyphenyl)pent-1-en-3-yn-1-yl)-2,6-dimethylpyridin-4(1H)-one;

(Z)-2-(3,4-dimethoxyphenyl)-3-(2,6-dimethyl-4-carbonylpyridine)-1(4H)-yl)acrylonitrile;

(E)-3-(3-cyclopropylmethoxy-4-methoxyphenyl)-2-(2,6-dimethyl-4-carbonylpyridin-1(4H)-yl)acrylonitrile;

(E)-3-(3-cyclopropylmethoxy-4-methoxyphenyl)-2-(2,6-dimethyl-4-carbonylpyridin-1(4H)-yl)acrylamide; and (E)-3-(3-cyclopropylmethoxy-4-methoxyphenyl)-2-(2,6-dimethyl-4-carbonylpyridine)-1(4H)-yl)-N,N-dimethylacrylamide.

* * * * *